United States Patent
Gillberg et al.

(10) Patent No.: US 10,975,045 B2
(45) Date of Patent: Apr. 13, 2021

(54) BENZOTHIAZEPINE COMPOUNDS AND THEIR USE AS BILE ACID MODULATORS

(71) Applicant: Albireo AB, Gothenburg (SE)

(72) Inventors: Per-Göran Gillberg, Mölndal (SE); Jan Mattsson, Kullavik (SE); Ingemar Starke, Gothenburg (SE); Santosh S. Kulkarni, Bangalore (IN)

(73) Assignee: Aibireo AB, Göteborg (SE)

( * ) Notice: Subject to any disclaimer, the term of this patent is extended or adjusted under 35 U.S.C. 154(b) by 0 days.

(21) Appl. No.: 16/805,153

(22) Filed: Feb. 28, 2020

(65) Prior Publication Data

US 2020/0247768 A1    Aug. 6, 2020

Related U.S. Application Data

(63) Continuation of application No. PCT/EP2020/052940, filed on Feb. 6, 2020.

(30) Foreign Application Priority Data

| Feb. 6, 2019 | (IN) | 201911004690 |
| Apr. 12, 2019 | (SE) | 1950463-8 |
| Dec. 4, 2019 | (IN) | 201911049986 |

(51) Int. Cl.
| *A61K 31/554* | (2006.01) |
| *C07D 281/02* | (2006.01) |
| *C07D 281/10* | (2006.01) |
| *A61P 1/16* | (2006.01) |

(52) U.S. Cl.
CPC .............. *C07D 281/10* (2013.01); *A61P 1/16* (2018.01)

(58) Field of Classification Search
CPC ........................... A61K 31/554; C07D 281/02
See application file for complete search history.

(56) References Cited

U.S. PATENT DOCUMENTS

| 3,539,380 | A | 11/1970 | Johnson |
| 4,507,235 | A | 3/1985 | Wunsch |
| 5,167,965 | A | 12/1992 | Schulz |
| 5,663,165 | A | 9/1997 | Brieaddy |
| 5,723,458 | A | 3/1998 | Brieaddy et al. |
| 5,811,388 | A | 9/1998 | Friend et al. |
| 5,817,652 | A | 10/1998 | Brieaddy et al. |
| 5,900,233 | A | 5/1999 | Day |
| 5,910,494 | A | 6/1999 | Brieaddy |
| 5,976,811 | A | 11/1999 | Mullner et al. |
| 5,994,391 | A | 11/1999 | Lee et al. |
| 5,998,400 | A | 12/1999 | Brieaddy et al. |
| 6,020,330 | A | 2/2000 | Enhsen et al. |
| 6,069,167 | A | 5/2000 | Sokol |
| 6,277,831 | B1 | 8/2001 | Frick et al. |
| 6,346,527 | B1 | 2/2002 | Takanaka et al. |
| 6,355,672 | B1 | 3/2002 | Yasuma et al. |
| 6,387,924 | B2 | 5/2002 | Lee et al. |
| 6,387,944 | B1 | 5/2002 | Frick et al. |
| 6,426,340 | B1 | 7/2002 | Gibson et al. |
| 6,562,860 | B1 | 5/2003 | Keller et al. |
| 6,642,269 | B2 | 11/2003 | Frick et al. |
| 6,676,979 | B2 | 1/2004 | Marlett et al. |
| 6,784,201 | B2 | 8/2004 | Lee et al. |
| 6,906,058 | B2 | 6/2005 | Starke et al. |
| 6,943,189 | B2 | 9/2005 | Keller et al. |
| 7,019,023 | B2 | 3/2006 | Frick et al. |
| 7,125,864 | B2 | 10/2006 | Starke et al. |
| 7,132,416 | B2 | 11/2006 | Starke et al. |
| 7,132,557 | B2 | 11/2006 | Wilkes et al. |
| 7,192,945 | B2 | 3/2007 | Starke et al. |
| 7,192,946 | B2 | 3/2007 | Starke et al. |
| 7,192,947 | B2 | 3/2007 | Starke et al. |
| 7,226,943 | B2 | 6/2007 | Starke et al. |
| 7,238,684 | B2 | 7/2007 | Starke et al. |
| 7,514,421 | B2 | 4/2009 | Abrahamsson et al. |
| 7,615,536 | B2 | 11/2009 | Frick et al. |
| 7,767,229 | B1 | 8/2010 | Milne et al. |
| 7,923,468 | B2 | 4/2011 | Frick et al. |
| 7,939,061 | B2 | 5/2011 | Prakash et al. |
| 7,956,085 | B2 | 6/2011 | Frick et al. |
| 8,048,413 | B2 | 11/2011 | Huguet |
| 8,067,584 | B2 | 11/2011 | Starke et al. |
| 8,101,583 | B2 | 1/2012 | Glombik et al. |
| 8,106,023 | B2 | 1/2012 | Glombik et al. |
| 9,295,677 | B2 | 3/2016 | Ling et al. |
| 9,339,480 | B2 | 5/2016 | Young et al. |
| 9,409,875 | B2 | 8/2016 | Bohlin et al. |
| 9,684,018 | B2 | 6/2017 | Horanzy |

(Continued)

FOREIGN PATENT DOCUMENTS

| DE | 3930168 | 3/1991 |
| DE | 19825804 | 8/2000 |

(Continued)

OTHER PUBLICATIONS

"A Long-Term, Open-Label Study of LUM001 With a Double-Blind, Placebo Controlled, Randomized Drug Withdrawal Period to Evaluate Safety and Efficacy in Children With Alagille Syndrome (ICONIC)," Clinical Trials.gov, Jun. 9, 2014, retrieved Oct. 3, 2014, http://clinicaltrials.gov/ct2/show/NCT02160782?term=LUM001 &rank=7, 4 pages.

(Continued)

*Primary Examiner* — Brenda L Coleman
(74) *Attorney, Agent, or Firm* — Fish & Richardson P.C.

(57) ABSTRACT

The invention relates to 1,5-benzothiazepine derivatives of formula (I). These compounds are bile acid modulators having apical sodium-dependent bile acid transporter (ASBT) and/or liver bile acid transport (LBAT) inhibitory activity. The invention also relates to pharmaceutical compositions comprising these compounds and to the use of these compounds in the treatment of cardiovascular diseases, fatty acid metabolism and glucose utilization disorders, gastrointestinal diseases and liver diseases.

9 Claims, No Drawings
Specification includes a Sequence Listing.

(56) References Cited

U.S. PATENT DOCUMENTS

| | | |
|---|---|---|
| 9,688,720 B2 | 6/2017 | Gillberg et al. |
| 9,694,018 B1 | 7/2017 | Gillberg et al. |
| 9,701,649 B2 | 7/2017 | Bohlin et al. |
| 9,745,276 B2 | 8/2017 | Bohlin et al. |
| 9,872,844 B2 | 1/2018 | Zernel et al. |
| 10,000,528 B2 | 6/2018 | Gillberg et al. |
| 10,011,633 B2 | 7/2018 | Gillberg et al. |
| 10,093,697 B2 | 10/2018 | Gillberg et al. |
| 1,044,160 A1 | 10/2019 | Gillberg et al. |
| 10,487,111 B2 | 11/2019 | Gillberg et al. |
| 10,709,755 B2 | 7/2020 | Ando et al. |
| 2002/0142054 A1 | 10/2002 | Marlett et al. |
| 2003/0125316 A1 | 7/2003 | Keller et al. |
| 2003/0143183 A1 | 7/2003 | Knudsen et al. |
| 2003/0153541 A1 | 8/2003 | Dudley et al. |
| 2003/0166927 A1 | 9/2003 | Starke et al. |
| 2003/0199515 A1 | 10/2003 | Mudipalli et al. |
| 2003/0215843 A1 | 11/2003 | Poupon et al. |
| 2004/0014806 A1 | 1/2004 | Bhat et al. |
| 2004/0038862 A1 | 2/2004 | Goodwin et al. |
| 2004/0062745 A1 | 4/2004 | Green et al. |
| 2004/0067933 A1 | 4/2004 | Starke et al. |
| 2004/0077625 A1 | 4/2004 | Tremont et al. |
| 2004/0082647 A1 | 4/2004 | Babiak et al. |
| 2004/0176438 A1 | 9/2004 | Tremont et al. |
| 2005/0009805 A1 | 1/2005 | Sasahara et al. |
| 2005/0038009 A1 | 2/2005 | Starke et al. |
| 2005/0113362 A1 | 5/2005 | Lindstedt et al. |
| 2005/0118326 A1 | 6/2005 | Anfinsen |
| 2005/0124557 A1 | 6/2005 | Lindqvist |
| 2005/0171204 A1 | 8/2005 | Lindstedt et al. |
| 2005/0197376 A1 | 9/2005 | Kayakiri et al. |
| 2005/0215882 A1 | 9/2005 | Chenevert et al. |
| 2005/0266080 A1 | 12/2005 | Desai et al. |
| 2006/0083790 A1 | 4/2006 | Anderberg et al. |
| 2007/0197522 A1 | 8/2007 | Edwards et al. |
| 2008/0207592 A1 | 8/2008 | Frick et al. |
| 2008/0300171 A1 | 12/2008 | Balkan et al. |
| 2009/0131395 A1 | 5/2009 | Antonelli et al. |
| 2010/0130472 A1 | 5/2010 | Young et al. |
| 2011/0003782 A1 | 1/2011 | Pellicciari |
| 2011/0152204 A1 | 6/2011 | Gedulin et al. |
| 2011/0294767 A1 | 12/2011 | Gedulin et al. |
| 2012/0114588 A1 | 5/2012 | Starke et al. |
| 2012/0157399 A1 | 6/2012 | Young et al. |
| 2013/0029938 A1 | 1/2013 | Aquino et al. |
| 2013/0059807 A1 | 3/2013 | Gedulin et al. |
| 2013/0108573 A1 | 5/2013 | Gedulin et al. |
| 2013/0109671 A1 | 5/2013 | Gedulin et al. |
| 2013/0225511 A1 | 8/2013 | Gillberg et al. |
| 2013/0236541 A1 | 9/2013 | Gillberg et al. |
| 2014/0275090 A1 | 9/2014 | Gedulin et al. |
| 2015/0031636 A1 | 1/2015 | Gillberg et al. |
| 2015/0031637 A1 | 1/2015 | Gillberg et al. |
| 2016/0039777 A1 | 2/2016 | Bohlin et al. |
| 2016/0146715 A1 | 5/2016 | Shim et al. |
| 2016/0193277 A1 | 7/2016 | Gillberg et al. |
| 2016/0194353 A1 | 7/2016 | Gillberg et al. |
| 2016/0229822 A1 | 8/2016 | Bohlin |
| 2016/0237049 A1 | 8/2016 | Bohlin |
| 2017/0143738 A1 | 5/2017 | Ando et al. |
| 2017/0143783 A1 | 5/2017 | Ando et al. |
| 2017/0182059 A1 | 6/2017 | Gillberg et al. |
| 2017/0182115 A1 | 6/2017 | Gillberg et al. |
| 2017/0240516 A1 | 8/2017 | Ymen et al. |
| 2018/0022776 A1 | 1/2018 | Gillberg et al. |
| 2018/0030088 A1 | 2/2018 | Gillberg et al. |
| 2018/0030089 A1 | 2/2018 | Gillberg et al. |
| 2018/0140219 A1 | 5/2018 | Yin et al. |
| 2018/0030009 A1 | 6/2018 | Gillberg et al. |
| 2018/0162904 A1 | 6/2018 | Gillberg et al. |
| 2018/0362577 A1 | 12/2018 | Gillberg et al. |
| 2019/0177286 A1 | 6/2019 | Ymen et al. |
| 2019/0367467 A1 | 12/2019 | Gillberg et al. |
| 2020/0002299 A1 | 1/2020 | Lundqvist |
| 2020/0247769 A1 | 8/2020 | Gillberg et al. |
| 2020/0330545 A1 | 10/2020 | Gillberg et al. |

FOREIGN PATENT DOCUMENTS

| | | |
|---|---|---|
| EP | 0278464 | 8/1988 |
| EP | 0489423 | 12/1991 |
| EP | 0372542 | 10/1992 |
| EP | 0573848 | 5/1993 |
| EP | 0549967 | 7/1993 |
| EP | 0624593 | 11/1994 |
| EP | 0624594 | 11/1994 |
| EP | 0624595 | 11/1994 |
| EP | 0624596 | 11/1994 |
| EP | 0864582 | 9/1998 |
| EP | 1173205 | 4/2000 |
| EP | 1535913 | 6/2005 |
| EP | 1719768 | 11/2006 |
| EP | 2144599 | 2/2008 |
| EP | 3210977 | 8/2017 |
| GB | 1573487 | 8/1980 |
| GB | 2262888 | 7/1996 |
| JP | 2000-513028 | 10/2000 |
| JP | B-3665055 | 6/2005 |
| JP | 2013-541584 | 11/2013 |
| JP | A-2013-542953 | 11/2013 |
| JP | H02258719 | 10/2019 |
| WO | WO 1991/03249 | 3/1991 |
| WO | WO 1993/16055 | 8/1993 |
| WO | WO 1994/00111 | 1/1994 |
| WO | WO 1994/18183 | 8/1994 |
| WO | WO 1994/18184 | 8/1994 |
| WO | WO 1996/05188 | 2/1996 |
| WO | WO 1996/08484 | 3/1996 |
| WO | WO 1996/16051 | 5/1996 |
| WO | WO 1997/33882 | 9/1997 |
| WO | WO 1998/03818 | 1/1998 |
| WO | WO 1998/07449 | 1/1998 |
| WO | WO 1998/38182 | 9/1998 |
| WO | WO 1998/40375 | 9/1998 |
| WO | WO 1998/56757 | 12/1998 |
| WO | WO 1999/01149 | 1/1999 |
| WO | WO 1999/32478 | 7/1999 |
| WO | WO 1999/35135 | 7/1999 |
| WO | WO 1999/64409 | 7/1999 |
| WO | WO 1999/64410 | 12/1999 |
| WO | WO 2000/01687 | 1/2000 |
| WO | WO 2000/38725 | 7/2000 |
| WO | WO 2000/38726 | 7/2000 |
| WO | WO 2000/38727 | 7/2000 |
| WO | WO 2000/38728 | 7/2000 |
| WO | WO 2000/38729 | 7/2000 |
| WO | WO 2000/47568 | 8/2000 |
| WO | WO 2000/61568 | 10/2000 |
| WO | WO 2000/62810 | 10/2000 |
| WO | WO 2001/34570 | 5/2001 |
| WO | WO 2001/60807 | 8/2001 |
| WO | WO 2001/66533 | 9/2001 |
| WO | WO 2001/68096 | 9/2001 |
| WO | WO 2001/68637 | 9/2001 |
| WO | WO 2002/08211 | 1/2002 |
| WO | WO 2002/32428 | 4/2002 |
| WO | WO 2002/50051 | 6/2002 |
| WO | WO 2002/53548 | 6/2002 |
| WO | WO 2003/020710 | 3/2003 |
| WO | WO 2003/022286 | 3/2003 |
| WO | WO 2003/022804 | 3/2003 |
| WO | WO 2003/022825 | 3/2003 |
| WO | WO 2003/022830 | 3/2003 |
| WO | WO 2003/043992 | 5/2003 |
| WO | WO 2003/051821 | 6/2003 |
| WO | WO 2003/051822 | 6/2003 |
| WO | WO 2003/061663 | 7/2003 |
| WO | WO 2003/091232 | 11/2003 |
| WO | WO 2003/106482 | 12/2003 |
| WO | WO 2004/006899 | 1/2004 |
| WO | WO 2004/056748 | 7/2004 |
| WO | WO 2004/076430 | 9/2004 |

(56) References Cited

FOREIGN PATENT DOCUMENTS

| WO | WO 2004/020421 | 10/2004 |
|---|---|---|
| WO | WO 2004/089350 | 10/2004 |
| WO | WO 2005/082874 | 9/2005 |
| WO | WO 2007/009655 | 1/2007 |
| WO | WO 2007/009656 | 1/2007 |
| WO | WO 2008/058628 | 5/2008 |
| WO | WO 2008/058630 | 5/2008 |
| WO | WO 2008/058631 | 5/2008 |
| WO | WO 2010/062861 | 6/2010 |
| WO | WO 2010/041268 | 9/2010 |
| WO | WO 2011/137135 | 11/2011 |
| WO | WO 2011/150286 | 12/2011 |
| WO | WO 2012/064266 | 5/2012 |
| WO | WO 2012/064267 | 5/2012 |
| WO | WO 2012/064268 | 5/2012 |
| WO | WO 2013/063512 | 5/2013 |
| WO | WO 2013/063526 | 5/2013 |
| WO | WO 2014/174066 | 10/2014 |
| WO | WO 2015/193788 | 12/2015 |
| WO | WO 2017/138876 | 8/2017 |
| WO | WO 2017/138877 | 8/2017 |
| WO | WO 2017/138878 | 8/2017 |
| WO | WO 2019/032027 | 2/2019 |

OTHER PUBLICATIONS

"Alagile Syndrome," Wikipedia, the free encyclopedia, posted on or about Feb. 11, 2005, retrieved Feb. 12, 2014, http://en.wikipedia.org/wiki/Alagille_syndrome, 3 pages.

"Albireo's Lead Compound in Cholestatic Liver Diseases, A4250, Projects Against Bile Acid-Mediated Cholestatic Liver Injury in Mice," Albireo Press Release, Apr. 11, 2014, 2 pages.

"An Extension Study to Evaluate the Long-Term Safety and Durability of Effect of LUM001 in the Treatment of Cholestatic Liver Disease in Subjects With Alagille Syndrome (IMAGINE)," Clinical Trials.gov, Jan. 23, 2014, retrieved on Oct. 3, 2014, http://clinicaltrials.gov/ct2/show/NCT02047318?term=LUM001&rank=3, 3 pages.

"An Extension Study to Evaluate the Long-Term Safety and Durability of Effect of LUM001 in the Treatment of Cholestatic Liver Disease in Subjects With Alagille Syndrome (IMAGINE-II)," Clincal Trials.gov, Apr. 16, 2014, retrieved on Oct. 3, 2014, http://clinicaltrials.gov/ct2/show/NCT02117713?term=LUM001&rank=2, 3 pages.

"Bowel Diversion Surgeries: Ileostomy, Colostomy, Ileoanal Reservoir and Continent Ileostomy," US Department of Health and Human Services: National Institute of Diabetes and Digestive and Kidney Diseases, Feb. 2009, retrieved on Jan. 27, 2014, http://digestive.niddk.nih.gov/ddiseases/pub/ileostomy/Bowel_Diversion_508.pdf, 4 pages.

"EASL Clinical Practice Guidelines: Management of cholestatic liver diseases," European Assoc. for the Study of the Liver, Journal of Hepatology, 2009, 51:237-267.

"Evaluation of LUM001 in the Reduction of Pruritus in Alagille Syndrome (ITCH)," Clinical Trials.gov, Feb. 5, 2014, retrieved on Oct. 3, 2014, http://clinicaltrials.gov/ct2/show/NCT02057692?term=LUM001&rank=5, 4 pages.

"IBAT inhibitor A4250 for Cholestatic Pruritus," ClinicalTrials.gov, Last updated Feb. 10, 2015, https://clinicaltrials.gov/ct2/show/NCT02360852?term=a4250&rank=1, 3 pages.

"Initiation of a Phase II Trial for A4250, the Company's Lead Compound for Cholestatic Liver Diseases and NASH," Albireo Pharma Press Release, Feb. 5, 2015, http://www.alberiopharma.com/News.aspx?PageID=1600872, 2 pages.

"Lumena Pharmaceuticals Now Dosing Patients in the INDIGO Phase 2 Clinical Trial of LUM001 in Pediatric Patients with Progressive Familial Intrahepatic Cholestasis," PR Newswire, May 9, 2014, retrieved on Oct. 3, 2014, http://www.prnewswire.com/news-releases/lumena-pharmaceuticals-now-dosing-patients-in-the-indigo-phase-2-clinical-trial-of-lum001-in-pediatric-patients-with-progressive-familial-intrahepatic-cholestasis-258609691.html, 3 pages.

"Open Label Study to Evaluate Efficacy and Long Term Safety of LUM001 in the Treatment of Cholestatic Liver Disease in Patients With Progressive Familial Intrahepatic Cholestasis (INDIGO)," Clinical Trials.gov, Feb. 5, 2014, retrieved on Oct. 3, 2014, http://clinicaltrials.gov/ct2/show/NCT02057718?term=LUM001&rank=4, 3 pages.

"Open Label Study to Evaluate Safety and Efficacy of LUM001 in Patients With Primary Sclerosing Cholangitis (CAMEO)," Clinical Trials.gov, Feb. 11, 2014, retrieved Oct. 3, 2014, http://clinicaltrials.gov/ct2/show/NCT02061540?term=LUM001&rank=6, 3 pages.

"Phase 2 Study to Evaluate LUM001 in Combination With Ursodeoxycholic Acid in Patients With Primary Biliary Cirrhosis (CLARITY)," Clinical Trials.gov, Jul. 17, 2013, retrieved Oct. 3, 2014, http://clinicaltrials.gov/ct2/show/NCT01904058?term=LUM001&rank=8, 3 pages.

"Progressive familial intrahepatic cholestasis," Wikipedia, the free encyclopedia, posted on or about Feb. 24, 2006, http://en.wikipedia.org/wiki/Progressive_familial_ intrahepatic_ cholestasis, 3 pages.

"Safety and Efficacy Study of LUM001 in the Treatment of Cholestatic Liver Disease in Patients With Alagille Syndrome (IMAGO)," Clinical Trials.gov, Jul. 16, 2013, http://clinicaltrials.gov/ct2/show/NCT01903460?term=LUM001&rank=1, 3 pages.

"What is Alagille Syndrome?," European Medicines Agency, Jan. 21, 2014, retrieved on Oct. 3, 2014, http://www.ema.europa.eu/docs/en_GB/document_library/Orphan_designation/2014/01/WC500159874.pdf, 6 pages.

AASLD: 2017 68th Annual Meeting of the American Association for the Study of Liver Diseases, Washington, DC, Oct. 20-24, 2017, (Abstract only).

Adams et al., "Hepascore: an accurate validated predictor of liver fibrosis in chronic hepatitis C infection," Clin. Chem. 2005, vol. 51(10), p. 1867-1873.

Alashkar et al., "Meeting Info.: 57th Annual Meeting of the American Society-of-Hematology," Orlando, FL, USA. Dec. 5-8, 2015, Amer Soc Hematol, Blood, 2015, 126(23).

Alissa et al., "Invited Review: Update on Progressive Familial Intrahepatic Cholestasis," Journal of Pediatric Gastroenterology and Nutrition, 2008, 46:241-252.

Alonso et al., "Histologic pathology of the liver in progressive familial intrahepatic cholestasis," Journal of Pediatric Gastroenterology and Nutrition, 14: 128-133, 1994.

Alvarez et al., "Reduced hepatic expression of farnesoid X receptor in hereditary cholestasis associated to mutation in ATP8B1," Hum Mol Genet, 2004, 13(20):2451-2460.

Alvarez, "Development of crystallization processes for pharmaceutical applications," LACCEI, 2007, 2E.3-1-2E.3-9.

Alvarez, Fernando; "Treatments in chronic cholestasis in children." Ann. Nestlé (2008) 66 p. 127-135.

American Diabetes Association, "Management of Dyslipidemia in Adults with Diabetes," Diabetes Care, Jan. 2003, 26(1).

Anakk et al., "Bile acids activate YAP to promote liver carcinogenesis," Cell Rep., Nov. 27, 2013, 5(4):1060-1069.

Angulo et al., "Independent Predictors of Liver Fibrosis in Patients With Nonalcoholic Steatohepatitis," Hepatology, Dec. 1999, 30(6): 1356-1362.

Angulo et al., "The NAFLD fibrosis score: a noninvasive system that identifies liver fibrosis in patients with NAFLD," Hepatology, 2007, vol. 45(4), p. 846-54.

Angulo, "Use of ursodeoxycholic acid in patients with liver disease," Current Gastroenterology Reports, Feb. 1, 2002, 4(1):37-44.

Anzivino et al., "ABCB4 and ABCB11 mutations in intrahepatic cholestasis of pregnancy in an Italian population," Dig Liver Dis., 2013, 45(3):226-232.

Appleby et al., "Effects of conventional and a novel colonic-release bile acid sequestrant, A3384, on fibroblast growth factor 19 and bile acid metabolism in healthy volunteers and patients with bile acid diarrhoea", United Eur. Gastroent. J., vol. 5, pp. 380-388, 2017.

Arnell et al., "Follow-up in children with progressive familial intrahepatic cholestasis after partial external biliary diversion," J Pediatr Gastroenterol Nutr., 2010, 51(4):494-499.

Artursson and Karlsson, "Correslation Between Oral Drug Absorption in Humans and Apparent Drug Permeability Coefficients in

(56) References Cited

OTHER PUBLICATIONS

Human Intestinal Epithelial (CACO-2) Cells," Biochemical and Biophysical Research Communications, Mar. 1991, 175(3):880-885.
Attili et al., "Bile Acid-induced Liver Toxicity: Relation to the Hydrophobic-Hydrophilic Balance of Bile Acids," Medical Hypotheses, 1986, 19:57-69.
Baghdasaryan et al., "Inhibition of intestinal bile acid absorption by ASBT inhibitor A4250 protects against bile acid-mediated cholestatic liver injury in mice," J. Hepatology, 2014, 60:S57.
Baghdasaryan et al., "Inhibition of intestinal bile acid absorption by ASBT inhibitor A4250 protects against bile acid-mediated cholestatic liver injury in mice," Presented at the EASL Conference, London, UK, Apr. 12, 2015, http://www.albireopharma.com/News.aspx?PageID=1591817, 22 pages.
Bajor et al., "Bile acids: short and long term effects in the intestine," Scandanavian J. Gastro., 2010, 45:645-664.
Balbach et al., "Pharmaceutical evaluation of early development candidates "the 100 mg-approach"," Int J Pharm, May 4, 2004, 275(1):1-12.
Banker et al., "Modern Pharmaceutics, 3ed", Marcel Dekker, New York, 1996, pp. 451 and 596.
Baumann, U. et al., "The ileal bile acid transport inhibitor A4250 decreases pruritus and serum bile acids in cholestatic liver diseases—an ongoing multiple dose, open-label, multicenter study," Hepatology, 2017, 66(1): S91 (Abstract only).
Bavin, "Polymorphism in Process Development," Chemistry and Industry, 527-529, 1989.
Beausejour et al., "Description of two new ABCB11 mutations responsible for type 2 benign recurrent intrahepatic cholestasis in a French-Canadian family," Can J Gastroenterol., 2011, 25(6):311-314.
Beraza et al., Nor-ursodeoxycholic acid reverses hepatocyte-specific nemo-dependnt steatohepatitis. Gut, 2011: 60: 387-396.
Billington et al., "Effects of bile salts on the plasma membranes of isolated rat hepatocytes," Bichem. J. 188: 321-327, 1980.
Blackmore et al., "Polymorphisms in ABCB11 and ATP8B1 Associated with Development of Severe Intrahepatic Cholestasis in Hodgkin's Lymphoma," J Clin Exp Hepatol., 2013, 3(2):159-161.
Bonge et al., "Cytostar-T Scintillating Microplate Assay for Measurement of Sodium-Dependent Bile Acid Uptake in Transfected HEK-293 Cells," Analytical Biochemistry, 2000, 282:94-101.
Bounford. University of Birmingham. Dissertation Abstracts International, (2016) vol. 75, No. 1C. Order No.: AA110588329. ProQuest Dissertations & Theses.
Brunt et al., "Nonalcoholic Steatohepatitis: A Proposal for Grading and Staging the Histological Lesions," American Jounral of Gastroenterology, Sep. 1999, 94(9): 2467-2474.
Brunzell and Hokanson, "Dislipidemia of Central Obesity and Insulin Resistance," Diabetes Care, 1999, 22(Suppl. 3):C10-C13.
Bull et al., "Genetic and morphological findings in progressive familial intrahepatic cholestasis (Byler disease [PFIC-1] and Byler syndrome): Evidence for Heterogeneity," Hepatology, 26: 1, 155-164, 1997.
Burrows, "Interventions for treating cholestasis in pregnancy," Cochrane Database Syst. Rev., 4:CD00493, 2001.
Byrne et al., "Missense mutations and single nucleotide polymorphisms in ABCB11 impair bile salt export pump processing and function or disrupt pre-messenger RNA splicing," Hepatology., 2009, 49(2):553-567.
Caira, "Crystalline Polymorphism of Organic Compounds," in: Topics in Current Chemistry, Jan. 1998, 198:163-208.
Camilleri, "Probiotics and irritable bowel syndrome: rationale, putative mechanisms, and evidence of clinical efficacy," Clin. Gastroenterol., 40(3):264-9, Mar. 2006.
Centeno, "Molecular mechanisms triggered by low-calcium diets," Nutrition research reviews., 22(2):163-74, Dec. 2009.
Chalasani et al., "The diagnosis and management of nonalcoholic fatty liver disease: Practice guidance from the American Association for the Study of Liver Diseases," Hepatology, 2018, 67(1):328-357.

Chauhan et al., "Pharmaceutical polymers," Encycl. Biomed. Polymers and Polymeric Biomaterials, 2016, 5929-5942.
Chen et al., "Bile salt export pump is dysregulated with altered farnesoid X receptor isoform expression in patients with hepatocelular carcinoma," Hepatologu, 57: 4, 1530-1541, 2013.
Chen et al., "Diagnosis of BSEP/ABCB11 mutations in Asian patients with cholestasis using denaturing high performance liquid chromatography," J Pediatr., 2008, 153(6):825-832.
Chen et al., "FIC1 and BSEP defects in Taiwanese patients with chronic intrahepatic cholestasis with low gamma-glutamyltranspeptidase levels," Journal of Pediatrics, 2002, 140(1):119-124.
Chen et al., "Inhibition of apical sodium-dependent bile acid transporter as a novel treatment for diabetes," Am J Physiol Endocrinol Metab, 2012, 302:E68-E76.
Chen et al., "Progressive Familial Intrahepatic Cholestasis, Type 1, Is Associated with Decreased Farnesoid X Receptor Activity," Gastroenterology, 2004, 126:756-764.
Chen et al., "Serum and urine metabolite profiling reveals potential biomarkers of human hepatocellular carcinoma," Molecular and Cellular Proteomics 10.7, 2011.
Chen et al., "The effects of diets enriched in beta-glucans on blood lipoprotein concentrations," J. Clin. Lipidol., 3(3):154-8, May 2009.
Chen et al., "Treatment effect of rifampicin on cholestasis," Internet Journal of Pharmacology, 4(2), 2006.
Chey et al., "A Randomized Placebo-Controlled Phase II b Trial of A3309, A Bile Acid Transporter Inhibitor, for Chronic Idiopathic Constipation," Am. J. Gastroenterology, May 2011, 106:1803-1812.
Chiang, "Bile acids: regulation of synthesis," J. Lipid Res, 2009, 50(10):1955-1966.
Copeland et al., "Novel splice-site mutation in ATP8B1 results in atypical progressive familial intrahepatic cholestasis type 1," J Gastroenterol Hepatol., 2013, 28(3):560-564.
Danese et al., "Analytical evaluation of three enzymatic assays for measuring total bile acids in plasma using a fully-automated clinical chemistry platform," PLoS One, 2017, 12(6):e0179200.
Das & Kar., Non alcoholic steatohepatitis. JAPI. 53, Mar. 2005.
Dashti et al., "A Phospholipidomic Analysis of All Defined Human Plasma Lipoproteins," Nature.com: Scientific Reports, Nov. 2011, DOI: 10.1038, 11 pages.
Davit_Spraul et al., "ATP8B1 and ABCB11 Analysis in 62 Children with Normal Gamma-Glutamyl Transferase Progressive Familial Intrahepatic Cholestasis (PFIC): Phenotypic Differences Between PFIC1 and PFIC2 and Natural History," Hepatology: Autoimmune, Cholestatic and Biliary Disease, May 2010, 1645-1655.
Davit-Spraul et al., "Liver transcript analysis reveals aberrant splicing due to silent and intronic variations in the ABCB11 gene," Mol Genet Metab., 2014, 113(3):225-229.
Davit-Spraul et al., "Progressive familial intrahepatic cholestasis," Orphanet Journal of Rare Diseases, Jan. 2009, 4:1-12.
Dawson et al., "Bile acid transporters" J. Lipid Res. 2009, 50, 2340-2357.
Dawson, "Role of the intestinal bile acid transporters in bile acid and drug disposition," Handb. Exp. Pharmacol. 2011, 201:169-203.
de Lédinghen et al., "Controlled attenuation parameter for the diagnosis of steatosis in non-alcoholic fatty liver disease," J Gastroenterol Hepatol., 2016, 31(4):848-855.
Declaration in U.S. Appl. No. 15/137,323, dated Apr. 6, 2019, 7 pages.
Declaration in U.S. Appl. No. 15/699,478, dated Apr. 4, 2019, 21 pages.
DeFronzo et al., "Insuline resistance, A multisurfaced syndrome responsible for NIDDM, obesity, hypertension, dyslipidemia and atherosclerotic cardiovascular disease," Diabetes Care, 1991, 14:173-194.
Deng et al., "Novel ATP8B1 mutation in an adult male with progressive familial intrahepatic cholestasis," World J Gastroenterol., 2012, 18(44):6504-6509.
Di Lascio et al., "Steato-Score: Non-Invasive Quantitative Assessment of Liver Fat by Ultrasound Imaging," Ultrasound Med Biol., 2018, 44(8):1585-1596.
Di Padova et al., "Double-blind placebo-controlled clinical trial of microporous chlestyramine in the treatment of intra- and extra-

(56) References Cited

OTHER PUBLICATIONS hepatic cholestasis: relationship between itching and serum bile acids," Methods Find Exp Clin Pharmacol., Dec. 1984, 6(12):773-776 (Abstract Only).

Dixon et al., "An expanded role for heterozygous mutations of ABCB4, ABCB11, ATP8B1, ABCC2 and TJP2 in intrahepatic cholestasis of pregnancy," Scientific Reports, 2017, 7(1):11823.

Dong et al., "Structure-activity relationship for FDA approved drugs as inhibitors of the human sodium taurocholate cotransporting polypeptide (NTCP).," Mol. Pharm. 2013, 10(3):1008-1019.

Dongiovanni et al., "Genetic Predisposition in NAFLD and NASH: Impact on Severity of Liver Disease and Response to Treatment," Curren Pharma Design, 2013, 19:5219-5238.

Drage et al., "Exon-skipping and mRNA decay in human liver tissue: molecular consequences of pathogenic bile salt export pump mutations," Sci Rep., 2016, vol. 6: 24827.

Drage et al., "Sequencing of FIC1, BSEP and MDR3 in a large cohort of patients with cholestasis revealed a high number of different genetic variants," J Hepatol. 2017, 67(6):1253-1264.

Droge et al., Zeitschrift fur Gastroenterologie 2015, 53(12) Abstract Number: A3-27. Meeting Info: 32. Jahrestagung der Deutschen Arbeitsgemeinschaft zum Studium der Leber. Dusseldorf, Germany. Jan. 22, 2016-Jan. 23, 2016.

Drumond et al., "Patients' appropriateness, acceptability, usability and preferences for pharmaceutical preparations: Results from a literature review on clinical evidence," Int. J. Pharm. 2017, 521(1-2):294-305.

Einspahr et al., "Protective role of wheat bran fiber: data from marker trials," Am. J. Med., 106(1A):32s-37s, Jan. 1999.

Ekkehard Sturm et al. The ileal bile acid transport inhibitor A4250 reduced pruritus and serum bile acid levels in children with cholestatic liver disease and pruritus: final results from a multiple-dose, open-label, multinational study Hepatology 2017; 66: 646-47 (Suppl. 1). doi: 10.1002/hep.29501.

Ellinger et al., "Partial external biliary diversion in bile salt export pump deficiency: Association between outcome and mutation," World J Gastroenterol., 2017, 23(29):5295-5303.

Ellis et al., "Zebrafish abcb11b mutant reveals strategies to restore bile excretion impaired by bile salt export pump deficiency," Hepatology, 2018, 67(4)1531-1545.

Engelen et al., "Oral size perception of particles: effect of size, type, viscosity and method," J. Text. Studies 2005, 36(4):373-386.

Espenshade and Hughes, "Regulation of Sterol Synthesis in Eukaryotes," Annu. Rev. Genet., 2007, 41:401-427.

Evason et al., "Morphologic findings in progressive familial intrahepatic cholestasis 2 (PFIC2): correlation with genetic and immunohistochemical studies," Am J Surg Pathol., 2011, 35(5):687-696.

Extended European Search Report in European Application No. 11840392.2, dated Feb. 24, 2014, 7 pages.

Extended European Search Report in European Application No. 11840481.3, dated Feb. 13, 2014, 10 pages.

Faubion et al., "Toxic bile salts induce rodent hepatocyte apoptosis via direct activation of Fas," The Journal of Clinical Investigation, 103: 1, 137-145, 1999.

Ferreira et al., Pediatric Transplantation 2013, 17(SUPPL. 1):99. Abstract Number: 239. Meeting Info: IPTA 7th Congress on Pediatric Transplantation. Warsaw, Poland. Jul. 13, 2013-Jul. 16, 2013.

Ferslew et al., "Altered Bile Acid Metabolome in Patients with Nonalcoholic Steatohepatitis," Dig Dis Sci., 2015, 60(11):3318-3328.

Folmer et al., "Differential effects of progressive familial intrahepatic cholestasis type 1 and benign recurrent intrahepatic cholestasis type 1 mutations on canalicular localization of ATP8B1," Hepatology., 2009, 50(5):1597-1605.

Forner et al., "Treatment of hepatocellular carcinoma," Critical Reviews in Oncology/Hematology, 2006, 60:89-98.

Francalanci et al., "Progressive familial intrahepatic cholestasis: Detection of new mutations and unusal modality of transmission," Digestive and Liver Disease 2010, 42(SUPPL. 1):516, Abstract Number: T.N.5.

Francalanci et al., Laboratory Investigation 2011, vol. 91, Supp. SUPPL. 1, pp. 360A. Abstract Number: 1526.

Gao et al., "Detection of hepatitis in children with idiopathic cholestatic bile salt export pump gene mutations," Shandong Yiyao, 2012, 52(10):14-16.

Gao et al., "Recent developments in the crystallization process: toward the pharmaceutical industry," Engineering, 2017, 3:343-353.

Gao et al., "The Identification of Two New ABCB11 Gene Mutations and the Treatment Outcome in a Young Adult with Benign Recurrent Intrahepatic Cholestasis: A Case Report," Hepatitis Monthly 2017, 17(10):e55087/1-e55087/6.

Gibney, "Shire Reports Topline Results from First of Three Placebo-Controlled Phase 2 Studies of SHP625 (LUM001) in Children with Alagille Syndrome," FierceBiotech.com, Apr. 9, 2015, http://www.firecebiotech.com/node/443176/print, 3 pages.

Gillberg et al., "The IBAT Inhibition by A3309—A Potential Mechanism for the Treatment of Constipation," Gastroenterology, 2010, 138(5), Supp 1, S-224.

Giovannoni et al., "Genetics and Molecular Modeling of New Mutations of Familial Intrahepatic Cholestasis in a Single Italian Center," PLoS One, 2015, 10(12):e0145021.

Glagov et al., "Compensatory enlargement of human atherosclerotic coronary arteries," N Engl. J. Med., May 1987, 316(22):1371-1375 (Abstract Only).

Goldschmidt et al., "Increased frequency of double and triple heterozygous gene variants in children with intrahepatic cholestasis," Hepatol Res., 2016, 46(4):306-311.

Govers et al., "Characterization of the adsorption of conjugated and unconjugated bile acids to insoluble, amorphous calcium phosphate", Journal of Lipid Research 35(5):741-748, 1994.

Griffin, et al., "A novel gene mutation in ABCB11 in siblings with progressive familial intrahepatic cholestasis type 2," Canadian Journal of Gastroenterology and Hepatology 2016, vol. 2016. Abstract Number: A200. Meeting Info: 2016 Canadian Digestive Diseases Week, CDDW 2016. Montreal, QC, United States. Feb. 26, 2016-Feb. 29, 2016.

Gunaydin et al., "Progressive familial intrahepatic cholestasis: diagnosis, management, and treatment," Hepat Med., 2018, 10:95-104.

Guorui et al., "Genetic diagnosis of progressive familial intrahepatic cholestasis type 2," Linchuang Erke Zazhi, 2013, 31(10):905-909.

Guzman et al., "Does Nonalcoholic Fatty Liver Disease Predispose Patients to Hepatocellular Carcinoma in the Absence of Cirrhosis?" Archives of pathology & laboratory medicine, Nov. 2008, 132(11):1761-1766.

Hancock et al., "Molecular Mobility of amorphous pharmaceutical solids below their glass transition temperatures," 12(6): 799-806, 1995.

Hao et al., "Application of high-throughput sequencing technologies with target capture/target next-generation sequencing in diagnosis of neonatal intrahepatic cholestasis causes by citrin deficiency (NICDD)," International Journal of Clinical and Experimental Pathology, 2017, 10(3):3480-3487.

Harmanci et al., "Late onset drug induced cholestasis in a living-related liver transplantation donor to son with progressive familial intrahepatic cholestasis," Experimental and Clinical Transplantation 2015, 13(2):76, Abstract Number: P62. Meeting Info: 1st Congress of the Turkic World Transplantation Society. Astana, Kazakhstan. May 20, 2015-May 22, 2015.

Hasegawa et al., "Intractable itch relieved by 4-phenylbutyrate therapy in patients with progressive familial intrahepatic cholestasis type 1," Orphanet J Rare Dis., 2014, 9:89.

Hayashi et al., "Assessment of ATP8B1 Deficiency in Pediatric Patients With Cholestasis Using Peripheral Blood Monocyte-Derived Macrophages," EBioMedicine, 2018, 27:187-199.

Hayashi et al., "Successful treatment with 4-phenylbutyrate in a patient with benign recurrent intrahepatic cholestasis type 2 refractory to biliary drainage and bilirubin absorption," Hepatol Res., 2016, 46(2):192-200.

Heathcote, "Management of primary biliary cirrhosis," Hepatology, 2000, 31(4):1005-1013.

hepc.liverfoundation.org' [online]. "Nonalcoholic Fatty Liver Disease," Brochure, 2016 [retrieved on Feb. 1, 2018]. Retrived from the

(56) References Cited

OTHER PUBLICATIONS

Internet: URL<http://hepc.liverfoundation.org/wp-content/uploads/2012/07/NAFLD-Brochure-2016.pdf>, 8 pages.
Herbst et al., "Taking the next step forward—Diagnosing inherited infantile cholestatic disorders with next generation sequencing," Mol Cell Probes, 2015, 29(5):291-298.
Higaki et al., "Inhibition of ileal na+/bile acid cotranporter by S-8921 reduces serum cholesteral and prevents atherosclerosis in rabbits", Arteriosclerosis, Thrombosis, and Vascular Biology 18(8):1304-1311, 1998.
Ho et al., "Polymorphic variants in the human bile salt export pump (BSEP; ABCB11): functional characterization and interindividual variability," Pharmacogenet Genomics, 2010, 20(1):45-57.
Hollands et al., "Ileal exclusion for Byler's disease: an alternative surgical approach with promising early results for pruritus," Journal of Pediatric Surgery, Feb. 1988, 33(2): 220-224.
Holz et al., "Can genetic testing guide the therapy of cholestatic pruritus? A case of benign recurrent intrahepatic cholestasis type 2 with severe nasobiliary drainage-refractory itch," Hepatol Commun., 2018, 2(2):152-154.
Holz et al., "Plasma separation and anion adsorption results in rapid improvement of nasobiliary drainage (NBD)-refractory pruritus in BRIC type 2," Zeitschrift fur Gastroenterologie 2016, vol. 54, No. 8. Abstract Number: KV275. Meeting Info: Viszeralmedizin 2016, 71. Jahrestagung der Deutschen Gesellschaft fur Gastroenterologie, Verdauungs- und Stoffwechselkrankheiten mit Sektion Endoskopie-10. Helbsttagung derDeutschen Gesellschaft fur Allgemein-und Viszeralchirurgie. Hamburg, Germany. Sep. 21, 2016-Sep. 24, 2016.
Hsu et al., "Adult progressive intrahepatic cholestasis associated with genetic variations in ATP8B1 and ABCB11," Hepatol Res., 2009, 39(6):625-631.
Hu et al., "Diagnosis of ABCB11 gene mutations in children with intrahepatic cholestasis using high resolution melting analysis and direct sequencing," Mol Med Rep., 2014, 10(3):1264-1274.
Huang et al., "Discovery of Potent, Nonsystemic Apical Sodium-Codependent Bile Acid Transporter Inhibitors (Part 2)," J. Med. Chem., 2005, 48:5853-5868.
Imagawa et al., "Clinical phenotype and molecular analysis of a homozygous ABCB11 mutation responsible for progressive infantile cholestasis," J Hum Genet. 2018, 63(5):569-577.
Imagawa et al., "Generation of a bile salt export pump deficiency model using patient-specific induced pluripotent stem cell-derived hepatocyte-like cells," Sci Rep., 2017, 7:41806.
Imagawa et al., "Splicing analysis using induced pluripotent stem cell-derived hepatocyte-like cells generated from a patient with progressive familial intrahepatic cholestatsis type 2," Journal of Pediatric Gastroenterology and Nutrition 2016, 63(2):551, Abstract Number: 166, Meeting Info: World Congress of Pediatric Gastroenterology, Hepatology and Nutrition 2016. Montreal, QC, Canada. Oct. 5, 2016-Oct. 8, 2016.
International Preliminary Report on Patentability for Application No. PCT/JP2015/068240, dated. Jan. 5, 2017, 12 pages (with English translation).
International Preliminary Report on Patentability for International Application No. PCT/EP2015/074573, dated Apr. 25, 2017, 8 pages.
International Preliminary Report on Patentability for International Application No. PCT/SE2011/051335, dated May 23, 2011, 7 pages.
International Preliminary Report on Patentability for International Application No. PCT/SE2011/051336, dated May 23, 2013, 11 pages.
International Search Report and Written Opinion for Application No. PCT/EP2014/058432, dated Jul. 11, 2014, 9 pages.
International Search Report and Written Opinion for Appln. No. PCT/EP2019/064602, dated Aug. 9, 2019, 11 pages.
International Search Report and Written Opinion for International Application No. PCT/EP2015/074573, dated Apr. 28, 2016, 11 pages.
International Search Report and Written Opinion for International Application No. PCT/SE2011/051335, dated Feb. 3, 2012, 12pages.
International Search Report and Written Opinion for International Application No. PCT/SE2011/051366, dated Feb. 22, 2012, 18 pages.
International Search Report and Written Opinion in Appln. No. PCT/SE2019/050603, dated Sep. 18, 2019, 11 pages.
International Search Report and Written Opinion in International Application No. PCT/SE2018/050802, dated Oct. 26, 2018.
International Search Report and Written Opinion in International Application No. PCT/SE2018/050803, dated Oct. 26, 2018.
International Search Report and Written Opinion in International Appln. No. PCT/EP2020/052940, dated Mar. 23, 2020, 12 pages.
International Search Report and Written Opinion in International Appln. No. PCT/EP2020/052942, dated Mar. 23, 2020, 9 pages.
International Search Report, Application No. PCT/JP2015/068240, dated Sep. 15, 2015, 11 pages (with English translation).
Ishak et al., "Histological grading and staging of chronic hepatitis," J. Hepatol. 1995, vol. 22, p. 696-699.
Ishibashi et al., "Hypercholesterolemia in low density lipoprotein receptor knockout mice and its reversal by adenovirus-mediated gene delivery", Journal of Clinical Investigation 92(2):883-893, 1993.
Ivashkin et al., "A novel mutation of ATP8B1 gene in young patient with familial intrahepatic cholestasis.," Hepatology International 2016, 10(1):S461, Abstract Number: LBO-38. Meeting Info: 25th Annual Conference of the Asian Pacific Association for the Study of the Liver, APASL 2016. Tokyo, Japan. Feb. 20, 2016-Feb. 24, 2016.
Jacquet et al., "Alagille Syndrome in Adult Patients: It is Never Too Late," American Journal of Kidney Diseases, May 2007, 49(5):705-709.
Jankowska et al., "[Cholestatic liver disease in children]," Przegl. Epidemiol., 56:16-21, 2002.
Jankowska et al., "Ileal exclusion in children with progressive familial intrahepatic cholestasis," J Pediatr Gastroenterol Nutr. 2014,58(1):92-95.
Jansen et al., "Endogenous bile acids as carcinogens," Journal of Hepatology, Sep. 2007, 47(3):434-435.
Jaquotot-Haerranz et al., "Clinical variability of mutations in the ABCB11 gene: a case report," Rev Esp Enferm Dig., 2013, 105(1):52-54.
Jericho et al., "Bile Acid Pool Dynamics in Progressive Familial Intrahepatic Cholestasis with Partial External Bile Diversion," Journal of Pediatric Gastroenterology and Nutrition, 2015, 60(3):368-374.
Jiang et al., "Non alcoholic steatohepatitis a precursor for hepatocellular carcinoma development," World Journal of Gastroenterology: WJG, Nov. 28, 2014, 20(44):16464-16473.
Jirsa et al., "Indel in the FIC1/ATP8B1 gene—a novel rare type of mutation associated with benign recurrent intrahepatic cholestasis," Hepatol Res. 2004, 30(1):1-3.
Jung et al., "Prenatal molecular diagnosis of inherited cholestatic diseases," J Pediatr Gastroenterol Nutr. 2007, 44(4):453-458.
Kagawa et al., "Phenotypic differences in PFIC2 and BRIC2 correlate with protein stability of mutant Bsep and impaired taurocholate secretion in MDCK II cells," Am J Physiol Gastrointest Liver Physiol., 2008, 294(1):G58-67.
Kang et al., "Progressive Familial Intrahepatic Cholestasis in Korea: A Clinicopathological Study of Five Patients," J Pathol Transl Med. May 16, 2019, 53(4):253-260.
Karpen and Dawson, "Not all (bile acids) who wander are lost: the first report of a patient with an isolated NTCP defect," Hepatology, 2015, 61(1):24-27.
Khosla et al., "Recurrent Post-partum Jaundice: Rare Genetic Disorder With Novel Genetic Mutations Identified," American Journal of Gastroenterology 2015, 110(1):S397. Meeting Info.: 80th Annual Scientific Meeting of the American-College-of-Gastroenterology. Honolulu, HI, USA. Oct. 16-21, 2015.
Kim, "Novel mutation of ABCB11 heterozygote associated with transient neonatal intrahepatic cholestasis," Journal of Pediatric Gastroenterology and Nutrition 2016, 62(1):620, Abstract Number: H-P-045. Meeting Info: 49th Annual Meeting of the European Society for Pediatric Gastroenterology, Hepatology and Nutrition, ESPGHAN 2016. Athens, Greece. May 25, 2016-May 28, 2016.

(56) References Cited

OTHER PUBLICATIONS

Kleiner et al., "Design and validation of a histological scoring system for nonalcoholic fatty liver disease," Hepatology, 2005, 41(6):1313-1321.

Klomp et al., "Characterization of mutations in ATP8B1 associated with hereditary cholestasis," Hepatology, 2004, 40(1):27-38.

Knisely et al., "Hepatocellular Carcinoma in ten children under five years of age with bile salt export pump deficiency," Hepatology, Aug. 2006, 44(2):478-486.

Kooistra, et al., "KLIFS: A structural kinase-ligand interaction database," Nucleic Acids Res., 2016, vol. 44, No. D1, pp. D365-D371.

Korman et al., "Assessment of Activity in Chronic Active Liver Disease," New England Journal of Medicine, 2010, 290(25):1399-1402.

Kosters et al., "Bile acid transporters in health and disease," Xenobiotica 2008, 38(7-8):1043-1071.

Kozarewicz, "Regulatory perspectives on acceptability testing of dosage forms in children," Int. J. Pharm. 2014, 469(2):245-248.

Krawczyk et al., "Prolonged cholestasis triggered by hepatitis A virus infection and variants of the hepatocanalicular phospholipid and bile salt transporters," Ann Hepatol., 2012, 11(5):710-714.

Kumar and Tandon, "Use of ursodeoxycholic acid in liver diseases," J. Gastroenterology and Hepatology, 2001, 16:3-14.

Kurata et al., "A novel class of apical sodium-dependent bile acid transporter inhibitors: the amphiphilic 4-oxo-1-phenyl-1,4-dihydroquinoline derivatives," Bioorganic & Medicinal Chemistry Letters, 2004, 14:1183-1186.

Kurbegov et al., Biliary diversion for progressive familial intrahepatic cholestasis: Improved liver morphology and bile acid profile, Gastroenterology, 125: 4, 1227-1234, 2003.

Lam et al., "A patient with novel ABCB11 gene mutations with phenotypic transition between BRIC2 and PFIC2," J Hepatol. 2006, 44(1):240-242.

Lam et al., "Levels of plasma membrane expression in progressive and benign mutations of the bile salt export pump (Bsep/Abcb11) correlate with severity of cholestatic diseases," Am J Physiol Cell Physiol. 2007, 293(5):C1709-16.

Lang et al,. "Genetic variability, haplotype structures, and ethnic diversity of hepatic transporters MDR3 (ABCB4) and bile salt export pump (ABCB11)," Drug Metab Dispos. 2006, 34(9):1582-1599.

Lang et al., "Mutations and polymorphisms in the bile salt export pump and the multidrug resistance protein 3 associated with drug-induced liver injury," Pharmacogenet Genomics, 2007, 17(1):47-60.

Lanzini et al., "Intestinal absorption of the bile acid analogue $^{75}$Se-homocholic acid-taurine is increased in primary biliary cirrhosis and reverts to normal during ursodeoycholic acid administrations," Gut, 2003, 52:1371-1375.

Lee et al., "Early Diagnosis of ABCB11 Spectrum Liver Disorders by Next Generation Sequencing," Pediatr Gastroenterol Hepatol Nutr. 2017, 20(2):114-123.

Lewis et al., "Effects of 2164U90 on ileal bile acid adsorption and serum cholesterol in rats and mice", Journal of Lipid Research 36(5):1098-1105, 1995.

Li et al., "ATP8B1 and ABCB11 mutations in Chinese patients with normal gamma-glutamyl transferase cholestasis: Phenotypic differences between progressive familial cholestasis type 1 and 2," Hepatology International 2017, 11(1):5180. Abstract Number: OP284.

Li et al., "Clinical feature and gene mutation analysis of one pedigree with progressive familial intrahepatic cholestasis type II," Hepatology International 2017, 11(1):5362, Abstract Number: PP0347. Meeting Info: 26th Annual Conference of the Asian Pacific Association for the Study of the Liver, APASL 2017. Shanghai, China. Feb. 15, 2017-Feb. 19, 2017.

Li et al., "Effect of Resistant Starch Film Properties on the Colon-Targeting Release of Drug From Coated Pellets", 152 J Control. Rel. e5, 2011.

Lichtinghagen R, et al., "The Enhanced Liver Fibrosis (ELF) score: normal values, influence factors and proposed cut-off values," J Hepatol. Aug. 2013;59(2):236-42.

Lin et al., "[Clinical and genetic analysis of an infant with progressive familial intrahepatic cholestasis type II].," Zhongguo Dang Dai Er Ke Za Zhi. 2018, 20(9)758-764 (with English abstract).

Ling, "Congenital cholestatic syndromes: What happens when children grow up?," Can J Gastroenterol, Nov. 11, 2007, 21(11):743-751.

Liu et al., "ABCB11 gene mutations in Chinese children with progressive intrahepatic cholestasis and low gamma glutamyltransferase," Liver International 2010, 30(6):809-815.

Liu et al., "Association of variants of ABCB11 with transient neonatal cholestasis," Pediatr Int. 2013, 55(2):138-144.

Liu et al., "Characterization of ATP8B1 gene mutations and a hot-linked mutation found in Chinese children with progressive intrahepatic cholestasis and low GGT," J Pediatr Gastroenterol Nutr., 2010, 50(2):179-183.

Liu et al., "Characterization of ATP8B1 mutations and a hot linked mutation found in Chinese children with progressive intrahepatic cholestasis and low GGT," Hepatology International 2009, 3(1):184-185, Abstract Number: PE405. Meeting Info: 19th Conference of the Asian Pacific Association for the Study of the Liver. Hong Kong, China. Feb. 13, 2009-Feb. 16, 2009.

Liu et al., "Homozygous p.Ser267Phe in SLC10A1 is associated with a new type of hypercholanemia and implications for personalized medicine," Scientific Reports, 2017, 7:9214.

Liu, et al., "Patient-centered pharmaceutical design to improve acceptability of medicines: similarities and differences in paediatric and geriatric populations," Drugs 2014, 74(16):1871-1889.

Loh et al., "Overview of milling techniques for improving the solubility of poorly water-soluble drugs," Asian J Pharm Sci., 2015, 10:225-274.

Longo et al., "Hyperlipidemia in chronic cholestatic liver disease," Curr. Treat. Options Gastrenterol., 2001, 4:111-114.

Lopez et al., "Effect of formulation variables on oral grittiness and preferences of multiparticulate formulations in adult volunteers," Eur. J. Pharm. Sci. 2016, 92:156-162.

Lopez et al., "Formulation approaches to pediatric oral drug delivery: benefits and limitations of current platforms," Expert Opin. Drug Deliv., 2015, 12(11):1727-1740.

Lv et al., "Noninvasive Quantitative Detection Methods of Liver Fat Content in Nonalcoholic Fatty Liver Disease," J Clin Transl Hepatol. 2018, 6(2):217-221.

Lykavieris et al., "Outcome of liver disease in children with Alagille syndrome: a study of 163 patients," Gut, 2001, 49:431-435.

Maggiore et al., "Relapsing features of bile salt export pump deficiency after liver transplantation in two patients with progressive familial intrahepatic cholestasis type 2," J Hepatol. 2010, 53(5):981-6.

Manghat and Wierzbicki, "Colesevelam hydrochloride: a specifically engineered bile acid sequestrant," Future Lipidology, 3(3):237-255, Jun. 2008.

Masahata et al., "Recurrence of Progressive Familial Intrahepatic Cholestasis Type 2 Phenotype After Living-donor Liver Transplantation: A Case Report," Transplant Proc. 2016, 48(9):3156-3162.

Matte et al., "Analysis of gene mutations in children with cholestasis of undefined etiology," J Pediatr Gastroenterol Nutr. 2010, 51(4):488-493.

McCullough et al., "The epidemiology and risk factors of NASH.", Blackwell Publishing, Chapter 3, 2005.

McKay et al., "Mutation detection in cholestatic patients using microarray resequencing of ATP8B1 and ABCB11 [version 2; peer review: 2 approved, 1 approved with reservations]," F1000 Res., 2013, 2:32.

McMichael and Potter, "Reproduction, endogenous and exogenous sex hormones, and colon cancer: a review and hypothesis," J. Natl. Cancer Inst., 65(6):1201-07, Dec. 1980.

McPherson et al., "Simple non-invasive fibrosis scoring systems can reliably exclude advanced fibrosis in patients with non-alcoholic fatty liver disease," Gut 2010, 59(9):1265-9.

MerckManuals.com', "Obesity," 2008, Merch Manual for Health Care Professionals, Section-Nutritional Disorders, Chapter- "Obe-

(56) References Cited

OTHER PUBLICATIONS sity and the metabolic syndrome," retrieved on Feb. 22, 2012, http://www.merchmanuals.com/professional/nutritional_disorders/obesity_and_the_metabolic_syndrome/metabolic_syndrome.html?qt=metabolicsyndrome&alt=sh, 10 pages.
Miloh et al., Gastroenterology 2006, vol. 130, No. 4, Suppl. 2, pp. A759-A760. Meeting Info.: Digestive Disease Week Meeting/107th Annual Meeting of the American-Gastroenterological Association. Los Angeles, CA, USA. May 19.
Mishra et al., "Investigation of organoleptic characteristics in the development of soft chews of calcium carbonate as mineral supplement," Yakugaku Zasshi 2009, 129(12):1537-1544.
Mistry et al., "Evidence of acceptability of oral paediatric medicines: a review," J. Pharm. Pharmacol. 2017, 69(4):361-376.
Mizuochi et al., "Characterization of urinary bile acids in a pediatric BRIC-1 patient: effect of rifampicin treatment," Clin Chim Acta. 2012, 413(15-16):1301-1304.
Moghadamrad et al., "Cholestasis in a patient with gallstones and a normal gamma-glutamyl transferase," Hepatology, 2013, 57(6):2539-2541.
Morissette et al., "High-throughput crystallization. polymorphs, salts, co-crystals and solvates of pharmaceutical solids," Advanced Drug Delivery Reviews, 2004, 56:275-300.
Mouzaki and Allard, "Non-alcoholic steatohepatitis: the therapeutic challenge of a global epidemic," Annals of Gastroenterology, 2012, 25: 207-217.
Mowat et al., "Respiratory chain complex III [correction of complex] in deficiency with pruritus: a novel vitamin responsive clinical feature," J. Pediatr., 134(3):352-4, Mar. 1999.
Nagasaka et al., "Depletion of high-density lipoprotein and appearance of triglyceride-rich low-density lipoprotein in a Japanese patient with FIC1 deficiency manifesting benign recurrent intrahepatic cholestasis," J Pediatr Gastroenterol Nutr., 2007, 45(1)96-105.
Nagase et al., "Preparation of Benzothiazepine derivatives with activity of bringing about high blood GLP-1 concentration," CAPLUS Database, Jul. 2002, retrieved from STN Database on Mar. 31, 2014, https://stneasy.cas.org/tmp/20140331/443268-0025347726-200/349520738.html, 2 pages.
Narchi et al., "Intrahepatic cholestasis in two omani siblings associated with a novel homozygous ATP8B1 mutation, c.379C>G (p.L127V).," Saudi J Gastroenterol. 2017, 23(5):303-305.
Neuman, et al., "Biomarkers in nonalcoholic fatty liver disease," Can. J. Gastroenterol. Hepatol. 2014, 28(11):607-618.
Ng et al., "Autoimmune haemolytic anaemia with giant cell hepatitis and concurrent bile salt export pump deficiency: Challenges in diagnosis and management," Journal of Pediatric Gastroenterology and Nutrition 2018, 66(2):860, Abstract Number: H-P-127. Meeting Info: 51st Annual Meeting European Society for Paediatric Gastroenterology, Hepatology and Nutrition, ESPGHAN 2018. Geneva, Switzerland. May 9, 2018-May 12, 2018.
Noe et al., "Impaired expression and function of the bile salt export pump due to three novel ABCB11 mutations in intrahepatic cholestasis," J Hepatol. 2005, 43(3):536-543.
O'Neill et al.,"Comparison of efficacy of plant stanol ester and sterol ester: short-term and longer-term studies," American Journal of Cardiology, 96(1A):29d-36D, Jul. 2005.
Okubo et al., "II, Daihyoteki Shikkan no Shinryo to Genkyo to Shorai Tenbo 6. Nanjisei Benpi," The Journal of the Japanese Society of Internal Medicine Jan. 10, 2013 (Jan. 10, 2013), 102(1), pp. 83-89.
Painter et al., "Sequence variation in the ATP8B1 gene and intrahepatic cholestasis of pregnancy," Eur J Hum Genet. 2005, 13(4):435-439.
Park et al., "Clinical and ABCB11 profiles in Korean infants with progressive familial intrahepatic cholestasis," World J Gastroenterol., 2016, 22(20):4901-4907.
Parker et al., "Molecular mechanisms underlying bile acid-stimulated glucagon-like peptide-1 secretion," British J. Pharmacology, 2012, 165:414-423.
Patani et al., "Bioisosterism: A Rational Approach in Drug Design," Chem Rev, 1996, 96:3147-3176.

Pauli-Magnus et al., "Enterohepatic transport of bile salts and genetics of cholestasis," Journal of Hepatology, 2005, 43(2):342-357.
Pauli-Magnus et al., "Impaired expression and function of the bile salt export pump due to three novel ABCB11 mutations in intrahepatic cholestasis," Hepatology 2003, vol. 38, No. 4 Suppl. 1, pp. 518A. print. Meeting Info.: 54th Annual Meeting of the American Association for the Study of Liver Diseases. Boston, MA, USA. Oct. 24-28, 2003. American Association for the Study of Liver Diseases.
Peng et al., "[Relationship between phenotype and genotype of ABCB11 deficiency in siblings and literature review].," Zhonghua er ke za zhi (Chinese journal of pediatrics) 2018, 56(6):440-444.
Perez et al., "Bile-acid-induced cell injury and protection," World J Gastroenterol, Apr. 2009, 15(14)1677-1689.
Perumpail et al., "Clinical epidemiology and disease burden of nonalcoholic fatty liver disease," World Journal of Gastroenterology, Dec. 2017, 23(47): 8263-8276.
Plump et al., "Severe hypercholesterolemia and atherosclerosis in apolipoprotein E-deficient mice created by homologous recombination in ES cells", Cell (71):343-353, 1992.
Podesta et al., "Treatment of pruritus of primary biliary cirrhosis with rifampin," Dig. Dis. Sci, 1991, 36(2):216-220.
Poupon et al., "Chronic Cholestatic Disease," J. Hepatology, 2000, 32(1):12-140.
Qiu et al., "Defects in myosin VB are associated with a spectrum of previously undiagnosed low γ-glutamyltransferase cholestasis," Hepatology 2017, 65(5)1655-1669.
Qiu et al., "Disruption of BSEP function in HepaRG cells alters bile acid disposition and is a susceptive factor to drug-induced cholestatic injury," Mol. Pharmaceutics, 13:4, 2016 (Abstract only).
Reeder et al., "Quantitative assessment of liver fat with magnetic resonance imaging and spectroscopy," J Magn Reson Imaging. 2011, 34(4):729-749.
Renga et al., "Role of FXR in regulating bile acid homeostasis and relevance for human diseases," Curr. Drug. Targets Immune Endocr. Metabol. Disord., 5(3):289-303, Sep. 2005.
Ricci, "Bridging studies in support of oral pediatric formulation development," Int. J. Pharmaceuticals, 2013, 457:323-326.
Rolo et al., "Bile acids affect liver mitochondrial bioenergetics: Possible relevance for cholestasis therapy," Toxocological Sciences, 57: 177-185, 2000.
Rumbo et al., Transplantation 2018, vol. 102, No. 7, Supp. Supplement 1, pp. 5848. Abstract Number: P.752. Meeting Info: 27th International Congress of the Transplantation Society, TTS 2018. Madrid, Spain. Jun. 30, 2018-Jul. 5, 2018.
Sanyal et al. The etiology of hepatocellular carcinonna and consequences of treatment. The Oncologist, 2010, 15 Suppl 4, 14-22.
Satapathy and Sanyal, "Epidemiology and Natural History of Non-alcoholic Fatty Liver Disease," Seminars in Liver Disease, Aug. 2015, 35(3): 221-235.
Sattler et al., "Functional analysis of previously uncharacterised disease-causing mutations of the bile salt export pump," Journal of Hepatology 2017, 66(1):5177. Meeting Info.: International Liver Congress/ 52nd Annual Meeting of the European-Association-for-the-Studyof-the-Liver. Amsterdam, Netherlands. Apr. 19-23, 2017. European Assoc Study Liver.
Scheimann et al., "Prevalence of Abcb 11 mutations among children with cholelithiasis," Gastroenterology 2007, 132(4)Suppl. 2:A452, Meeting Info.: Digestive Disease Week Meeting/108th Annual Meeting of the American-GastroenterologicalAssociation. Washington, DC, USA. May 19-24, 2007. Amer Gastroenterol Assoc; Amer Assoc Study Liver Dis; Amer Soc Gastrointestinal Endoscopy; Soc Surg Alimentary Tract.
Scheuer, "Primary Biliary Cirrhosis," Proc. R. Soc. Med., Dec. 1967, 60:1257-1260.
Schiller, "Review article: the therapy of constipation", Alimentary Pharmacology and Therapeutics 15(6):749-763, 2001.
Schumpelick et al., "[Ulcerative colitis—late functional results of ileoanal pouch anastomosis]," Chirung, 69(10):1013-19, Oct. 1998.
Sciveres. "Relapsing features of bile salt export pump (BSEP) deficiency in a patient successfully transplanted for progressive familial intrahepatic cholestasis type 2 (PFIC2).," Digestive and

(56) References Cited

OTHER PUBLICATIONS

Liver Disease 2010, 42(5):5329. Abstract Number: CO18. Meeting Info: 17th National Congress SIGENP. Pescara, Italy. Oct. 7, 2010-Oct. 9, 2010.
Shah et al., "Progressive Familial Intrahepatic Cholestasis Type 2 in an Indian Child," J Pediatr Genet. 2017, 6(2):126-127.
Shah et al., "Role of Caco-2 Cell Monolayers in Prediction of Intestinal Drug Absorption," Biotechnol. Prog., 2006, 22:186-198.
Shang et al., "Colesevelam improves insulin resistance in a diet-induced obesity (F-DIO) rat model by increasing the release of GLP-1," Am J. Physiol Gastroint Liver Physiol, 2010, 298:G419-G424.
Shaprio et al., "DHPLC screening for mutations in progressive familial intrahepatic cholestasis patients," J Hum Genet. 2010, 55(5):308-313.
Sharma et al., "Spectrum of genomic variations in Indian patients with progressive familial intrahepatic cholestasis," BMC Gastroenterol, 2018, 18(1):107.
Sharma et al., "Spectrum of sequence variations in Indian patients with progressive familial intrahepatic cholestasis show several novel polymorphisms," Indian Journal of Gastroenterology 2017, 36(1):A99. Abstract Number: M-20. Meeting Info: 58th Annual Conference of the Indian Society of Gastroenterology, ISGCON 2017. Bhubaneswar, India. Dec. 14, 2017-Dec. 17, 2017.
Sherrif et al., "Hepatotoxicity from anabolic androgenic steroids marketed as dietary supplements: contribution from ATP8B1/ABCB11 mutations?," Liver international: official journal of the International Association for the Study of the Liver, 2013, 33(8):1266-1270.
Shimizu et al., "Living-related liver transplantation for siblings with progressive familial intrahepatic cholestasis 2, with novel genetic findings," Am J Transplant. 2011, 11(2):394-398.
Simons, "The fate of the orally administered bile acid sequestrant, polidexide, in humans," Clin. Exp. Pharmacol. Physiol., 3(1):99-101, Jan.-Feb. 1976.
Singhal et al., "Drug polymorphism and dosage form design: a practical perspective," Adv Drug Deliv Rev, Feb. 23, 2004, 56(3):335-347.
Sirtori, "Mechanisms of lipid-lowering agents," Cardiology, 78(3):226-35, 1991.
Sohn et al., "Benign Recurrent Intrahepatic Cholestasis Type 2 in Siblings with Novel ABCB11 Mutations," Pediatr Gastroenterol Hepatol Nutr. 2019, 22(2):201-206.
Sorrentino et al., "A Clinical-Morphological Study on Cholestatic Presentation of Nonalcoholic Fatty Liver Disease," Digestive Disease and Sciences, Jun. 2005, 50(6):1130-1135.
Sprong et al., "Dietary Calcium Phosphate Promotes Listeria monosytogenes colonization and translocation in rats red diets containing corn oil but not milk fat1", J. Nutrition (US) 132(6):1269-1274, 2002.
Squires et al., "Clinical Variability After Partial External Biliary Diversion in Familial Intrahepatic Cholestasis 1 Deficiency," J Pediatr Gastroenterol Nutr. 2017, 64(3):425-430.
Staels and Kuipers, "Bile acid sequestrants and the treatment of type 2 diabetes mellitus," Drugs, 67(10):1383-92, 2007.
Stein, "Managing Dyslipidemia in the High-Risk Patient," Am J. Cardiol., 2002, 89:50-57.
Stindt et al., "A novel mutation within a transmembrane helix of the bile salt export pump (BSEP, ABCB11) with delayed development of cirrhosis," Liver Int. 2013, 33(10):1527-1735.
Stolz et al., "Severe and protracted cholestasis in 44 young men taking bodybuilding supplements: assessment of genetic, clinical and chemical risk factors," Aliment Pharmacol Ther. 2019, 49(9):1195-1204.
Stone et al., "Biochemical characterization of P4-ATPase mutations identified in patients with progressive familial intrahepatic cholestasis," J Biol Chem. 2012, 287(49):41139-51.
Strautnieks et al., "Severe bile salt export pump deficiency: 82 different ABCB11 mutations in 109 families," Gastroenterology. 2008, 134(4):1203-1214.
Sun et al., "Bile acids promote diethylnitrosamine-induced hepatocellular carcinoma via increased inflammatory signaling," American Journal of Physiology-Gastrointestinal and Liver Physiology, May 5, 2016, 311(1):G91-104.
Suzuki and Takada, "Mechanisms of regulation of bile acid transport in the small intestine," Falk Symposium, 165:76-81, 2009.
Swedish Office Aciton in SW Appln. No. 1950463-8, dated Sep. 26, 2019, 3 pages.
Swedish Office Action for Swedish Appln. No. 1850915-8, dated Feb. 15, 2019, 6 pages.
Swedish Office Action in SW Appln. No. 1950464-6, dated Sep. 26, 2019, 3 pages.
Swedish Office Action in Swedish Appln. No. 1850761-6, dated Dec. 17, 2018, 8 pages.
Swedish Office Action in Swedish Appln. No. 1850762-4, dated Dec. 27, 2018, 7 pages.
Swedish Search Report for Swedish Appln. No. 1850915-8, dated Feb. 15, 2019, 2 pages.
Swedish Search Report in SW Appln. No. 1950463-8, dated Sep. 26, 2019, 2 pages.
Swedish Search Report in SW Appln. No. 1950464-6, dated Sep. 26, 2015, 3 pages.
Swedish Search Report in Swedish Appln. No. 1850761-6, dated Dec. 17, 2018, 3 pages.
Swedish Search Report in Swedish Appln. No. 1850762-4, dated Dec. 27, 2018, 3 pages.
Takahashi et al., "Gradual improvement of liver function after administration of ursodeoxycholic acid in an infant with a novel ABCB11 gene mutation with phenotypic continuum between BRIC2 and PFIC2," Eur J Gastroenterol Hepatol. 2007, 19(11):942-6.
Tanaka et al., "Genetic and Familial considerations of Primary Biliary Cirrhosis," Am. J. Gastroenterology, 2001, 96(1): 8-15.
Tian et al., "Factors affecting crystallization of hydrates," J. Pharm. Pharmacol., 2010, 62:1534-1546.
Tibesar et al., "Two Cases of Progressive Familial Intrahepatic Cholestasis Type 2 Presenting with Severe Coagulopathy without Jaundice," Case Rep Pediatr. 2014, 2014:185923.
Togawa et al., "Diversity of ATP8B1 mutations in japanese patients with intrahepatic cholestasis associated with low gamma-glutamyl transpeptidase level," Journal of Pediatric Gastroenterology and Nutrition 2018, 67(1):5363, Abstract Number: 615.
Tollefson et al., "A novel class of apical sodium co-dependent bile acid transporter inhibitors: the 1,2-Benzothiazepines", Bioorganic and Medicinal Chemistry Letters 12:3727-3730, 2003.
Treepongkaruna et al., "Novel ABCB11 mutations in a Thai infant with progressive familial intrahepatic cholestasis," World J Gastroenterol. 2009, 15(34):4339-4342.
Tremont et al., "Discovery of Potent, Nonsystemic Apical Sodium-Codependent Bile Acid Transporter Inhibitors (Part 1)," J. Med. Chem, 2005, 48:5837-5852.
Tyle, "Effect of size, shape and hardness of particles in suspension on oral texture and palatability," Acta Psychologica 1993, 84(1):111-118.
Uegaki et al., "Successful treatment with colestimide for a bout of cholestasis in a Japanese patient with benign recurrent intrahepatic cholestasis caused by ATP8B1 mutation," Intern Med. 2008, 47(7):599-602.
Van der Woerd et al., "Analysis of aberrant pre-messenger RNA splicing resulting from mutations in ATP8B1 and efficient in vitro rescue by adapted U1 small nuclear RNA," Hepatology 2015, 61(4):1382-1391.
Van der Woerd et al., "Mutational analysis of ATP8B1 in patients with chronic pancreatitis," PLoS One. 2013, 8(11):e80553.
Van Heek et al., "In vivo metabolism-based discovery of a potent cholesterol absorptions inhibitor, sch58235, in the rat and rhesus monkey through the identification of the active metabolites of sch48461," J. Pharmacol. Exp. Med, 1997, 283(1):157-163.
Van Mil et al., "Benign recurrent intrahepatic cholestasis type 2 is caused by mutations in ABCB11," Gastroenterology. 2004, 127(2):379-384.
Van Tilberg et al., "Na+-dependent bile acid transport in the ileum: the balance between diarrhea and constipation", Gastroenterology 98(1):25-32, 1989.

(56) References Cited

OTHER PUBLICATIONS

Varma et al., "Retargeting of bile salt export pump and favorable outcome in children with progressive familial intrahepatic cholestasis type 2," Hepatology 2015, 62(1):198-206.
Vaz et al., "Sodium taurocholate cotransporting polypeptide (SLC10A1) deficiency: conjugated hypercholanemia without a clear clinical phenotype," Hepatology, 2015, 61(1):260-267.
Vertommen and Kinget, "The influence of five selected processing and formulation variables on the particle size, particle size distribution, and friability of pellets produced in a rotary processor," Drug Dev. Ind. Pharm. 1997, vol. 23, p. 39-46.
Vippagunta et al., "Crystalline solids", Advanced Drug Delivery Reviews 48:3-26, 2001.
Vitale et al., "Cryptogenic cholestasis in young and adults: ATP8B1, ABCB11, ABCB4, and TJP2 gene variants analysis by high-throughput sequencing," J Gastroenterol. 2018, 53(8):945-958.
Waisbourd-Zinman et al., "A Rare BSEP Mutation Associated with a Mild Form of Progressive Familial Intrahepatic Cholestasis Type 2," Ann Hepatol. 2017, 16(3):465-468.
Walkowiak-Tomczak, "Characteristics of plums as a raw material with valuable nutritive and dietary properties—a review," Pol. J. Food Nutr. Sci., 58(4):401-405, 2008.
Walsh et al., "Patient acceptability, safety and access: A balancing act for selecting age-appropriate oral dosage forms for paediatric and geriatric populations," Int. J. Pharm. 2017, 536(2):547-562.
Wang et al., "Bile acid receptors and liver cancer," Curr. Pathobiol Rep, Mar. 2013, 1(1):29-35.
Wang et al., "Increased hepatocellular carcinoma risk in chronic hepatitis B patients with persistently elevated serum total bile acid: a retrospective cohort study," Scientific reports, Dec. 1, 2016, 6:38180, 9 pages.
Wang et al., "Splicing analysis of rare/novel synonymous or intronic variants identified in ABCB11 heterozygotes presenting as progressive intrahepatic cholestasis with low γ-glutamyltransferase," Hepatol Res. 2018, 48(7):574-584.
Wang et al., "The Features of GGT in Patients with ATP8B1 or ABCB11 Deficiency Improve the Diagnostic Efficiency," PLoS One. 2016; 11(4):e0153114.
Watts and Illum, "Colonic Drug Delivery," Drug Development and Industrial Pharmacy, 1997, 23(9):893-913.
Welberg et al., "Calcium and the prevention of colon cancer", Scandinavian J. Gasteroenterology Suppl. 188:52-59, 1991.
Whitington et al., "Partial external diversion of bile for the treatment of intractable pruitus associated with intrahepatic cholestasis," Gastroenterology, 95: 1, 130-136, 1988 (Abstract only).
Williams et al., Foye's Principles of Medicinal Chemistry, 5th Edition, 2002, 59-63.
Wolff, "Burger's Medicinal Chemistry, 5ed, Part I", John Wiley & Sons, 1995, pp. 975-977.
Wong et al., "Utility of oligonucleotide array-based comparative genomic hybridization for detection of target gene deletions," Clin Chem. 2008, 54(7)1141-1148.
Woolbright et al., "Novel insight into mechanisms of cholestatic liver injury," World Journal of Gastroenterology, 18: 36, 4985-4993, 2012.
Wu et al., "Discovery of a highly potent, nonabsorbable apical sodium-dependent bile acid transporter inhibitor (GSK2330672) for treatment of type 2 diabetes," J. Med. Chem., 2013, 53(12):5094-5117.
Xie et al., "Dysregulated hepatic bile acids collaboratively promote liver carcinogenesis," Int J Cancer, Oct. 15, 2016, 139(8):1764-1775.
Yang et al., "Partial external biliary diversion in children with progressive familial intrahepatic cholestasis and alagille disease," Journal of Pediatric Gastroenterology and Nutrition, 49: 216-221, 2009.
Yerushalmi et al., "Bile acid-induced rat hepatocyte apoptosis is inhibited by antioxidants and blockers of the mitochondrial," Hepatology, 33: 3, 616-626, 2001.
Zarenezhad et al., "Investigation of Common Variations of ABCB4, ATP8B1 and ABCB11 Genes in Patients with Progressive Familial Intrahepatic Cholestasis," Hepatitis Monthly: 2017, 17(2):e43500.
Zhang et al., "Effect of bile duct ligation on bile acid composition in mouse serum and liver," Liver int, 32: 1, 58-69, 2012.
Zhang et al., Abcb11 deficiency induces cholestasis coupled to impaired B-Fatty acid oxidation in mice, Journal of biological chemistry, 287: 29, 24784-2479, 2012.
Morotti et al., "Progressive Familial Intrahepatic Cholestasis (PFIC) Type 1, 2, and 3: A Review of the Liver Pathology Findings," Seminars in Liver Disease, Feb. 2011, 31(1):3-10.

SEQUENCE LISTING

```
<160> NUMBER OF SEQ ID NOS: 4

<210> SEQ ID NO 1
<211> LENGTH: 1251
<212> TYPE: PRT
<213> ORGANISM: Homo sapiens

<400> SEQUENCE: 1

Met Ser Thr Glu Arg Asp Ser Glu Thr Thr Phe Asp Glu Asp Ser Gln
1               5                   10                  15

Pro Asn Asp Glu Val Val Pro Tyr Ser Asp Asp Glu Thr Glu Asp Glu
            20                  25                  30

Leu Asp Asp Gln Gly Ser Ala Val Glu Pro Glu Gln Asn Arg Val Asn
        35                  40                  45

Arg Glu Ala Glu Glu Asn Arg Glu Pro Phe Arg Lys Glu Cys Thr Trp
    50                  55                  60

Gln Val Lys Ala Asn Asp Arg Lys Tyr His Glu Gln Pro His Phe Met
65                  70                  75                  80

Asn Thr Lys Phe Leu Cys Ile Lys Glu Ser Lys Tyr Ala Asn Asn Ala
                85                  90                  95

Ile Lys Thr Tyr Lys Tyr Asn Ala Phe Thr Phe Ile Pro Met Asn Leu
            100                 105                 110

Phe Glu Gln Phe Lys Arg Ala Ala Asn Leu Tyr Phe Leu Ala Leu Leu
        115                 120                 125

Ile Leu Gln Ala Val Pro Gln Ile Ser Thr Leu Ala Trp Tyr Thr Thr
    130                 135                 140

Leu Val Pro Leu Leu Val Val Leu Gly Val Thr Ala Ile Lys Asp Leu
```

-continued

```
            145                 150                 155                 160
Val Asp Asp Val Ala Arg His Lys Met Asp Lys Glu Ile Asn Asn Arg
                165                 170                 175
Thr Cys Glu Val Ile Lys Asp Gly Arg Phe Lys Val Ala Lys Trp Lys
                180                 185                 190
Glu Ile Gln Val Gly Asp Val Ile Arg Leu Lys Lys Asn Asp Phe Val
                195                 200                 205
Pro Ala Asp Ile Leu Leu Leu Ser Ser Ser Glu Pro Asn Ser Leu Cys
            210                 215                 220
Tyr Val Glu Thr Ala Glu Leu Asp Gly Glu Thr Asn Leu Lys Phe Lys
225                 230                 235                 240
Met Ser Leu Glu Ile Thr Asp Gln Tyr Leu Gln Arg Glu Asp Thr Leu
                245                 250                 255
Ala Thr Phe Asp Gly Phe Ile Glu Cys Glu Glu Pro Asn Asn Arg Leu
                260                 265                 270
Asp Lys Phe Thr Gly Thr Leu Phe Trp Arg Asn Thr Ser Phe Pro Leu
                275                 280                 285
Asp Ala Asp Lys Ile Leu Leu Arg Gly Cys Val Ile Arg Asn Thr Asp
            290                 295                 300
Phe Cys His Gly Leu Val Ile Phe Ala Gly Ala Asp Thr Lys Ile Met
305                 310                 315                 320
Lys Asn Ser Gly Lys Thr Arg Phe Lys Arg Thr Lys Ile Asp Tyr Leu
                325                 330                 335
Met Asn Tyr Met Val Tyr Thr Ile Phe Val Val Leu Ile Leu Leu Ser
                340                 345                 350
Ala Gly Leu Ala Ile Gly His Ala Tyr Trp Glu Ala Gln Val Gly Asn
            355                 360                 365
Ser Ser Trp Tyr Leu Tyr Asp Gly Glu Asp Asp Thr Pro Ser Tyr Arg
370                 375                 380
Gly Phe Leu Ile Phe Trp Gly Tyr Ile Ile Val Leu Asn Thr Met Val
385                 390                 395                 400
Pro Ile Ser Leu Tyr Val Ser Val Glu Val Ile Arg Leu Gly Gln Ser
                405                 410                 415
His Phe Ile Asn Trp Asp Leu Gln Met Tyr Tyr Ala Glu Lys Asp Thr
                420                 425                 430
Pro Ala Lys Ala Arg Thr Thr Thr Leu Asn Glu Gln Leu Gly Gln Ile
            435                 440                 445
His Tyr Ile Phe Ser Asp Lys Thr Gly Thr Leu Thr Gln Asn Ile Met
450                 455                 460
Thr Phe Lys Lys Cys Cys Ile Asn Gly Gln Ile Tyr Gly Asp His Arg
465                 470                 475                 480
Asp Ala Ser Gln His Asn His Asn Lys Ile Glu Gln Val Asp Phe Ser
                485                 490                 495
Trp Asn Thr Tyr Ala Asp Gly Lys Leu Ala Phe Tyr Asp His Tyr Leu
                500                 505                 510
Ile Glu Gln Ile Gln Ser Gly Lys Glu Pro Glu Val Arg Gln Phe Phe
            515                 520                 525
Phe Leu Leu Ala Val Cys His Thr Val Met Val Asp Arg Thr Asp Gly
                530                 535                 540
Gln Leu Asn Tyr Gln Ala Ala Ser Pro Asp Glu Gly Ala Leu Val Asn
545                 550                 555                 560
Ala Ala Arg Asn Phe Gly Phe Ala Phe Leu Ala Arg Thr Gln Asn Thr
                565                 570                 575
```

```
Ile Thr Ile Ser Glu Leu Gly Thr Glu Arg Thr Tyr Asn Val Leu Ala
            580                 585                 590

Ile Leu Asp Phe Asn Ser Asp Arg Lys Arg Met Ser Ile Ile Val Arg
            595                 600                 605

Thr Pro Glu Gly Asn Ile Lys Leu Tyr Cys Lys Gly Ala Asp Thr Val
            610                 615                 620

Ile Tyr Glu Arg Leu His Arg Met Asn Pro Thr Lys Gln Glu Thr Gln
625                 630                 635                 640

Asp Ala Leu Asp Ile Phe Ala Asn Glu Thr Leu Arg Thr Leu Cys Leu
                645                 650                 655

Cys Tyr Lys Glu Ile Glu Glu Lys Glu Phe Thr Glu Trp Asn Lys Lys
            660                 665                 670

Phe Met Ala Ala Ser Val Ala Ser Thr Asn Arg Asp Glu Ala Leu Asp
            675                 680                 685

Lys Val Tyr Glu Glu Ile Glu Lys Asp Leu Ile Leu Leu Gly Ala Thr
            690                 695                 700

Ala Ile Glu Asp Lys Leu Gln Asp Gly Val Pro Glu Thr Ile Ser Lys
705                 710                 715                 720

Leu Ala Lys Ala Asp Ile Lys Ile Trp Val Leu Thr Gly Asp Lys Lys
                725                 730                 735

Glu Thr Ala Glu Asn Ile Gly Phe Ala Cys Glu Leu Leu Thr Glu Asp
            740                 745                 750

Thr Thr Ile Cys Tyr Gly Glu Asp Ile Asn Ser Leu Leu His Ala Arg
            755                 760                 765

Met Glu Asn Gln Arg Asn Arg Gly Gly Val Tyr Ala Lys Phe Ala Pro
            770                 775                 780

Pro Val Gln Glu Ser Phe Phe Pro Pro Gly Gly Asn Arg Ala Leu Ile
785                 790                 795                 800

Ile Thr Gly Ser Trp Leu Asn Glu Ile Leu Leu Glu Lys Lys Thr Lys
                805                 810                 815

Arg Asn Lys Ile Leu Lys Leu Lys Phe Pro Arg Thr Glu Glu Glu Arg
            820                 825                 830

Arg Met Arg Thr Gln Ser Lys Arg Arg Leu Glu Ala Lys Lys Glu Gln
            835                 840                 845

Arg Gln Lys Asn Phe Val Asp Leu Ala Cys Glu Cys Ser Ala Val Ile
            850                 855                 860

Cys Cys Arg Val Thr Pro Lys Gln Lys Ala Met Val Val Asp Leu Val
865                 870                 875                 880

Lys Arg Tyr Lys Lys Ala Ile Thr Leu Ala Ile Gly Asp Gly Ala Asn
                885                 890                 895

Asp Val Asn Met Ile Lys Thr Ala His Ile Gly Val Gly Ile Ser Gly
            900                 905                 910

Gln Glu Gly Met Gln Ala Val Met Ser Ser Asp Tyr Ser Phe Ala Gln
            915                 920                 925

Phe Arg Tyr Leu Gln Arg Leu Leu Leu Val His Gly Arg Trp Ser Tyr
            930                 935                 940

Ile Arg Met Cys Lys Phe Leu Arg Tyr Phe Phe Tyr Lys Asn Phe Ala
945                 950                 955                 960

Phe Thr Leu Val His Phe Trp Tyr Ser Phe Phe Asn Gly Tyr Ser Ala
                965                 970                 975

Gln Thr Ala Tyr Glu Asp Trp Phe Ile Thr Leu Tyr Asn Val Leu Tyr
            980                 985                 990
```

| | | | | | | | | | | | |
|---|---|---|---|---|---|---|---|---|---|---|---|
|Thr|Ser|Leu|Pro|Val|Leu|Leu|Met|Gly|Leu|Leu|Asp|Gln|Asp|Val|Ser|
| |995| | | | |1000| | | | |1005| | | | |

Asp Lys Leu Ser Leu Arg Phe Pro Gly Leu Tyr Ile Val Gly Gln
    1010                1015                 1020

Arg Asp Leu Leu Phe Asn Tyr Lys Arg Phe Phe Val Ser Leu Leu
    1025                1030                 1035

His Gly Val Leu Thr Ser Met Ile Leu Phe Phe Ile Pro Leu Gly
    1040                1045                 1050

Ala Tyr Leu Gln Thr Val Gly Gln Asp Gly Glu Ala Pro Ser Asp
    1055                1060                 1065

Tyr Gln Ser Phe Ala Val Thr Ile Ala Ser Ala Leu Val Ile Thr
    1070                1075                 1080

Val Asn Phe Gln Ile Gly Leu Asp Thr Ser Tyr Trp Thr Phe Val
    1085                1090                 1095

Asn Ala Phe Ser Ile Phe Gly Ser Ile Ala Leu Tyr Phe Gly Ile
    1100                1105                 1110

Met Phe Asp Phe His Ser Ala Gly Ile His Val Leu Phe Pro Ser
    1115                1120                 1125

Ala Phe Gln Phe Thr Gly Thr Ala Ser Asn Ala Leu Arg Gln Pro
    1130                1135                 1140

Tyr Ile Trp Leu Thr Ile Ile Leu Ala Val Ala Val Cys Leu Leu
    1145                1150                 1155

Pro Val Val Ala Ile Arg Phe Leu Ser Met Thr Ile Trp Pro Ser
    1160                1165                 1170

Glu Ser Asp Lys Ile Gln Lys His Arg Lys Arg Leu Lys Ala Glu
    1175                1180                 1185

Glu Gln Trp Gln Arg Arg Gln Gln Val Phe Arg Arg Gly Val Ser
    1190                1195                 1200

Thr Arg Arg Ser Ala Tyr Ala Phe Ser His Gln Arg Gly Tyr Ala
    1205                1210                 1215

Asp Leu Ile Ser Ser Gly Arg Ser Ile Arg Lys Lys Arg Ser Pro
    1220                1225                 1230

Leu Asp Ala Ile Val Ala Asp Gly Thr Ala Glu Tyr Arg Arg Thr
    1235                1240                 1245

Gly Asp Ser
    1250

<210> SEQ ID NO 2
<211> LENGTH: 3756
<212> TYPE: DNA
<213> ORGANISM: Homo sapiens

<400> SEQUENCE: 2

```
atgagtacag aaagagactc agaaacgaca tttgacgagg attctcagcc taatgacgaa        60
gtggttccct acagtgatga tgaaacagaa gatgaacttg atgaccaggg gtctgctgtt       120
gaaccagaac aaaaccgagt caacagggaa gcagaggaga accggagcc attcagaaaa        180 gaatgtacat ggcaagtcaa agcaaacgat cgcaagtacc acgaacaacc tcactttatg       240
aacacaaaat tcttgtgtat taaggagagt aaatatgcga ataatgcaat taaaacatac       300
aagtacaacg catttacctt tataccaatg aatctgtttg agcagtttaa gagagcagcc       360
aatttatatt tcctggctct tcttatctta caggcagttc ctcaaatctc taccctggct       420
tggtacacca cactagtgcc cctgcttgtg gtgctgggcg tcactgcaat caagacctg        480 gtggacgatg tggctcgcca taaaatggat aaggaaatca caataggac gtgtgaagtc       540
```

```
attaaggatg gcaggttcaa agttgctaag tggaaagaaa ttcaagttgg agacgtcatt      600
cgtctgaaaa aaaatgattt tgttccagct gacattctcc tgctgtctag ctctgagcct      660
aacagcctct gctatgtgga aacagcagaa ctggatggag aaaccaattt aaaatttaag      720
atgtcacttg aaatcacaga ccagtacctc caaagagaag atacattggc tacatttgat      780
ggttttattg aatgtgaaga acccaataac agactagata agtttacagg aacactattt      840
tggagaaaca caagttttcc tttggatgct gataaaattt tgttacgtgg ctgtgtaatt      900
aggaacaccg atttctgcca cggcttagtc attttttgcag gtgctgacac taaaataatg      960
aagaatagtg ggaaaaccag atttaaaaga actaaaattg attacttgat gaactacatg     1020
gtttacacga tctttgttgt tcttattctg cttcctgctg tcttgccat cggccatgct       1080 tattgggaag cacaggtggg caattcctct tggtacctct atgatggaga agacgataca      1140
ccctcctacc gtggattcct cattttctgg ggctatatca ttgttctcaa caccatggta     1200
cccatctctc tctatgtcag cgtggaagtg attcgtcttg acagagtca cttcatcaac       1260 tgggacctgc aaatgtacta tgctgagaag gacacacccg caaagctag aaccaccaca      1320 ctcaatgaac agctcgggca gatccattat atcttctctg ataagacggg gacactcaca      1380
caaaatatca tgacctttaa aaagtgctgt atcaacgggc agatatatgg ggaccatcgg     1440
gatgcctctc aacacaacca caacaaaata gagcaagttg attttagctg aatacatat      1500 gctgatggga agcttgcatt ttatgaccac tatcttattg agcaaatcca gtcagggaaa     1560
gagccagaag tacgacagtt cttcttcttg ctcgcagttt gccacacagt catggtggat      1620
aggactgatg gtcagctcaa ctaccaggca gcctctcccg atgaaggtgc cctggtaaac      1680
gctgccagga actttggctt tgccttcctc gccaggaccc agaacaccat caccatcagt     1740
gaactgggca ctgaaaggac ttacaatgtt cttgccattt tggacttcaa cagtgaccgg      1800
aagcgaatgt ctatcattgt aagaacccca gaaggcaata tcaagcttta ctgtaaaggt     1860
gctgacactg ttatttatga acggttacat cgaatgaatc ctactaagca agaaacacag      1920
gatgccctgg atatctttgc aaatgaaact cttagaaccc tatgcctttg ctacaaggaa     1980
attgaagaaa aagaatttac agaatggaat aaaagtttta ggctgccag tgtggcctcc      2040 accaaccggg acgaagctct ggataaagta tatgaggaga ttgaaaaaga cttaattctc     2100
ctgggagcta cagctattga agacaagcta caggatggag ttccagaaac catttcaaaa      2160
cttgcaaaag ctgacattaa gatctgggtg cttactggag acaaaaagga aactgctgaa     2220
aatataggat ttgcttgtga acttctgact gaagacacca ccatctgcta tggggaggat      2280
attaattctc ttcttcatgc aaggatggaa aaccagagga atagaggtgg cgtctacgca     2340
aagtttgcac ctcctgtgca ggaatctttt tttccacccg tgaaaaccg tgccttaatc      2400 atcactggtt cttggttgaa tgaaattctt ctcgagaaaa agaccaagag aaataagatt      2460
ctgaagctga agttcccaag aacagaagaa gaaagacgga tgcggaccca agtaaaagg     2520 aggctagaag ctaagaaaga gcagcggcag aaaaacttg tggacctggc ctgcgagtgc      2580
agcgcagtca tctgctgccg cgtcaccccc aagcagaagg ccatggtggt ggacctggtg     2640
aagaggtaca agaaagccat cacgctggcc atcggagatg gggccaatga cgtgaacatg     2700
atcaaaactg cccacattgg cgttggaata agtggacaag aaggaatgca agctgtcatg     2760
tcgagtgact attcctttgc tcagttccga tatctgcaga ggctactgct ggtgcatggc     2820
cgatggtctt acataaggat gtgcaagttc ctacgatact tcttttacaa aaactttgcc     2880
```

```
tttactttgg ttcatttctg gtactccttc ttcaatggct actctgcgca gactgcatac    2940
gaggattggt tcatcaccct ctacaacgtg ctgtacacca gcctgcccgt gctcctcatg    3000
gggctgctcg accaggatgt gagtgacaaa ctgagcctcc gattccctgg gttatacata    3060
gtgggacaaa gagacttact attcaactat aagagattct ttgtaagctt gttgcatggg    3120
gtcctaacat cgatgatcct cttcttcata cctcttggag cttatctgca aaccgtaggg    3180
caggatggag aggcaccttc cgactaccag tcttttgccg tcaccattgc ctctgctctt    3240
gtaataacag tcaatttcca gattggcttg gatacttctt attggacttt tgtgaatgct    3300
ttttcaattt ttggaagcat tgcactttat tttggcatca tgtttgactt tcatagtgct    3360
ggaatacatg ttctctttcc atctgcattt caatttacag gcacagcttc aaacgctctg    3420
agacagccat acatttggtt aactatcatc ctggctgttg ctgtgtgctt actaccegtc    3480 gttgccattc gattcctgtc aatgaccatc tggccatcag aaagtgataa gatccagaag    3540
catcgcaagc ggttgaaggc ggaggagcag tggcagcgac ggcagcaggt gttccgccgg    3600
ggcgtgtcaa cgcggcgctc ggcctacgcc ttctcgcacc agcggggcta cgcggacctc    3660
atctcctccg ggcgcagcat ccgcaagaag cgctcgccgc ttgatgccat cgtggcggat    3720
ggcaccgcgg agtacaggcg caccggggac agctga                              3756
```

<210> SEQ ID NO 3
<211> LENGTH: 1321
<212> TYPE: PRT
<213> ORGANISM: Homo sapiens

<400> SEQUENCE: 3

```
Met Ser Asp Ser Val Ile Leu Arg Ser Ile Lys Lys Phe Gly Glu Glu
1               5                   10                  15

Asn Asp Gly Phe Glu Ser Asp Lys Ser Tyr Asn Asn Asp Lys Lys Ser
            20                  25                  30

Arg Leu Gln Asp Glu Lys Lys Gly Asp Gly Val Arg Val Gly Phe Phe
        35                  40                  45

Gln Leu Phe Arg Phe Ser Ser Ser Thr Asp Ile Trp Leu Met Phe Val
    50                  55                  60

Gly Ser Leu Cys Ala Phe Leu His Gly Ile Ala Gln Pro Gly Val Leu
65                  70                  75                  80

Leu Ile Phe Gly Thr Met Thr Asp Val Phe Ile Asp Tyr Asp Val Glu
                85                  90                  95

Leu Gln Glu Leu Gln Ile Pro Gly Lys Ala Cys Val Asn Asn Thr Ile
            100                 105                 110

Val Trp Thr Asn Ser Ser Leu Asn Gln Asn Met Thr Asn Gly Thr Arg
        115                 120                 125

Cys Gly Leu Leu Asn Ile Glu Ser Glu Met Ile Lys Phe Ala Ser Tyr
    130                 135                 140

Tyr Ala Gly Ile Ala Val Ala Val Leu Ile Thr Gly Tyr Ile Gln Ile
145                 150                 155                 160

Cys Phe Trp Val Ile Ala Ala Arg Gln Ile Gln Lys Met Arg Lys
                165                 170                 175

Phe Tyr Phe Arg Arg Ile Met Arg Met Glu Ile Gly Trp Phe Asp Cys
            180                 185                 190

Asn Ser Val Gly Glu Leu Asn Thr Arg Phe Ser Asp Asp Ile Asn Lys
        195                 200                 205

Ile Asn Asp Ala Ile Ala Asp Gln Met Ala Leu Phe Ile Gln Arg Met
    210                 215                 220
```

```
Thr Ser Thr Ile Cys Gly Phe Leu Leu Gly Phe Phe Arg Gly Trp Lys
225                 230                 235                 240

Leu Thr Leu Val Ile Ser Val Ser Pro Leu Ile Gly Ile Gly Ala
        245                 250                 255

Ala Thr Ile Gly Leu Ser Val Ser Lys Phe Thr Asp Tyr Glu Leu Lys
            260                 265                 270

Ala Tyr Ala Lys Ala Gly Val Ala Asp Glu Val Ile Ser Ser Met
    275                 280                 285

Arg Thr Val Ala Ala Phe Gly Gly Glu Lys Arg Glu Val Glu Arg Tyr
    290                 295                 300

Glu Lys Asn Leu Val Phe Ala Gln Arg Trp Gly Ile Arg Lys Gly Ile
305                 310                 315                 320

Val Met Gly Phe Phe Thr Gly Phe Val Trp Cys Leu Ile Phe Leu Cys
                325                 330                 335

Tyr Ala Leu Ala Phe Trp Tyr Gly Ser Thr Leu Val Leu Asp Glu Gly
            340                 345                 350

Glu Tyr Thr Pro Gly Thr Leu Val Gln Ile Phe Leu Ser Val Ile Val
        355                 360                 365

Gly Ala Leu Asn Leu Gly Asn Ala Ser Pro Cys Leu Glu Ala Phe Ala
370                 375                 380

Thr Gly Arg Ala Ala Thr Ser Ile Phe Glu Thr Ile Asp Arg Lys
385                 390                 395                 400

Pro Ile Ile Asp Cys Met Ser Glu Asp Gly Tyr Lys Leu Asp Arg Ile
            405                 410                 415

Lys Gly Glu Ile Glu Phe His Asn Val Thr Phe His Tyr Pro Ser Arg
            420                 425                 430

Pro Glu Val Lys Ile Leu Asn Asp Leu Asn Met Val Ile Lys Pro Gly
        435                 440                 445

Glu Met Thr Ala Leu Val Gly Pro Ser Gly Ala Gly Lys Ser Thr Ala
    450                 455                 460

Leu Gln Leu Ile Gln Arg Phe Tyr Asp Pro Cys Glu Gly Met Val Thr
465                 470                 475                 480

Val Asp Gly His Asp Ile Arg Ser Leu Asn Ile Gln Trp Leu Arg Asp
            485                 490                 495

Gln Ile Gly Ile Val Glu Gln Glu Pro Val Leu Phe Ser Thr Thr Ile
        500                 505                 510

Ala Glu Asn Ile Arg Tyr Gly Arg Glu Asp Ala Thr Met Glu Asp Ile
    515                 520                 525

Val Gln Ala Ala Lys Glu Ala Asn Ala Tyr Asn Phe Ile Met Asp Leu
530                 535                 540

Pro Gln Gln Phe Asp Thr Leu Val Gly Glu Gly Gly Gly Gln Met Ser
545                 550                 555                 560

Gly Gly Gln Lys Gln Arg Val Ala Ile Ala Arg Ala Leu Ile Arg Asn
            565                 570                 575

Pro Lys Ile Leu Leu Leu Asp Met Ala Thr Ser Ala Leu Asp Asn Glu
            580                 585                 590

Ser Glu Ala Met Val Gln Glu Val Leu Ser Lys Ile Gln His Gly His
        595                 600                 605

Thr Ile Ile Ser Val Ala His Arg Leu Ser Thr Val Arg Ala Ala Asp
        610                 615                 620

Thr Ile Ile Gly Phe Glu His Gly Thr Ala Val Glu Arg Gly Thr His
625                 630                 635                 640
```

Glu Glu Leu Leu Glu Arg Lys Gly Val Tyr Phe Thr Leu Val Thr Leu
                    645                 650                 655

Gln Ser Gln Gly Asn Gln Ala Leu Asn Glu Glu Asp Ile Lys Asp Ala
                660                 665                 670

Thr Glu Asp Asp Met Leu Ala Arg Thr Phe Ser Arg Gly Ser Tyr Gln
            675                 680                 685

Asp Ser Leu Arg Ala Ser Ile Arg Gln Arg Ser Lys Ser Gln Leu Ser
        690                 695                 700

Tyr Leu Val His Glu Pro Pro Leu Ala Val Val Asp His Lys Ser Thr
705                 710                 715                 720

Tyr Glu Glu Asp Arg Lys Asp Lys Asp Ile Pro Val Gln Glu Val
            725                 730                 735

Glu Pro Ala Pro Val Arg Arg Ile Leu Lys Phe Ser Ala Pro Glu Trp
                740                 745                 750

Pro Tyr Met Leu Val Gly Ser Val Gly Ala Ala Val Asn Gly Thr Val
            755                 760                 765

Thr Pro Leu Tyr Ala Phe Leu Phe Ser Gln Ile Leu Gly Thr Phe Ser
    770                 775                 780

Ile Pro Asp Lys Glu Glu Gln Arg Ser Gln Ile Asn Gly Val Cys Leu
785                 790                 795                 800

Leu Phe Val Ala Met Gly Cys Val Ser Leu Phe Thr Gln Phe Leu Gln
                805                 810                 815

Gly Tyr Ala Phe Ala Lys Ser Gly Glu Leu Leu Thr Lys Arg Leu Arg
            820                 825                 830

Lys Phe Gly Phe Arg Ala Met Leu Gly Gln Asp Ile Ala Trp Phe Asp
        835                 840                 845

Asp Leu Arg Asn Ser Pro Gly Ala Leu Thr Thr Arg Leu Ala Thr Asp
    850                 855                 860

Ala Ser Gln Val Gln Gly Ala Ala Gly Ser Gln Ile Gly Met Ile Val
865                 870                 875                 880

Asn Ser Phe Thr Asn Val Thr Val Ala Met Ile Ile Ala Phe Ser Phe
                885                 890                 895

Ser Trp Lys Leu Ser Leu Val Ile Leu Cys Phe Phe Pro Phe Leu Ala
            900                 905                 910

Leu Ser Gly Ala Thr Gln Thr Arg Met Leu Thr Gly Phe Ala Ser Arg
        915                 920                 925

Asp Lys Gln Ala Leu Glu Met Val Gly Gln Ile Thr Asn Glu Ala Leu
    930                 935                 940

Ser Asn Ile Arg Thr Val Ala Gly Ile Gly Lys Glu Arg Arg Phe Ile
945                 950                 955                 960

Glu Ala Leu Glu Thr Glu Leu Glu Lys Pro Phe Lys Thr Ala Ile Gln
                965                 970                 975

Lys Ala Asn Ile Tyr Gly Phe Cys Phe Ala Phe Ala Gln Cys Ile Met
            980                 985                 990

Phe Ile Ala Asn Ser Ala Ser Tyr Arg Tyr Gly Gly Tyr Leu Ile Ser
        995                 1000                1005

Asn Glu Gly Leu His Phe Ser Tyr Val Phe Arg Val Ile Ser Ala
    1010                1015                1020

Val Val Leu Ser Ala Thr Ala Leu Gly Arg Ala Phe Ser Tyr Thr
    1025                1030                1035

Pro Ser Tyr Ala Lys Ala Lys Ile Ser Ala Ala Arg Phe Phe Gln
    1040                1045                1050

Leu Leu Asp Arg Gln Pro Pro Ile Ser Val Tyr Asn Thr Ala Gly

| | | | |
|---|---|---|---|
| | | 1055 | 1060 | 1065 |

Glu Lys Trp Asp Asn Phe Gln Gly Lys Ile Asp Phe Val Asp Cys
    1070                        1075                        1080

Lys Phe Thr Tyr Pro Ser Arg Pro Asp Ser Gln Val Leu Asn Gly
    1085                        1090                        1095

Leu Ser Val Ser Ile Ser Pro Gly Gln Thr Leu Ala Phe Val Gly
    1100                        1105                        1110

Ser Ser Gly Cys Gly Lys Ser Thr Ser Ile Gln Leu Leu Glu Arg
    1115                        1120                        1125

Phe Tyr Asp Pro Asp Gln Gly Lys Val Met Ile Asp Gly His Asp
    1130                        1135                        1140

Ser Lys Lys Val Asn Val Gln Phe Leu Arg Ser Asn Ile Gly Ile
    1145                        1150                        1155

Val Ser Gln Glu Pro Val Leu Phe Ala Cys Ser Ile Met Asp Asn
    1160                        1165                        1170

Ile Lys Tyr Gly Asp Asn Thr Lys Glu Ile Pro Met Glu Arg Val
    1175                        1180                        1185

Ile Ala Ala Ala Lys Gln Ala Gln Leu His Asp Phe Val Met Ser
    1190                        1195                        1200

Leu Pro Glu Lys Tyr Glu Thr Asn Val Gly Ser Gln Gly Ser Gln
    1205                        1210                        1215

Leu Ser Arg Gly Glu Lys Gln Arg Ile Ala Ile Ala Arg Ala Ile
    1220                        1225                        1230

Val Arg Asp Pro Lys Ile Leu Leu Leu Asp Glu Ala Thr Ser Ala
    1235                        1240                        1245

Leu Asp Thr Glu Ser Glu Lys Thr Val Gln Val Ala Leu Asp Lys
    1250                        1255                        1260

Ala Arg Glu Gly Arg Thr Cys Ile Val Ile Ala His Arg Leu Ser
    1265                        1270                        1275

Thr Ile Gln Asn Ala Asp Ile Ile Ala Val Met Ala Gln Gly Val
    1280                        1285                        1290

Val Ile Glu Lys Gly Thr His Glu Glu Leu Met Ala Gln Lys Gly
    1295                        1300                        1305

Ala Tyr Tyr Lys Leu Val Thr Thr Gly Ser Pro Ile Ser
    1310                        1315                        1320

<210> SEQ ID NO 4
<211> LENGTH: 3966
<212> TYPE: DNA
<213> ORGANISM: Homo sapiens

<400> SEQUENCE: 4

```
atgtctgact cagtaattct tcgaagtata aagaaatttg gagaggagaa tgatggtttt      60
gagtcagata atcatataa taatgataag aaatcaaggt tacaagatga aagaaaggt      120 gatggcgtta gagttggctt ctttcaattg tttcggtttt cttcatcaac tgacatttgg     180
ctgatgtttg tgggaagttt gtgtgcattt ctccatggaa tagcccagcc aggcgtgcta     240 ctcattttg gcacaatgac agatgttttt attgactacg acgttgagtt acaagaactc     300
cagattccag gaaaagcatg tgtgaataac accattgtat ggactaacag ttccctcaac     360
cagaacatga caaatggaac acgttgtggg ttgctgaaca tcgagagcga aatgatcaaa     420
tttgccagtt actatgctgg aattgctgtc gcagtactta tcacaggata tattcaaata     480
tgcttttggg tcattgccgc agctcgtcag atacagaaaa tgagaaaatt ttactttagg     540
```

```
agaataatga gaatggaaat agggtggttt gactgcaatt cagtggggga gctgaataca       600
agattctctg atgatattaa taaaatcaat gatgccatag ctgaccaaat ggccttttc        660 attcagcgca tgacctcgac catctgtggt ttcctgttgg gattttcag gggttggaaa        720 ctgaccttgg ttattatttc tgtcagccct ctcattggga ttggagcagc caccattggt       780
ctgagtgtgt ccaagtttac ggactatgag ctgaaggcct atgccaaagc aggggtggtg       840
gctgatgaag tcatttcatc aatgagaaca gtggctgctt ttggtggtga gaaaagagag       900
gttgaaaggt atgagaaaaa tcttgtgttc gcccagcgtt ggggaattag aaaaggaata       960
gtgatgggat tctttactgg attcgtgtgg tgtctcatct ttttgtgtta tgcactggcc      1020
ttctggtacg gctccacact tgtcctggat gaaggagaat atacaccagg aacccttgtc      1080 cagatttttcc tcagtgtcat agtaggagct ttaaatcttg gcaatgcctc tccttgtttg     1140
gaagcctttg caactggacg tgcagcagcc accagcattt tgagacaat agacaggaaa       1200 cccatcattg actgcatgtc agaagatggt tacaagttgg atcgaatcaa gggtgaaatt      1260
gaattccata atgtgacctt ccattatcct tccagaccag aggtgaagat tctaaatgac      1320
ctcaacatgg tcattaaacc agggaaatg acagctctgg taggacccag tggagctgga      1380
aaaagtacag cactgcaact cattcagcga ttctatgacc cctgtgaagg aatggtgacc      1440
gtggatggcc atgacattcg ctctcttaac attcagtggc ttagagatca gattgggata      1500
gtggagcaag agccagttct gttctctacc accattgcag aaaatattcg ctatggcaga     1560
gaagatgcaa caatggaaga catagtccaa gctgccaagg aggccaatgc ctacaacttc     1620
atcatggacc tgccacagca atttgacacc cttgttggag aaggaggagg ccagatgagt     1680
ggtggccaga acaaagggt agctatcgcc agagccctca tccgaaatcc aagattctg        1740 cttttggaca tggccacctc agctctggac aatgagagtg aagccatggt gcaagaagtg     1800
ctgagtaaga ttcagcatgg gcacacaatc atttcagttg ctcatcgctt gtctacggtc     1860
agagctgcag ataccatcat tggttttgaa catggcactg cagtggaaag agggacccat     1920
gaagaattac tggaaaggaa aggtgtttac ttcactctag tgactttgca aagccaggga     1980
aatcaagctc ttaatgaaga ggacataaag gatgcaactg aagatgacat gcttgcgagg     2040 accttagca gagggagcta ccaggatagt ttaagggctt ccatccggca acgctccaag       2100
tctcagcttt cttacctggt gcacgaacct ccattagctg ttgtagatca taagtctacc     2160
tatgaagaag atagaaagga caaggacatt cctgtgcagg aagaagttga acctgcccca     2220
gttaggagga ttctgaaatt cagtgctcca gaatggccct acatgctggt agggtctgtg     2280
ggtgcagctg tgaacgggac agtcacaccc ttgtatgcct ttttattcag ccagattctt     2340
gggacttttt caattcctga taagaggaa caaaggtcac agatcaatgg tgtgtgccta      2400 cttttttgtag caatgggctg tgtatctctt ttcacccaat ttctacaggg atatgccttt     2460
gctaaatctg gggagctcct aacaaaaagg ctacgtaaat ttggtttcag ggcaatgctg     2520
gggcaagata ttgcctggtt tgatgacctc agaaatagcc ctggagcatt gacaacaaga     2580
cttgctacag atgcttccca agttcaaggg gctgccggct ctcagatcgg gatgatagtc     2640
aattccttca ctaacgtcac tgtggccatg atcattgcct tctccttag ctggaagctg       2700 agcctggtca tcttgtgctt cttccccttc ttggctttat caggagccac acagaccagg     2760
atgttgacag gatttgcctc tcgagataag caggccctgg agatggtggg acagattaca     2820
aatgaagccc tcagtaacat ccgcactgtt gctggaattg aaaggagag gcggttcatt     2880 gaagcacttg agactgagct ggagaagccc ttcaagacag ccattcagaa agccaatatt     2940
```

-continued

```
tacggattct gctttgcctt tgcccagtgc atcatgttta ttgcgaattc tgcttcctac    3000
agatatggag gttacttaat ctccaatgag gggctccatt tcagctatgt gttcagggtg    3060
atctctgcag ttgtactgag tgcaacagct cttggaagag ccttctctta cacccccaagt   3120 tatgcaaaag ctaaaatatc agctgcacgc tttttttcaac tgctggaccg acaaccccca   3180
atcagtgtat acaatactgc aggtgaaaaa tgggacaact tccaggggaa gattgatttt    3240
gttgattgta aatttacata tccttctcga cctgactcgc aagttctgaa tggtctctca    3300
gtgtcgatta gtccagggca gacactggcg tttgttggga gcagtggatg tggcaaaagc    3360
actagcattc agctgttgga acgtttctat gatcctgatc aagggaaggt gatgatagat    3420
ggtcatgaca gcaaaaaagt aaatgtccag ttcctccgct caaacattgg aattgtttcc    3480
caggaaccag tgttgtttgc ctgtagcata atggacaata tcaagtatgg agacaacacc    3540
aaagaaattc ccatggaaag agtcatagca gctgcaaaac aggctcagct gcatgatttt    3600
gtcatgtcac tcccagagaa atatgaaact aacgttgggt cccaggggtc tcaactctct    3660
agaggggaga aacaacgcat tgctattgct cgggccattg tacgagatcc taaaatcttg    3720
ctactagatg aagccacttc tgccttagac acagaaagtg aaaagacggt gcaggttgct    3780
ctagacaaag ccagagaggg tcggacctgc attgtcattg cccatcgctt gtccaccatc    3840
cagaacgcgg atatcattgc tgtcatggca caggggggtgg tgattgaaaa ggggacccat    3900
gaagaactga tggcccaaaa aggagcctac tacaaactag tcaccactgg atccccatc    3960 agttga                                                               3966
```

BENZOTHIAZEPINE COMPOUNDS AND THEIR USE AS BILE ACID MODULATORS

CROSS-REFERENCE TO RELATED APPLICATIONS

This application is a Continuation under 35 U.S.C. § 111(a) of International Application No. PCT/EP2020/052940, filed on Feb. 6, 2020, which claims priority to Indian Application No. 201911004690, filed Feb. 6, 2019; Swedish Application No. 1950463-8, filed Apr. 12, 2019; and Indian Application No. 201911049986, filed Dec. 4, 2019, the disclosures of which are incorporated herein by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing filename: NP0414WO_2020-02-06_seqlist_ST25.txt, date created: Feb. 5, 2020, file size≈35 kilobytes.

TECHNICAL FIELD

The invention relates to 1,5-benzothiazepine derivatives of formula (I). These compounds are bile acid modulators having apical sodium-dependent bile acid transporter (ASBT) and/or liver bile acid transport (LBAT) inhibitory activity. The invention also relates to pharmaceutical compositions comprising these compounds and to the use of these compounds in the treatment of cardiovascular diseases, fatty acid metabolism and glucose utilization disorders, gastrointestinal diseases and liver diseases.

BACKGROUND

Bile acids are physiological detergents that play an important role in the intestinal absorption and transport of lipids, nutrients and vitamins. They are also signaling molecules that activate nuclear receptors and cell signaling pathways that regulate lipid, glucose and energy metabolism. Bile acids are steroid acids that are synthesized from cholesterol in the liver and stored in the gallbladder as mixed micelles. During digestion, the duodenum triggers the release of hormones that cause the gallbladder to contract, thereby releasing bile acids in the small intestine where they enable absorption of fat-soluble vitamins and cholesterol. When they reach the ileum, bile acids are reabsorbed from the intestine and secreted into portal blood to return to the liver via the portal venous circulation. Over 90% of the bile acids are thus recycled and returned to the liver. These bile acids are then transported across the sinusoidal membrane of hepatocytes and re-secreted across the canalicular membrane into bile. In this first pass, 75-90% of bile acids are taken up by hepatocytes, completing one round of enterohepatic circulation. The fraction of bile acids that escapes being cleared in the liver enters the systemic circulation where the free bile acids are filtered by the renal glomerulus, efficiently reclaimed in the proximal tubules and exported back into the systemic circulation. Interestingly, most of the bile acids secreted across the canalicular membrane into bile are derived from the recirculating pool with less than 10% coming from new de novo hepatic synthesis. The small fraction of bile acids that is not reabsorbed in the ileum reaches the colon. Within the intestinal lumen, the primary bile acids are transformed into secondary bile acids under the action of intestinal bacteria, mainly by single or dual dehydroxylation reactions of the steroid nucleus. The bile acids that escape intestinal absorption are thereafter excreted into the faeces.

Overall, the efficient transport system helps maintain a constant bile acid pool, ensuring sufficiently high levels of conjugated bile acids in the intestine to promote lipid absorption as well as reduce the small intestinal bacterial load. The system also minimizes fecal and urinary bile acid loss and protects the intestinal and hepatobiliary compartments by eliminating potentially cytotoxic detergents (as reviewed by Kosters and Karpen (Xenobiotica 2008, vol. 38, p. 1043-1071); by Chiang (J. Lipid Res. 2009, vol. 50, p. 1955-1966); and by Dawson (Handb. Exp. Pharmacol. 2011, vol. 201, p. 169-203)).

The regulation of the bile acid pool size has been found to play a key role in cholesterol homeostasis by hepatic conversion of cholesterol to bile acid, which represents a major route for elimination of cholesterol from the body. The liver plays an essential role in removing endogenous and xenobiotic compounds from the body. The normal hepatobiliary secretion and enterohepatic circulation are required for the elimination of endogenous compounds such as cholesterol and bilirubin and their metabolites from the body, thereby maintaining lipid and bile acid homeostasis. (Kosters and Karpen, Xenobiotica 2008, vol. 38, p. 1043-1071).

The reabsorption of bile acids in the ileum may be inhibited by apical sodium-dependent bile acid transporter (ASBT) inhibitor compounds. Inhibition of bile acid reabsorption has been reported useful in the treatment of several diseases, including dyslipidemia, diabetes, obesity, constipation, cholestatic liver diseases, non-alcoholic steatohepatitis and other hepatic diseases. A number of ASBT inhibitor compounds has been disclosed over the past decades, see e.g. WO 93/16055, WO 94/18183, WO 94/18184, WO 96/05188, WO 96/08484, WO 96/16051, WO 97/33882, WO 98/03818, WO 98/07449, WO 98/40375, WO 99/35135, WO 99/64409, WO 99/64410, WO 00/47568, WO 00/61568, WO 00/38725, WO 00/38726, WO 00/38727, WO 00/38728, WO 00/38729, WO 01/66533, WO 01/68096, WO 02/32428, WO 02/50051, WO 03/020710, WO 03/022286, WO 03/022825, WO 03/022830, WO 03/061663, WO 03/091232, WO 03/106482, WO 2004/006899, WO 2004/076430, WO 2007/009655, WO 2007/009656, WO 2011/137135, DE 19825804, EP 864582, EP 489423, EP 549967, EP 573848, EP 624593, EP 624594, EP 624595, EP 624596, EP 0864582, EP 1173205 and EP 1535913.

Despite the number of ASBT inhibitor compounds that have been previously reported, there is a need for additional bile acid modulating compounds that have an optimized profile with respect to potency, selectivity and bioavailability.

DETAILED DESCRIPTION OF THE INVENTION

It has been discovered that certain 1,5-benzothiazepine derivates are potent inhibitors of apical sodium-dependent bile acid transporter (ASBT) and/or liver bile acid transporter (LBAT), and may be useful for treating diseases wherein inhibition of bile acid circulation is desirable.

In a first aspect, the invention relates to a compound of formula (I)

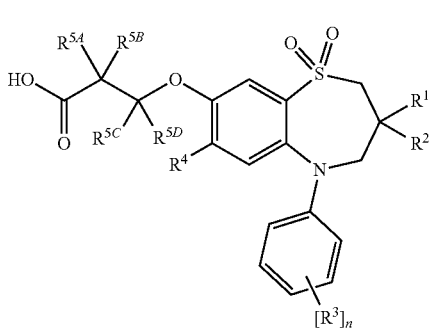

(I)

wherein
- $R^1$ and $R^2$ are each independently $C_{1-4}$ alkyl;
- $R^3$ is independently selected from the group consisting of hydrogen, halogen, hydroxy, $C_{1-4}$ alkyl, $C_{1-4}$ haloalkyl, $C_{1-4}$ alkoxy, $C_{1-4}$ haloalkoxy, cyano, nitro, amino, N—($C_{1-4}$ alkyl)amino, N,N-di($C_{1-4}$ alkyl)amino and N-(aryl-$C_{14}$ alkyl)amino;
- n is an integer 1, 2 or 3;
- $R^4$ is selected from the group consisting of hydrogen, halogen, hydroxy, cyano, $C_{1-4}$ alkyl, $C_{3-6}$ cycloalkyl, $C_{1-4}$ alkoxy, $C_{3-6}$ cycloalkyloxy, $C_{1-4}$ alkylthio, $C_{3-6}$ cycloalkylthio, amino, N—($C_{1-4}$ alkyl)-amino and N,N-di($C_{1-4}$ alkyl)amino; and
- $R^{5A}$, $R^{5B}$, $R^{5C}$ and $R^{5D}$ are each independently selected from the group consisting of hydrogen, halogen, hydroxy, amino, $C_{1-4}$ alkyl and $C_{1-4}$ alkoxy;

or a pharmaceutically acceptable salt thereof;
with the proviso that the compound is not racemic 3-((7-bromo-3-butyl-3-ethyl-1,1-dioxido-5-phenyl-2,3,4,5-tetrahydro-1,5-benzothiazepin-8-yl)oxy)propanoic acid.

In some embodiments, $R^1$ is n-butyl.

In some embodiments, $R^2$ is $C_{2-4}$ alkyl. In a preferred embodiment, $R^2$ is methyl. In another preferred embodiment, $R^2$ is ethyl. In another preferred embodiment, $R^2$ is n-propyl. In yet another preferred embodiment, $R^2$ is n-butyl.

In some embodiments, $R^3$ is independently selected from the group consisting of hydrogen, halogen, hydroxy, amino, cyano, $C_{1-4}$ haloalkyl, $C_{1-4}$ alkoxy and $C_{1-4}$ haloalkoxy. In another embodiment, $R^3$ is hydrogen. In a preferred embodiment, $R^3$ is independently selected from the group consisting of hydrogen, fluoro, chloro, bromo, hydroxy, cyano, trifluoromethyl, methoxy and trifluoromethoxy.

In a preferred embodiment, n is 1, i.e. the phenyl-ring is substituted with only one substituent $R^3$. In another preferred embodiment, $R^3$ is in the para-position.

In some embodiments, $R^4$ is selected from the group consisting of halogen, hydroxy, cyano, $C_{1-4}$ alkyl, $C_{1-4}$ alkoxy, $C_{1-4}$ alkylthio, amino, N—($C_{1-4}$ alkyl)amino and N,N-di($C_{1-4}$ alkyl)amino. In a preferred embodiment, $R^4$ is selected from the group consisting of fluoro, chloro, bromo, hydroxy, cyano, methyl, methoxy, ethoxy, methylthio, ethylthio, amino, methylamino and dimethylamino. In another embodiment, $R^4$ is selected from the group consisting of fluoro, chloro, bromo, methoxy, ethoxy, methylthio, ethylthio and dimethylamino. In another embodiment, $R^4$ is selected from the group consisting of chloro, bromo, methylthio and dimethylamino.

In some embodiments, $R^{5A}$, $R^{5B}$, $R^{5C}$ and $R^{5D}$ are each independently selected from the group consisting of hydrogen, halogen, hydroxy, amino and $C_{1-4}$ alkyl. In some embodiments, $R^{5A}$ and $R^{5B}$ are each independently selected from the group consisting of hydrogen, halogen, hydroxy, amino, methyl and methoxy. In some embodiments, $R^{5A}$ and $R^{5B}$ are each independently selected from the group consisting of hydrogen, halogen, hydroxy, amino and methyl. In some embodiments, $R^{5C}$ and $R^{5D}$ are each independently hydrogen or methyl. In another embodiment, $R^{5C}$ is hydrogen or methyl and $R^{5D}$ is hydrogen.

In a preferred embodiment, the compound of formula (I) is a compound of formula (I-a):

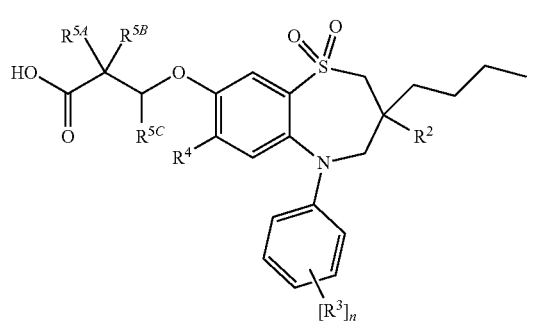

(I-a)

wherein
- $R^2$ is $C_{1-4}$ alkyl;
- $R^3$ is independently selected from the group consisting of hydrogen, halogen, hydroxy, cyano, $C_{1-4}$ haloalkyl, $C_{1-4}$ alkoxy and $C_{1-4}$ haloalkoxy;
- n is an integer 1 or 2;
- $R^4$ is selected from the group consisting of halogen, hydroxy, cyano, $C_{1-4}$ alkyl, $C_{1-4}$ alkoxy, $C_{1-4}$ alkylthio, amino, N—($C_{1-4}$ alkyl)amino and N,N-di($C_{1-4}$ alkyl)amino;
- $R^{5A}$ and $R^{5B}$ are each independently selected from the group consisting of hydrogen, halogen, hydroxy, amino and $C_{1-4}$ alkyl;
- $R^{5C}$ is hydrogen or $C_{1-4}$ alkyl;

or a pharmaceutically acceptable salt thereof.

In another preferred embodiment, the compound of formula (I) is a compound of formula (I-b):

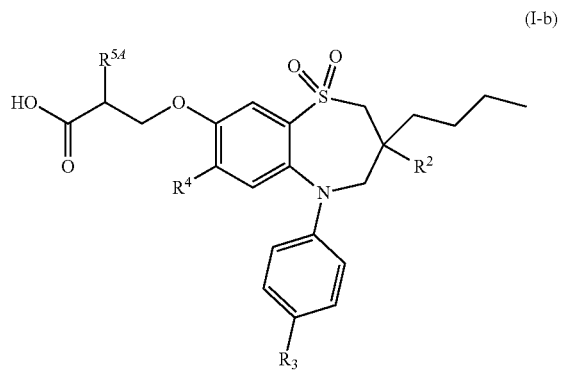

(I-b)

wherein
- $R^2$ is methyl, ethyl, n-propyl or n-butyl;
- $R^3$ is selected from the group consisting of hydrogen, fluoro, chloro, bromo, hydroxy, cyano, trifluoromethyl, methoxy, and trifluoromethoxy;

R[4] is selected from the group consisting of selected from the group consisting of fluoro, chloro, bromo, hydroxy, cyano, methoxy, ethoxy, methylthio, ethylthio and dimethylamino; and R[5A] is selected from the group consisting of hydrogen, halogen, hydroxy, amino and methyl; or a pharmaceutically acceptable salt thereof.

In another preferred embodiment, the compound of formula (I) is a compound of formula (I-b) as defined above, yet wherein R[3] is selected from the group consisting of hydrogen, fluoro, chloro, bromo, hydroxy and methoxy; and R[4] is selected from the group consisting of fluoro, chloro, bromo, methoxy, ethoxy, methylthio, ethylthio and dimethylamino.

Preferred compounds of the invention are compounds of formula (I-b), as defined above, wherein R[2] to R[5A] are as indicated in Table 1 below, or a pharmaceutically acceptable salt thereof:

TABLE 1

| R[2] | R[3] | R[4] | R[5A] |
|---|---|---|---|
| CH$_3$ | H | SCH$_3$ | H |
| CH$_3$ | F | SCH$_3$ | H |
| CH$_3$ | OCH$_3$ | SCH$_3$ | H |
| CH$_3$ | OH | SCH$_3$ | H |
| CH$_3$ | Cl | SCH$_3$ | H |
| CH$_3$ | H | SCH$_3$ | OH |
| CH$_3$ | F | SCH$_3$ | OH |
| CH$_3$ | OCH$_3$ | SCH$_3$ | OH |
| CH$_3$ | OH | SCH$_3$ | OH |
| CH$_3$ | Cl | SCH$_3$ | OH |
| CH$_3$ | H | N(CH$_3$)$_2$ | H |
| CH$_3$ | F | N(CH$_3$)$_2$ | H |
| CH$_3$ | OCH$_3$ | N(CH$_3$)$_2$ | H |
| CH$_3$ | OH | N(CH$_3$)$_2$ | H |
| CH$_3$ | Cl | N(CH$_3$)$_2$ | H |
| CH$_3$ | H | N(CH$_3$)$_2$ | OH |
| CH$_3$ | F | N(CH$_3$)$_2$ | OH |
| CH$_3$ | OCH$_3$ | N(CH$_3$)$_2$ | OH |
| CH$_3$ | OH | N(CH$_3$)$_2$ | OH |
| CH$_3$ | Cl | N(CH$_3$)$_2$ | OH |
| CH$_2$CH$_3$ | H | SCH$_3$ | H |
| CH$_2$CH$_3$ | F | SCH$_3$ | H |
| CH$_2$CH$_3$ | OCH$_3$ | SCH$_3$ | H |
| CH$_2$CH$_3$ | OH | SCH$_3$ | H |
| CH$_2$CH$_3$ | Cl | SCH$_3$ | H |
| CH$_2$CH$_3$ | H | SCH$_3$ | OH |
| CH$_2$CH$_3$ | F | SCH$_3$ | OH |
| CH$_2$CH$_3$ | OCH$_3$ | SCH$_3$ | OH |
| CH$_2$CH$_3$ | OH | SCH$_3$ | OH |
| CH$_2$CH$_3$ | Cl | SCH$_3$ | OH |
| CH$_2$CH$_3$ | H | N(CH$_3$)$_2$ | H |
| CH$_2$CH$_3$ | F | N(CH$_3$)$_2$ | H |
| CH$_2$CH$_3$ | OCH$_3$ | N(CH$_3$)$_2$ | H |
| CH$_2$CH$_3$ | OH | N(CH$_3$)$_2$ | H |
| CH$_2$CH$_3$ | Cl | N(CH$_3$)$_2$ | H |
| CH$_2$CH$_3$ | H | N(CH$_3$)$_2$ | OH |
| CH$_2$CH$_3$ | F | N(CH$_3$)$_2$ | OH |
| CH$_2$CH$_3$ | OCH$_3$ | N(CH$_3$)$_2$ | OH |
| CH$_2$CH$_3$ | OH | N(CH$_3$)$_2$ | OH |
| CH$_2$CH$_3$ | Cl | N(CH$_3$)$_2$ | OH |
| CH$_2$CH$_2$CH$_2$CH$_3$ | H | SCH$_3$ | H |
| CH$_2$CH$_2$CH$_2$CH$_3$ | F | SCH$_3$ | H |
| CH$_2$CH$_2$CH$_2$CH$_3$ | OCH$_3$ | SCH$_3$ | H |
| CH$_2$CH$_2$CH$_2$CH$_3$ | OH | SCH$_3$ | H |
| CH$_2$CH$_2$CH$_2$CH$_3$ | Cl | SCH$_3$ | H |
| CH$_2$CH$_2$CH$_2$CH$_3$ | H | SCH$_3$ | OH |
| CH$_2$CH$_2$CH$_2$CH$_3$ | F | SCH$_3$ | OH |
| CH$_2$CH$_2$CH$_2$CH$_3$ | OCH$_3$ | SCH$_3$ | OH |
| CH$_2$CH$_2$CH$_2$CH$_3$ | OH | SCH$_3$ | OH |
| CH$_2$CH$_2$CH$_2$CH$_3$ | Cl | SCH$_3$ | OH |
| CH$_2$CH$_2$CH$_2$CH$_3$ | H | N(CH$_3$)$_2$ | H |
| CH$_2$CH$_2$CH$_2$CH$_3$ | F | N(CH$_3$)$_2$ | H |
| CH$_2$CH$_2$CH$_2$CH$_3$ | OCH$_3$ | N(CH$_3$)$_2$ | H |
| CH$_2$CH$_2$CH$_2$CH$_3$ | OH | N(CH$_3$)$_2$ | H |
| CH$_2$CH$_2$CH$_2$CH$_3$ | Cl | N(CH$_3$)$_2$ | H |
| CH$_2$CH$_2$CH$_2$CH$_3$ | H | N(CH$_3$)$_2$ | OH |
| CH$_2$CH$_2$CH$_2$CH$_3$ | F | N(CH$_3$)$_2$ | OH |
| CH$_2$CH$_2$CH$_2$CH$_3$ | OCH$_3$ | N(CH$_3$)$_2$ | OH |
| CH$_2$CH$_2$CH$_2$CH$_3$ | OH | N(CH$_3$)$_2$ | OH |
| CH$_2$CH$_2$CH$_2$CH$_3$ | Cl | N(CH$_3$)$_2$ | OH |

In a particular embodiment, the compound of formula (I) is selected from the group consisting of:
(S)-3-((7-bromo-3-butyl-3-ethyl-1,1-dioxido-5-phenyl-2,3,4,5-tetrahydro-1,5-benzothiazepin-8-yl)oxy)propanoic acid;
(R)-3-((7-bromo-3-butyl-3-ethyl-1,1-dioxido-5-phenyl-2,3,4,5-tetrahydro-1,5-benzothiazepin-8-yl)oxy)propanoic acid;
3-((7-bromo-3,3-dibutyl-1,1-dioxido-5-phenyl-2,3,4,5-tetrahydro-1,5-benzothiazepin-8-yl)oxy)propanoic acid;
3-((3-butyl-7-chloro-3-ethyl-1,1-dioxido-5-phenyl-2,3,4,5-tetrahydro-1,5-benzothiazepin-8-yl)oxy)propanoic acid;
(S)-3-((3-butyl-7-chloro-3-ethyl-1,1-dioxido-5-phenyl-2,3,4,5-tetrahydro-1,5-benzothiazepin-8-yl)oxy)propanoic acid;
(R)-3-((3-butyl-7-chloro-3-ethyl-1,1-dioxido-5-phenyl-2,3,4,5-tetrahydro-1,5-benzothiazepin-8-yl)oxy)propanoic acid;
3-((3,3-dibutyl-7-chloro-1,1-dioxido-5-phenyl-2,3,4,5-tetrahydro-1,5-benzothiazepin-8-yl)oxy)propanoic acid;
3-((3,3-dibutyl-7-(methylthio)-1,1-dioxido-5-phenyl-2,3,4,5-tetrahydro-1,5-benzothiazepin-8-yl)oxy)-2-hydroxypropanoic acid;
(S)-3-((3,3-dibutyl-7-(methylthio)-1,1-dioxido-5-phenyl-2,3,4,5-tetrahydro-1,5-benzothiazepin-8-yl)oxy)-2-hydroxypropanoic acid;
(R)-3-((3,3-dibutyl-7-(methylthio)-1,1-dioxido-5-phenyl-2,3,4,5-tetrahydro-1,5-benzothiazepin-8-yl)oxy)-2-hydroxypropanoic acid;
3-((3-butyl-3-ethyl-7-(methylthio)-1,1-dioxido-5-phenyl-2,3,4,5-tetrahydro-1,5-benzothiazepin-8-yl)oxy)propanoic acid;
(S)-3-((3-butyl-3-ethyl-7-(methylthio)-1,1-dioxido-5-phenyl-2,3,4,5-tetrahydro-1,5-benzothiazepin-8-yl)oxy)propanoic acid;
(R)-3-((3-butyl-3-ethyl-7-(methylthio)-1,1-dioxido-5-phenyl-2,3,4,5-tetrahydro-1,5-benzothiazepin-8-yl)oxy)propanoic acid;
3-((3,3-dibutyl-7-(methylthio)-1,1-dioxido-5-phenyl-2,3,4,5-tetrahydro-1,5-benzothiazepin-8-yl)oxy)propanoic acid;
3-((3-butyl-7-(dimethylamino)-3-ethyl-1,1-dioxido-5-phenyl-2,3,4,5-tetrahydro-1,5-benzothiazepin-8-yl)oxy)propanoic acid;
(S)-3-((3-butyl-7-(dimethylamino)-3-ethyl-1,1-dioxido-5-phenyl-2,3,4,5-tetrahydro-1,5-benzothiazepin-8-yl)oxy)propanoic acid;
(R)-3-((3-butyl-7-(dimethylamino)-3-ethyl-1,1-dioxido-5-phenyl-2,3,4,5-tetrahydro-1,5-benzothiazepin-8-yl)oxy)propanoic acid;
3-((3,3-dibutyl-7-(methylthio)-1,1-dioxido-5-phenyl-2,3,4,5-tetrahydro-1,5-benzothiazepin-8-yl)oxy)-2-hydroxy-2-methylpropanoic acid;
(S)-3-((3,3-dibutyl-7-(methylthio)-1,1-dioxido-5-phenyl-2,3,4,5-tetrahydro-1,5-benzothiazepin-8-yl)oxy)-2-hydroxy-2-methylpropanoic acid;

(R)-3-((3,3-dibutyl-7-(methylthio)-1,1-dioxido-5-phenyl-2,3,4,5-tetrahydro-1,5-benzothiazepin-8-yl)oxy)-2-hydroxy-2-methylpropanoic acid;

3-((3-butyl-3-methyl-7-(methylthio)-1,1-dioxido-5-phenyl-2,3,4,5-tetrahydro-1,5-benzothiazepin-8-yl)oxy)propanoic acid;

(S)-3-((3-butyl-3-methyl-7-(methylthio)-1,1-dioxido-5-phenyl-2,3,4,5-tetrahydro-1,5-benzothiazepin-8-yl)oxy)propanoic acid;

(R)-3-((3-butyl-3-methyl-7-(methylthio)-1,1-dioxido-5-phenyl-2,3,4,5-tetrahydro-1,5-benzothiazepin-8-yl)oxy)propanoic acid;

3-((3,3-dibutyl-5-(3,4-difluorophenyl)-7-(methylthio)-1,1-dioxido-2,3,4,5-tetrahydro-1,5-benzothiazepin-8-yl)oxy)propanoic acid;

3-((3,3-dibutyl-5-(4-fluorophenyl)-7-(methylthio)-1,1-dioxido-2,3,4,5-tetrahydro-1,5-benzothiazepin-8-yl)oxy)propanoic acid;

3-((3-ethyl-7-(methylthio)-1,1-dioxido-5-phenyl-3-propyl-2,3,4,5-tetrahydro-1,5-benzothiazepin-8-yl)oxy)propanoic acid;

O-(3-butyl-3-ethyl-7-(methylthio)-1,1-dioxido-5-phenyl-2,3,4,5-tetrahydro-1,5-benzothiazepin-8-yl)serine;

3-((3-butyl-7-(dimethylamino)-3-methyl-1,1-dioxido-5-phenyl-2,3,4,5-tetrahydro-1,5-benzothiazepin-8-yl)oxy)propanoic acid;

(S)-3-((3-butyl-7-(dimethylamino)-3-methyl-1,1-dioxido-5-phenyl-2,3,4,5-tetrahydro-1,5-benzothiazepin-8-yl)oxy)propanoic acid;

(R)-3-((3-butyl-7-(dimethylamino)-3-methyl-1,1-dioxido-5-phenyl-2,3,4,5-tetrahydro-1,5-benzothiazepin-8-yl)oxy)propanoic acid;

3-((3-butyl-7-chloro-3-ethyl-1,1-dioxido-5-phenyl-2,3,4,5-tetrahydro-1,5-benzothiazepin-8-yl)oxy)butanoic acid;

(S)-3-(((R)-3-butyl-7-chloro-3-ethyl-1,1-dioxido-5-phenyl-2,3,4,5-tetrahydro-1,5-benzothiazepin-8-yl)oxy)butanoic acid;

(R)-3-(((R)-3-butyl-7-chloro-3-ethyl-1,1-dioxido-5-phenyl-2,3,4,5-tetrahydro-1,5-benzothiazepin-8-yl)oxy)butanoic acid;

(S)-3-(((S)-3-butyl-7-chloro-3-ethyl-1,1-dioxido-5-phenyl-2,3,4,5-tetrahydro-1,5-benzothiazepin-8-yl)oxy)butanoic acid;

(R)-3-(((S)-3-butyl-7-chloro-3-ethyl-1,1-dioxido-5-phenyl-2,3,4,5-tetrahydro-1,5-benzothiazepin-8-yl)oxy)butanoic acid;

3-((3-butyl-3-methyl-7-(methylthio)-1,1-dioxido-5-phenyl-2,3,4,5-tetrahydro-1,5-benzothiazepin-8-yl)oxy)-2-hydroxypropanoic acid;

(S)-3-(((R)-3-butyl-3-methyl-7-(methylthio)-1,1-dioxido-5-phenyl-2,3,4,5-tetrahydro-1,5-benzothiazepin-8-yl)oxy)-2-hydroxypropanoic acid;

(R)-3-(((R)-3-butyl-3-methyl-7-(methylthio)-1,1-dioxido-5-phenyl-2,3,4,5-tetrahydro-1,5-benzothiazepin-8-yl)oxy)-2-hydroxypropanoic acid;

(S)-3-(((S)-3-butyl-3-methyl-7-(methylthio)-1,1-dioxido-5-phenyl-2,3,4,5-tetrahydro-1,5-benzothiazepin-8-yl)oxy)-2-hydroxypropanoic acid;

(R)-3-(((S)-3-butyl-3-methyl-7-(methylthio)-1,1-dioxido-5-phenyl-2,3,4,5-tetrahydro-1,5-benzothiazepin-8-yl)oxy)-2-hydroxypropanoic acid;

3-((3-butyl-3-methyl-7-(methylthio)-1,1-dioxido-5-phenyl-2,3,4,5-tetrahydro-1,5-benzothiazepin-8-yl)oxy)-2-hydroxy-2-methylpropanoic acid;

(S)-3-(((R)-3-butyl-3-methyl-7-(methylthio)-1,1-dioxido-5-phenyl-2,3,4,5-tetrahydro-1,5-benzothiazepin-8-yl)oxy)-2-hydroxy-2-methylpropanoic acid;

(R)-3-(((R)-3-butyl-3-methyl-7-(methylthio)-1,1-dioxido-5-phenyl-2,3,4,5-tetrahydro-1,5-benzothiazepin-8-yl)oxy)-2-hydroxy-2-methylpropanoic acid;

(S)-3-(((S)-3-butyl-3-methyl-7-(methylthio)-1,1-dioxido-5-phenyl-2,3,4,5-tetrahydro-1,5-benzothiazepin-8-yl)oxy)-2-hydroxy-2-methylpropanoic acid;

(R)-3-(((S)-3-butyl-3-methyl-7-(methylthio)-1,1-dioxido-5-phenyl-2,3,4,5-tetrahydro-1,5-benzothiazepin-8-yl)oxy)-2-hydroxy-2-methylpropanoic acid;

3-((3-butyl-3-ethyl-7-(methylthio)-1,1-dioxido-5-phenyl-2,3,4,5-tetrahydro-1,5-benzothiazepin-8-yl)oxy)-2-fluoro-2-methyl propanoic acid;

(S)-3-(((R)-3-butyl-3-ethyl-7-(methylthio)-1,1-dioxido-5-phenyl-2,3,4,5-tetrahydro-1,5-benzothiazepin-8-yl)oxy)-2-fluoro-2-methylpropanoic acid;

(R)-3-(((R)-3-butyl-3-ethyl-7-(methylthio)-1,1-dioxido-5-phenyl-2,3,4,5-tetrahydro-1,5-benzothiazepin-8-yl)oxy)-2-fluoro-2-methyl propanoic acid;

(S)-3-(((S)-3-butyl-3-ethyl-7-(methylthio)-1,1-dioxido-5-phenyl-2,3,4,5-tetrahydro-1,5-benzothiazepin-8-yl)oxy)-2-fluoro-2-methylpropanoic acid;

(R)-3-(((S)-3-butyl-3-ethyl-7-(methylthio)-1,1-dioxido-5-phenyl-2,3,4,5-tetrahydro-1,5-benzothiazepin-8-yl)oxy)-2-fluoro-2-methyl propanoic acid;

O—((S)-3-butyl-3-ethyl-7-(methylthio)-1,1-dioxido-5-phenyl-2,3,4,5-tetrahydro-1,5-benzothiazepin-8-yl)-D-serine;

O—((R)-3-butyl-3-ethyl-7-(methylthio)-1,1-dioxido-5-phenyl-2,3,4,5-tetrahydro-1,5-benzothiazepin-8-yl)-D-serine;

3-((3-butyl-3-ethyl-5-(4-fluorophenyl)-7-(methylthio)-1,1-dioxido-2,3,4,5-tetrahydro-1,5-benzothiazepin-8-yl)oxy)propanoic acid;

(S)-3-((3-butyl-3-ethyl-5-(4-fluorophenyl)-7-(methylthio)-1,1-dioxido-2,3,4,5-tetrahydro-1,5-benzothiazepin-8-yl)oxy)propanoic acid;

(R)-3-((3-butyl-3-ethyl-5-(4-fluorophenyl)-7-(methylthio)-1,1-dioxido-2,3,4,5-tetrahydro-1,5-benzothiazepin-8-yl)oxy)propanoic acid;

3-((3-butyl-3-ethyl-7-(methylthio)-1,1-dioxido-5-phenyl-2,3,4,5-tetrahydro-1,5-benzothiazepin-8-yl)oxy)-2-hydroxypropanoic acid;

(S)-3-(((R)-3-butyl-3-ethyl-7-(methylthio)-1,1-dioxido-5-phenyl-2,3,4,5-tetrahydro-1,5-benzothiazepin-8-yl)oxy)-2-hydroxypropanoic acid;

(R)-3-(((R)-3-butyl-3-ethyl-7-(methylthio)-1,1-dioxido-5-phenyl-2,3,4,5-tetrahydro-1,5-benzothiazepin-8-yl)oxy)-2-hydroxypropanoic acid;

(S)-3-(((S)-3-butyl-3-ethyl-7-(methylthio)-1,1-dioxido-5-phenyl-2,3,4,5-tetrahydro-1,5-benzothiazepin-8-yl)oxy)-2-hydroxypropanoic acid;

(R)-3-(((S)-3-butyl-3-ethyl-7-(methylthio)-1,1-dioxido-5-phenyl-2,3,4,5-tetrahydro-1,5-benzothiazepin-8-yl)oxy)-2-hydroxypropanoic acid;

3-((3-butyl-3-ethyl-5-(4-fluorophenyl)-7-(methylthio)-1,1-dioxido-2,3,4,5-tetrahydro-1,5-benzothiazepin-8-yl)oxy)-2-hydroxypropanoic acid;

(S)-3-(((R)-3-butyl-3-ethyl-5-(4-fluorophenyl)-7-(methylthio)-1,1-dioxido-2,3,4,5-tetrahydro-1,5-benzothiazepin-8-yl)oxy)-2-hydroxypropanoic acid;

(R)-3-(((R)-3-butyl-3-ethyl-5-(4-fluorophenyl)-7-(methylthio)-1,1-dioxido-2,3,4,5-tetrahydro-1,5-benzothiazepin-8-yl)oxy)-2-hydroxypropanoic acid;

(S)-3-(((S)-3-butyl-3-ethyl-5-(4-fluorophenyl)-7-(methylthio)-1,1-dioxido-2,3,4,5-tetrahydro-1,5-benzothiazepin-8-yl)oxy)-2-hydroxypropanoic acid;

(R)-3-(((S)-3-butyl-3-ethyl-5-(4-fluorophenyl)-7-(methylthio)-1,1-dioxido-2,3,4,5-tetrahydro-1,5-benzothiazepin-8-yl)oxy)-2-hydroxypropanoic acid;

3-((3-butyl-3-ethyl-7-methoxy-1,1-dioxido-5-phenyl-2,3,4,5-tetrahydro-1,5-benzothiazepin-8-yl)oxy)propanoic acid;

(S)-3-((3-butyl-3-ethyl-7-methoxy-1,1-dioxido-5-phenyl-2,3,4,5-tetrahydro-1,5-benzothiazepin-8-yl)oxy)propanoic acid;

(R)-3-((3-butyl-3-ethyl-7-methoxy-1,1-dioxido-5-phenyl-2,3,4,5-tetrahydro-1,5-benzothiazepin-8-yl)oxy)propanoic acid;

3-((3,3-dibutyl-7-methoxy-1,1-dioxido-5-phenyl-2,3,4,5-tetrahydro-1,5-benzothiazepin-8-yl)oxy)propanoic acid;

3-((3,3-dibutyl-7-(methylthio)-1,1-dioxido-5-phenyl-2,3,4,5-tetrahydro-1,5-benzothiazepin-8-yl)oxy)-2-methoxypropanoic acid;

(R)-3-((3,3-dibutyl-7-(methylthio)-1,1-dioxido-5-phenyl-2,3,4,5-tetrahydro-1,5-benzothiazepin-8-yl)oxy)-2-methoxypropanoic acid;

(S)-3-((3,3-dibutyl-7-(methylthio)-1,1-dioxido-5-phenyl-2,3,4,5-tetrahydro-1,5-benzothiazepin-8-yl)oxy)-2-methoxypropanoic acid;

3-((3-butyl-3-ethyl-7-(methylthio)-1,1-dioxido-5-phenyl-2,3,4,5-tetrahydro-1,5-benzothiazepin-8-yl)oxy)-2-hydroxy-2-methylpropanoic acid;

(S)-3-(((R)-3-butyl-3-ethyl-7-(methylthio)-1,1-dioxido-5-phenyl-2,3,4,5-tetrahydro-1,5-benzothiazepin-8-yl)oxy)-2-hydroxy-2-methylpropanoic acid;

(R)-3-(((R)-3-butyl-3-ethyl-7-(methylthio)-1,1-dioxido-5-phenyl-2,3,4,5-tetrahydro-1,5-benzothiazepin-8-yl)oxy)-2-hydroxy-2-methylpropanoic acid;

(S)-3-(((S)-3-butyl-3-ethyl-7-(methylthio)-1,1-dioxido-5-phenyl-2,3,4,5-tetrahydro-1,5-benzothiazepin-8-yl)oxy)-2-hydroxy-2-methylpropanoic acid;

(R)-3-(((S)-3-butyl-3-ethyl-7-(methylthio)-1,1-dioxido-5-phenyl-2,3,4,5-tetrahydro-1,5-benzothiazepin-8-yl)oxy)-2-hydroxy-2-methylpropanoic acid;

3-((3-butyl-5-(4-fluorophenyl)-3-methyl-7-(methylthio)-1,1-dioxido-2,3,4,5-tetrahydro-1,5-benzothiazepin-8-yl)oxy)propanoic acid;

(S)-3-((3-butyl-5-(4-fluorophenyl)-3-methyl-7-(methylthio)-1,1-dioxido-2,3,4,5-tetrahydro-1,5-benzothiazepin-8-yl)oxy)propanoic acid;

(R)-3-((3-butyl-5-(4-fluorophenyl)-3-methyl-7-(methylthio)-1,1-dioxido-2,3,4,5-tetrahydro-1,5-benzothiazepin-8-yl)oxy)propanoic acid;

3-((3-butyl-5-(4-fluorophenyl)-3-methyl-7-(methylthio)-1,1-dioxido-2,3,4,5-tetrahydro-1,5-benzothiazepin-8-yl)oxy)-2-hydroxypropanoic acid;

(S)-3-(((R)-3-butyl-5-(4-fluorophenyl)-3-methyl-7-(methylthio)-1,1-dioxido-2,3,4,5-tetrahydro-1,5-benzothiazepin-8-yl)oxy)-2-hydroxypropanoic acid;

(R)-3-(((R)-3-butyl-5-(4-fluorophenyl)-3-methyl-7-(methylthio)-1,1-dioxido-2,3,4,5-tetrahydro-1,5-benzothiazepin-8-yl)oxy)-2-hydroxypropanoic acid;

(S)-3-(((S)-3-butyl-5-(4-fluorophenyl)-3-methyl-7-(methylthio)-1,1-dioxido-2,3,4,5-tetrahydro-1,5-benzothiazepin-8-yl)oxy)-2-hydroxypropanoic acid;

(R)-3-(((S)-3-butyl-5-(4-fluorophenyl)-3-methyl-7-(methylthio)-1,1-dioxido-2,3,4,5-tetrahydro-1,5-benzothiazepin-8-yl)oxy)-2-hydroxypropanoic acid;

3-((3-butyl-3-ethyl-7-(methylamino)-1,1-dioxido-5-phenyl-2,3,4,5-tetrahydro-1,5-benzothiazepin-8-yl)oxy)propanoic acid;

(S)-3-((3-butyl-3-ethyl-7-(methylamino)-1,1-dioxido-5-phenyl-2,3,4,5-tetrahydro-1,5-benzothiazepin-8-yl)oxy)propanoic acid; and (R)-3-((3-butyl-3-ethyl-7-(methylamino)-1,1-dioxido-5-phenyl-2,3,4,5-tetrahydro 5-benzothiazepin-8-yl)oxy)propanoic acid;

or a pharmaceutically acceptable salt thereof.

In some embodiments, the invention relates to a compound of formula (I), as defined above, with the proviso that the compound is not racemic 3-((7-bromo-3-butyl-3-ethyl-1,1-dioxido-5-phenyl-2,3,4,5-tetrahydro-1,5-benzothiazepin-8-yl)oxy)propanoic acid or any enantiomers thereof.

As used herein, the term "halo" refers to fluoro, chloro, bromo and iodo.

As used herein, the term "$C_{1-6}$ alkyl" refers to a straight or branched alkyl group having from 1 to 6 carbon atoms, and the term "$C_{1-4}$ alkyl" refers to a straight or branched alkyl group having from 1 to 4 carbon atoms. Examples of $C_{1-4}$ alkyl include methyl, ethyl, n-propyl, isopropyl, n-butyl, isobutyl, sec-butyl and tert-butyl.

As used herein, the term "$C_{1-4}$ haloalkyl" refers to a straight or branched $C_{1-4}$ alkyl group, as defined herein, wherein one or more hydrogen atoms have been replaced with halogen. Examples of $C_{1-4}$ haloalkyl include chloromethyl, fluoroethyl and trifluoromethyl.

As used herein, the terms "$C_{1-4}$ alkoxy" and "$C_{1-4}$ alkylthio" refer to a straight or branched $C_{1-4}$ alkyl group attached to the remainder of the molecule through an oxygen or sulphur atom, respectively.

As used herein, the term "$C_{3-6}$ cycloalkyl" refers to a monocyclic saturated hydrocarbon ring having from 3 to 6 carbon atoms. Examples of $C_{3-6}$ cycloalkyl include cyclopropyl, cyclobutyl, cyclopentyl and cyclohexyl.

The term "aryl" denotes an aromatic monocyclic ring composed of 6 carbon atoms or an aromatic bicyclic ring system composed of 10 carbon atoms. Examples of aryl include phenyl, naphthyl and azulenyl.

The term "amino" refers to an —$NH_2$ group. As used herein, the terms "N—($C_{1-4}$ alkyl)amino" and "N,N-di($C_{1-4}$ alkyl)amino" refer to an amino group wherein one or both hydrogen atom(s), respectively, are replaced with a straight or branched $C_{1-4}$ alkyl group. Examples of N—($C_{1-4}$ alkyl) amino include methylamino, ethylamino and tert-butylamino, and examples of N,N-di-($C_{1-4}$ alkyl)amino include dimethylamino and diethylamino.

As used herein, the term "N-(aryl-$C_{1-4}$ alkyl)amino" refers to an amino group wherein a hydrogen atom is replaced with an aryl-$C_{1-4}$ alkyl group. Examples of N-(aryl-$C_{1-4}$ alkyl)amino include benzylamino and phenylethylamino.

As used herein, the term "pharmaceutically acceptable" refers to those compounds, materials, compositions and/or dosage forms that are suitable for human pharmaceutical use and that are generally safe, non-toxic and neither biologically nor otherwise undesirable.

As used herein, the term "about" refers to a value or parameter herein that includes (and describes) embodiments that are directed to that value or parameter per se. For example, description referring to "about 20" includes description of "20." Numeric ranges are inclusive of the numbers defining the range. Generally speaking, the term "about" refers to the indicated value of the variable and to all values of the variable that are within the experimental error of the indicated value (e.g., within the 95% confidence interval for the mean) or within 10 percent of the indicated value, whichever is greater.

The 1,5-benzothiazepine compounds of formula (I), or pharmaceutically acceptable salts thereof, are inhibitors of the apical sodium-dependent bile acid transporter (ASBT inhibitors), of the liver bile acid transporter (LBAT inhibitors), or of both the apical sodium-dependent bile acid and liver bile acid transporters (dual ASBT/LBAT inhibitors). They are therefore useful in the treatment or prevention of conditions, disorders and diseases wherein inhibition of bile acid circulation is desirable, such as cardiovascular diseases, fatty acid metabolism and glucose utilization disorders, gastrointestinal diseases and liver diseases.

Cardiovascular diseases and disorders of fatty acid metabolism and glucose utilization include, but are not limited to, hypercholesterolemia; disorders of fatty acid metabolism; type 1 and type 2 diabetes mellitus; complications of diabetes, including cataracts, micro- and macrovascular diseases, retinopathy, neuropathy, nephropathy and delayed wound healing, tissue ischaemia, diabetic foot, arteriosclerosis, myocardial infarction, acute coronary syndrome, unstable angina pectoris, stable angina pectoris, stroke, peripheral arterial occlusive disease, cardiomyopathy, heart failure, heart rhythm disorders and vascular restenosis; diabetes-related diseases such as insulin resistance (impaired glucose homeostasis), hyperglycemia, hyperinsulinemia, elevated blood levels of fatty acids or glycerol, obesity, dyslipidemia, hyperlipidemia including hypertriglyceridemia, metabolic syndrome (syndrome X), atherosclerosis and hypertension; and for increasing high density lipoprotein levels.

Gastrointestinal diseases and disorders include constipation (including chronic constipation, functional constipation, chronic idiopathic constipation (CIC), intermittent/sporadic constipation, constipation secondary to diabetes mellitus, constipation secondary to stroke, constipation secondary to chronic kidney disease, constipation secondary to multiple sclerosis, constipation secondary to Parkinson's disease, constipation secondary to systemic sclerosis, drug induced constipation, irritable bowel syndrome with constipation (IBS-C), irritable bowel syndrome mixed (IBS-M), pediatric functional constipation and opioid induced constipation); Crohn's disease; primary bile acid malabsorption; irritable bowel syndrome (IBS); inflammatory bowel disease (IBD); ileal inflammation; and reflux disease and complications thereof, such as Barrett's esophagus, bile reflux esophagitis and bile reflux gastritis.

A liver disease as defined herein is any disease in the liver and in organs connected therewith, such as the pancreas, portal vein, the liver parenchyma, the intrahepatic biliary tree, the extrahepatic biliary tree, and the gall bladder. In some cases, a liver disease a bile acid-dependent liver disease. Liver diseases and disorders include, but are not limited to an inherited metabolic disorder of the liver; inborn errors of bile acid synthesis; congenital bile duct anomalies; biliary atresia; post-Kasai biliary atresia; post-liver transplantation biliary atresia; neonatal hepatitis; neonatal cholestasis; hereditary forms of cholestasis; cerebrotendinous xanthomatosis; a secondary defect of BA synthesis; Zellweger's syndrome; cystic fibrosis-associated liver disease; alpha1-antitrypsin deficiency; Alagilles syndrome (ALGS); Byler syndrome; a primary defect of bile acid (BA) synthesis; progressive familial intrahepatic cholestasis (PFIC) including PFIC-1, PFIC-2, PFIC-3 and non-specified PFIC, post-biliary diversion PFIC and post-liver transplant PFIC; benign recurrent intrahepatic cholestasis (BRIC) including BRIC1, BRIC2 and non-specified BRIC, post-biliary diversion BRIC and post-liver transplant BRIC; autoimmune hepatitis; primary biliary cirrhosis (PBC); liver fibrosis; non-alcoholic fatty liver disease (NAFLD); non-alcoholic steatohepatitis (NASH); portal hypertension; cholestasis; Down syndrome cholestasis; drug-induced cholestasis; intrahepatic cholestasis of pregnancy (jaundice during pregnancy); intrahepatic cholestasis; extrahepatic cholestasis; parenteral nutrition associated cholestasis (PNAC); low phospholipid-associated cholestasis; lymphedema cholestasis syndrome 1 (LSC1); primary sclerosing cholangitis (PSC); immunoglobulin G4 associated cholangitis; primary biliary cholangitis; cholelithiasis (gall stones); biliary lithiasis; choledocholithiasis; gallstone pancreatitis; Caroli disease; malignancy of bile ducts; malignancy causing obstruction of the biliary tree; biliary strictures; AIDS cholangiopathy; ischemic cholangiopathy; pruritus due to cholestasis or jaundice; pancreatitis; chronic autoimmune liver disease leading to progressive cholestasis; hepatic steatosis; alcoholic hepatitis; acute fatty liver; fatty liver of pregnancy; drug-induced hepatitis; iron overload disorders; congenital bile acid synthesis defect type 1 (BAS type 1); drug-induced liver injury (DILI); hepatic fibrosis; congenital hepatic fibrosis; hepatic cirrhosis; Langerhans cell histiocytosis (LCH); neonatal ichthyosis sclerosing cholangitis (NISCH); erythropoietic protoporphyria (EPP); idiopathic adulthood ductopenia (IAD); idiopathic neonatal hepatitis (INH); non syndromic paucity of interlobular bile ducts (NS PILBD); North American Indian childhood cirrhosis (NAIC); hepatic sarcoidosis; amyloidosis; necrotizing enterocolitis; serum bile acid-caused toxicities, including cardiac rhythm disturbances (e.g., atrial fibrillation) in setting of abnormal serum bile acid profile, cardiomyopathy associated with liver cirrhosis ("cholecardia"), and skeletal muscle wasting associated with cholestatic liver disease; viral hepatitis (including hepatitis A, hepatitis B, hepatitis C, hepatitis D and hepatitis E); hepatocellular carcinoma (hepatoma); cholangiocarcinoma; bile acid-related gastrointestinal cancers; and cholestasis caused by tumours and neoplasms of the liver, of the biliary tract and of the pancreas. Compounds of formula (I), or pharmaceutically acceptable salts thereof, are also useful in the enhancement of corticosteroid therapy in liver disease.

Other diseases that may be treated or prevented by the compounds of formula (I), or pharmaceutically acceptable salts thereof, include hyperabsorption syndromes (including abetalipoproteinemia, familial hypobetalipoproteinemia (FHBL), chylomicron retention disease (CRD) and sitosterolemia); hypervitaminosis and osteopetrosis; hypertension; glomerular hyperfiltration; pruritus of renal failure; The compounds are also useful in the protection against liver- or metabolic disease-associated kidney injury.

The transport of bile acids in the human body is controlled by the action of the members of the SLC10 family of solute carrier proteins, in particular by the $Na^+$-taurocholate cotransporting polypeptide (NTCP, also called liver bile acid transporter (LBAT); gene symbol SLC10A1), which is expressed in the sinusoidal membrane of hepatocytes, and by the apical sodium dependent bile acid transporter (ASBT, also called ileal bile acid transporter (IBAT), ISBT, ABAT or NTCP2; gene symbol SLC10A2), which is expressed in the apical membrane of ileal enterocytes, proximal renal tubule cells, biliary epithelium, large cholangiocytes and gallbladder epithelial cells. In the liver, bile acids are efficiently extracted from portal blood by the liver bile acid transporter (LBAT) and re-secreted across the canalicular membrane by the bile salt export pump (BSEP; gene symbol ABCB11). The reabsorption of bile acids in the ileum is handled by the apical sodium-dependent bile acid transporter (ASBT), where it is commonly referred to as ileal bile acid transporter (IBAT). Both LBAT and ASBT function as electrogenic sodium-solute cotransporters that move two or more $Na^+$ ions per molecule of solute.

Xenobiotics and endobiotics, including bile acids, are taken up by the liver from portal blood and secreted into bile by distinct transport proteins with individualized substrate specificities. Glycine- and taurine-conjugated bile acids exist in anionic form and are unable to cross membranes by diffusion, and thus, are completely dependent on membrane transport proteins to enter or exit the hepatocyte (Kosters and Karpen, Xenobiotica 2008, vol. 38, p. 1043-1071). ASBT and LBAT prefer glycine- and taurine-conjugated bile salts over their unconjugated counterparts and demonstrate a higher affinity for dihydroxy bile salts than for trihydroxy bile salts. No non-bile acid substrates have been identified for ASBT yet, however, LBAT was also found to transport a variety of steroid sulfates, hormones and xenobiotics.

LBAT is not as thoroughly characterized as ASBT in terms of drug inhibition requirements. Dong et al. have identified FDA approved drugs that inhibit human LBAT and compared LBAT and ASBT inhibition requirements. A series of LBAT inhibition studies were performed using FDA approved drugs, in concert with iterative computational model development. Screening studies identified 27 drugs as novel LBAT inhibitors, including irbesartan (Ki=11.9 µM) and ezetimibe (Ki=25.0 µM). The common feature pharmacophore indicated that two hydrophobes and one hydrogen bond acceptor were important for inhibition of LBAT. From 72 drugs screened in vitro, a total of 31 drugs inhibited LBAT, while 51 drugs (i.e. more than half) inhibited ASBT. Hence, while there was inhibitor overlap, ASBT unexpectedly was more permissive to drug inhibition than was LBAT, and this may be related to LBAT's possessing fewer pharmacophore features (Dong et al., Mol. Pharm. 2013, vol. 10, p. 1008-1019).

Vaz et al. describe the identification of LBAT deficiency as a new inborn error of metabolism with a relatively mild clinical phenotype. The identification of LBAT deficiency confirms that this transporter is the main import system for conjugated bile salts into the liver, but also indicates that auxiliary transporters are able to sustain the enterohepatic cycle in its absence (Vaz et al., Hepatology 2015, vol. 61, p. 260-267). These findings support the hypothesis that LBAT inhibition is a safe mechanism of action, as the hepatocytes still have the possibility to take up the necessary amount of bile acids.

Liu et al. describe the identification of a new type of hypercholanemia that is associated with homozygosity for the p.Ser267Phe mutation in SLC10A1 (LBAT). The allele frequency of this mutation in gene SLC10A1 varies in different populations, with the highest incidence occurring in Southern China (8% and 12% in Chinese Han and Dai respectively) and in Vietnam (11%). This "hidden" hypercholanemia was believed to affect 0.64% of the Southern Han, 1.44% of the Dai Chinese population, and 1.21% of the Vietnamese population. An increase in conjugated and unconjugated serum BA levels in the homozygous individuals was also observed. Liu et al. suggest that this finding is most likely due to reduced BA transport from the portal circulation into hepatocytes. This supports the hypothesis that the physiological function of the enterohepatic circulation is not only to recycle bile acids but also to clear bile acids from the circulation to achieve homeostasis (Karpen and Dawson, Hepatology 2015, vol. 61, p. 24-27). Alternatively, the liver may synthesize increased levels of bile acids to compensate for the reduced enterohepatic recirculation in the homozygous carriers. As LBAT also transports unconjugated bile acids, the increase of the unconjugated bile acids in this study was not surprising (Liu et al., Scientific Reports 2017, 7: 9214, p. 1-7).

LBAT has been found to be downregulated in several forms of cholestatic liver injury and cholestasis, whereas ASBT has been found to be downregulated in a variety of gastrointestinal disorders such as Crohn's disease, primary bile acid malabsorption, inflammatory bowel disease, and ileal inflammation but upregulated in cholestasis. LBAT also functions as a cellular receptor for viral entry of the hepatitis B virus (HBV) and hepatitis D virus (HDV), which in turn is the major cause of liver disease and hepatocellular carcinoma.

ASBT inhibition has been investigated for decreasing plasma cholesterol levels and improving insulin resistance, as well as to relieving the hepatic bile acid burden in cholestatic liver disease. In addition, ASBT inhibition has been found to restore insulin levels and normoglycemia, thus establishing ASBT inhibition as a promising treatment for type 2 diabetes mellitus. ASBT inhibitors are also used for treatment of functional constipation.

As ASBT is predominantly expressed in the ileum (where it is often referred to as IBAT), ASBT inhibitors need not be systemically available. On the other hand, ASBT is also expressed in the proximal tubule cells of the kidneys. ASBT inhibitors that are systemically available may therefore also inhibit the reuptake of bile acids in the kidneys. It is believed that this would lead to increased levels of bile acids in urine, and to an increased removal of bile acids from the body via the urine. Systemically available ASBT inhibitors that exert their effect not only in the ileum but also in the kidneys are therefore expected to lead to a greater reduction of bile acid levels than non-systemically available ASBT inhibitors that only exert their effect in the ileum.

Compounds having a high ASBT inhibiting potency are particularly suitable for the treatment of liver diseases that cause cholestasis, such as progressive familial intrahepatic cholestasis (PFIC), Alagilles syndrome, biliary atresia and non-alcoholic steatohepatitis (NASH).

Biliary atresia is a rare pediatric liver disease that involves a partial or total blockage (or even absence) of large bile ducts. This blockage or absence causes cholestasis that leads to the accumulation of bile acids that damages the liver. In some embodiments, the accumulation of bile acids occurs in the extrahepatic biliary tree. In some embodiments, the accumulation of bile acids occurs in the intrahepatic biliary tree. The current standard of care is the Kasai procedure, which is a surgery that removes the blocked bile ducts and directly connects a portion of the small intestine to the liver. There are currently no approved drug therapies for this disorder.

Provided herein are methods for treating biliary atresia in a subject in need thereof, the methods comprising administration of a therapeutically effective amount of a compound of formula (I), or a pharmaceutically acceptable salt thereof. In some embodiments, the subject has undergone the Kasai procedure prior to administration of a compound of formula (I), or a pharmaceutically acceptable salt thereof. In some embodiments, the subject is administered a compound of formula (I), or a pharmaceutically acceptable salt thereof, prior to undergoing the Kasai procedure. In some embodiments, the treatment of biliary atresia decreases the level of serum bile acids in the subject. In some embodiments, the level of serum bile acids is determined by, for example, an ELISA enzymatic assay or the assays for the measurement of total bile acids as described in Danese et al., PLoS One. 2017, vol. 12(6): e0179200, which is incorporated by reference herein in its entirety. In some embodiments, the level of serum bile acids can decrease by, for example, 10% to 40%, 20% to 50%, 30% to 60%, 40% to 70%, 50% to 80%, or by more than 90% of the level of serum bile acids prior to administration of a compound of formula (I), or a pharmaceutically acceptable salt thereof. In some embodiments, the treatment of bilary atresia includes treatment of pruritus.

PFIC is a rare genetic disorder that is estimated to affect between one in every 50,000 to 100,000 children born worldwide and causes progressive, life-threatening liver disease.

One manifestation of PFIC is pruritus, which often results in a severely diminished quality of life. In some cases, PFIC leads to cirrhosis and liver failure. Current therapies include Partial External Biliary Diversion (PEBD) and liver transplantation, however, these options can carry substantial risk of post-surgical complications, as well as psychological and social issues.

Three alternative gene defects have been identified that correlate to three separate PFIC subtypes known as types 1, 2 and 3.

PFIC, type 1, which is sometimes referred to as "Byler disease," is caused by impaired bile secretion due to mutations in the ATP8B1 gene, which codes for a protein that helps to maintain an appropriate balance of fats known as phospholipids in cell membranes in the bile ducts. An imbalance in these phospholipids is associated with cholestasis and elevated bile acids in the liver. Subjects affected by PFIC, type 1 usually develop cholestasis in the first months of life and, in the absence of surgical treatment, progress to cirrhosis and end-stage liver disease before the end of the first decade of life.

PFIC, type 2, which is sometimes referred to as "Byler syndrome," is caused by impaired bile salt secretion due to mutations in the ABCB11 gene, which codes for a protein, known as the bile salt export pump, that moves bile acids out of the liver. Subjects with PFIC, type 2 often develop liver failure within the first few years of life and are at increased risk of developing a type of liver cancer known as hepatocellular carcinoma.

PFIC, type 3, which typically presents in the first years of childhood with progressive cholestasis, is caused by mutations in the ABCB4 gene, which codes for a transporter that moves phospholipids across cell membranes.

In addition, TJP2 gene, NR1H4 gene or Myo5b gene mutations have been proposed to be causes of PFIC. In addition, some subjects with PFIC do not have a mutation in any of the ATP8B1, ABCB11, ABCB4, TJP2, NR1H4 or Myo5b genes. In these cases, the cause of the condition is unknown.

Exemplary mutations of the ATP8B1 gene or the resulting protein are listed in Tables 2 and 3, with numbering based on the human wild type ATP8B1 protein (e.g., SEQ ID NO: 1) or gene (e.g., SEQ ID NO: 2). Exemplary mutations of the ABCB11 gene or the resulting protein are listed in Tables 4 and 5, with numbering based on the human wild type ABCB11 protein (e.g., SEQ ID NO: 3) or gene (e.g., SEQ ID NO: 4).

As can be appreciated by those skilled in the art, an amino acid position in a reference protein sequence that corresponds to a specific amino acid position in SEQ ID NO: 1 or 3 can be determined by aligning the reference protein sequence with SEQ ID NO: 1 or 3 (e.g., using a software program, such as ClustalW2). Changes to these residues (referred to herein as "mutations") may include single or multiple amino acid substitutions, insertions within or flanking the sequences, and deletions within or flanking the sequences. As can be appreciated by those skilled in the art, an nucleotide position in a reference gene sequence that corresponds to a specific nucleotide position in SEQ ID NO: 2 or 4 can be determined by aligning the reference gene sequence with SEQ ID NO: 2 or 4 (e.g., using a software program, such as ClustalW2). Changes to these residues (referred to herein as "mutations") may include single or multiple nucleotide substitutions, insertions within or flanking the sequences, and deletions within or flanking the sequences. See also Kooistra, et al., "KLIFS: A structural kinase-ligand interaction database," Nucleic Acids Res. 2016, vol. 44, no. D1, pp. D365-D371, which is incorporated by reference in its entirety herein.

```
Canonical protein sequence of ATP8B1 - Uniprot ID O43520
                                                        (SEQ ID NO: 1)
         MSTERDSETT FDEDSQPNDE VVPYSDDETE DELDDQGSAV EPEQNRVNRE AEENREPFRK

ECTWQVKAND RKYHEQPHFM NTKFLCIKES KYANNAIKTY KYNAFTFIPM NLFEQFKRAA

NLYFLALLIL QAVPQISTLA WYTTLVPLLV VLGVTAIKDL VDDVARHKMD KEINNRTCEV

IKDGRFKVAK WKEIQVGDVI RLKKNDFVPA DILLLSSSEP NSLCYVETAE LDGETNLKFK

MSLEITDQYL QREDTLATFD GFIECEEPNN RLDKFTGTLF WRNTSFPLDA DKILLRGCVI

RNTDFCHGLV IFAGADTKIM KNSGKTRFKR TKIDYLMNYM VYTIFVVLIL LSAGLAIGHA

YWEAQVGNSS WYLYDGEDDT PSYRGFLIFW GYIIVLNTMV PISLYVSVEV IRLGQSHFIN

WDLQMYYAEK DTPAKARTTT LNEQLGQIHY IFSDKTGTLT QNIMTFKKCC INGQIYGDHR

DASQHNHNKI EQVDFSWNTY ADGKLAFYDH YLIEQIQSGK EPEVRQFFFL LAVCHTVMVD

RTDGQLNYQA ASPDEGALVN AARNFGFAFL ARTQNTITIS ELGTERTYNV LAILDFNSDR

KRMSIIVRTP EGNIKLYCKG ADTVIYERLH RMNPTKQETQ DALDIFANET LRTLCLCYKE

IEEKEFTEWN KKFMAASVAS TNRDEALDKV YEEIEKDLIL LGATAIEDKL QDGVPETISK

LAKADIKIWV LTGDKKETAE NIGFACELLT EDTTICYGED INSLLHARME NQRNRGGVYA
```

-continued

```
KFAPPVQESF FPPGGNRALI ITGSWLNEIL LEKKTKRNKI LKLKFPRTEE ERRMRTQSKR
RLEAKKEQRQ KNFVDLACEC SAVICCRVTP KQKAMVVDLV KRYKKAITLA IGDGANDVNM
IKTAHIGVGI SGQEGMQAVM SSDYSFAQFR YLQRLLLVHG RWSYIRMCKF LRYFFYKNFA
FTLVHFWYSF FNGYSAQTAY EDWFITLYNV LYTSLPVLLM GLLDQDVSDK LSLRFPGLYI
VGQRDLLFNY KRFFVSLLHG VLTSMILFFI PLGAYLQTVG QDGEAPSDYQ SFAVTIASAL
VITVNFQIGL DTSYWTFVNA FSIFGSIALY FGIMFDFHSA GIHVLFPSAF QFTGTASNAL
RQPYIWLTII LAVAVCLLPV VAIRFLSMTI WPSESDKIQK HRKRLKAEEQ WQRRQQVFRR
GVSTRRSAYA FSHQRGYADL ISSGRSIRKK RSPLDAIVAD GTAEYRRTGD S
```

Canonical DNA Sequence for ATP8B1
(SEQ ID NO: 2)

```
ATG AGT ACA GAA AGA GAC TCA GAA ACG ACA TTT GAC GAG GAT TCT CAG CCT
AAT GAC GAA GTG GTT CCC TAC AGT GAT GAT GAA ACA GAA GAT GAA CTT GAT
GAC CAG GGG TCT GCT GTT GAA CCA GAA CAA AAC CGA GTC AAC AGG GAA GCA
GAG GAG AAC CGG GAG CCA TTC AGA AAA GAA TGT ACA TGG CAA GTC AAA GCA
AAC GAT CGC AAG TAC CAC GAA CAA CCT CAC TTT ATG AAC ACA AAA TTC TTG
TGT ATT AAG GAG AGT AAA TAT GCG AAT AAT GCA ATT AAA ACA TAC AAG TAC
AAC GCA TTT ACC TTT ATA CCA ATG AAT CTG TTT GAG CAG TTT AAG AGA GCA
GCC AAT TTA TAT TTC CTG GCT CTT CTT ATC TTA CAG GCA GTT CCT CAA ATC
TCT ACC CTG GCT TGG TAC ACC ACA CTA GTG CCC CTG CTT GTG GTG CTG GGC
GTC ACT GCA ATC AAA GAC CTG GTG GAC GAT GTG GCT CGC CAT AAA ATG GAT
AAG GAA ATC AAC AAT AGG ACG TGT GAA GTC ATT AAG GAT GGC AGG TTC AAA
GTT GCT AAG TGG AAA GAA ATT CAA GTT GGA GAC GTC ATT CGT CTG AAA AAA
AAT GAT TTT GTT CCA GCT GAC ATT CTC CTG CTG TCT AGC TCT GAG CCT AAC
AGC CTC TGC TAT GTG AAA ACA GCA GAA CTG GAT GGA GAA ACC AAT TTA AAA
TTT AAG ATG TCA CTT GAA ATC ACA GAC CAG TAC CTC CAA AGA GAA GAT ACA
TTG GCT ACA TTT GAT GGT TTT ATT GAA TGT GAA GAA CCC AAT AAC AGA CTA
GAT AAG TTT ACA GGA ACA CTA TTT TGG AGA AAC ACA AGT TTT CCT TTG GAT
GCT GAT AAA ATT TTG TTA CGT GGC TGT GTA ATT AGG AAC ACC GAT TTC TGC
CAC GGC TTA GTC ATT TTT GCA GGT GCT GAC ACT AAA ATA ATG AAG AAT AGT
GGG AAA ACC AGA TTT AAA AGA ACT AAA ATT GAT TAC TTG ATG AAC TAC ATG
GTT TAC ACG ATC TTT GTT GTT CTT ATT CTG CTT TCT GCT GGT CTT GCC ATC
GGC CAT GCT TAT TGG GAA GCA CAG GTG GGC AAT TCC TCT TGG TAC CTC TAT
GAT GGA GAA GAC GAT ACA CCC TCC TAC CGT GGA TTC CTC ATT TTC TGG GGC
TAT ATC ATT GTT CTC AAC ACC ATG GTA CCC ATC TCT CTC TAT GTC AGC GTG
GAA GTG ATT CGT CTT GGA CAG AGT CAC TTC ATC AAC TGG GAC CTG CAA ATG
TAC TAT GCT GAG AAG GAC ACA CCC GCA AAA GCT AGA ACC ACC ACA CTC AAT
GAA CAG CTC GGG CAG ATC CAT TAT ATC TTC TCT GAT AAG ACG GGG ACA CTC
ACA CAA AAT ATC ATG ACC TTT AAA AAG TGC TGT ATC AAC GGG CAG ATA TAT
GGG GAC CAT CGG GAT GCC TCT CAA CAC AAC CAC AAC AAA ATA GAG CAA GTT
GAT TTT AGC TGG AAT ACA TAT GCT GAT GGG AAG CTT GCA TTT TAT GAC CAC
TAT CTT ATT GAG CAA ATC CAG TCA GGG AAA GAG CCA GAA GTA CGA CAG TTC
TTC TTC TTG CTC GCA GTT TGC CAC ACA GTC ATG GTG GAT AGG ACT GAT GGT
```

-continued

```
CAG CTC AAC TAC CAG GCA GCC TCT CCC GAT GAA GGT GCC CTG GTA AAC GCT
GCC AGG AAC TTT GGC TTT GCC TTC CTC GCC AGG ACC CAG AAC ACC ATC ACC
ATC AGT GAA CTG GGC ACT GAA AGG ACT TAC AAT GTT CTT GCC ATT TTG GAC
TTC AAC AGT GAC CGG AAG CGA ATG TCT ATC ATT GTA AGA ACC CCA GAA GGC
AAT ATC AAG CTT TAC TGT AAA GGT GCT GAC ACT GTT ATT TAT GAA CGG TTA
CAT CGA ATG AAT CCT ACT AAG CAA GAA ACA CAG GAT GCC CTG GAT ATC TTT
GCA AAT GAA ACT CTT AGA ACC CTA TGC CTT TGC TAC AAG GAA ATT GAA GAA
AAA GAA TTT ACA GAA TGG AAT AAA AAG TTT ATG GCT GCC AGT GTG GCC TCC
ACC AAC CGG GAC GAA GCT CTG GAT AAA GTA TAT GAG GAG ATT GAA AAA GAC
TTA ATT CTC CTG GGA GCT ACA GCT ATT GAA GAC AAG CTA CAG GAT GGA GTT
CCA GAA ACC ATT TCA AAA CTT GCA AAA GCT GAC ATT AAG ATC TGG GTG CTT
ACT GGA GAC AAA AAG GAA ACT GCT GAA AAT ATA GGA TTT GCT TGT GAA CTT
CTG ACT GAA GAC ACC ACC ATC TGC TAT GGG GAG GAT ATT AAT TCT CTT CTT
CAT GCA AGG ATG GAA AAC CAG AGG AAT AGA GGT GGC GTC TAC GCA AAG TTT
GCA CCT CCT GTG CAG GAA TCT TTT TTT CCA CCC GGT GGA AAC CGT GCC TTA
ATC ATC ACT GGT TCT TGG TTG AAT GAA ATT CTT CTC GAG AAA AAG ACC AAG
AGA AAT AAG ATT CTG AAG CTG AAG TTC CCA AGA ACA GAA GAA GAA AGA CGG
ATG CGG ACC CAA AGT AAA AGG AGG CTA GAA GCT AAG AAA GAG CAG CGG CAG
AAA AAC TTT GTG GAC CTG GCC TGC GAG TGC AGC GCA GTC ATC TGC TGC CGC
GTC ACC CCC AAG CAG AAG GCC ATG GTG GTG GAC CTG GTG AAG AGG TAC AAG
AAA GCC ATC ACG CTG GCC ATC GGA GAT GGG GCC AAT GAC GTG AAC ATG ATC
AAA ACT GCC CAC ATT GGC GTT GGA ATA AGT GGA CAA GAA GGA ATG CAA GCT
GTC ATG TCG AGT GAC TAT TCC TTT GCT CAG TTC CGA TAT CTG CAG AGG CTA
CTG CTG GTG CAT GGC CGA TGG TCT TAC ATA AGG ATG TGC AAG TTC CTA CGA
TAC TTC TTT TAC AAA AAC TTT GCC TTT ACT TTG GTT CAT TTC TGG TAC TCC
TTC TTC AAT GGC TAC TCT GCG CAG ACT GCA TAC GAG GAT TGG TTC ATC ACC
CTC TAC AAC GTG CTG TAC ACC AGC CTG CCC GTG CTC CTC ATG GGG CTG CTC
GAC CAG GAT GTG AGT GAC AAA CTG AGC CTC CGA TTC CCT GGG TTA TAC ATA
GTG GGA CAA AGA GAC TTA CTA TTC AAC TAT AAG AGA TTC TTT GTA AGC TTG
TTG CAT GGG GTC CTA ACA TCG ATG ATC CTC TTC TTC ATA CCT CTT GGA GCT
TAT CTG CAA ACC GTA GGG CAG GAT GGA GAG GCA CCT TCC GAC TAC CAG TCT
TTT GCC GTC ACC ATT GCC TCT GCT CTT GTA ATA ACA GTC AAT TTC CAG ATT
GGC TTG GAT ACT TCT TAT TGG ACT TTT GTG AAT GCT TTT TCA ATT TTT GGA
AGC ATT GCA CTT TAT TTT GGC ATC ATG TTT GAC TTT CAT AGT GCT GGA ATA
CAT GTT CTC TTT CCA TCT GCA TTT CAA TTT ACA GGC ACA GCT TCA AAC GCT
CTG AGA CAG CCA TAC ATT TGG TTA ACT ATC ATC CTG GCT GTT GCT GTG TGC
TTA CTA CCC GTC GTT GCC ATT CGA TTC CTG TCA ATG ACC ATC TGG CCA TCA
GAA AGT GAT AAG ATC CAG AAG CAT CGC AAG CGG TTG AAG GCG GAG GAG CAG
TGG CAG CGA CGG CAG CAG GTG TTC CGC CGG GGC GTG TCA ACG CGG CGC TCG
GCC TAC GCC TTC TCG CAC CAG CGG GGC TAC GCG GAC CTC ATC TCC TCC GGG
```

-continued

```
CGC AGC ATC CGC AAG AAG CGC TCG CCG CTT GAT GCC ATC GTG GCG GAT GGC

ACC GCG GAG TAC AGG CGC ACC GGG GAC AGC TGA
```

TABLE 2

Exemplary ATP8B1 Mutations

Amino acid position 3 (e.g., T3K)[27]
Amino acid position 23 (e.g., P23L)[5]
Amino acid position 45 (e.g., N45T)[5,8,9]
Amino acid position 46 (e.g., R46X)[4,25]
Amino acid position 62 (e.g., C62R)[28]
Amino acid position 63 (e.g., T63T)[41]
Amino acid position 70 (e.g., D70N)[1,6]
Amino acid position 71 (e.g., R71H)[43]
Amino acid position 78 (e.g., H78Q)[19]
Amino acid position 82 (e.g., T82T)[41]
Amino acid position 92 (e.g., Y92Y)[41]
Amino acid position 93 (e.g., A93A)[6]
Amino acid position 96 (e.g., A96G)[27]
Amino acid position 114 (e.g., E114Q)[8]
Amino acid position 127 (e.g., L127P[6], L127V[36])
Amino acid position 177 (e.g., T177T)[6]
Amino acid position 179 (e.g., E179X)[29]
Δ Amino acid positions 185-282[44]
Amino acid position 197 (e.g., G197Lfs*10)[22]
Amino acid position 201 (e.g., R201S[27], R201H[35])
Amino acid position 203 (e.g., K203E[5,8], K203R[9], K203fs[25])
Amino acid position 205 (e.g., N205fs[6], N205Kfs*2[35])
Amino acid position 209 (e.g., P209T)[4]
Amino acid position 217 (e.g., S217N)[43]
Amino acid position 232 (e.g., D232D)[30]
Amino acid position 233 (e.g., G233R)[38]
Amino acid position 243 (e.g., L243fs*28)[33]
Amino acid position 265 (e.g., C265R)[25]
Amino acid position 271 (e.g., R271X[13], R271R[30])
Amino acid position 288 (e.g., L288S)[6]
Amino acid position 294 (e.g., L294S)[43]
Amino acid position 296 (e.g., R296C)[11]
Amino acid position 305 (e.g., F305I)[28]
Amino acid position 306 (e.g., C306R)[23]
Amino acid position 307 (e.g., H307L)[35]
Amino acid position 308 (e.g., G308V[1], G308D[6], G308S[35])
Amino acid position 314 (e.g., G314S)[13]
Amino acid position 320 (e.g., M320Vfs*13)[11]
Amino acid position 337 (e.g., M337R)[18]
Amino acid position 338 (e.g., N338K)[18]
Amino acid position 340 (e.g., M340V)[18]
Amino acid position 344 (e.g., I344F)[6,20]
Amino acid position 349 (e.g., I349T)[41]
Amino acid position 358 (e.g., G358R)[28]
Amino acid position 367 (e.g., G367G)[41]
Amino acid position 368 (e.g., N368D)[41]
Amino acid position 393 (e.g., I393V)[27]
Amino acid position 403 (e.g., S403Y)[6]
Amino acid position 407 (e.g., S407N)[40]
Amino acid position 412 (e.g., R412P)[6]
Amino acid position 415 (e.g., Q415R)[27]
Amino acid position 422 (e.g., D422H)[35]
Amino acid position 429 (e.g., E429A)[6]
Amino acid position 446 (e.g., G446R)[4,11]
Amino acid position 453 (e.g., S453Y)[6]
Amino acid position 454 (e.g., D454G)[6]
Amino acid position 455 (e.g., K455N)[43]
Amino acid position 456 (e.g., T456M[3,6], T456K[35])
Amino acid position 457 (e.g., G457G[6], G457fs*6[33])
Amino acid position 469 (e.g., C469G)[41]
Amino acid position 478 (e.g., H478H)[41]
Amino acid position 500 (e.g., Y500H)[6]
Amino acid position 525 (e.g., R525X)[4]
Δ Amino acid position 529[6]
Amino acid position 535 (e.g., H535L[6], H535N[41])
Amino acid position 553 (e.g., P553P)[43]
Amino acid position 554 (e.g., D554N[1,6], D554A[35])
Δ Amino acid positions 556-628[44]
Δ Amino acid positions 559-563[35]
Amino acid position 570 (e.g., L570L)[41]
Amino acid position 577 (e.g., I577V)[19]

TABLE 2-continued

Exemplary ATP8B1 Mutations

Amino acid position 581 (e.g., E581K)[35]
Amino acid positions 554 and 581 (e.g., D554A + E581K)[35]
Amino acid position 585 (e.g., E585X)[21]
Amino acid position 600 (e.g., R600W[2,4], R600Q[6])
Amino acid position 602 (e.g., R602X)[3,6]
Amino acid position 628 (e.g., R628W)[6]
Amino acid position 631 (e.g., R631Q)[28]
Δ Amino acid positions 645-699[4]
Amino acid position 661 (e.g., I661T)[1,4,6]
Amino acid position 665 (e.g., E665X)[4,6]
Amino acid position 672 (e.g., K672fs[6], K672Vfs*1[35])
Amino acid position 674 (e.g., M674T)[19]
Amino acid positions 78 and 674 (e.g., H78Q/M674T)[19]
Amino acid position 684 (e.g., D684D)[41]
Amino acid position 688 (e.g., D688G)[6]
Amino acid position 694 (e.g., I694T[6], I694N[17])
Amino acid position 695 (e.g., E695K)[27]
Amino acid position 709 (e.g., K709fs[6], K709Qfs*41[13])
Amino acid position 717 (e.g., T717N)[4]
Amino acid position 733 (e.g., G733R)[6]
Amino acid position 757 (e.g., Y757X)[4]
Amino acid position 749 (e.g., L749P)[21]
Amino acid position 792 (e.g., P792fs)[6]
Δ Amino acid position 795-797[6]
Amino acid position 809 (e.g., I809L)[27]
Amino acid position 814 (e.g., K814N)[28]
Amino acid position 833 (e.g., R833Q[27], R833W[41])
Amino acid position 835 (e.g., K835Rfs*36)[35]
Amino acid position 845 (e.g., K845fs)[25]
Amino acid position 849 (e.g., R849Q)[24]
Amino acid position 853 (e.g., F853S, F853fs)[6]
Amino acid position 867 (e.g., R867C[1], R867fs[6], R867H[23])
Amino acid position 885 (e.g., K885T)[41]
Amino acid position 888 (e.g., T888T)[41]
Amino acid position 892 (e.g., G892R)[6]
Amino acid position 912 (e.g., G912R)[35]
Amino acid position 921 (e.g., S921S)[41]
Amino acid position 924 (e.g., Y924C)[28]
Amino acid position 930 (e.g., R930X[6], R930Q[28])
Amino acid position 941 (e.g., R941X)[35]
Amino acid position 946 (e.g., R946T)[41]
Amino acid position 952 (e.g., R952Q[5,9,15], R952X[6])
Amino acid position 958 (e.g., N958fs)[6]
Amino acid position 960 (e.g., A960A)[41]
Δ Amino acid position 971[43]
Amino acid position 976 (e.g., A976E[41], A976A[43])
Amino acid position 981 (e.g., E981K)[20]
Amino acid position 994 (e.g., S994R)[4]
Amino acid position 1011 (e.g., L1011fs*18)[33]
Amino acid position 1012 (e.g., S1012I)[10]
Amino acid position 1014 (e.g., R1014X)[6,11]
Amino acid position 1015 (e.g., F1015L)[27]
Amino acid position 1023 (e.g., Q1023fs)[6]
Amino acid position 1040 (e.g., G1040R)[1,6]
Amino acid position 1044 (e.g., S0144L)[34]
Amino acid position 1047 (e.g., L1047fs)[6]
Amino acid position 1050 (e.g., I1050K)[31]
Amino acid position 1052 (e.g., L1052R)[28]
Amino acid position 1095 (e.g., W1095X)[11]
Amino acid position 1098 (e.g., V1098X)[35]
Amino acid position 1131 (e.g., Q1131X)[44]
Amino acid position 1142 (e.g., A1142Tfs*35)[43]
Amino acid position 1144 (e.g., Y1144Y)[43]
Amino acid position 1150 (e.g., I1150T)[41]
Amino acid position 1152 (e.g., A1152T)[30]
Amino acid position 1159 (e.g., P1159P)[25,43]
Amino acid position 1164 (e.g., R1164X)[6]
Amino acid position 1193 (e.g., R1193fs*39)[33]
Amino acid position 1197 (e.g., V1197L)[41]
Amino acid position 1208 (e.g., A1208fs)[6]
Amino acid position 1209 (e.g., Y1209Lfs*28)[4]

TABLE 2-continued

Exemplary ATP8B1 Mutations

Amino acid position 1211 (e.g., F1211L)[27]
Amino acid position 1219 (e.g., D1219H[5], D1219G[27])
Amino acid position 1223 (e.g., S1223S)[41]
Amino acid position 1233 (e.g., P1233P)[41]
Amino acid position 1241 (e.g., G1241fs)[6]
Amino acid position 1248 (e.g., T1248T)[43]
Splice site mutation IVS3 + 1_+3delGTG[6]
Splice site mutation IVS3 − 2A > G[6]
IVS6 + 5T > G[17,25]
Splice site mutation IVS8 + 1G > T[6]
IVS9 − G > A[26]
IVS12 + 1G > A[25]
Splice site mutation IVS17 − 1G > A[6]
Splice site mutation IVS18 + 2T > C[6]
Splice site mutation IVS20 − 4CT > AA
Splice site mutation IVS21 + 5G > A[6]
Splice site mutation IVS23 − 3C > A[6]
Splice site mutation IVS26 + 2T > A[6]
g.24774-42062del[4]
c.-4C > G[41]
c.145C > T[12]
c.181 − 72G > A[9]
c.182 − 5T > A[41]
c.182 − 72G > A[41]
c.246A > G[9]
c.239G > A[39]
c.279 + 1_279 + 3delGTG[46]
c.280 − 2A > G[46]
c.625_62715delinsACAGTAAT[46]
c.554 + 122C > T[9]
c.555 − 3T > C[27]
c.625 + 5 G > T[4]
Amino acid position 209 (e.g., P209T) and c.625 + 5 G > T[4]
c.628 − 30G > A[41]
c.628 − 31C > T[41]
c.698 + 1G > T[46]
c.698 + 20C > T[41]
c.782 − 1G > A[46]
c.782 − 34G > A[41]
Δ795-797[14]
c.782 − 1G > A[4]
c.852A > C[27]
c.941 − 1G > A[46]
c.1014C > T[9]
c.1029 + 35G > A[9]
c.1221-8C.G[41]
1226delA[16]
c.1429 + 1G > A[46]
c.1429 + 2T > G[13]
c.1429 + 49G > A[41]
c.1430 − 42A > G[41]
c.1493T > C[12]
c.1587_1589delCTT[46]
c.1630 + 2T > G[27]
c.1631 − 10T > A[41]
c.1637 − 37T > C[41]
1660 G > A[14]
1798 C > T[14]
1799 G > A[14]
c.1819 − 39_41delAA[9]
c.1819 + 1G > A[31]
c.1820 − 27G > A[41]
c.1918 + 8C > T[27]
c.1933 − 1G > AK[46]
c.2097 + 2T > C[32]
c.2097 + 60T > G[41]
c.2097 + 89T > C[41]
c.2097 + 97T > G[41]
c.2210 − 114T > C[9]
2210delA[16]
c.2210 − 45_50dupATAAAA[9]
c.2285 + 29C · T[41]
c.2285 + 32A > G[41]
c.2286 − 4_2286-3delinsAA[46]
c.2418 + 5G > A[46]
c.2707 + 3G > C[27]
c.2707 + 9T > G[41]
c.2707 + 43A > G[41]
c.2709 − 59T > C[41]
c.2931 + 9A > G[41]
c.2931 + 59T > A[41]
c.2932 − 3C > A[46]
c.2932 + 59T > A[9]
c.2937A > C[27]
c.3016 − 9C > A[31]
c.3033-3034del[19]
3122delTCCTA/insACATCGATGTTGATGTTAGG[45]
3318 G > A[14]
c.3400 + 2T > A[46]
c.3401 − 175C > T[9]
c.3401 − 167C > T[9]
c.3401 − 108C > T[9]
c.3531 + 8G > T[9,15]
c.3532 − 15C > T[9]
Δ Phe ex 15[4]
Ex1_Ex13del[6]
Ex2_Ex6del[33]
Ex12_Ex14del[27]
Skipped Exon 24[45]
del5'UTR-ex18[11]
c.*11C > T[41]
c.*1101 + 366G > A[7]
g.92918del565[31]
GC preceding exon 16 (e.g., resulting in a 4 bp deletion)[42]
Frameshift from the 5' end of exon 16[42]
5' 1.4 kb deletion[46]

TABLE 3

Selected ATP8B1 Mutations Associated with PFIC-1

Amino acid position 23 (e.g., P23L)[5]
Amino acid position 78 (e.g., H78Q)[19]
Amino acid position 93 (e.g., A93A)[6]
Amino acid position 96 (e.g., A96G)[27]
Amino acid position 127 (e.g., L127P)[6]
Amino acid position 197 (e.g., G197Lfs*10)[22]
Amino acid position 205 (e.g., N205fs)[6]
Amino acid position 209 (e.g., P209T)[4]
Amino acid position 233 (e.g., G233R)[38]
Amino acid position 243 (e.g., L243fs*28)[33]
Amino acid position 288 (e.g., L288S)[6]
Amino acid position 296 (e.g., R296C)[11]
Amino acid position 308 (e.g., G308V[1,6])
Amino acid position 320 (e.g., M320Vfs*13)[11]
Amino acid position 403 (e.g., S403Y)[6]
Amino acid position 407 (e.g., S407N)[40]
Amino acid position 412 (e.g., R412P)[6]
Amino acid position 415 (e.g., Q415R)[27]
Amino acid position 429 (e.g., E429A)[6]
Amino acid position 446 (e.g., G446R)[4]
Amino acid position 456 (e.g., T456M)[3,6]
Amino acid position 457 (e.g., G457G[6], G457fs*6[33])
Amino acid position 500 (e.g., Y500H)[6]
Amino acid position 525 (e.g., R525X)[4]
Δ Amino acid position 529[6]
Amino acid position 535 (e.g., H535L)[6]
Amino acid position 554 (e.g., D554N)[1,6]
Amino acid position 577 (e.g., I577V)[19]
Amino acid position 585 (e.g., E585X)[21]
Amino acid position 600 (e.g., R600W)[4]
Amino acid position 602 (e.g., R602X)[3,6]
Amino acid position 661 (e.g., I661T)[4,6]
Amino acid position 665 (e.g., E665X)[4,6]
Δ Amino acid positions 645-699[4]
Amino acid position 672 (e.g., K672fs)[6]
Amino acid position 674 (e.g., M674T)[19]
Amino acid positions 78 and 674 (e.g., H78Q/M674T)[19]
Amino acid position 688 (e.g., D688G)[6]
Amino acid position 694 (e.g., I694N)[17]
Amino acid position 695 (e.g., E695K)[27]
Amino acid position 709 (e.g., K709fs)[6]
Amino acid position 717 (e.g., T717N)[4]

TABLE 3-continued

Selected ATP8B1 Mutations Associated with PFIC-1

Amino acid position 733 (e.g., G733R)[6]
Amino acid position 749 (e.g., L749P)[21]
Amino acid position 757 (e.g., Y757X)[4]
Amino acid position 792 (e.g., P792fs)[6]
Amino acid position 809 (e.g., I809L)[27]
Amino acid position 853 (e.g., F853S, F853fs)[6]
Amino acid position 867 (e.g., R867fs)[6]
Amino acid position 892 (e.g., G892R)[6]
Amino acid position 930 (e.g., R930X[6], R952Q[15])
Amino acid position 952 (e.g., R952X)[6]
Amino acid position 958 (e.g., N958fs)[6]
Amino acid position 981 (e.g., E981K)[20]
Amino acid position 994 (e.g., S994R)[4]
Amino acid position 1014 (e.g., R1014X)[6,11]
Amino acid position 1015 (e.g., F1015L)[27]
Amino acid position 1023 (e.g., Q1023fs)[6]
Amino acid position 1040 (e.g., G1040R)[1,6]
Amino acid position 1047 (e.g., L1047fs)[6]
Amino acid position 1095 (e.g., W1095X)[11]
Amino acid position 1208 (e.g., A1208fs)[6]
Amino acid position 1209 (e.g., Y1209Lfs*28)[4]
Amino acid position 1211 (e.g., F1211L)[27]
Amino acid position 1219 (e.g., D1219H[5], D1219G[27])
Splice site mutation IVS3 + 1_+3delGTG[6]
Splice site mutation IVS3 − 2A > G[6]
IVS6 + 5T > G[17]
Splice site mutation IVS8 + 1G > T[6]
IVS9 − G > A[26]
Splice site mutation IVS17 − 1G > A[6]
Splice site mutation IVS18 + 2T > C[6]
Splice site mutation IVS21 + 5G > A[6]
g.24774-42062del[4]
c.145C > T[12]
c.239G > A[39]
c.625 + 5 G > T[4]
Amino acid position 209 (e.g., P209T) and c.625 + 5 G > T[4]
c.782 − 1G > A[4]
c.1493T > C[12]
c.1630 + 2T > G[27]
1660 G > A[14]
c.2707 + 3G > C[27]
c.2097 + 2T > C[32]
c.3033-3034del[19]
3318 G > A[14]
c.3158 + 8G > T[15]
Δ Phe ex 15[4]
Ex1_Ex13del[6]
Ex2_Ex6del[33]
Ex12_Ex14del[27]
del5'UTR-ex18[11]
c.*1101 + 366G > A[7]
GC preceding exon 16 (e.g., resulting in a 4 bp deletion)[42]
Frameshift from the 5' end of exon 16[42]

[A]A mutation to 'X' denotes an early stop codon

REFERENCES FOR TABLES 2 AND 3

[1] Folmer et al., Hepatology. 2009, vol. 50(5), p. 1597-1605.
[2] Hsu et al., Hepatol Res. 2009, vol. 39(6), p. 625-631.
[3] Alvarez et al., Hum Mol Genet. 2004, vol. 13(20), p. 2451-2460.
[4] Davit-Spraul et al., Hepatology 2010, vol. 51(5), p. 1645-1655.
[5] Vitale et al., J Gastroenterol. 2018, vol. 53(8), p. 945-958.
[6] Klomp et al., Hepatology 2004, vol. 40(1), p. 27-38.
[7] Zarenezhad et al., Hepatitis Monthly: 2017, vol. 17(2); e43500.
[8] Dixon et al., Scientific Reports 2017, vol. 7, 11823.
[9] Painter et al., Eur J Hum Genet. 2005, vol. 13(4), p. 435-439.
[10] Deng et al., World J Gastroenterol. 2012, vol. 18(44), p. 6504-6509.
[11] Giovannoni et al., PLoS One. 2015, vol. 10(12): e0145021.
[12] Li et al., Hepatology International 2017, vol. 11, No. 1, Supp. Supplement 1, pp. S180. Abstract Number: OP284.
[13] Togawa et al., Journal of Pediatric Gastroenterology and Nutrition 2018, vol. 67, Supp. Supplement 1, pp. S363. Abstract Number: 615.
[14] Miloh et al., Gastroenterology 2006, vol. 130, No. 4, Suppl. 2, pp. A759-A760. Meeting Info.: Digestive Disease Week Meeting/107th Annual Meeting of the American-Gastroenterological-Association. Los Angeles, Calif., USA. May 19.
[15] Dröge et al., Zeitschrift fur Gastroenterologie 2015, vol. 53, No. 12. Abstract Number: A3-27. Meeting Info: 32. Jahrestagung der Deutschen Arbeitsgemeinschaft zum Studium der Leber. Dusseldorf, Germany. 22 Jan. 2016-23 Jan. 2016
[16] Mizuochi et al., Clin Chim Acta. 2012, vol. 413(15-16), p. 1301-1304.
[17] Liu et al., Hepatology International 2009, vol. 3, No. 1, p. 184-185. Abstract Number: PE405. Meeting Info: 19th Conference of the Asian Pacific Association for the Study of the Liver. Hong Kong, China. 13 Feb. 2009-16 Feb. 2009
[18] McKay et al., Version 2. F1000Res. 2013; 2: 32. DOI: 10.12688/f1000research.2-32.v2
[19] Hasegawa et al., Orphanet J Rare Dis. 2014, vol. 9:89.
[20] Stone et al., J Biol Chem. 2012, vol. 287(49), p. 41139-51.
[21] Kang et al., J Pathol Transl Med. 2019 May 16. doi: 10.4132/jptm.2019.05.03. [Epub ahead of print]
[22] Sharma et al., BMC Gastroenterol. 2018, vol. 18(1), p. 107.
[23] Uegaki et al., Intern Med. 2008, vol. 47(7), p. 599-602.
[24] Goldschmidt et al., Hepatol Res. 2016, vol. 46(4), p. 306-311.
[25] Liu et al., J Pediatr Gastroenterol Nutr. 2010, vol. 50(2), p. 179-183.
[26] Jung et al., J Pediatr Gastroenterol Nutr. 2007, vol. 44(4), p. 453-458.
[27] Bounford. University of Birmingham. Dissertation Abstracts International, (2016) Vol. 75, No. 1C. Order No.: AAI10588329. ProQuest Dissertations & Theses.
[28] Stolz et al., Aliment Pharmacol Ther. 2019, vol. 49(9), p. 1195-1204.
[29] Ivashkin et al., Hepatology International 2016, vol. 10, No. 1, Supp. SUPPL. 1, pp. S461. Abstract Number: LBO-38. Meeting Info: 25th Annual Conference of the Asian Pacific Association for the Study of the Liver, APASL 2016. Tokyo, Japan. 20 Feb. 2016-24 Feb. 2016
[30] Blackmore et al., J Clin Exp Hepatol. 2013, vol. 3(2), p. 159-161.
[31] Matte et al., J Pediatr Gastroenterol Nutr. 2010, vol. 51(4), p. 488-493.
[32] Squires et al., J Pediatr Gastroenterol Nutr. 2017, vol. 64(3), p. 425-430.
[33] Hayshi et al., EBioMedicine. 2018, vol. 27, p. 187-199.
[34] Nagasaka et al., J Pediatr Gastroenterol Nutr. 2007, vol. 45(1), p. 96-105.
[35] Wang et al., PLoS One. 2016; vol. 11(4): e0153114.
[36] Narchi et al., Saudi J Gastroenterol. 2017, vol. 23(5), p. 303-305.
[37] Alashkar et al., Blood 2015, vol. 126, No. 23. Meeting Info.: 57th Annual Meeting of the American-Society-of-Hematology. Orlando, Fla., USA. Dec. 5-8, 2015. Amer Soc Hematol.
[38] Ferreira et al., Pediatric Transplantation 2013, vol. 17, Supp. SUPPL. 1, pp. 99. Abstract Number: 239. Meeting Info: IPTA 7th Congress on Pediatric Transplantation. Warsaw, Poland. 13 Jul. 2013-16 Jul. 2013.
[39] Pauli-Magnus et al., J Hepatol. 2005, vol. 43(2), p. 342-357.
[40] Jericho et al., Journal of Pediatric Gastroenterology and Nutrition 2015, vol. 60(3), p. 368-374.
[41] van der Woerd et al., PLoS One. 2013, vol. 8(11): e80553.
[42] Copeland et al., J Gastroenterol Hepatol. 2013, vol. 28(3), p. 560-564.
[43] Dröge et al., J Hepatol. 2017, vol. 67(6), p. 1253-1264.
[44] Chen et al., Journal of Pediatrics 2002, vol. 140(1), p. 119-124.
[45] Jirsa et al., Hepatol Res. 2004, vol. 30(1), p. 1-3.
[46] van der Woerd et al., Hepatology 2015, vol. 61(4), p. 1382-1391.

In some embodiments, the mutation in ATP8B1 is selected from L127P, G308V, T456M, D554N, F529del, I661T, E665X, R930X, R952X, R1014X, and G1040R.

```
Canonical Protein Sequence of ABCB11 - Uniprot ID O95342
                                                     (SEQ ID NO: 3)
MSDSVILRSI KKFGEENDGF ESDKSYNNDK KSRLQDEKKG DGVRVGFFQL FRFSSSTDIW

LMFVGSLCAF LHGIAQPGVL LIFGTMTDVF IDYDVELQEL QIPGKACVNN TIVWTNSSLN

QNMTNGTRCG LLNIESEMIK FASYYAGIAV AVLITGYIQI CFWVIAAARQ IQKMRKFYFR

RIMRMEIGWF DCNSVGELNT RFSDDINKIN DAIADQMALF IQRMTSTICG FLLGFFRGWK

LTLVIISVSP LIGIGAATIG LSVSKFTDYE LKAYAKAGVV ADEVISSMRT VAAFGGEKRE

VERYEKNLVF AQRWGIRKGI VMGFFTGFVW CLIFLCYALA FWYGSTLVLD EGEYTPGTLV

QIFLSVIVGA LNLGNASPCL EAFATGRAAA TSIFETIDRK PIIDCMSEDG YKLDRIKGEI

EFHNVTFHYP SRPEVKILND LNMVIKPGEM TALVGPSGAG KSTALQLIQR FYDPCEGMVT

VDGHDIRSLN IQWLRDQIGI VEQEPVLFST TIAENIRYGR EDATMEDIVQ AAKEANAYNF

IMDLPQQFDT LVGEGGGQMS GGQKQRVAIA RALIRNPKIL LLDMATSALD NESEAMVQEV

LSKIQHGHTI ISVAHRLSTV RAADTIIGFE HGTAVERGTH EELLERKGVY FTLVTLQSQG

NQALNEEDIK DATEDDMLAR TFSRGSYQDS LRASIRQRSK SQLSYLVHEP PLAVVDHKST

YEEDRKDKDI PVQEEVEPAP VRRILKFSAP EWPYMLVGSV GAAVNGTVTP LYAFLFSQIL

GTFSIPDKEE QRSQINGVCL LFVAMGCVSL FTQFLQGYAF AKSGELLTKR LRKFGFRAML

GQDIAWFDDL RNSPGALTTR LATDASQVQG AAGSQIGMIV NSFTNVTVAM IIAFSFSWKL

SLVILCFFPF LALSGATQTR MLTGFASRDK QALEMVGQIT NEALSNIRTV AGIGKERRFI

EALETELEKP FKTAIQKANI YGFCFAFAQC IMFIANSASY RYGGYLISNE GLHFSYVFRV

ISAVVLSATA LGRAFSYTPS YAKAKISAAR FFQLLDRQPP ISVYNTAGEK WDNFQGKIDF

VDCKFTYPSR PDSQVLNGLS VSISPGQTLA FVGSSGCGKS TSIQLLERFY DPDQGKVMID

GHDSKKVNVQ FLRSNIGIVS QEPVLFACSI MDNIKYGDNT KEIPMERVIA AAKQAQLHDF

VMSLPEKYET NVGSQGSQLS RGEKQRIAIA RAIVRDPKIL LLDEATSALD TESEKTVQVA

LDKAREGRTC IVIAHRLSTI QNADIIAVMA QGVVIEKGTH EELMAQKGAY YKLVTTGSPI S
Canonical DNA Sequence of ABCB11
                                                     (SEQ ID NO: 4)
ATG TCT GAC TCA GTA ATT CTT CGA AGT ATA AAG AAA TTT GGA GAG GAG AAT

GAT GGT TTT GAG TCA GAT AAA TCA TAT AAT AAT GAT AAG AAA TCA AGG TTA

CAA GAT GAG AAG AAA GGT GAT GGC GTT AGA GTT GGC TTC TTT CAA TTG TTT

CGG TTT TCT TCA ACT GAC ATT TGG CTG ATG TTT GTG GGA AGT TTG TGT

GCA TTT CTC CAT GGA ATA GCC CAG CCA GGC GTG CTA CTC ATT TTT GGC ACA

ATG ACA GAT GTT TTT ATT GAC TAC GAC GTT GAG TTA CAA GAA CTC CAG ATT

CCA GGA AAA GCA TGT GTG AAT AAC ACC ATT GTA TGG ACT AAC AGT TCC CTC

AAC CAG AAC ATG ACA AAT GGA ACA CGT TGT GGG TTG CTG AAC ATC GAG AGC

GAA ATG ATC AAA TTT GCC AGT TAC TAT GCT GGA ATT GCT GTC GCA GTA CTT

ATC ACA GGA TAT ATT CAA ATA TGC TTT TGG GTC ATT GCC GCA GCT CGT CAG

ATA CAG AAA ATG AGA AAA TTT TAC TTT AGG AGA ATA ATG AGA ATG GAA ATA
```

-continued

```
GGG TGG TTT GAC TGC AAT TCA GTG GGG GAG CTG AAT ACA AGA TTC TCT GAT
GAT ATT AAT AAA ATC AAT GAT GCC ATA GCT GAC CAA ATG GCC CTT TTC ATT
CAG CGC ATG ACC TCG ACC ATC TGT GGT TTC CTG TTG GGA TTT TTC AGG GGT
TGG AAA CTG ACC TTG GTT ATT ATT TCT GTC AGC CCT CTC ATT GGG ATT GGA
GCA GCC ACC ATT GGT CTG AGT GTG TCC AAG TTT ACG GAC TAT GAG CTG AAG
GCC TAT GCC AAA GCA GGG GTG GTG GCT GAT GAA GTC ATT TCA TCA ATG AGA
ACA GTG GCT GCT TTT GGT GGT GAG AAA AGA GAG GTT GAA AGG TAT GAG AAA
AAT CTT GTG TTC GCC CAG CGT TGG GGA ATT AGA AAA GGA ATA GTG ATG GGA
TTC TTT ACT GGA TTC GTG TGG TGT CTC ATC TTT TTG TGT TAT GCA CTG GCC
TTC TGG TAC GGC TCC ACA CTT GTC CTG GAT GAA GGA GAA TAT ACC AGG A
ACC CTT GTC CAG ATT TTC CTC AGT GTC ATA GTA GGA GCT TTA AAT CTT GGC
AAT GCC TCT CCT TGT TTG GAA GCC TTT GCA ACT GGA CGT GCA GCA GCC ACC
AGC ATT TTT GAG ACA ATA GAC AGG AAA CCC ATC ATT GAC TGC ATG TCA GAA
GAT GGT TAC AAG TTG GAT CGA ATC AAG GGT GAA ATT GAA TTC CAT AAT GTG
ACC TTC CAT TAT CCT TCC AGA CCA GAG GTG AAG ATT CTA AAT GAC CTC AAC
ATG GTC ATT AAA CCA GGG GAA ATG ACA GCT CTG GTA GGA CCC AGT GGA GCT
GGA AAA AGT ACA GCA CTG CAA CTC ATT CAG CGA TTC TAT GAC CCC TGT GAA
GGA ATG GTG ACC GTG GAT GGC CAT GAC ATT CGC TCT CTT AAC ATT CAG TGG
CTT AGA GAT CAG ATT GGG ATA GTG GAG CAA GAG CCA GTT CTG TTC TCT ACC
ACC ATT GCA GAA AAT ATT CGC TAT GGC AGA GAA GAT GCA ACA ATG GAA GAC
ATA GTC CAA GCT GCC AAG GAG GCC AAT GCC TAC AAC TTC ATC ATG GAC CTG
CCA CAG CAA TTT GAC ACC CTT GTT GGA GAA GGA GGA GGC CAG ATG AGT GGT
GGC CAG AAA CAA AGG GTA GCT ATC GCC AGA GCC CTC ATC CGA AAT CCC AAG
ATT CTG CTT TTG GAC ATG GCC ACC TCA GCT CTG GAC AAT GAG AGT GAA GCC
ATG GTG CAA GAA GTG CTG AGT AAG ATT CAG CAT GGG CAC ACA ATC ATT TCA
GTT GCT CAT CGC TTG TCT ACG TCA GAT CTG CAG ATA CCA TCA TTG GTT TTT
GAA CAT GGC ACT GCA GTG GAA AGA GGG ACC CAT GAA GAA TTA CTG GAA AGG
AAA GGT GTT TAC TTC ACT CTA GTG ACT TTG CAA AGC AGG GAA TCA AGC T
CTT AAT GAA GAG GAC ATA AAG GAT GCA ACT GAA GAT GAC ATG CTT GCG AGG
ACC TTT AGC AGA GGG AGC TAC CAG GAT AGT TTA AGG GCT TCC ATC CGG CAA
CGC TCC AAG TCT CAG CTT TCT TAC CTG GTG CAC GAA CCT CCA TTA GCT GTT
GTA GAT CAT AAG TCT ACC TAT GAA GAA GAT AGA AAG GAC AAG GAC ATT CCT
GTG CAG GAA GAA GTT GAA CCT GCC CCA GTT AGG AGG ATT CTG AAA TTC AGT
GCT CCA GAA TGG CCC TAC ATG CTG GTA GGG TCT GTG GGT GCA GCT GTG AAC
GGG ACA GTC ACA CCC TTG TAT GCC TTT TTA TTC AGC CAG ATT CTT GGG ACT
TTT TCA ATT CCT GAT AAA GAG GAA CAA AGG TCA CAG ATC AAT GGT GTG TGC
CTA CTT TTT GTA GCA ATG GGC TGT GTA TCT CTT TTC ACC CAA TTT CTA CAG
GGA TAT GCC TTT GCT AAA TCT GGG GAG CTC CTA ACA AAA AGG CTA CGT AAA
TTT GGT TTC AGG GCA ATG CTG GGG CAA GAT ATT GCC TGG TTT GAT GAC CTC
AGA AAT AGC CCT GGA GCA TTG ACA ACA AGA CTT GCT ACA GAT GCT TCC CAA
```

-continued

```
GTT CAA GGG GCT GCC GGC TCT CAG ATC GGG ATG ATA GTC AAT TCC TTC ACT

AAC GTC ACT GTG GCC ATG ATC ATT GCC TTC TCC TTT AGC TGG AAG CTG AGC

CTG GTC ATC TTG TGC TTC TTC CCC TTC TTG GCT TTA TCA GGA GCC ACA CAG

ACC AGG ATG TTG ACA GGA TTT GCC TCT CGA GAT AAG CAG GCC CTG GAG ATG

GTG GGA CAG ATT ACA AAT GAA GCC CTC AGT AAC ATC CGC ACT GTT GCT GGA

ATT GGA AAG GAG AGG CGG TTC ATT GAA GCA CTT GAG ACT GAG CTG GAG AAG

CCC TTC AAG ACA GCC ATT CAG AAA GCC AAT ATT TAC GGA TTC TGC TTT GCC

TTT GCC CAG TGC ATC ATG TTT ATT GCG AAT TCT GCT TCC TAC AGA TAT GGA

GGT TAC TTA ATC TCC AAT GAG GGG CTC CAT TTC AGC TAT GTG TTC AGG GTG

ATC TCT GCA GTT GTA CTG AGT GCA ACA GCT CTT GGA AGA GCC TTC TCT TAC

ACC CCA AGT TAT GCA AAA GCT AAA ATA TCA GCT GCA CGC TTT TTT CAA CTG

CTG GAC CGA CAA CCC CCA ATC AGT GTA TAC AAT ACT GCA GGT GAA AAA TGG

GAC AAC TTC AGG GGA AAG ATT GAT TTT GTT GAT TGT AAA TTT ACA TAT CCT

TCT CGA CCT GAC TCG CAA GTT CTG AAT GGT CTC TCA GTG TCG ATT AGT CCA

GGG CAG ACA CTG GCG TTT GTT GGG AGC AGT GGA TGT GGC AAA AGC ACT AGC

ATT CAG CTG TTG GAA CGT TTC TAT GAT CCT GAT CAA GGG AAG GTG ATG ATA

GAT GGT CAT GAC AGC AAA AAA GTA AAT GTC CAG TTC CTC CGC TCA AAC ATT

GGA ATT GTT CCA GAA CCA GTG TTG TTT GCC TGT AGC ATA ATG GAC AAT

ATC AAG TAT GGA GAC AAC ACC AAA GAA ATT CCC ATG GAA AGA GTC ATA GCA

GCT GCA AAA CAG GCT CAG CTG CAT GAT TTT GTC ATG TCA CTC CCA GAG AAA

TAT GAA ACT AAC GTT GGG TCC CAG GGG TCT CAA CTC TCT AGA GGG GAG AAA

CAA CGC ATT GCT ATT GCT CGG GCC ATT GTA CGA GAT CCT AAA ATC TTG CTA

CTA GAT GAA GCC ACT TCT GCC TTA GAC ACA GAA AGT GAA AAG ACG GTG CAG

GTT GCT CTA GAC AAA GCC AGA GAG GGT CGG ACC TGC ATT GTC ATT GCC CAT

CGC TTG TCC ACC ATC CAG AAC GCG GAT ATC ATT GCT GTC ATG GCA CAG GGG

GTG GTG ATT GAA AAG GGG ACC CAT GAA GAA CTG ATG GCC CAA AAA GGA GCC

TAC TAC AAA CTA GTC ACC ACT GGA TCC CCC ATC AGT TGA
```

TABLE 4

| Exemplary ABCB11 Mutations |
| --- |
| Amino acid position 1 (e.g., M1V)[9] |
| Amino acid position 4 (e.g., S4X)[4,64] |
| Amino acid position 8 (e.g., R8X)[88] |
| Amino acid position 19 (e.g., G19R)[56] |
| Amino acid position 24 (e.g., K24X)[35] |
| Amino acid position 25 (e.g., S25X)[5,14] |
| Amino acid position 26 (e.g., Y26Ifs*7)[38] |
| Amino acid position 36 (e.g., D36D)[27] |
| Amino acid position 38 (e.g., K38Rfs*24)[73] |
| Amino acid position 43 (e.g., V43I)[57] |
| Amino acid position 49 (e.g., Q49X)[73] |
| Amino acid position 50 (e.g., L50S, L50W)[57] |
| Amino acid position 52 (e.g., R52W[26], R52R[28]) |
| Amino acid position 56 (e.g., S56L)[58] |
| Amino acid position 58 (e.g., D58N)[62] |
| Amino acid position 62 (e.g., M62K)[9] |
| Amino acid position 66 (e.g., S66N)[17] |
| Amino acid position 68 (e.g., C68Y)[41] |
| Amino acid position 50 (e.g., L50S)[5,7] |
| Amino acid position 71 (e.g., L71H)[73] |
| Amino acid position 74 (e.g., I74R)[71] |
| Amino acid position 77 (e.g., P77A)[73] |
| Amino acid position 87 (e.g., T87R)[67] |
| Amino acid position 90 (e.g., F90F)[7,27] |
| Amino acid position 93 (e.g., Y93S[13], Y93X[88]) |
| Amino acid position 96 (e.g., E96X)[88] |
| Amino acid position 97 (e.g., L97X)[39] |
| Amino acid position 101 (e.g., Q101Dfs*8)[9] |
| Amino acid position 107 (e.g., C107R)[36] |
| Amino acid position 112 (e.g., I112T)[9] |
| Amino acid position 114 (e.g., W114R)[2,9] |
| Amino acid position 123 (e.g. M123T)[67] |
| Amino acid position 127 (e.g., T127Hfs*6)[5] |
| Amino acid position 129 (e.g., C129Y)[25] |
| Amino acid position 130 (e.g., G130G)[77] |
| Amino acid position 134 (e.g., I134I)[28] |
| Amino acid position 135 (e.g., E135K[7,13], E135L[17]) |
| Amino acid position 137 (e.g., E137K)[7] |
| Amino acid position 157 (e.g., Y157C)[5] |
| Amino acid position 161 (e.g., C161X)[39] |
| Amino acid position 164 (e.g., V164Gfs*7[30], V164I[85]) |
| Amino acid position 167 (e.g., A167S[4], A167V[7], A167T[9,17]) |

TABLE 4-continued

| Exemplary ABCB11 Mutations |
|---|
| Amino acid position 181 (e.g., R181I)[35] |
| Amino acid position 182 (e.g., I182K)[9] |
| Amino acid position 183 (e.g., M183V[8], M183T[9]) |
| Amino acid position 185 (e.g., M185I)[73] |
| Amino acid position 186 (e.g., E186G)[2,7,22] |
| Amino acid position 188 (e.g., G188W)[73] |
| Amino acid position 194 (e.g., S194P)[7] |
| Amino acid position 198 (e.g., L198P)[7] |
| Amino acid position 199 (e.g., N199Ifs*15X)[88] |
| Amino acid position 206 (e.g., I206V)[28] |
| Amino acid position 212 (e.g., A212T)[73] |
| Amino acid position 217 (e.g., M217R)[88] |
| Amino acid position 225 (e.g., T225P)[57] |
| Amino acid position 226 (e.g., S226L)[9] |
| Amino acid position 232 (e.g., L232Cfs*9)[9] |
| Amino acid position 233 (e.g., L233S)[86] |
| Amino acid position 238 (e.g., G238V)[2,7] |
| Amino acid position 242 (e.g., T242I)[5,7] |
| Amino acid position 245 (e.g., I245Tfs*26)[57] |
| Amino acid position 256 (e.g., A256G)[9] |
| Amino acid position 260 (e.g., G260D)[7] |
| Amino acid position 269 (e.g., Y269Y)[27] |
| Amino acid position 277 (e.g., A277E)[77] |
| Amino acid position 283 (e.g., E283D)[73] |
| Amino acid positions 212 and 283 (e.g., A212T + E283D)[73] |
| Amino acid position 284 (e.g., V284L[7,39], V284A[7], V284D[23]) |
| Amino acid position 297 (e.g., E297G[1,2,5,7], E297K[7]) |
| Amino acid position 299 (e.g., R299K)[28] |
| Amino acid position 303 (e.g., R303K[8], R303M[63] R303fsX321[83]) |
| Amino acid position 304 (e.g., Y304X)[26] |
| Amino acid position 312 (e.g., Q312H)[7] |
| Amino acid position 313 (e.g., R313S)[5,7] |
| Amino acid position 314 (e.g., W314X)[57] |
| Amino acid position 318 (e.g., K318Rfs*26)[29] |
| Amino acid position 319 (e.g., G319G)[7] |
| Amino acid position 327 (e.g., G327E)[5,7] |
| Amino acid position 330 (e.g., W330X)[24] |
| Amino acid position 336 (e.g., C336S)[2,7] |
| Amino acid position 337 (e.g., Y337H)[21,27] |
| Amino acid position 342 (e.g., W342G)[50] |
| Amino acid position 354 (e.g., R354X)[9] |
| Amino acid position 361 (e.g., Q361X[57], Q361R[74]) |
| Amino acid position 366 (e.g., V366V[28], V366D[57]) |
| Amino acid position 368 (e.g., V368Rfs*27)[5] |
| Amino acid position 374 (e.g., G374S)[3] |
| Amino acid position 380 (e.g., L380Wfs*18)[5] |
| Amino acid position 382 (e.g., A382G)[88] |
| Δ Amino acid positions 382-388[5] |
| Δ Amino acid positions 383-389[57] |
| Amino acid position 387 (e.g., R387H)[9] |
| Amino acid position 390 (e.g., A390P)[5,7] |
| Amino acid position 395 (e.g., E395E)[28] |
| Amino acid position 404 (e.g., D404G)[9] |
| Amino acid position 410 (e.g., G410D)[5,7] |
| Amino acid position 413 (e.g., L413W)[5,7] |
| Amino acid position 415 (e.g., R415X)[42] |
| Amino acid position 416 (e.g., I416I)[27] |
| Amino acid position 420 (e.g., I420T)[9] |
| Amino acid position 423 (e.g., H423R)[13] |
| Amino acid position 432 (e.g., R432T)[1,2,7] |
| Amino acid position 436 (e.g., K436N)[40] |
| Amino acid position 440 (e.g., D440E)[88] |
| Amino acid position 444 (e.g., V444A)[2] |
| Amino acid position 454 (e.g., V454X)[49] |
| Amino acid position 455 (e.g., G455E)[9] |
| Amino acid position 457 (e.g., S457Vfs*23)[88] |
| Amino acid position 461 (e.g., K461E)[2,7] |
| Amino acid position 462 (e.g., S462R)[88] |
| Amino acid position 463 (e.g., T463I)[5,7] |
| Amino acid position 466 (e.g., Q466K)[5,7] |
| Amino acid position 470 (e.g., R470Q[5,7], R470X[9]) |
| Amino acid position 471 (e.g., Y472X)[5] |
| Amino acid position 472 (e.g., Y472C[5,27], Y472X[14]) |
| Amino acid position 473 (e.g., D473Q[35], D473V[88]) |
| Amino acid position 475 (e.g., C475X)[29] |
| Amino acid position 481 (e.g., V481E)[5,7] |
| Amino acid position 482 (e.g., D482G)[2,5,7] |
| Amino acid position 484 (e.g., H484Rfs*5)[9] |
| Amino acid position 487 (e.g., R487H[2], R487P[5]) |
| Amino acid position 490 (e.g., N490D)[5,7] |
| Amino acid position 493 (e.g., W493X)[8] |
| Amino acid positon 496 (e.g., D496V)[88] |
| Amino acid position 498 (e.g., I498T)[2,7] |
| Amino acid position 499 (e.g., G499E)[73] |
| Amino acid position 501 (e.g., V501G)[68] |
| Amino acid position 504 (e.g., E504K)[79] |
| Amino acid position 510 (e.g., T510T)[7] |
| Amino acid position 512 (e.g., I512T)[5,7] |
| Amino acid position 515 (e.g., N515T[5,7], N515D[64]) |
| Amino acid position 516 (e.g., I516M)[17] |
| Amino acid position 517 (e.g., R517H)[5,7] |
| Amino acid position 520 (e.g., R520X)[5] |
| Amino acid position 523 (e.g., A523G)[13] |
| Amino acid position 528 (e.g., I528Sfs*21[5], I528X[9], I528T[73]) |
| Amino acid position 535 (e.g., A535A[7], A535X[89]) |
| Amino acid position 540 (e.g., F540L)[46] |
| Amino acid position 541 (e.g., I541L[5,7], I541T[5,17]) |
| Amino acid position 546 (e.g., Q546K[39], Q546H[73]) |
| Amino acid position 548 (e.g., F548Y)[5,7] |
| Amino acid position 549 (e.g., D549V)[9] |
| Amino acid position 554 (e.g., E554K)[21] |
| Amino acid position 556 (e.g., G556R)[67] |
| Amino acid position 558 (e.g., Q558H)[23] |
| Amino acid position 559 (e.g., M559T)[57] |
| Amino acid position 562 (e.g., G562D[5,7], G562S[73]) |
| Amino acid position 570 (e.g., A570T[2,5,7], A570V[26]) |
| Amino acid position 575 (e.g., R575X[2,5], R575Q[21]) |
| Amino acid position 580 (e.g., L580P)[57] |
| Amino acid position 586 (e.g., T586I)[7] |
| Amino acid position 587 (e.g., S587X)[73] |
| Amino acid position 588 (e.g., A588V[5,7], A588P[73]) |
| Amino acid position 591 (e.g., N591S)[2,7] |
| Amino acid position 593 (e.g., S593R)[2,7] |
| Amino acid position 597 (e.g., V597V[9], V597L[13]) |
| Amino acid positon 603 (e.g., K603K)[55] |
| Amino acid position 609 (e.g., H609Hfs*46)[26] |
| Amino acid position 610 (e.g., I610Gfs*45[9], I610T[57])[9] |
| Amino acid position 615 (e.g., H615R)[26] |
| Amino acid position 616 (e.g., R616G[28], R616H[73]) |
| Amino acid position 619 (e.g., T619A)[28] |
| Amino acid position 623 (e.g., A623A)[28] |
| Amino acid position 625 (e.g., T625Nfs*5)[26] |
| Amino acid position 627 (e.g., I627T)[7] |
| Amino acid position 628 (e.g., G628Wfs*3)[70] |
| Amino acid position 636 (e.g., E636G)[2] |
| Amino acid position 648 (e.g., G648Vfs*6[5], G648V[50]) |
| Amino acid position 655 (e.g., T655I)[7] |
| Amino acid position 669 (e.g., I669V)[26] |
| Amino acid position 676 (e.g., D676Y)[11] |
| Amino acid position 677 (e.g., M677V)[7,13] |
| Amino acid position 679 (e.g., A679V)[58] |
| Amino acid position 685 (e.g., G685W)[60] |
| Amino acid position 696 (e.g., R696W[27], R696Q[58]) |
| Amino acid position 698 (e.g., R698H[7,9], R698K[61], R698C[88]) |
| Amino acid position 699 (e.g., S699P)[9] |
| Amino acid positon 701 (e.g., S701P)[58] |
| Amino acid position 702 (e.g., Q702X)[89] |
| Amino acid position 709 (e.g., E709K)[7] |
| Amino acid position 710 (e.g., P710P)[7] |
| Amino acid position 712 (e.g., L712L)[28] |
| Amino acid position 721 (e.g., Y721C)[88] |
| Amino acid position 729 (e.g., D724N)[39] |
| Amino acid position 731 (e.g., P731S)[23] |
| Amino acid position 740 (e.g., P740Qfs*6)[73] |
| Amino acid position 758 (e.g., G758R)[5] |
| Amino acid position 766 (e.g., G766R)[5,24] |
| Amino acid position 772 (e.g., Y772X)[5] |
| Amino acid positon 804 (e.g., A804A)[7] |
| Amino acid position 806 (e.g., G806D[44], G806G[55]) |
| Amino acid position 809 (e.g., S809F)[81] |
| Amino acid position 817 (e.g., G817G)[88] |
| Amino acid position 818 (e.g., Y818F)[7] |
| Amino acid position 824 (e.g., G824E)[42] |
| Amino acid position 825 (e.g., G825G)[73] |
| Amino acid position 830 (e.g., R830Gfs*28)[73] |
| Amino acid position 832 (e.g., R832C[7,26], R832H[41]) |

TABLE 4-continued

Exemplary ABCB11 Mutations

Amino acid position 842 (e.g., D842G)[2]
Amino acid position 848 (e.g., D848N)[73]
Amino acid position 855 (e.g., G855R)[11]
Amino acid position 859 (e.g., T859R)[5,7]
Amino acid position 865 (e.g., A865V)[27]
Amino acid position 866 (e.g., S866A)[57]
Amino acid position 868 (e.g., V868P)[73]
Amino acid position 869 (e.g., Q869P)[73]
Amino acid position 875 (e.g., Q875X)[73]
Amino acid position 877 (e.g., G877R)[56]
Amino acid position 879 (e.g., I879R)[88]
Amino acid position 893 (e.g., A893V)[57]
Amino acid position 901 (e.g., S901R[17], S901I[73])
Amino acid position 903 (e.g., V903G)[57]
Δ Amino acid position 919[12]
Amino acid position 923 (e.g., T923P)[2,7]
Amino acid position 926 (e.g., A926P)[2,7]
Amino acid position 928 (e.g., R928X[15], R928Q[40])
Amino acid position 930 (e.g., K930X[5], K930Efs*79[5,10], K930Efs*49[26])
Amino acid position 931 (e.g., Q931P)[27]
Amino acid position 945 (e.g., S945N)[57]
Amino acid position 948 (e.g., R948C)[5,7,26]
Amino acid position 958 (e.g., R958Q)[28]
Amino acid position 969 (e.g., K969K)[88]
Δ Amino acid positions 969-972[5]
Amino acid position 973 (e.g., T973I)[57]
Amino acid position 976 (e.g., Q976R[58], Q976X[88])
Amino acid position 979 (e.g., N979D)[5,7]
Amino acid position 981 (e.g., Y981Y)[28]
Amino acid position 982 (e.g., G982R)[2,5,7]
Amino acid positions 444 and 982 (e.g., V444A + G982R)[38]
Amino acid position 995 (e.g., A995A)[28]
Amino acid position 1001 (e.g., R1001R)[9]
Amino acid position 1003 (e.g., G1003R)[24]
Amino acid position 1004 (e.g., G1004D)[2,7]
Amino acid position 1027 (e.g., S1027R)[26]
Amino acid position 1028 (e.g., A1028A[7,10,88], A1028E[88])
Amino acid position 1029 (e.g., T1029K)[5]
Amino acid position 1032 (e.g., G1032R)[12]
Amino acid position 1041 (e.g., Y1041X)[9]
Amino acid position 1044 (e.g., A1044P)[88]
Amino acid position 1050 (e.g., R1050C)[2,7,57]
Amino acid position 1053 (e.g., Q1053X)[57]
Amino acid position 1055 (e.g., L1055P)[36]
Amino acid position 1057 (e.g., R1057X[2], R1057Q[58])
Amino acid position 1058 (e.g., Q1058Hfs*38[9], Q1058fs*38[17], Q1058X[73])
Amino acid position 1061 (e.g., I1061Vfs*34)[9]
Amino acid position 1083 (e.g., C1083Y)[47]
Amino acid position 1086 (e.g., T1086T)[28]
Amino acid position 1090 (e.g., R1090X)[2,5]
Amino acid position 1099 (e.g., L1099Lfs*38)[26]
Amino acid position 1100 (e.g., S1100Qfs*38)[13]
Amino acid position 1110 (e.g., A1110E)[5,7]
Amino acid position 1112 (e.g., V1112F)[70]
Amino acid position 1116 (e.g., G1116R[7], G1116F[9,17], G1116E[36])
Amino acid position 1120 (e.g., S1120N)[88]
Amino acid position 1128 (e.g., R1128H[2,7], R1128C[5,7,13])
Amino acid position 1131 (e.g., D1131V)[27]
Amino acid position 1144 (e.g., S1144R)[7]
Amino acid position 1147 (e.g., V1147X)[5]
Amino acid position 1153 (e.g., R1153C[2,5,7], R1153H[5])
Amino acid position 1154 (e.g., S1154P)[5,7]
Amino acid position 1162 (e.g., E1162X)[39]
Δ Amino acid position 1165[88]
Amino acid position 1164 (e.g., V1164Gfs*7)
Amino acid position 1173 (e.g., N1173D)[57]
Amino acid position 1175 (e.g., K1175T)[58]
Amino acid position 1186 (e.g., E1186K)[7]
Amino acid position 1192 (e.g., A1192Efs*50)[9]
Amino acid position 1196 (e.g., Q1196X)[88]
Amino acid position 1197 (e.g., L1197G)[7]
Amino acid position 1198 (e.g., H1198R)[27]
Amino acid position 1204 (e.g., L1204P)[88]
Amino acid position 1208 (e.g. Y1208C)[73]
Amino acid position 1210 (e.g., T1210P[5,7], T1210F[57])
Amino acid position 1211 (e.g., N1211D)[7]
Amino acid position 1212 (e.g., V1212F)[36]
Amino acid position 1215 (e.g., Q1215X)[5]
Amino acid position 1221 (e.g., R1221K)[53]
Amino acid position 1223 (e.g., E1223D)[7]
Amino acid position 1226 (e.g., R1226P)[73]
Amino acid position 1228 (e.g., A1228V)[7]
Amino acid position 1231 (e.g., R1231W[5,7], R1231Q[5,7])
Amino acid position 1232 (e.g., A1232D)[17]
Amino acid position 1235 (e.g., R1235X)[5,12]
Amino acid position 1242 (e.g., L1242I)[5,7]
Amino acid position 1243 (e.g., D1243G)[67]
Amino acid position 1249 (e.g., L1249X)[73]
Amino acid position 1256 (e.g., T1256fs*1296)[83]
Amino acid position 1268 (e.g., R1268Q)[2,7]
Amino acid position 1276 (e.g., R1276H)[30]
Amino acid position 1283 (e.g., A1283A[28], A1283V[88])
Amino acid position 1292 (e.g., G1292V)[73]
Amino acid position 1298 (e.g., G1298R)[5]
Amino acid position 1302 (e.g., E1302X)[5]
Amino acid position 1311 (e.g., Y1311X)[57]
Amino acid position 1316 (e.g., T1316Lfs*64)[15]
Amino acid position 1321 (e.g., S1321N)[57]
Intron 4 ((+3)A > C)[1]
IVS4 − 74A > T[89]
Splice site mutation 3' Intron 5 c.3901G > A[5]
Splice site mutation 5; Intron 7 c.6111G > A[5]
Splice site mutation IVS7 + 1G > A[14]
IVS7 + 5G > A[40]
IVS8 + 1G > C[76]
Splice site mutation 5' Intron 9 c.9081delG[5]
Splice site mutation 5' Intron 9 c.9081G > T[5]
Splice site mutation 5' Intron 9 c.9081G > A[5]
Splice site mutation IVS9 + 1G > T[14]
Splice site mutation 3' Intron 13 c.143513_1435-8del[5]
Splice site mutation IVS13del-13ˆ-8[14]
Splice site mutation 3' Intron 16 c.20128T > G[5]
Splice site mutation IVS16 − 8T > G[14]
Splice site mutation 5' Intron 18 c.21781G > T[5]
Splice site mutation 5' Intron 18 c.21781G > A[5]
Splice site mutation 5' Intron 18 c.21781G > C[5]
Splice site mutation 3' Intron 18 c.21792A > G[5]
Splice site mutation IVS18 + 1G > A[14]
Splice site mutation 5' Intron 19 c.2343 + 1G > T[5]
Splice site mutation 5' Intron 19 c.2343 + 2T > C[5]
Splice site mutation IVS19 + 2T > C[14]
Splice site mutation IVS19 + 1G > A[22]
Splice site mutation 3' Intron 21 c.26112A > T[5]
IVS22 + 3A > G[89]
IVS 23 − 8 G − A[36]
IVS24 + 5G > A[51]
Splice site mutation 5' Intron 24 c.32131delG[5]
IVS35 − 6C > G[89]
Putative splice mutation 1198 − 1G > C[17]
Putative splice mutation 1810 − 3C > G[17]
Putative splice mutation 2178 + 1G > A[17]
Putative splice mutation 2344 − 1G > T[17]
Putative splice mutation c.2611 − 2A > T[39]
Putative splice mutation 3213 + 1_3213 + 2delinsA[17]
c.-24C > A[44,78]
c.76 13 G > T[9]
c.77 − 19T > A[52]
c.90_93delGAAA[18]
c.124G > A[69]
c.150 + 3 A > C[10]
174C > T[54]
c.245T > C[87]
c.249_250insT[18]
270T > C[54]
402C > T[54]
585G > C[54]
c.611 + 1G > A[70]
c.611 + 4A > G[36]
c.612 − 15_−6del10bp[55]
c.625A > C[31]
c.627 + 5G > T[31]
c.625A > C/c.627 + 5G > T[31]
696G > T[54]
c. 784 + 1G > C[49]
807T > C[54]

TABLE 4-continued

Exemplary ABCB11 Mutations c.886C > T[31]
c.890A > G[59]
c.908 + 1G > A[57]
c.908 + 5G > A[55]
c.908delG[59]
c.909 − 15A > G[66]
957A > G[54]
c.1084 − 2A > G[57]
1145 1 bp deletion[90]
1281C > T[54,57]
c.1309 − 165C > T[19]
c.1434 + 174G > A[19]
c.1434 + 70C > T[19]
c.1530C > A[57]
c.1587 − 1589delCTT[31]
c.1621A > C[33,59]
c.1638 + 32T > C[66]
c.1638 + 80C > T[66]
1671C > T[54]
1791G > T[54]
1939delA[14]
c.2075 + 3A > G[53]
c.2081T > A[31]
c.2093G > A[65]
2098delA[16]
c.2138 − 8T > G[67]
2142A > G[54]
c.2178 + 1G > T[36,39]
c.2179 − 17C > A[66]
c.2344 − 157T > G[66]
c.2344 − 17T > C[66]
c.2417G > A[78]
c.2541delG[87]
c.2620C > T[32,33]
c.2815 − 8A > G[55]
c.3003A > G[37]
c.3084A > G[48,54]
c.3213 + 4 A > G[9,37]
c.3213 + 5 G > A[9]
c.3268C > T[75]
3285A > G[54]
c.3382C > T[75]
3435A > G[54]
c.3491delT[72]
c.3589C > T[57]
c.3765(+1 + 5)del5[42]
c.3766 − 34A > G[66]
c.3767-3768insC[6]
c.3770delA[67]
c.3826C > T[72]
c.3846C > T[57]
c.3929delG[67]
c.*236A > G[66]
1145delC[8]
Ex13_Ex17del[82]

TABLE 5

Selected ABCB11 Mutations Associated with PFIC-2

Amino acid position 1 (e.g., M1V)[9]
Amino acid position 4 (e.g., S4X)[64]
Amino acid position 19 (e.g., G19R)[56]
Amino acid position 25 (e.g., S25X)[14]
Amino acid position 26 (e.g., Y26Ifs*7)[38]
Amino acid position 50 (e.g., L50S)[7,57]
Amino acid position 52 (e.g., R52W)[26]
Amino acid position 58 (e.g., D58N)[62]
Amino acid position 62 (e.g., M62K)[9]
Amino acid position 66 (e.g., S66N)[17]
Amino acid position 68 (e.g., C68Y)[41]
Amino acid position 93 (e.g., Y93S)[13]
Amino acid position 101 (e.g., Q101Dfs*8)[9]
Amino acid position 107 (e.g., C107R)[36]
Amino acid position 112 (e.g., I112T)[9]

TABLE 5-continued

Selected ABCB11 Mutations Associated with PFIC-2

Amino acid position 114 (e.g., W114R)[2,9]
Amino acid position 129 (e.g., C129Y)[25]
Amino acid position 135 (e.g., E135K[13], E135L[17])
Amino acid position 167 (e.g., A167V[7], A167T[9,17])
Amino acid position 182 (e.g., I182K)[9]
Amino acid position 183 (e.g., M183V[8], M183T[9])
Amino acid position 225 (e.g., T225P)[57]
Amino acid position 226 (e.g., S226L)[9]
Amino acid position 232 (e.g., L232Cfs*9)[9]
Amino acid position 233 (e.g., L233S)[86]
Amino acid position 238 (e.g., G238V)[2,7]
Amino acid position 242 (e.g., T242I)[7]
Amino acid position 245 (e.g., I245Tfs*26)[57]
Amino acid position 256 (e.g., A256G)[9]
Amino acid position 260 (e.g., G260D)[57]
Amino acid position 284 (e.g., V284L)[7]
Amino acid position 297 (e.g., E297G)[2,7]
Amino acid position 303 (e.g., R303K[8], R303M[63], R303fsX321[83])
Amino acid position 304 (e.g., Y304X)[26]
Amino acid position 312 (e.g., Q312H)[7]
Amino acid position 313 (e.g., R313S)[7]
Amino acid position 314 (e.g., W314X)[57]
Amino acid position 318 (e.g., K318Rfs*26)[29]
Amino acid position 327 (e.g., G327E)[7]
Amino acid position 330 (e.g., V330X)[24]
Amino acid position 336 (e.g., C336S)[2,7]
Amino acid position 337 (e.g., Y337H)[21]
Amino acid position 342 (e.g., W342G)[50]
Amino acid position 354 (e.g., R354X)[9]
Amino acid position 361 (e.g., Q361X)[57]
Amino acid position 366 (e.g., V366D)[57]
Amino acid position 386 (e.g., G386X)[34]
Δ Amino acid positions 383-389[57]
Amino acid position 387 (e.g., R387H)[9]
Amino acid position 390 (e.g., A390P)[7]
Amino acid position 410 (e.g., G410D)[7]
Amino acid position 413 (e.g., L413W)[7]
Amino acid position 415 (e.g., R415X)[42]
Amino acid position 420 (e.g., I420T)[9]
Amino acid position 454 (e.g., V454X)[49]
Amino acid position 455 (e.g., G455E)[9]
Amino acid position 461 (e.g., K461E)[2,7]
Amino acid position 463 (e.g., T463I)[7]
Amino acid position 466 (e.g., Q466K)[7]
Amino acid position 470 (e.g., R470Q[7], R470X[9])
Amino acid position 472 (e.g., Y472X[14], Y472C[27])
Amino acid position 475 (e.g., C475X)[29]
Amino acid position 481 (e.g., V481E)[7]
Amino acid position 482 (e.g., D482G)[2,7]
Amino acid position 484 (e.g., H484Rfs*5)[9]
Amino acid position 487 (e.g., R487H[2], R487P[84])
Amino acid position 490 (e.g., N490D)[7]
Amino acid position 493 (e.g., W493X)[8]
Amino acid position 498 (e.g., I498T)[7]
Amino acid position 501 (e.g., V501G)[68]
Amino acid position 512 (e.g., I512T)[7]
Amino acid position 515 (e.g., N515T[7], N515D[64])
Amino acid position 516 (e.g., I516M)[17]
Amino acid position 517 (e.g., R517H)[7]
Amino acid position 520 (e.g., R520X)[57]
Amino acid position 523 (e.g., A523G)[13]
Amino acid position 528 (e.g., I528X)[9]
Amino acid position 540 (e.g., F540L)[46]
Amino acid position 541 (e.g., I541L[7], I541T[17])
Amino acid position 548 (e.g., F548Y)[7]
Amino acid position 549 (e.g., D549V)[9]
Amino acid position 554 (e.g., E554K)[21]
Amino acid position 559 (e.g., M559T)[57]
Amino acid position 562 (e.g., G562D)[7]
Amino acid position 570 (e.g., A570T[7], A570V[26])
Amino acid position 575 (e.g., R575X[2], R575Q[21])
Amino acid position 588 (e.g., A588V)[7]
Amino acid position 591 (e.g., N591S)[9,17]
Amino acid position 593 (e.g., S593R)[2,7]
Amino acid position 597 (e.g., V597V[9], V597L[13])
Amino acid positions 591 and 597 (e.g., N591S + V597V)[9]
Amino acid position 603 (e.g., K603K)[55]
Amino acid position 609 (e.g., H609Hfs*46)[26]

TABLE 5-continued

Selected ABCB11 Mutations Associated with PFIC-2

Amino acid position 610 (e.g., I610Gfs*45)[9]
Amino acid position 615 (e.g., H615R)[26]
Amino acid position 625 (e.g., T625Nfs*5)[26]
Amino acid position 627 (e.g., I627T)[7]
Amino acid position 636 (e.g., E636G)[2]
Amino acid position 669 (e.g., I669V)[26]
Amino acid position 698 (e.g., R609H)[9]
Amino acid positions 112 and 698 (e.g., I112T + R698H)[9]
Amino acid position 699 (e.g., S699P)[9]
Amino acid position 766 (e.g., G766R)[24]
Amino acid position 806 (e.g., G806G)[55]
Amino acid position 824 (e.g., G824E)[42]
Amino acid position 832 (e.g., R832C[7,26], R832H[41])
Amino acid position 842 (e.g., D842G)[2]
Amino acid position 859 (e.g., T859R)[7]
Amino acid position 865 (e.g., A865V)[45]
Amino acid position 877 (e.g., G877R)[56]
Amino acid position 893 (e.g., A893V)[57]
Amino acid position 901 (e.g., S901R)[17]
Amino acid position 903 (e.g., V903G)[57]
Δ Amino acid position 919[12]
Amino acid position 928 (e.g., R928X)[15,21]
Amino acid position 930 (e.g., K930Efs*79[10], K930Efs*49[26])
Amino acid position 948 (e.g., R948C)[7,26]
Amino acid position 979 (e.g., N979D)[7]
Amino acid position 982 (e.g., G982R)[2,7]
Amino acid positions 444 and 982 (e.g., V444A + G982R)[38]
Amino acid position 1001 (e.g., R1001R)[9]
Amino acid position 1003 (e.g., G1003R)[24]
Amino acid position 1004 (e.g., G1004D)[2,7]
Amino acid position 1027 (e.g., S1027R)[26]
Amino acid position 1028 (e.g., A1028A)[10]
Amino acid position 1032 (e.g., G1032R)[12]
Amino acid position 1041 (e.g., Y1041X)[9]
Amino acid position 1050 (e.g., R1050C)[57]
Amino acid position 1053 (e.g., Q1053X)[57]
Amino acid position 1055 (e.g., L1055P)[36]
Amino acid position 1057 (e.g., R1057X)[2]
Amino acid position 1058 (e.g., Q1058Hfs*38[9], Q1058fs*38[17])
Amino acid position 1061 (e.g., I1061Vfs*34)[9]
Amino acid position 1083 (e.g., C1083Y)[47]
Amino acid position 1090 (e.g., R1090X)[2]
Amino acid position 1099 (e.g., L1099Lfs*38)[26]
Amino acid position 1100 (e.g., S1100Qfs*38)[13]
Amino acid position 1110 (e.g., A1110E)[7]
Amino acid position 1116 (e.g., G1116R[7], G1116F[9,17], G1116E[36])
Amino acid position 1128 (e.g., R1128C)[7,13]
Amino acid position 1131 (e.g., D1131V)[27]
Amino acid position 1144 (e.g., S1144R)[7]
Amino acid position 1153 (e.g., R1153C[2,7], R1153H[7,26])
Amino acid position 1154 (e.g., S1154P)[7]
Amino acid position 1173 (e.g., N1173D)[57]
Amino acid position 1192 (e.g., A1192Efs*50)[9]
Amino acid position 1198 (e.g., H1198R)[27]
Amino acid position 1210 (e.g., T1210P[7], T1210F[57])
Amino acid position 1211 (e.g., N1211D)[7]
Amino acid position 1212 (e.g., V1212F)[36]
Amino acid position 1231 (e.g., R1231W[7], R1223Q[7])
Amino acid position 1232 (e.g., A1232D)[17]
Amino acid position 1235 (e.g., R1235X)[12]
Amino acid position 1242 (e.g., L1242I)[7]
Amino acid position 1256 (e.g., T1256fs*1296)[83]
Amino acid position 1268 (e.g., R1268Q)[2,7]
Amino acid position 1302 (e.g. E1302X)[57]
Amino acid position 1311 (e.g., Y1311X)[57]
Amino acid position 1316 (e.g., T1316Lfs*64)[15]
Intron 4 ((+3)A > C)[1]
Splice site mutation IVS7 + 1G > A[14]
IVS8 + 1G > C[76]
Splice site mutation IVS9 + 1G > T[14]
Splice site mutation IVS13del-13´-8[14]
Splice site mutation IVS16 − 8T > G[14]
Splice site mutation IVS18 + 1G > A[14]
Splice site mutation IVS19 + 2T > C[14]
IVS 23 − 8 G − A[36]
IVS24 + 5G > A[51]
Putative splice mutation 1198 − 1G > C[17]
Putative splice mutation 1810 − 3C > G[17]
Putative splice mutation 2178 + 1G > A[17]
Putative splice mutation 2344 − 1G > T[17]
Putative splice mutation 3213 + 1_3213 + 2delinsA[17]
c.-24C > A[78]
c.76 13 G > T[9]
c.77 − 19T > A[52]
c.90_93delGAAA[18]
c.124G > A[69]
c.150 + 3 A > C[10]
c.249_250insT[18]
c.611 + 1G > A[84]
c.611 + 4A > G[36]
c.612 − 15_-6del10bp[55]
c.625A > C[31]
c.627 + 5G > T[31]
c.625A > C/c.627 + 5G > T[31]
c.886C > T[31]
c.890A > G[59]
c.908 + 1G > A[57]
c.908 + 5G > A[55]
c.908delG[59]
1273 1 bp deletion[91]
c.1084 − 2A > G[57]
c.1445A > G[59]
c.1587-1589delCTT[31]
c.1621A > C[59]
1939delA[14]
c.2081T > A[31]
2098delA[16]
c.2343 + 1 G > T[80]
c.2178 + 1G > T[36]
c.2417G > A[78]
c.2620C > T[32]
c.2815 − 8A > G[55]
c.3003A > G[37]
c.3213 + 4 A > G[9,37]
c.3213 + 5 G > A[9]
c.3268C > T[75]
c.3382C > T[75]
c.3765(+1 + 5)del5[42]
c.3767-3768insC[6]
1145delC[8]
Ex13_Ex17del[82]

[a] A mutation to 'X' denotes an early stop codon

REFERENCES FOR TABLES 4 AND 5

[1] Noe et al., J Hepatol. 2005, vol. 43(3), p. 536-543.
[2] Lam et al., Am J Physiol Cell Physiol. 2007, vol. 293(5), p. C1709-16.
[3] Stindt et al., Liver Int. 2013, vol. 33(10), p. 1527-1735.
[4] Gao et al., Shandong Yiyao 2012, vol. 52(10), p. 14-16.
[5] Strautnieks et al., Gastroenterology. 2008, vol. 134(4), p. 1203-1214.
[6] Kagawa et al., Am J Physiol Gastrointest Liver Physiol. 2008, vol. 294(1), p. G58-67.
[7] Byrne et al., Hepatology. 2009, vol. 49(2), p. 553-567.
[8] Chen et al., J Pediatr. 2008, vol. 153(6), p. 825-832.
[9] Davit-Spraul et al., Hepatology 2010, vol. 51(5), p. 1645-1655.
[10] Dröge et al., Sci Rep. 2016, vol. 6: 24827.
[11] Lang et al., Pharmacogenet Genomics. 2007, vol. 17(1), p. 47-60.
[12] Ellinger et al., World J Gastroenterol. 2017, vol. 23(29), p.: 5295-5303.
[13] Vitale et al., J Gastroenterol. 2018, vol. 53(8), p. 945-958.
[14] Knisely et al., Hepatology. 2006, vol. 44(2), p. 478-86.
[15] Ellis et al., Hepatology. 2018, vol. 67(4), p. 1531-1545.
[16] Lam et al., J Hepatol. 2006, vol. 44(1), p. 240-242.
[17] Varma et al., Hepatology 2015, vol. 62(1), p. 198-206.

[18] Treepongkaruna et al., World J Gastroenterol. 2009, vol. 15(34), p. 4339-4342.
[19] Zarenezhad et al., Hepatitis Monthly: 2017, vol. 17(2); e43500.
[20] Hayashi et al., Hepatol Res. 2016, vol. 46(2), p. 192-200.
[21] Guorui et al., Linchuang Erke Zazhi 2013, vol. 31(10), 905-909.
[22] van Mil et al., Gastroenterology. 2004, vol. 127(2), p. 379-384.
[23] Anzivino et al., Dig Liver Dis. 2013, vol. 45(3), p. 226-232.
[24] Park et al., World J Gastroenterol. 2016, vol. 22(20), p. 4901-4907.
[25] Imagawa et al., J Hum Genet. 2018, vol. 63(5), p. 569-577.
[26] Giovannoni et al., PLoS One. 2015, vol. 10(12): e0145021.
[27] Hu et al., Mol Med Rep. 2014, vol. 10(3), p. 1264-1274.
[28] Lang et al., Drug Metab Dispos. 2006, vol. 34(9), p. 1582-1599.
[29] Masahata et al., Transplant Proc. 2016, vol. 48(9), p. 3156-3162.
[30] Holz et al., Hepatol Commun. 2018, vol. 2(2), p. 152-154.
[31] Li et al., Hepatology International 2017, vol. 11, No. 1, Supp. Supplement 1, pp. S180. Abstract Number: OP284.
[32] Francalanci et al., Laboratory Investigation 2011, vol. 91, Supp. SUPPL. 1, pp. 360A. Abstract Number: 1526.
[33] Francalanci et al., Digestive and Liver Disease 2010, vol. 42, Supp. SUPPL. 1, pp. S16. Abstract Number: T.N.5.
[34] Shah et al., J Pediatr Genet. 2017, vol. 6(2), p. 126-127.
[35] Gao et al., Hepatitis Monthly 2017, vol. 17(10), e55087/1-e55087/6.
[36] Evason et al., Am J Surg Pathol. 2011, vol. 35(5), p. 687-696.
[37] Davit-Spraul et al., Mol Genet Metab. 2014, vol. 113(3), p. 225-229.
[38] Maggiore et al., J Hepatol. 2010, vol. 53(5), p. 981-6.
[39] McKay et al., Version 2. F1000Res. 2013; 2: 32. DOI: 10.12688/f1000research.2-32.v2
[40] Liu et al., Pediatr Int. 2013, vol. 55(2), p. 138-144.
[41] Waisbourd-Zinman et al., Ann Hepatol. 2017, vol. 16(3), p. 465-468.
[42] Griffin, et al., Canadian Journal of Gastroenterology and Hepatology 2016, vol. 2016. Abstract Number: A200. Meeting Info: 2016 Canadian Digestive Diseases Week, CDDW 2016. Montreal, QC, United States. 26 Feb. 2016-29 Feb. 2016
[43] Qiu et al., Hepatology 2017, vol. 65(5), p. 1655-1669.
[44] Imagawa et al., Sci Rep. 2017, 7:41806.
[45] Kang et al., J Pathol Transl Med. 2019 May 16. doi: 10.4132/jptm.2019.05.03. [Epub ahead of print]
[46] Takahashi et al., Eur J Gastroenterol Hepatol. 2007, vol. 19(11), p. 942-6.
[47] Shimizu et al., Am J Transplant. 2011, vol. 11(2), p. 394-398.
[48] Krawczyk et al., Ann Hepatol. 2012, vol. 11(5), p. 710-744.
[49] Sharma et al., BMC Gastroenterol. 2018, vol. 18(1), p. 107.
[50] Sattler et al., Journal of Hepatology 2017, vol. 66, No. 1, Suppl. S, pp. S177. Meeting Info.: International Liver Congress/52nd Annual Meeting of the European-Association-for-the-Study-of-the-Liver. Amsterdam, NETHERLANDS. Apr. 19-23, 2017. European Assoc Study Liver.
[51] Jung et al., J Pediatr Gastroenterol Nutr. 2007, vol. 44(4), p. 453-458.
[52] Sciveres. Digestive and Liver Disease 2010, vol. 42, Supp. SUPPL. 5, pp. S329. Abstract Number: CO18. Meeting Info: 17th National Congress SIGENP. Pescara, Italy. 7 Oct. 2010-9 Oct. 2010
[53] Sohn et al., Pediatr Gastroenterol Hepatol Nutr. 2019, vol. 22(2), p. 201-206.
[54] Ho et al., Pharmacogenet Genomics. 2010, vol. 20(1), p. 45-57.
[55] Wang et al., Hepatol Res. 2018, vol. 48(7), p. 574-584.
[56] Shaprio et al., J Hum Genet. 2010, vol. 55(5), p. 308-313.
[57] Bounford. University of Birmingham. Dissertation Abstracts International, (2016) Vol. 75, No. 1C. Order No.: AAI10588329. ProQuest Dissertations & Theses.
[58] Stolz et al., Aliment Pharmacol Ther. 2019, vol. 49(9), p. 1195-1204.
[59] Jankowska et al., J Pediatr Gastroenterol Nutr. 2014, vol. 58(1), p. 92-95.
[60] Kim. Journal of Pediatric Gastroenterology and Nutrition 2016, vol. 62, Supp. SUPPL. 1, pp. 620. Abstract Number: H-P-045. Meeting Info: 49th Annual Meeting of the European Society for Paediatric Gastroenterology, Hepatology and Nutrition, ESPGHAN 2016. Athens, Greece. 25 May 2016-28 May 2016.
[61] Pauli-Magnus et al., Hepatology 2003, vol. 38, No. 4 Suppl. 1, pp. 518A. print. Meeting Info.: 54th Annual Meeting of the American Association for the Study of Liver Diseases. Boston, Mass., USA. Oct. 24-28, 2003. American Association for the Study of Liver Diseases.
[62] Li et al., Hepatology International 2017, vol. 11, No. 1, Supp. Supplement 1, pp. S362. Abstract Number: PP0347. Meeting Info: 26th Annual Conference of the Asian Pacific Association for the Study of the Liver, APASL 2017. Shanghai, China. 15 Feb. 2017-19 Feb. 2017.
[63] Rumbo et al., Transplantation 2018, vol. 102, No. 7, Supp. Supplement 1, pp. S848. Abstract Number: P.752. Meeting Info: 27th International Congress of The Transplantation Society, TTS 2018. Madrid, Spain. 30 Jun. 2018-5 Jul. 2018.
[64] Lee et al., Pediatr Gastroenterol Hepatol Nutr. 2017, vol. 20(2), p. 114-123.
[65] Sherrif et al., Liver international: official journal of the International Association for the Study of the Liver 2013, vol. 33, No. 8, pp. 1266-1270.
[66] Blackmore et al., J Clin Exp Hepatol. 2013, vol. 3(2), p. 159-161.
[67] Matte et al., J Pediatr Gastroenterol Nutr. 2010, vol. 51(4), p. 488-493.
[68] Lin et al., Zhongguo Dang Dai Er Ke Za Zhi. 2018, vol. 20(9), p. 758-764.
[69] Harmanci et al., Experimental and Clinical Transplantation 2015, vol. 13, Supp. SUPPL. 2, pp. 76. Abstract Number: P62. Meeting Info: 1st Congress of the Turkic World Transplantation Society. Astana, Kazakhstan. 20 May 2015-22 May 2015.
[70] Herbst et al., Mol Cell Probes. 2015, vol. 29(5), p. 291-298.
[71] Moghadamrad et al., Hepatology. 2013, vol. 57(6), p. 2539-2541.
[72] Holz et al., Zeitschrift fur Gastroenterologie 2016, vol. 54, No. 8. Abstract Number: KV275. Meeting Info: Viszeralmedizin 2016, 71. Jahrestagung der Deutschen Gesellschaft fur Gastroenterologie, Verdauungs- und Stoffwechselkrankheiten mit Sektion Endoskopie—10. Herbsttagung der Deutschen Gesellschaft fur Allgemein- und Viszeralchirurgie. Hamburg, Germany. 21 Sep. 2016-24 Sep. 2016.

[73] Wang et al., PLoS One. 2016; vol. 11(4): e0153114.
[74] Hao et al., International Journal of Clinical and Experimental Pathology 2017, vol. 10(3), p. 3480-3487.
[75] Arnell et al., J Pediatr Gastroenterol Nutr. 2010, vol. 51(4), p. 494-499.
[76] Sharma et al., Indian Journal of Gastroenterology 2017, vol. 36, No. 1, Supp. Supplement 1, pp. A99. Abstract Number: M-20. Meeting Info: 58th Annual Conference of the Indian Society of Gastroenterology, ISGCON 2017. Bhubaneswar, India. 14 Dec. 2017-17 Dec. 2017.
[77] Beauséjour et al., Can J Gastroenterol. 2011, vol. 25(6), p. 311-314.
[78] Imagawa et al., Journal of Pediatric Gastroenterology and Nutrition 2016, vol. 63, Supp. Supplement 2, pp. S51. Abstract Number: 166. Meeting Info: World Congress of Pediatric Gastroenterology, Hepatology and Nutrition 2016. Montreal, QC, Canada. 5 Oct. 2016-8 Oct. 2016.
[79] Peng et al., Zhonghua er ke za zhi (Chinese journal of pediatrics) 2018, vol. 56, No. 6, pp. 440-444.
[80] Tibesar et al., Case Rep Pediatr. 2014, vol. 2014: 185923.
[81] Ng et al., Journal of Pediatric Gastroenterology and Nutrition 2018, vol. 66, Supp. Supplement 2, pp. 860. Abstract Number: H-P-127. Meeting Info: 51st Annual Meeting European Society for Paediatric Gastroenterology, Hepatology and Nutrition, ESPGHAN 2018. Geneva, Switzerland. 9 May 2018-12 May 2018.
[82] Wong et al., Clin Chem. 2008, vol. 54(7), p. 1141-1148.
[83] Pauli-Magnus et al., J Hepatol. 2005, vol. 43(2), p. 342-357.
[84] Jericho et al., Journal of Pediatric Gastroenterology and Nutrition. 60, vol. 3, p. 368-374.
[85] Scheimann et al., Gastroenterology 2007, vol. 132, No. 4, Suppl. 2, pp. A452. Meeting Info.: Digestive Disease Week Meeting/108th Annual Meeting of the American-Gastroenterological-Association. Washington, D.C., USA. May 19-24, 2007. Amer Gastroenterol Assoc; Amer Assoc Study Liver Dis; Amer Soc Gastrointestinal Endoscopy; Soc Surg Alimentary Tract.
[86] Jaquotot-Haerranz et al., Rev Esp Enferm Dig. 2013, vol. 105(1), p. 52-54.
[87] Khosla et al., American Journal of Gastroenterology 2015, vol. 110, No. Suppl. 1, pp. S397. Meeting Info.: 80th Annual Scientific Meeting of the American-College-of-Gastroenterology. Honolulu, Hi., USA. Oct. 16-21, 2015.
[88] Dröge et al., J Hepatol. 2017, vol. 67(6), p. 1253-1264.
[89] Liu et al., Liver International 2010, vol. 30(6), p. 809-815.
[90] Chen et al., Journal of Pediatrics 2002, vol. 140(1), p. 119-124.
[91] U.S. Pat. No. 9,295,677

In some embodiments, the mutation in ABCB11 is selected from A167T, G238V, V284L, E297G, R470Q, R470X, D482G, R487H, A570T, N591S, A865V, G982R, R1153C, and R1268Q.

Provided are methods of treating PFIC (e.g., PFIC-1 and PFIC-2) in a subject that includes performing an assay on a sample obtained from the subject to determine whether the subject has a mutation associated with PFIC (e.g., a ATP8B1, ABCB11, ABCB4, TJP2, NR1H4 or Myo5b mutation), and administering (e.g., specifically or selectively administering) a therapeutically effective amount of a compound of formula (I), or a pharmaceutically acceptable salt thereof, to the subject determined to have a mutation associated with PFIC. In some embodiments, the mutation is a ATP8B1 or ABCB11 mutation. For example, a mutation as provided in any one of Tables 1-4. In some embodiments, the mutation in ATP8B1 is selected from L127P, G308V, T456M, D554N, F529del, I661T, E665X, R930X, R952X, R1014X, and G1040R. In some embodiments, the mutation in ABCB11 is selected from A167T, G238V, V284L, E297G, R470Q, R470X, D482G, R487H, A570T, N591S, A865V, G982R, R1153C, and R1268Q.

Also provided are methods for treating PFIC (e.g., PFIC-1 and PFIC-2) in a subject in need thereof, the method comprising: (a) detecting a mutation associated with PFIC (e.g., a ATP8B1, ABCB11, ABCB4, TJP2, NR1H4 or Myo5b mutation) in the subject; and (b) administering to the subject a therapeutically effective amount of a compound of formula (I), or a pharmaceutically acceptable salt thereof. In some embodiments, methods for treating PFIC can include administering a therapeutically effective amount of a compound of formula (I), or a pharmaceutically acceptable salt thereof, to a subject having a mutation associated with PFIC (e.g., a ATP8B1, ABCB11, ABCB4, TJP2, NR1H4 or Myo5b mutation). In some embodiments, the mutation is a ATP8B1 or ABCB11 mutation. For example, a mutation as provided in any one of Tables 1-4. In some embodiments, the mutation in ATP8B1 is selected from L127P, G308V, T456M, D554N, F529del, I661T, E665X, R930X, R952X, R1014X, and G1040R. In some embodiments, the mutation in ABCB11 is selected from A167T, G238V, V284L, E297G, R470Q, R470X, D482G, R487H, A570T, N591S, A865V, G982R, R1153C, and R1268Q.

In some embodiments, the subject is determined to have a mutation associated with PFIC in a subject or a biopsy sample from the subject through the use of any art recognized tests, including next generation sequencing (NGS). In some embodiments, the subject is determined to have a mutation associated with PFIC using a regulatory agency-approved, e.g., FDA-approved test or assay for identifying a mutation associated with PFIC in a subject or a biopsy sample from the subject or by performing any of the non-limiting examples of assays described herein. Additional methods of diagnosing PFIC are described in Gunaydin, M. et al., Hepat Med. 2018, vol. 10, p. 95-104, incorporated by reference in its entirety herein.

In some embodiments, the treatment of PFIC (e.g., PFIC-1 or PFIC-2) decreases the level of serum bile acids in the subject. In some embodiments, the level of serum bile acids is determined by, for example, an ELISA enzymatic assay or the assays for the measurement of total bile acids as described in Danese et al., PLoS One. 2017, vol. 12(6): e0179200, which is incorporated by reference herein in its entirety. In some embodiments, the level of serum bile acids can decrease by, for example, 10% to 40%, 20% to 50%, 30% to 60%, 40% to 70%, 50% to 80%, or by more than 90% of the level of serum bile acids prior to administration of a compound of formula (I), or a pharmaceutically acceptable salt thereof. In some embodiments, the treatment of PFIC includes treatment of pruritus.

Since LBAT is expressed on hepatocytes, LBAT and dual ASBT/LBAT inhibitor substances need to have at least some bioavailability and free fraction in blood. Because LBAT inhibitor compounds only need to survive from the intestine to the liver, it is expected that a relatively low systemic exposure of such compounds will be sufficient, thereby minimizing the potential risk for any side effects in the rest of the body. It is expected that inhibition of LBAT and ASBT will have at least additive effects in decreasing the intrahepatic bile acid concentration. It is also expected that a dual ASBT/LBAT inhibitor may be able to reduce bile acid levels without inducing diarrhoea, as is sometimes observed with ASBT inhibitors.

Compounds having a high LBAT inhibiting potency and sufficient bioavailability are expected to be particularly suitable for the treatment of hepatitis. Compounds having a dual ASBT/LBAT inhibiting potency and sufficient bioavailability are expected to be particularly suitable for the treatment of non-alcoholic steatohepatitis (NASH).

NASH is a common and serious chronic liver disease that resembles alcoholic liver disease, but that occurs in people who drink little or no alcohol. In NASH patients, fat accumulation in the liver, known as nonalcoholic fatty liver disease (NAFLD) or steatosis, and other factors such as high LDL cholesterol and insulin resistance induce chronic inflammation in the liver and may lead to progressive scarring of tissue, known as fibrosis, and cirrhosis, followed eventually by liver failure and death. Patients with NASH have been found to have significantly higher total serum bile acid concentrations than healthy subjects under fasting conditions (2.2- to 2.4-fold increase in NASH) and at all post-prandial time points (1.7- to 2.2-fold increase in NASH). These are driven by increased taurine- and glycine-conjugated primary and secondary bile acids. Patients with NASH exhibited greater variability in their fasting and post-prandial bile acid profile. These results indicate that patients with NASH have higher fasting and post-prandial exposure to bile acids, including the more hydrophobic and cytotoxic secondary species. Increased bile acid exposure may be involved in liver injury and the pathogenesis of NAFLD and NASH (Ferslew et al., Dig Dis Sci. 2015, vol. 60, p. 3318-3328). It is therefore likely that ASBT and/or LBAT inhibition will be beneficial for the treatment of NASH.

NAFLD is characterized by hepatic steatosis with no secondary causes of hepatic steatosis including excessive alcohol consumption, other known liver diseases, or long-term use of a steatogenic medication (Chalasani et al., Hepatology 2018, vol. 67(1), p. 328-357). NAFLD can be categorized into non-alcoholic fatty liver (NAFL) and non-alcoholic steatohepatitis (NASH). According to Chalasani et al., NAFL is defined as the presence of ≥5% hepatic steatosis without evidence of hepatocellular injury in the form of hepatocyte ballooning. NASH is defined as the presence of ≥5% hepatic steatosis and inflammation with hepatocyte injury (e.g., ballooning), with or without any liver fibrosis. NASH is also commonly associated with hepatic inflammation and liver fibrosis, which can progress to cirrhosis, end-stage liver disease, and hepatocellular carcinoma. While liver fibrosis is not always present in NASH, the severity of the fibrosis, when present, can be linked to long-term outcomes.

There are many approaches used to assess and evaluate whether a subject has NAFLD and if so, the severity of the disease, including differentiating whether the NAFLD is NAFL or NASH. In some embodiments, the severity of NAFLD can be assessed using the NAS. In some embodiments, treatment of NAFLD can be assessed using the NAS. In some embodiments, the NAS can be determined as described in Kleiner et al., *Hepatology*. 2005, 41(6):1313-1321, which is hereby incorporated by reference in its entirety. See, for example, Table 6 for a simplified NAS scheme adapted from Kleiner.

TABLE 6

Example of the NAFLD Activity Score (NAS) with Fibrosis Stage

| Feature | Degree | Score |
|---|---|---|
| Steatosis | <5% | 0 |
| | 5-33% | 1 |

TABLE 6-continued

Example of the NAFLD Activity Score (NAS) with Fibrosis Stage

| Feature | Degree | Score |
|---|---|---|
| | >33-66% | 2 |
| | >66% | 3 |
| Lobular Inflammation | No foci | 0 |
| | <2 foci/200x | 1 |
| | 2-4 foci/200x | 2 |
| | >4 foci/200x | 3 |
| Ballooning degeneration | None | 0 |
| | Few | 1 |
| | Many cells/Prominent ballooning | 2 |
| Fibrosis | None | 0 |
| | Perisinusoidal or periportal | 1 |
| | Perisinusoidal & portal/periportal | 2 |
| | Bridging fibrosis | 3 |
| | Cirrhosis | 4 |

In some embodiments, the NAS is determined non-invasively, for example, as described in U.S. Application Publication No. 2018/0140219, which is incorporated by reference herein in its entirety. In some embodiments, the NAS is determined for a sample from the subject prior to administration of a compound of formula (I), or a pharmaceutically acceptable salt thereof. In some embodiments, the NAS is determined during the period of time or after the period of time of administration of a compound of formula (I), or a pharmaceutically acceptable salt thereof. In some embodiments, a lower NAS score during the period of time or after the period of time of administration of a compound of formula (I), or a pharmaceutically acceptable salt thereof compared to prior to administration of the compound of formula (I), or a pharmaceutically acceptable salt thereof indicates treatment of NAFLD (e.g., NASH). For example, a decrease in the NAS by 1, by 2, by 3, by 4, by 5, by 6, or by 7 indicates treatment of NAFLD (e.g., NASH). In some embodiments, the NAS following administration of a compound of formula (I), or a pharmaceutically acceptable salt thereof, is 7 or less. In some embodiments, the NAS during the period of time of administration of a compound of formula (I), or a pharmaceutically acceptable salt thereof, is 5 or less, 4 or less, 3 or less, or 2 or less. In some embodiments, the NAS during the period of time of administration of a compound of formula (I), or a pharmaceutically acceptable salt thereof, is 7 or less. In some embodiments, the NAS during the period of time of administration of a compound of formula (I), or a pharmaceutically acceptable salt thereof, is 5 or less, 4 or less, 3 or less, or 2 or less. In some embodiments, the NAS after the period of time of administration of a compound of formula (I), or a pharmaceutically acceptable salt thereof, is 7 or less. In some embodiments, the NAS after the period of time of administration of a compound of formula (I), or a pharmaceutically acceptable salt thereof, is 5 or less, 4 or less, 3 or less, or 2 or less.

Additional approaches of assessing and evaluating NASH in a subject include determining one or more of hepatic steatosis (e.g., accumulation of fat in the liver); hepatic inflammation; biomarkers indicative of one or more of liver damage, hepatic inflammation, liver fibrosis, and/or liver cirrhosis (e.g., serum markers and panels). Further examples of physiological indicators of NASH can include liver morphology, liver stiffness, and the size or weight of the subject's liver. In some embodiments, NASH in the subject is evidenced by an accumulation of hepatic fat and detection of a biomarker indicative of liver damage. For example, elevated serum ferritin and low titers of serum autoantibodies can be common features of NASH.

In some embodiments, methods to assess NASH include magnetic resonance imaging, either by spectroscopy or by proton density fat fraction (MRI-PDFF) to quantify steatosis, transient elastography (FIBROSCAN®), hepatic venous pressure gradient (HPVG), hepatic stiffness measurement with MRE for diagnosing significant liver fibrosis and/or cirrhosis, and assessing histological features of liver biopsy. In some embodiments, magnetic resonance imaging is used to detect one or more of steatohepatitis (NASH-MRI), liver fibrosis (Fibro-MRI), and steatosis. See, for example, U.S. Application Publication Nos. 2016/146715 and 2005/0215882, each of which are incorporated herein by reference in their entireties.

In some embodiments, treatment of NASH can include a decrease of one or more symptoms associated with NASH; reduction in the amount of hepatic steatosis; a decrease in the NAS; a decrease in hepatic inflammation; a decrease in the level of biomarkers indicative of one or more of liver damage, inflammation, liver fibrosis, and/or liver cirrhosis; and a reduction in fibrosis and/or cirrhosis, a lack of further progression of fibrosis and/or cirrhosis, or a slowing of the progression of fibrosis and/or cirrhosis in the subject following administration of one or more doses of a compound of formula (I), or a pharmaceutically acceptable salt thereof.

In some embodiments, treatment of NASH comprises a decrease of one or more symptoms associated with NASH in the subject. Exemplary symptoms can include one or more of an enlarged liver, fatigue, pain in the upper right abdomen, abdominal swelling, enlarged blood vessels just beneath the skin's surface, enlarged breasts in men, enlarged spleen, red palms, jaundice, and pruritus. In some embodiments, the subject is asymptomatic. In some embodiments, the total body weight of the subject does not increase. In some embodiments, the total body weight of the subject decreases. In some embodiments, the body mass index (BMI) of the subject does not increase. In some embodiments, the body mass index (BMI) of the subject decreases. In some embodiments, the waist and hip (WTH) ratio of the subject does not increase. In some embodiments, the waist and hip (WTH) ratio of the subject decreases.

In some embodiments, treatment of NASH can be assessed by measuring hepatic steatosis. In some embodiments, treatment of NASH comprises a reduction in hepatic steatosis following administration of a compound of formula (I), or a pharmaceutically acceptable salt thereof, as described herein. In some embodiments, hepatic steatosis is determined by one or more methods selected from the group consisting of ultrasonography, computed tomography (CT), magnetic resonance imaging, magnetic resonance spectroscopy (MRS), magnetic resonance elastography (MRE), transient elastography (TE) (e.g., FIBROSCAN®), measurement of liver size or weight, or by liver biopsy (see, e.g., Di Lascio et al., Ultrasound Med Biol. 2018, vol. 44(8), p. 1585-1596; Lv et al., J Clin Transl Hepatol. 2018, vol. 6(2), p. 217-221; Reeder et al., J Magn Reson Imaging. 2011, vol. 34(4), spcone; and de Lédinghen V, et al., J Gastroenterol Hepatol. 2016, vol. 31(4), p. 848-855, each of which are incorporated herein by reference in their entireties). A subject diagnosed with NASH can have greater than about 5% hepatic steatosis, for example, greater than about 5% to about 25%, about 25% to about 45%, about 45% to about 65%, or greater than about 65% hepatic steatosis. In some embodiments, a subject with greater than about 5% to about 33% hepatic steatosis has stage 1 hepatic steatosis, a subject with about 33% to about 66% hepatic steatosis has stage 2 hepatic steatosis, and a subject with greater than about 66% hepatic steatosis has stage 3 hepatic steatosis.

In some embodiments, the amount of hepatic steatosis is determined prior to administration of a compound of formula (I), or a pharmaceutically acceptable salt thereof. In some embodiments, the amount of hepatic steatosis is determined during the period of time or after the period of time of administration of the compound of formula (I), or a pharmaceutically acceptable salt thereof. In some embodiments, a reduction in the amount of hepatic steatosis during the period of time or after the period of time of administration of the compound of formula (I), or a pharmaceutically acceptable salt thereof, compared to prior to administration of the compound of formula (I), or a pharmaceutically acceptable salt thereof, indicates treatment of NASH. For example, a reduction in the amount of hepatic steatosis by about 1% to about 50%, about 25% to about 75%, or about 50% to about 100% indicates treatment of NASH. In some embodiments, a reduction in the amount of hepatic steatosis by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% indicates treatment of NASH.

In some embodiments, the presence of hepatic inflammation is determined by one or more methods selected from the group consisting of biomarkers indicative of hepatic inflammation and a liver biopsy sample(s) from the subject. In some embodiments, the severity of hepatic inflammation is determined from a liver biopsy sample(s) from the subject. For example, hepatic inflammation in a liver biopsy sample can be assessed as described in Kleiner et al., Hepatology 2005, vol. 41(6), p. 1313-1321 and Brunt et al., Am J Gastroenterol 1999, vol. 94, p. 2467-2474, each of which are hereby incorporated by reference in their entireties. In some embodiments, the severity of hepatic inflammation is determined prior to administration of a compound of formula (I), or a pharmaceutically acceptable salt thereof. In some embodiments, the severity of hepatic inflammation is determined during the period of time or after the period of time of administration of a compound of formula (I), or a pharmaceutically acceptable salt thereof. In some embodiments, a decrease in the severity of hepatic inflammation during the period of time or after the period of time of administration of a compound of formula (I), or a pharmaceutically acceptable salt thereof, compared to prior to administration of the compound of formula (I), or a pharmaceutically acceptable salt thereof, indicates treatment of NASH. For example, a decrease in the severity of hepatic inflammation by about 1% to about 50%, about 25% to about 75%, or about 50% to about 100% indicates treatment of NASH. In some embodiments, a decrease in the severity of hepatic inflammation by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% indicates treatment of NASH.

In some embodiments, treatment of NASH comprises treatment of fibrosis and/or cirrhosis, e.g., a decrease in the severity of fibrosis, a lack of further progression of fibrosis and/or cirrhosis, or a slowing of the progression of fibrosis and/or cirrhosis. In some embodiments, the presence of fibrosis and/or cirrhosis is determined by one or more methods selected from the group consisting of transient elastography (e.g., FIBROSCAN®), non-invasive markers of hepatic fibrosis, and histological features of a liver biopsy. In some embodiments, the severity (e.g., stage) of fibrosis is determined by one or more methods selected from the group consisting of transient elastography (e.g., FIBROSCAN®), a fibrosis-scoring system, biomarkers of hepatic fibrosis (e.g., non-invasive biomarkers), and hepatic venous pressure gradient (HVPG). Non-limiting examples of fibrosis scoring systems include the NAFLD fibrosis scoring system (see, e.g., Angulo et al., Hepatology 2007, vol. 45(4), p. 846-54), the fibrosis scoring system in Brunt et al., Am. J. Gastroenterol. 1999, vol. 94, p. 2467-2474, the fibrosis scoring system in Kleiner et al., Hepatology 2005, vol. 41(6), p. 1313-1321, and the ISHAK fibrosis scoring system (see Ishak et al., J. Hepatol. 1995, vol. 22, p. 696-699), the contents of each of which are incorporated by reference herein in their entireties.

In some embodiments, the severity of fibrosis is determined prior to administration of a compound of formula (I), or a pharmaceutically acceptable salt thereof. In some embodiments, the severity of fibrosis is determined during the period of time or after the period of time of administration of a compound of formula (I), or a pharmaceutically acceptable salt thereof. In some embodiments, a decrease in the severity of fibrosis during the period of time or after the period of time of administration of a compound of formula (I), or a pharmaceutically acceptable salt thereof, compared to prior to administration of the compound of formula (I), or a pharmaceutically acceptable salt thereof, indicates treatment of NASH. In some embodiments, a decrease in the severity of fibrosis, a lack of further progression of fibrosis and/or cirrhosis, or a slowing of the progression of fibrosis and/or cirrhosis indicates treatment of NASH. In some embodiments, the severity of fibrosis is determined using a scoring system such as any of the fibrosis scoring systems described herein, for example, the score can indicate the stage of fibrosis, e.g., stage 0 (no fibrosis), stage 1, stage 2, stage 3, and stage 4 (cirrhosis) (see, e.g., Kleiner et al). In some embodiments, a decrease in the stage of the fibrosis is a decrease in the severity of the fibrosis. For example, a decrease by 1, 2, 3, or 4 stages is a decrease in the severity of the fibrosis. In some embodiments, a decrease in the stage, e.g., from stage 4 to stage 3, from stage 4 to stage 2, from stage 4 to stage 1, from stage 4 to stage 0, from stage 3 to stage 2, from stage 3 to stage 1, from stage 3 to stage 0, from stage 2 to stage 1, from stage 2 to stage 0, or from stage 1 to stage 0 indicates treatment of NASH. In some embodiments, the stage of fibrosis decreases from stage 4 to stage 3, from stage 4 to stage 2, from stage 4 to stage 1, from stage 4 to stage 0, from stage 3 to stage 2, from stage 3 to stage 1, from stage 3 to stage 0, from stage 2 to stage 1, from stage 2 to stage 0, or from stage 1 to stage 0 following administration of a compound of formula (I), or a pharmaceutically acceptable salt thereof, compared to prior to administration of the compound of formula (I), or a pharmaceutically acceptable salt thereof. In some embodiments, the stage of fibrosis decreases from stage 4 to stage 3, from stage 4 to stage 2, from stage 4 to stage 1, from stage 4 to stage 0, from stage 3 to stage 2, from stage 3 to stage 1, from stage 3 to stage 0, from stage 2 to stage 1, from stage 2 to stage 0, or from stage 1 to stage 0 during the period of time of administration of a compound of formula (I), or a pharmaceutically acceptable salt thereof, compared to prior to administration of the compound of formula (I), or a pharmaceutically acceptable salt thereof. In some embodiments, the stage of fibrosis decreases from stage 4 to stage 3, from stage 4 to stage 2, from stage 4 to stage 1, from stage 4 to stage 0, from stage 3 to stage 2, from stage 3 to stage 1, from stage 3 to stage 0, from stage 2 to stage 1, from stage 2 to stage 0, or from stage 1 to stage 0 after the period of time of administration of a compound of formula (I), or a pharmaceutically acceptable salt thereof, compared to prior to administration of the compound of formula (I), or a pharmaceutically acceptable salt thereof.

In some embodiments, the presence of NASH is determined by one or more biomarkers indicative of one or more of liver damage, inflammation, liver fibrosis, and/or liver cirrhosis or scoring systems thereof. In some embodiments, the severity of NASH is determined by one or more biomarkers indicative of one or more of liver damage, inflammation, liver fibrosis, and/or liver cirrhosis or scoring systems thereof. The level of the biomarker can be determined by, for example, measuring, quantifying, and monitoring the expression level of the gene or mRNA encoding the biomarker and/or the peptide or protein of the biomarker. Non-limiting examples of biomarkers indicative of one or more of liver damage, inflammation, liver fibrosis, and/or liver cirrhosis and/or scoring systems thereof include the aspartate aminotransferase (AST) to platelet ratio index (APRI); the aspartate aminotransferase (AST) and alanine aminotransferase (ALT) ratio (AAR); the FIB-4 score, which is based on the APRI, alanine aminotransferase (ALT) levels, and age of the subject (see, e.g., McPherson et al., Gut 2010, vol. 59(9), p. 1265-9, which is incorporated by reference herein in its entirety); hyaluronic acid; pro-inflammatory cytokines; a panel of biomarkers consisting of α2-macroglobulin, haptoglobin, apolipoprotein A1, bilirubin, gamma glutamyl transpeptidase (GGT) combined with a subject's age and gender to generate a measure of fibrosis and necroinflammatory activity in the liver (e.g., FIBROTEST®, FIBROSURE®), a panel of biomarkers consisting of bilirubin, gamma-glutamyltransferase, hyaluronic acid, α2-macroglobulin combined with the subject's age and sex (e.g., HEPASCORE®; see, e.g., Adams et al., Clin. Chem. 2005, vol. 51(10), p. 1867-1873), and a panel of biomarkers consisting of tissue inhibitor of metalloproteinase-1, hyaluronic acid, and α2-macroglobulin (e.g., FIBROSPECT®); a panel of biomarkers consisting of tissue inhibitor of metalloproteinases 1 (TIMP-1), amino-terminal propeptide of type III procollagen (PIIINP) and hyaluronic acid (HA) (e.g., the Enhanced Liver Fibrosis (ELF) score, see, e.g., Lichtinghagen R, et al., J Hepatol. 2013 August; 59(2):236-42, which is incorporated by reference herein in its entirety). In some embodiments, the presence of fibrosis is determined by one or more of the FIB-4 score, a panel of biomarkers consisting of α2-macroglobulin, haptoglobin, apolipoprotein A1, bilirubin, gamma glutamyl transpeptidase (GGT) combined with a subject's age and gender to generate a measure of fibrosis and necroinflammatory activity in the liver (e.g., FIBROTEST®, FIBROSURE®), a panel of biomarkers consisting of bilirubin, gamma-glutamyltransferase, hyaluronic acid, α2-macroglobulin combined with the subject's age and sex (e.g., HEPASCORE®; see, e.g., Adams et al., Clin. Chem. 2005, vol. 51(10), p. 1867-1873), and a panel of biomarkers consisting of tissue inhibitor of metalloproteinase-1, hyaluronic acid, and α2-macroglobulin (e.g., FIBROSPECT®); and a panel of biomarkers consisting of tissue inhibitor of metalloproteinases 1 (TIMP-1), amino-terminal propeptide of type III procollagen (PIIINP) and hyaluronic acid (HA) (e.g., the Enhanced Liver Fibrosis (ELF) score). In some embodiments, the level of aspartate aminotransferase (AST) does not increase. In some embodiments, the level of aspartate aminotransferase (AST) decreases. In some embodiments, the level of alanine aminotransferase (ALT) does not increase. In some embodiments, the level of alanine aminotransferase (ALT) decreases. In some embodiments, the "level" of an enzyme refers to the concentration of the enzyme, e.g., within blood. For example, the level of AST or ALT can be expressed as Units/L.

In some embodiments, the severity of fibrosis is determined by one or more of the FIB-4 score, a panel of biomarkers consisting of α2-macroglobulin, haptoglobin, apolipoprotein A1, bilirubin, gamma glutamyl transpeptidase (GGT) combined with a subject's age and gender to generate a measure of fibrosis and necroinflammatory activity in the liver (e.g., FIBROTEST®, FIBROSURE®), a panel of biomarkers consisting of bilirubin, gamma-glutamyltransferase, hyaluronic acid, α2-macroglobulin combined with the subject's age and sex (e.g., HEPASCORE®; see, e.g., Adams et al., Clin. Chem. 2005, vol. 51(10), p. 1867-1873, which is incorporated by reference herein in its entirety), and a panel of biomarkers consisting of tissue inhibitor of metalloproteinase-1, hyaluronic acid, and α2-macroglobulin (e.g., FIBROSPECT®); and a panel of biomarkers consisting of tissue inhibitor of metalloproteinases 1 (TIMP-1), amino-terminal propeptide of type III procollagen (PIIINP) and hyaluronic acid (HA) (e.g., the Enhanced Liver Fibrosis (ELF) score).

In some embodiments, hepatic inflammation is determined by the level of liver inflammation biomarkers, e.g., pro-inflammatory cytokines. Non-limiting examples of biomarkers indicative of liver inflammation include interleukin-(IL) 6, interleukin-(IL) 1β, tumor necrosis factor (TNF)-α, transforming growth factor (TGF)-β, monocyte chemotactic protein (MCP)-1, C-reactive protein (CRP), PAI-1, and collagen isoforms such as Col1a1, Col1a2, and Col4a1 (see, e.g., Neuman, et al., Can. J. Gastroenterol. Hepatol. 2014, vol. 28(11), p. 607-618 and U.S. Pat. No. 9,872,844, each of which are incorporated by reference herein in their entireties). Liver inflammation can also be assessed by change of macrophage infiltration, e.g., measuring a change of CD68 expression level. In some embodiments, liver inflammation can be determined by measuring or monitoring serum levels or circulating levels of one or more of interleukin-(IL) 6, interleukin-(IL) 1β, tumor necrosis factor (TNF)-α, transforming growth factor (TGF)-β, monocyte chemotactic protein (MCP)-1, and C-reactive protein (CRP).

In some embodiments, the level of one or more biomarkers indicative of one or more of liver damage, inflammation, liver fibrosis, and/or liver cirrhosis is determined for a sample from the subject prior to administration of a compound of formula (I), or a pharmaceutically acceptable salt thereof. In some embodiments, the level of one or more biomarkers indicative of one or more of liver damage, inflammation, liver fibrosis, and/or liver cirrhosis is determined during the period of time or after the period of time of administration of a compound of formula (I), or a pharmaceutically acceptable salt thereof. In some embodiments, a decrease in the level of one or more biomarkers indicative of one or more of liver damage, inflammation, liver fibrosis, and/or liver cirrhosis during the period of time or after the period of time of administration of a compound of formula (I), or a pharmaceutically acceptable salt thereof, compared to prior to administration of the compound of formula (I), or a pharmaceutically acceptable salt thereof, indicates treatment of NASH. For example, a decrease in the level of one or more biomarkers indicative of one or more of liver damage, inflammation, liver fibrosis, and/or liver cirrhosis by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% indicates treatment of NASH. In some embodiments, the decrease in the level of one or more biomarkers indicative of one or more of liver damage, inflammation, liver fibrosis, and/or liver cirrhosis following administration of the compound of formula (I), or a pharmaceutically acceptable salt thereof, is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%. In some embodiments, the level of one or more biomarkers indicative of one or more of liver damage, inflammation, liver fibrosis, and/or liver cirrhosis during the period of time of administration of a compound of formula (I), or a pharmaceutically acceptable salt thereof, is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%. In some embodiments, the level of one or more biomarkers indicative of one or more of liver damage, inflammation, liver fibrosis, and/or liver cirrhosis after the period of time of administration of a compound of formula (I), or a pharmaceutically acceptable salt thereof, is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%.

In some embodiments, the treatment of NASH decreases the level of serum bile acids in the subject. In some embodiments, the level of serum bile acids is determined by, for example, an ELISA enzymatic assay or the assays for the measurement of total bile acids as described in Danese et al., PLoS One. 2017, vol. 12(6): e0179200, which is incorporated by reference herein in its entirety. In some embodiments, the level of serum bile acids can decrease by, for example, 10% to 40%, 20% to 50%, 30% to 60%, 40% to 70%, 50% to 80%, or by more than 90% of the level of serum bile acids prior to administration of a compound of formula (I), or a pharmaceutically acceptable salt thereof. In some embodiments, the NASH is NASH with attendant cholestasis. In cholestasis, the release of bile, including bile acids, from the liver is blocked. Bile acids can cause hepatocyte damage (see, e.g., Perez M J, Briz O. World J. Gastroenterol. 2009, vol. 15(14), p. 1677-1689) likely leading to or increasing the progression of fibrosis (e.g., cirrhosis) and increasing the risk of hepatocellular carcinoma (see, e.g., Sorrentino P et al., *Dig. Dis. Sci.* 2005, vol. 50(6), p. 1130-1135 and Satapathy S K and Sanyal A J. *Semin. Liver Dis.* 2015, vol. 35(3), p. 221-235, each of which are incorporated by reference herein in their entireties). In some embodiments, the treatment of NASH includes treatment of pruritus. In some embodiments, the treatment of NASH with attendant cholestasis includes treatment of pruritus. In some embodiments, a subject with NASH with attendant cholestasis has pruritus.

Exemplary biomarkers for NASH are provided in Table 7.

TABLE 7

Exemplary NASH biomarkers

Liver Fibrosis Biomarkers

Aspartate aminotransferase (AST) to platelet ratio index (APRI)
Aspartate aminotransferase (AST) and alanine aminotransferase (ALT) ratio (AAR)
FIB-4 score[1]
Hyaluronic acid
Pro-inflammatory cytokines
A panel including α2-macroglobulin, haptoglobin, apolipoprotein A1, bilirubin, gamma glutamyl transpeptidase (GGT) combined with a subject's age and gender to generate a measure of fibrosis and necroinflammatory activity in the liver (e.g., FIBROTEST ®, FIBROSURE ®)
A panel including bilirubin, gamma-glutamyltransferase, hyaluronic acid, α2-macroglobulin combined with the subject's age and sex (e.g., HEPASCORE ®[2])
A panel including tissue inhibitor of metalloproteinase-1, hyaluronic acid, and α2-macroglobulin (e.g., FIBROSPECT ®)
A panel including tissue inhibitor of metalloproteinases 1 (TIMP-1), amino-terminal propeptide of type III procollagen (PIIINP) and hyaluronic acid (HA) (e.g., the Enhanced Liver Fibrosis (ELF) score[3])
Liver inflammation biomarkers[4,5]

Interleukin-(IL) 6
Interleukin-(IL) 1β
Tumor necrosis factor (TNF)-α
Transforming growth factor (TGF)-β
Monocyte chemotactic protein (MCP)-1
C-reactive protein (CRP)
PAI-1
Collagen isoforms (e.g., Col1a1, Col1a2, and Col4a1)
Change of macrophage infiltration (e.g., a change of CD68 expression level)

References for Table 7
[1]McPherson et al., Gut. 2010, vol. 59(9), p. 1265-1269.
[2]Adams, et al. Clin Chem. 2005, vol. 51(10), p. 1867-1873.
[3]Lichtinghagen, et al. J Hepatol. 2013, vol. 59(2), p. 236-242.
[4]Neuman, et al. Can J Gastroenterol Hepatol. 2014, vol. 28(11), p. 607-618.
[5]U.S. Pat. No. 9,872,844

Some compounds of formula (I), or pharmaceutically acceptable salts thereof, may show a higher free fraction in plasma. In some embodiments, the free fraction is greater than about 0.2%, such as greater than about 0.4%, such as greater than about 0.6%, such as greater than about 0.8%, such as greater than about 1.0%, such as greater than about 1.25%, such as greater than about 1.5%, such as greater than about 1.75%, such as greater than about 2.0%, such as greater than about 2.5%, such as greater than about 3%, such as greater than about 4%, such as greater than about 5%, such as greater than about 7.5%, such as greater than about 10%, or such as greater than about 20%.

Some compounds of formula (I), or pharmaceutically acceptable salts thereof, may be excreted in urine. In some embodiments, the fraction of the compound that is excreted in urine is greater than about 0.2%, such as greater than about 0.4%, such as greater than about 0.6%, such as greater than about 0.8%, such as greater than about 1.0%, such as greater than about 2%, such as greater than about 3%, such as greater than about 5%, such as greater than about 7.5%, such as greater than about 10%, such as greater than about 15%, such as greater than about 20%, such as greater than about 30%, or such as greater than about 50%.

Following absorption from the intestine, some compounds of formula (I), or pharmaceutically acceptable salts thereof, may be circulated via the enterohepatic circulation. In some embodiments, the fraction of the compound that is circulated via the enterohepatic circulation is greater than about 0.1%, such as greater than about 0.2%, such as greater than about 0.3%, such as greater than about 0.5%, such as greater than about 1.0%, such as greater than about 1.5%, such as greater than about 2%, such as greater than about 3%, such as greater than about 5%, such as greater than about 7%, such as greater than about 10%, such as greater than about 15%, such as greater than about 20%, such as greater than about 30% or such as greater than about 50%.

Some compounds of formula (I), or pharmaceutically acceptable salts thereof, may cause renal excretion of bile salts. In some embodiments, the fraction of circulating bile acids that is excreted by the renal route is greater than about 1%, such as greater than about 2%, such as greater than about 5%, such as greater than about 7%, such as greater than about 10%, such as greater than about 15%, such as greater than about 20%, or such as greater than about 25%.

Some compounds of formula (I), or pharmaceutically acceptable salts thereof, may show improved or optimal permeability. The permeability may be measured in Caco2 cells, and values are given as Papp (apparent permeability) values in cm/s. In some embodiments, the permeability is greater than at least about $0.1 \times 10^{-6}$ cm/s, such as greater than about $0.2 \times 10^{-6}$ cm/s, such as greater than about $0.4 \times 10^{-6}$ cm/s, such as greater than about $0.7 \times 10^{-6}$ cm/s, such as greater than about $1.0 \times 10^{-6}$ cm/s, such as greater than about $2 \times 10^{-6}$ cm/s, such as greater than about $3 \times 10^{-6}$ cm/s, such as greater than about $5 \times 10^{-6}$ cm/s, such as greater than about $7 \times 10^{-6}$ cm/s, such as greater than about $10 \times 10^{-6}$ cm/s, such as greater than about $15 \times 10^{-6}$ cm/s.

Some compounds of formula (I), or pharmaceutically acceptable salts thereof, may show an improved or optimal bioavailability. In some embodiments, the oral bioavailability is greater than about 5%, such as greater than about 7%, such as greater than about 10%, such as greater than about 15%, such as greater than about 20%, such as greater than about 30%, such as greater than about 40%, such as greater than about 50%, such as greater than about 60%, such as greater than about 70% or such as greater than about 80%. In other embodiments, the oral bioavailability is between about 10 and about 90%, such as between about 20 and about 80%, such as between about 30 and about 70% or such as between about 40 and about 60%.

Some compounds of formula (I), or pharmaceutically acceptable salts thereof, may be a substrate to relevant transporters in the kidney.

Some compounds of formula (I), or pharmaceutically acceptable salts thereof, may give rise to concentrations of bile acids in the intestine, the liver and in serum that do not cause adverse gastrointestinal effects.

Some compounds of formula (I), or pharmaceutically acceptable salts thereof, may decrease the concentration of bile acids in the liver without causing gastrointestinal disorders such as diarrhoea.

As used herein, the terms "treatment", "treat" and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

A suitable pharmaceutically acceptable salt of a compound of the invention is, for example, a base-addition salt of a compound of the invention which is sufficiently acidic, such as an alkali metal salt (e.g., a sodium or potassium salt), an alkaline earth metal salt (e.g., a calcium or magnesium salt), an ammonium salt, or a salt with an organic base which affords a physiologically acceptable cation, for example a salt with methylamine, dimethylamine, trimethylamine, piperidine, morpholine or tris-(2-hydroxyethyl)amine.

Some compounds of formula (I), or pharmaceutically acceptable salts thereof, may have chiral centres and/or geometric isomeric centres (E- and Z-isomers). It is to be understood that the invention encompasses all such optical isomers, diastereoisomers and geometric isomers that possess ASBT and/or LBAT inhibitory activity. The invention also encompasses any and all tautomeric forms of compounds of formula (I), or pharmaceutically acceptable salts thereof, that possess ASBT and/or LBAT inhibitory activity. Certain compounds of formula (I), or pharmaceutically acceptable salts thereof, may exist in unsolvated as well as solvated forms, such as, for example, hydrated forms. It is to be understood that the invention encompasses all such solvated forms that possess ASBT and/or LBAT inhibitory activity.

In another aspect, the invention relates to a pharmaceutical composition comprising a therapeutically effective amount of a compound of formula (I), or a pharmaceutically acceptable salt thereof, and one or more pharmaceutically acceptable excipients. The excipients may e.g. include fillers, binders, disintegrants, glidants and lubricants. In general, pharmaceutical compositions may be prepared in a conventional manner using conventional excipients.

Examples of suitable fillers include, but are not limited to, dicalcium phosphate dihydrate, calcium sulfate, lactose (such as lactose monohydrate), sucrose, mannitol, sorbitol, cellulose, microcrystalline cellulose, dry starch, hydrolyzed starches and pregelatinized starch. In certain embodiments, the filler is mannitol and/or microcrystalline cellulose.

Examples of suitable binders include, but are not limited to, starch, pregelatinized starch, gelatin, sugars (such as sucrose, glucose, dextrose, lactose and sorbitol), polyethylene glycol, waxes, natural and synthetic gums (such as acacia gum and tragacanth gum), sodium alginate, cellulose derivatives (such as hydroxypropylmethylcellulose (or hypromellose), hydroxypropylcellulose and ethylcellulose) and synthetic polymers (such as acrylic acid and methacrylic acid copolymers, methacrylic acid copolymers, methyl methacrylate copolymers, aminoalkyl methacrylate copolymers, polyacrylic acid/polymethacrylic acid copolymers and polyvinylpyrrolidone (povidone)). In certain embodiments, the binder is hydroxypropylmethylcellulose (hypromellose).

Examples of suitable disintegrants include, but are not limited to, dry starch, modified starch (such as (partially) pregelatinized starch, sodium starch glycolate and sodium carboxymethyl starch), alginic acid, cellulose derivatives (such as sodium carboxymethylcellulose, hydroxypropyl cellulose, and low substituted hydroxypropyl cellulose (L-HPC)) and cross-linked polymers (such as carmellose, croscarmellose sodium, carmellose calcium and cross-linked PVP (crospovidone)). In certain embodiments, the disintegrant is croscarmellose sodium.

Examples of suitable glidants and lubricants include, but are not limited to, talc, magnesium stearate, calcium stearate, stearic acid, glyceryl behenate, colloidal silica, aqueous silicon dioxide, synthetic magnesium silicate, fine granulated silicon oxide, starch, sodium lauryl sulfate, boric acid, magnesium oxide, waxes (such as carnauba wax), hydrogenated oil, polyethylene glycol, sodium benzoate, polyethylene glycol, and mineral oil. In certain embodiments, the glidant or lubricant is magnesium stearate or colloidal silica.

The pharmaceutical composition may be conventionally coated with one or more coating layers.

Enteric coating layers or coating layers for delayed or targeted release of the compound of formula (I), or pharmaceutically acceptable salts thereof, are also contemplated. The coating layers may comprise one or more coating agents, and may optionally comprise plasticizers and/or pigments (or colorants).

Example of suitable coating agents include, but are not limited to, cellulose-based polymers (such as ethylcellulose, hydroxypropylmethylcellulose (or hypromellose), hydroxypropylcellulose, cellulose acetate phthalate, cellulose acetate succinate, hydroxypropyl methylcellulose acetate succinate and hydroxypropyl methylcellulose phthalate), vinyl-based polymers (such as polyvinyl alcohol) and polymers based on acrylic acid and derivatives thereof (such as acrylic acid and methacrylic acid copolymers, methacrylic acid copolymers, methyl methacrylate copolymers, aminoalkyl methacrylate copolymers, polyacrylic acid/polymethacrylic acid copolymers). In certain embodiments, the coating agent is hydroxypropylmethylcellulose. In other embodiments, the coating agent is polyvinyl alcohol.

Examples of suitable plasticizers include, but are not limited to, triethyl citrate, glyceryl triacetate, tributyl citrate, diethyl phthalate, acetyl tributyl citrate, dibutyl phthalate, dibutyl sebacate and polyethylene glycol. In certain embodiments, the plasticizer is polyethylene glycol.

Examples of suitable pigments include, but are not limited to, titanium dioxide, iron oxides (such as yellow, brown, red or black iron oxides) and barium sulfate.

The pharmaceutical composition may be in a form that is suitable for oral administration, for parenteral injection (including intravenous, subcutaneous, intramuscular and intravascular injection), for topical administration of for rectal administration. In a preferred embodiment, the pharmaceutical composition is in a form that is suitable for oral administration, such as a tablet or a capsule.

The dosage required for the therapeutic or prophylactic treatment will depend on the route of administration, the severity of the disease, the age and weight of the patient and other factors normally considered by the attending physician, when determining the appropriate regimen and dosage level for a particular patient.

The amount of the compound to be administered will vary for the patient being treated, and may vary from about 1 µg/kg of body weight to about 50 mg/kg of body weight per day. A unit dose form, such as a tablet or capsule, will usually contain about 1 to about 250 mg of active ingredient, such as about 1 to about 100 mg, or such as about 1 to about 50 mg, or such as about 1 to about 20 mg, e.g. about 2.5 mg, or about 5 mg, or about 10 mg, or about 15 mg. The daily dose can be administered as a single dose or divided into one, two, three or more unit doses. An orally administered daily dose of a bile acid modulator is preferably within about 0.1 to about 250 mg, more preferably within about 1 to about 100 mg, such as within about 1 to about 5 mg, such as within about 1 to about 10 mg, such as within about 1 to about 15 mg, or such as within about 1 to about 20 mg.

In another aspect, the invention relates to a compound of formula (I)

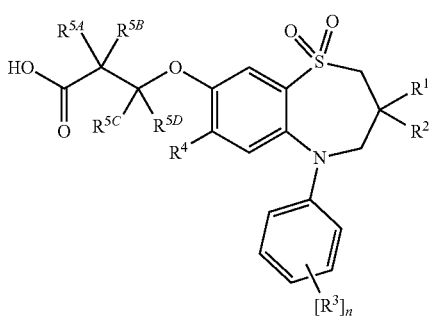

(I)

wherein
- $R^1$ and $R^2$ are each independently $C_{1-4}$ alkyl;
- $R^3$ is independently selected from the group consisting of hydrogen, halogen, hydroxy, $C_{1-4}$ alkyl, $C_{1-4}$ haloalkyl, $C_{1-4}$ alkoxy, $C_{1-4}$ haloalkoxy, cyano, nitro, amino, N—($C_{1-4}$ alkyl)amino, N,N-di($C_{1-4}$ alkyl)amino and N-(aryl-$C_{1-4}$ alkyl)amino;
- n is an integer 1, 2 or 3;
- $R^4$ is selected from the group consisting of hydrogen, halogen, hydroxy, cyano, $C_{1-4}$ alkyl, $C_{3-6}$ cycloalkyl, $C_{1-4}$ alkoxy, $C_{3-6}$ cycloalkyloxy, $C_{1-4}$ alkylthio, $C_{3-6}$ cycloalkylthio, amino, N—($C_{1-4}$ alkyl)-amino and N,N-di($C_{1-4}$ alkyl)amino; and
- $R^{5A}$, $R^{5B}$, $R^{5C}$ and $R^{5D}$ are each independently selected from the group consisting of hydrogen, halogen, hydroxy, amino, $C_{1-4}$ alkyl and $C_{1-4}$ alkoxy;

or a pharmaceutically acceptable salt thereof, for use as a medicament.

In another aspect, the invention relates to a compound of formula (I), or a pharmaceutically acceptable salt thereof, for use in the treatment or prevention of any of the diseases recited herein. The invention also relates to the use of a compound of formula (I), or a pharmaceutically acceptable salt thereof, in the manufacture of a medicament for the treatment or prevention of any of the diseases recited herein. The invention also relates to a method of treating or preventing any of the diseases recited herein in a subject, such as man, comprising administering to the subject in need of such treatment or prevention a therapeutically effective amount of a compound of formula (I), or a pharmaceutically acceptable salt thereof.

Combination Therapy

In one aspect of the invention, the compounds of formula (I), or pharmaceutically acceptable salts thereof, are administered in combination with at least one other therapeutically active agent, such as with one, two, three or more other therapeutically active agents. The compound of formula (I), or a pharmaceutically acceptable salt thereof, and the at least one other therapeutically active agent may be administered simultaneously, sequentially or separately. Therapeutically active agents that are suitable for combination with the compounds of formula (I) include, but are not limited to, known active agents that are useful in the treatment of any of the aforementioned conditions, disorders and diseases.

In one embodiment, compounds of formula (I), or pharmaceutically acceptable salts thereof, are administered in combination with another ASBT inhibitor. Suitable ASBT inhibitors are disclosed in WO 93/16055, WO 94/18183, WO 94/18184, WO 96/05188, WO 96/08484, WO 96/16051, WO 97/33882, WO 98/03818, WO 98/07449, WO 98/40375, WO 99/35135, WO 99/64409, WO 99/64410, WO 00/47568, WO 00/61568, WO 00/38725, WO 00/38726, WO 00/38727, WO 00/38728, WO 00/38729, WO 01/66533, WO 01/68096, WO 02/32428, WO 02/50051, WO 03/020710, WO 03/022286, WO 03/022825, WO 03/022830, WO 03/061663, WO 03/091232, WO 03/106482, WO 2004/006899, WO 2004/076430, WO 2007/009655, WO 2007/009656, WO 2011/137135, DE 19825804, EP 864582, EP 489423, EP 549967, EP 573848, EP 624593, EP 624594, EP 624595, EP 624596, EP 0864582, EP 1173205 and EP 1535913, all of which are incorporated herein by reference in their entireties.

In another embodiment, compounds of formula (I), or pharmaceutically acceptable salts thereof, are administered in combination with a bile acid binder (also referred to as a bile acid sequestrant, or a resin), such as colesevelam, cholestyramine or cholestipol. In a preferred embodiment of such a combination, the bile acid binder is formulated for colon release. Examples of such formulations are disclosed in e.g. WO 2017/138877, WO 2017/138878, WO 2019/032026 and WO 2019/032027, all of which are incorporated herein by reference in their entireties.

In another embodiment, compounds of formula (I), or pharmaceutically acceptable salts thereof, are administered in combination with a DPP-IV inhibitor, including gliptins such as sitagliptin, vildagliptin, saxagliptin, linagliptin, gemigliptin, anagliptin, teneligliptin, alogliptin, trelagliptin, omarigliptin, evogliptin, gosogliptin and dutogliptin, or a pharmaceutically acceptable salt thereof.

In another embodiment, compounds of formula (I), or pharmaceutically acceptable salts thereof, are administered in combination with an HMG CoA reductase inhibitor, such as fluvastatin, lovastatin, pravastatin, simvastatin, atorvastatin, pitavastatin cerivastatin, mevastatin, rosuvastatin, bervastatin or dalvastatin, or a pharmaceutically acceptable salt thereof.

In another embodiment, compounds of formula (I), or pharmaceutically acceptable salts thereof, are administered in combination with a cholesterol absorption inhibitor such as ezetimibe, or a pharmaceutically acceptable salt thereof.

In another embodiment, compounds of formula (I), or pharmaceutically acceptable salts thereof, are administered in combination with a PPAR alpha agonist, including fibrates such as clofibrate, bezafibrate, ciprofibrate, clinofribrate, clofibride, fenofibrate, gemfibrozil, ronifibrate and simfribrate, or a pharmaceutically acceptable salt thereof.

In another embodiment, compounds of formula (I), or pharmaceutically acceptable salts thereof, are administered in combination with a PPAR gamma agonist, including thiazolidinediones such as pioglitazone, rosiglitazone and lobeglitazone, or a pharmaceutically acceptable salt thereof.

In another embodiment, compounds of formula (I), or pharmaceutically acceptable salts thereof, are administered in combination with a dual PPAR alpha/gamma agonist, including glitazars such as saroglitazar, aleglitazar, muraglitazar or tesaglitazar, or a pharmaceutically acceptable salt thereof.

In another embodiment, compounds of formula (I), or pharmaceutically acceptable salts thereof, are administered in combination with a dual PPAR alpha/delta agonist, such as elafibranor.

In yet another embodiment, compounds of formula (I), or pharmaceutically acceptable salts thereof, are administered in combination with a pan PPAR agonist (i.e. a PPAR agonist that has activity across all subtypes: α, γ and δ), such as IVA337.

In another embodiment, compounds of formula (I), or pharmaceutically acceptable salts thereof, are administered in combination with a farnesoid X receptor (FXR) modulators, including FXR agonists such as cafestol, chenodeoxycholic acid, 6α-ethyl-chenodeoxycholic acid (obeticholic acid; INT-747), fexaramine, tropifexor, cilofexor and MET409.

In another embodiment, compounds of formula (I), or pharmaceutically acceptable salts thereof, are administered in combination with a TGR5 receptor modulator, including TGR5 agonists such as 6α-ethyl-23(S)-methylcholic acid (INT-777).

In another embodiment, compounds of formula (I), or pharmaceutically acceptable salts thereof, are administered in combination with a dual FXR/TGR5 agonist such as INT-767.

In another embodiment, compounds of formula (I), or pharmaceutically acceptable salts thereof, are administered in combination with ursodeoxycholic acid (UDCA). In yet another embodiment, compounds of formula (I), or pharmaceutically acceptable salts thereof, are administered in combination with nor-ursodeoxycholic acid (nor-UDCA).

In another embodiment, compounds of formula (I), or pharmaceutically acceptable salts thereof, are administered in combination with an FGF19 modulator, such as NGM282.

In another embodiment, compounds of formula (I), or pharmaceutically acceptable salts thereof, are administered in combination with an FGF21 agonist, such as BMS-986036.

In another embodiment, compounds of formula (I), or pharmaceutically acceptable salts thereof, are administered in combination with an integrin inhibitor, such as PLN-74809 and PLN-1474.

In another embodiment, compounds of formula (I), or pharmaceutically acceptable salts thereof, are administered in combination with a CCR2/CCR5 inhibitor, such as cenicriviroc.

In another embodiment, compounds of formula (I), or pharmaceutically acceptable salts thereof, are administered in combination with a caspase protease inhibitor, such as emricasan.

In another embodiment, compounds of formula (I), or pharmaceutically acceptable salts thereof, are administered in combination with a galectin-3 inhibitor, such as GR-MD-02.

In another embodiment, compounds of formula (I), or pharmaceutically acceptable salts thereof, are administered in combination with a stearoyl-CoA desaturase (SCD) Inhibitor, such as aramchol (arachidyl amido cholanoic acid).

In another embodiment, compounds of formula (I), or pharmaceutically acceptable salts thereof, are administered in combination with an apoptosis signal-regulating kinase 1 (ASK1) inhibitor, such as selonsertib.

In another embodiment, compounds of formula (I), or pharmaceutically acceptable salts thereof, are administered in combination with an LOXL2 inhibitor, such as simtuzumab.

In another embodiment, compounds of formula (I), or pharmaceutically acceptable salts thereof, are administered in combination with an ACC inhibitor, such as GS-0976.

In another embodiment, compounds of formula (I), or pharmaceutically acceptable salts thereof, are administered in combination with a thyroid hormone receptor-β agonist, such as MGL3196.

In another embodiment, compounds of formula (I), or pharmaceutically acceptable salts thereof, are administered in combination with a GLP-1 agonist such as liraglutide.

In another embodiment, compounds of formula (I), or pharmaceutically acceptable salts thereof, are administered in combination with a dual glucagon-like peptide and glucagon receptor agonists, such as SAR425899.

In another embodiment, compounds of formula (I), or pharmaceutically acceptable salts thereof, are administered in combination with a mitochondrial pyruvate carrier inhibitor, such as MSDC-0602K.

In another embodiment, compounds of formula (I), or pharmaceutically acceptable salts thereof, are administered in combination with an anti-oxidant agent, such as vitamin E.

In another embodiment, compounds of formula (I), or pharmaceutically acceptable salts thereof, are administered in combination with an SGLT1 inhibitor, an SGLT2 inhibitor or a dual SGLT1 and SGLT2 inhibitor. Examples of such compounds are dapagliflozin, sotagliflozin, canagliflozin, empagliflozin, LIK066 and SGL5213.

In another embodiment, compounds of formula (I), or pharmaceutically acceptable salts thereof, are administered in combination with a diacylglycerol O-Acyltransferase 2 (DGAT2) inhibitor, such as DGAT2RX and PF-06865571.

In another embodiment, compounds of formula (I), or pharmaceutically acceptable salts thereof, are administered in combination with a fatty acid synthase (FASN) Inhibitor, such as TVB-2640.

In another embodiment, compounds of formula (I), or pharmaceutically acceptable salts thereof, are administered in combination with an AMP-activated protein kinase (AMPK) activator, such as PXL-770.

In another embodiment, compounds of formula (I), or pharmaceutically acceptable salts thereof, are administered in combination with a glucocorticoid receptor antagonist (GR), a mineralocorticoid receptor antagonist (MR), or a dual GR/MR antagonist. Examples of such compounds are MT-3995 and CORT-118335.

In another embodiment, compounds of formula (I), or pharmaceutically acceptable salts thereof, are administered in combination with a cannabinoid receptor 1 (CB1) antagonist, such as IM102.

In another embodiment, compounds of formula (I), or pharmaceutically acceptable salts thereof, are administered in combination with a Klothoβ (KLB) and fibroblast growth factor receptor (FGFR) activator, such as MK-3655 (previously known as NGM-313).

In another embodiment, compounds of formula (I), or pharmaceutically acceptable salts thereof, are administered in combination with a chemokine (c-c motif) ligand 24 (CCL24) inhibitor, such as CM101.

In another embodiment, compounds of formula (I), or pharmaceutically acceptable salts thereof, are administered in combination with an A3 antagonist, such as PBF-1650.

In another embodiment, compounds of formula (I), or pharmaceutically acceptable salts thereof, are administered in combination with a P2x7 receptor antagonist, such as SGM 1019.

In another embodiment, compounds of formula (I), or pharmaceutically acceptable salts thereof, are administered in combination with P2Y13 receptor agonists, such as CER-209.

In another embodiment, compounds of formula (I), or pharmaceutically acceptable salts thereof, are administered in combination with a sulfated oxysterol, such as Dur-928.

In another embodiment, compounds of formula (I), or pharmaceutically acceptable salts thereof, are administered in combination with a leukotriene D4 (LTD4) receptor antagonist, such as MN-001.

In another embodiment, compounds of formula (I), or pharmaceutically acceptable salts thereof, are administered in combination with a type 1 natural killer T cell (NKT1) inhibitor, such as GRI-0621.

In another embodiment, compounds of formula (I), or pharmaceutically acceptable salts thereof, are administered in combination with an anti-lipopolysaccharide (LPS) compound, such as IMM-124E.

In another embodiment, compounds of formula (I), or pharmaceutically acceptable salts thereof, are administered in combination with a VAP1 inhibitor, such as B11467335.

In another embodiment, compounds of formula (I), or pharmaceutically acceptable salts thereof, are administered in combination with an A3 adenosine receptor agonist, such as CF-102.

In another embodiment, compounds of formula (I), or pharmaceutically acceptable salts thereof, are administered in combination with a SIRT-1 activator, such as NS-20.

In another embodiment, compounds of formula (I), or pharmaceutically acceptable salts thereof, are administered in combination with a nicotinic acid receptor 1 agonist, such as ARI-3037MO.

In another embodiment, compounds of formula (I), or pharmaceutically acceptable salts thereof, are administered in combination with a TLR4 antagonist, such as JKB-121.

In another embodiment, compounds of formula (I), or pharmaceutically acceptable salts thereof, are administered in combination with a ketohexokinase inhibitor, such as PF-06835919.

In another embodiment, compounds of formula (I), or pharmaceutically acceptable salts thereof, are administered in combination with an adiponectin receptor agonist, such as ADP-335.

In another embodiment, compounds of formula (I), or pharmaceutically acceptable salts thereof, are administered in combination with an autotaxin inhibitor, such as PAT-505 and PF8380.

In another embodiment, compounds of formula (I), or pharmaceutically acceptable salts thereof, are administered in combination with a chemokine (c-c motif) receptor 3 (CCR3) antagonist, such as bertilimumab.

In another embodiment, compounds of formula (I), or pharmaceutically acceptable salts thereof, are administered in combination with a chloride channel stimulator, such as cobiprostone and lubiprostone.

In another embodiment, compounds of formula (I), or pharmaceutically acceptable salts thereof, are administered in combination with a heat shock protein 47 (HSP47) inhibitor, such as ND-L02-s0201.

In another embodiment, compounds of formula (I), or pharmaceutically acceptable salts thereof, are administered in combination with a sterol regulatory element-binding protein (SREBP) transcription factor inhibitor, such as CAT-2003 and MDV-4463.

In another embodiment, compounds of formula (I), or pharmaceutically acceptable salts thereof, are administered in combination with a bisguanidine, such as metformin.

In another embodiment, compounds of formula (I), or pharmaceutically acceptable salts thereof, are administered in combination with insulin.

In another embodiment, compounds of formula (I), or pharmaceutically acceptable salts thereof, are administered in combination with a glycogen phosphorylase inhibitor and/or a glucose-6-phosphatase inhibitor.

In another embodiment, compounds of formula (I), or pharmaceutically acceptable salts thereof, are administered in combination with a sulfonylurea, such as glipizid, glibenklamid and glimepirid.

In another embodiment, compounds of formula (I), or pharmaceutically acceptable salts thereof, are administered in combination with a meglitinide, such as repaglinide, nateglinide and ormiglitinide.

In another embodiment, compounds of formula (I), or pharmaceutically acceptable salts thereof, are administered in combination with a glucosidase inhibitor, such as acarbose or miglitol.

In another embodiment, compounds of formula (I), or pharmaceutically acceptable salts thereof, are administered in combination with a squalene synthase inhibitor, such as TAK-475.

In another embodiment, compounds of formula (I), or pharmaceutically acceptable salts thereof, are administered in combination with a PTPB1 inhibitor, such as trodusquemine, ertiprotafib, JTT-551 and claramine.

Preparation of Compounds

The compounds of the invention can be prepared as a free acid or a pharmaceutically acceptable salt thereof by the processes described below. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in *Greene's Protective Groups in Organic Synthesis* by P. G. M Wutz and T. W. Greene, 4th Edition, John Wiley & Sons, Hoboken, 2006.

General Methods

All solvents used were of analytical grade. Commercially available anhydrous solvents were routinely used for reactions. Starting materials were available from commercial sources or prepared according to literature procedures. 7-Bromo-3,3-dibutyl-8-methoxy-5-phenyl-2,3,4,5-tetrahydro-1,5-benzothiazepine 1,1-dioxide and 3,3-dibutyl-8-hydroxy-7-(methylthio)-5-phenyl-2,3,4,5-tetrahydro-1,5-benzothiazepine 1,1-dioxide may be prepared as described in WO 02/50051 (method 26). 7-Bromo-3-butyl-3-ethyl-8-hydroxy-5-phenyl-2,3,4,5-tetrahydro-1,5-benzothiazepine 1,1-dioxide may be prepared as described in WO 96/16051 (Example 21). 3-butyl-3-ethyl-8-methoxy-7-(methylamino)-5-phenyl-2,3,4,5-tetrahydro-1,5-benzothiazepine 1,1-dioxide may be prepared as described in WO 2019/234077 (Intermediate 154). Room temperature refers to 20-25° C. Solvent mixture compositions are given as volume percentages or volume ratios.

LCMS:

Instrument name: Agilent 1290 infinity II.

Method A: Mobile phase: A: 0.1% HCOOH in $H_2O$: ACN (95:5), B: ACN; flow rate: 1.5 mL/min; column: ZORBAX XDB C-18 (50×4.6 mm) 3.5 µM.

Method B: Mobile phase: A: 10 mM $NH_4HCO_3$ in water, B: ACN; flow rate: 1.2 mL/min; column: XBridge C8 (50×4.6 mm), 3.5 µM.

Method C: Mobile phase: A: 0.1% HCOOH in water: ACN (95:5), B: ACN; flow rate: 1.5 mL/min; column: ATLANTIS dC18 (50×4.6 mm), 5 µM.

Method D: Mobile phase: A: 10 mM $NH_4OAc$ in water, B: ACN; flow rate: 1.2 mL/min; column: Zorbax Extend C18 (50×4.6 mm) 5 µM.

Method E: Mobile phase: A: 0.1% TFA in water: ACN (95:5), B: 0.1% TFA in ACN; flow rate: 1.5 mL/min; column: XBridge C8 (50×4.6 mm), 3.5 µM.

Method F: Mobile phase: A: 0.1% TFA in water, B: 0.1% TFA in ACN; flow Rate: 0.8 mL/min; column: ZORBAX ECLIPSE PLUS C18 (50×2.1 mm), 1.8 µM.

Method G: Mobile phase: A: 0.1% TFA in water, B: 0.1% TFA in ACN; flow Rate: 0.8 mL/min; column: Acquity UPLC BEH C18 (2.1×50 mm), 1.7 µm.

UPLC:
Instrument name: waters Acquity I Class
Method A: Mobile Phase: A: 0.1% HCOOH in water, B: 0.1% HCOOH in ACN; Flow Rate: 0.8 mL/min; Column: Acquity UPLC HSS T3 (2.1×50) mm; 1.8 µm.

HPLC:
Instrument name: Agilent 1260 Infinity II series instruments as followed using % with UV detection (maxplot).
Method A: Mobile phase: A: 10 mM NH$_4$HCO$_3$ in water, B: ACN; flow rate: 1.0 mL/min; column: XBridge C8 (50×4.6 mm, 3.5 µm).
Method B: Mobile phase: A: 0.1% TFA in water, B: 0.1% TFA in ACN; flow rate: 2.0 mL/min; column: XBridge C8 (50×4.6 mm, 3.5 µm).
Method C: Mobile phase: A: 10 mM NH$_4$OAc in milli-q water, B: ACN; flow rate: 1.0 ml/min; column: Phenomenex Gemini C18 (150×4.6 mm, 3.0 µm).
Method D: Mobile phase: A: 10 mM NH$_4$HCO$_3$ in milli-q water, B: ACN; flow rate: 1.0 ml/min; column: X-Bridge C8 (50×4.6 mm, 3.5 µm).

Chiral SFC:
Instrument name: PIC SFC 10 (analytical) (analytical)
Ratio between CO$_2$ and co-solvent is ranging between 60:40 and 80:20
Method A: Mobile phase: 0.5% isopropylamine in IPA; flow rate: 3 mL/min; column: YMC Amylose-SA (250×4.6 mm, 5 µm).
Method B: Mobile Phase: 0.5% isopropylamine in IPA; flow rate: 3 mL/min; column: Chiralpak AD-H (250×4.6 mm, 5 µm).
Method C: Mobile Phase: 20 mM ammonia in methanol; flow rate: 3 mL/min; column: YMC Cellulose-SC (250×4.6 mm, 5 µm).
Method D: Mobile Phase: methanol; flow rate: 3 mL/min; column: Lux A1 (250×4.6 mm, 5 µm).
Method E: Mobile Phase: 0.5% isopropylamine in methanol; flow rate: 5 mL/min; column: Lux C4.
Method F: Mobile Phase: 0.5% isopropylamine in methanol; flow rate: 3 mL/min; column: YMC Cellulose-SC.
Method G: Mobile Phase: 0.5% isopropylamine in methanol; flow rate: 3 mL/min; column: Lux A1.
Method H: Mobile Phase: 0.5% isopropylamine in IPA; flow rate: 3 mL/min; column: Lux A1 (250×4.6 mm, 5 µm).
Method I: Mobile Phase: 0.5% isopropylamine in methanol; flow rate: 3 mL/min; column: Chiral CCS (250×4.6 mm, 5 µm).
Method J: Mobile Phase: 0.5% isopropylamine in IPA; flow rate: 5 mL/min; column: YMC Cellulose-SC AD-H (250×4.6 mm, 5 µm).
Method K: Mobile Phase: 0.5% Isopropylamine in methanol; flow rate: 4 mL/min; column: (R,R)-Whelk-01 (250×4.6 mm, 5 µm).
Method L: Mobile Phase: 0.5% isopropylamine in IPA; flow rate: 3 mL/min; column: Chiralcel OX-H (250×4.6 mm, 5 µm).
Method M: Mobile Phase: 0.5% isopropylamine in IPA; flow rate: 5 mL/min; column: YMC Cellulose-SC (250×4.6 mm, 5 µm).
Method N: Mobile phase: methanol, flow rate: 5 mL/min; column: Chiralcel OX-H (250×4.6 mm, 5 µm).

Prep-HPLC:
Instrument name: Agilent 1290 Infinity II
Method A: Mobile phase: A: 0.1% TFA in water; Mobile phase; B: 0.1% TFA in CAN; flow rate: 2.0 mL/min; Column: X-Bridge C8 (50×4.6 mm, 3.5 µM).
Method B: Mobile phase: A: 10 mM NH$_4$OAc in water; B: ACN; flow rate: 35 mL/min; column: X select C18 (30×150 mm, 5 µm).
Method C: Mobile phase: A: 10 mM NH$_4$HCO$_3$ in water; B: ACN; flow rate: 1.0 mL/min; column: XBridge C8 (50×4.6 mm, 3.5 µm).
Method D: Mobile phase: A: 0.1% HCOOH in water; B: ACN; flow rate: 1.0 mL/min; column: X-select C18 (30×150 mm, 5 µm).

Chiral Preparative SFC:
Instrument name: PIC SFC 100 and PSC SFC 400
Ratio between CO$_2$ and co-solvent is ranging between 60:40 and 80:20
Method A: Mobile phase: 0.5% isopropylamine in IPA; flow rate: 3 mL/min; column: YMC Amylose-SA (250×30 mm, 5 µm).
Method B: Mobile Phase: 0.5% isopropylamine in IPA; flow rate: 3 mL/min; column: Chiralpak AD-H (250×30 mm, 5 µm).
Method C: Mobile phase: 20 mM ammonia in methanol; flow rate: 3 mL/min; column: YMC Cellulose-SC (250×30 mm, 5 µm).
Method D: Mobile phase: methanol; flow rate: 3 mL/min; column: Chiral CCS (250×30 mm, 5 µm).
Method E: Mobile phase: methanol; flow rate: 3 mL/min; column: Lux A1 (250×30 mm, 5 µm).
Method F: Mobile Phase: 0.5% isopropylamine in IPA; flow rate: 3 mL/min; column: Lux A1 (250×30 mm, 5 µm).
Method G: Mobile phase: 0.5% isopropylamine in methanol; flow rate: 3 mL/min; column: Chiral CCS (250×30 mm, 5 µm).
Method H: Mobile phase: 0.5% isopropylamine in IPA; flow rate: 5 mL/min; column: YMC Amylose-SC (250×30 mm, 5 µm).
Method J: Mobile phase: 0.5% isopropylamine in IPA; flow rate: 3 mL/min; column: Chiralcel OX-H (250×30 mm, 5 µm).
Method K: Mobile phase: 0.5% isopropylamine in methanol; flow rate: 5 mL/min; column: YMC Cellulose-SC (250×30 mm, 5 µm).
Method L: Mobile phase: methanol; flow rate: 5 mL/min; column: Chiralcel OX-H (250×30 mm, 5 µm).

Chiral Preparative HPLC:
Instrument name: Agilent 1260 Infinity II
Method A: Mobile phase: A: 0.1% TFA in n-hexane; B: ethanol; flow rate: 15 mL/min; Column: Chiralpak IA (250×19 mm, 5.0 µm).

Abbreviations

ACN acetonitrile
DCM dichloromethane
DMAP 4-dimethylaminopyridine
DMF dimethylformamide
IPA isopropyl alcohol
LCMS liquid chromatography—mass spectrometry
HPLC high-performance liquid chromatography
PE petroleum ether
SFC supercritical fluid chromatography
TFA trifluoroacetic acid THF tetrahydrofuran
TLC thin layer chromatography
UPLC ultra performance liquid chromatography The invention will now be described by the following examples which do not limit the invention in any respect. All cited documents and references are incorporated by reference.

EXAMPLES

Intermediate 1

Ethyl (E)-3-((7-bromo-3-butyl-3-ethyl-1,1-dioxido-5-phenyl-2,3,4,5-tetrahydro-1,5-benzothiazepin-8-yl)oxy)acrylate and ethyl (Z)-3-((7-bromo-3-butyl-3-ethyl-1,1-dioxido-5-phenyl-2,3,4,5-tetrahydro-1,5-benzothiazepin-8-yl)oxy)acrylate

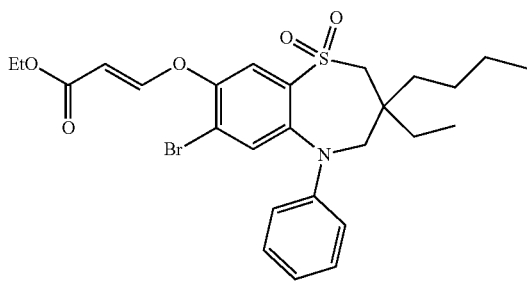 [SMILES: CCCCC1(CC)CN(c2ccccc2)c2cc(Br)c(O/C=C/C(=O)OCC)cc2S(=O)(=O)C1]

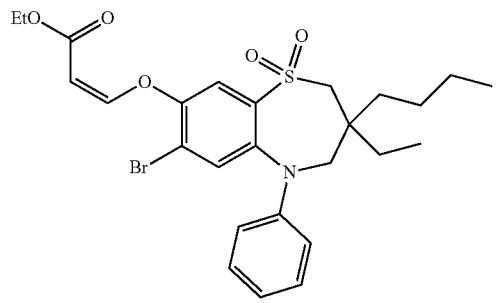

To a stirred solution of 7-bromo-3-butyl-3-ethyl-8-hydroxy-5-phenyl-2,3,4,5-tetrahydro-1,5-benzothiazepine 1,1-dioxide (0.5 g, 1.1 mmol) in dry DMF (20 mL), ethyl (E)-3-bromoacrylate (0.59 g, 3.3 mmol), sodium carbonate (0.35 g, 3.3 mmol) and tetra-butyl ammonium bromide (0.035 g, 0.1 mmol) were added at room temperature and the reaction mixture was heated at 85-90° C. for 5 hours. After completion of the reaction (monitored by TLC), the reaction mixture was poured into ice-cold water and extracted with EtOAc (3×15 mL). The combined organic layer was washed with brine (20 mL), dried over anhydrous $Na_2SO_4$ and concentrated under vacuum to afford the crude title compound as a mixture of the (E)- and (Z)-isomers (1:1 ratio). The mixture was purified by Isolera column chromatography (eluent: 8-9% EtOAc/PE; Silica gel: 230-400 mesh) to afford the first eluting fraction corresponding to the (E)-isomer and the second eluting fraction corresponding to the (Z)-isomer.

(E)-isomer: Yield: 32% (0.28 g, off-white solid). $^1$H NMR (400 MHz, DMSO-$d_6$): δ 7.80 (d, J=12.2 Hz, 1H), 7.66 (s, 1H), 7.38-7.25 (m, 4H), 7.10-7.04 (m, 2H), 5.47 (d, J=12.3 Hz, 1H), 4.13 (q, J=7.1 Hz, 2H), 3.81-3.78 (m, 2H), 3.46 (s, 2H), 1.54-1.50 (m, 1H), 1.43-1.30 (m, 3H), 1.21 (t, J=7.08 Hz, 3H), 1.12-0.98 (m, 4H), 0.74-0.71 (m, 6H). LCMS: (Method A) 552.1 (M+2), Rt. 3.33 min, 97.8% (Max).

(Z)-isomer: Yield: 41% (0.23 g, off-white solid). $^1$H NMR (400 MHz, DMSO-$d_6$): δ 7.60 (s, 1H), 7.37-7.31 (m, 2H), 7.21-7.19 (m, 3H), 7.07-7.03 (m, 2H), 5.32 (d, J=6.9 Hz, 1H), 4.11 (q, J=6.9 Hz, 2H), 3.78-3.74 (m, 2H), 3.42-3.38 (m, 2H), 1.51-1.29 (m, 4H), 1.22 (t, J=7.2 Hz, 3H), 1.08-1.01 (m, 4H), 0.73-0.71 (m, 6H). LCMS: (Method A) 552.1 (M+2), Rt. 3.18 min, 98.2% (Max).

Intermediate 2

(E)-3-((7-Bromo-3-butyl-3-ethyl-1,1-dioxido-5-phenyl-2,3,4,5-tetrahydro-1,5-benzothiazepin-8-yl)oxy)acrylic acid

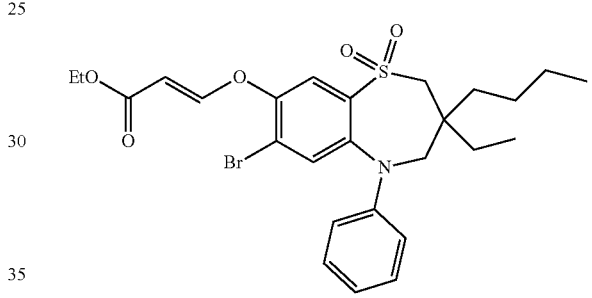

To a stirred solution of ethyl (E)-3-((7-bromo-3-butyl-3-ethyl-1,1-dioxido-5-phenyl-2,3,4,5-tetrahydro-1,5-benzothiazepin-8-yl)oxy)acrylate (Intermediate 1; 0.28 g, 0.48 mmol) in a mixture of 1,4-dioxane and water (3 mL; 5:1), lithium hydroxide (0.04 g, 0.96 mmol) was added and the resulting mixture was stirred for at room temperature for 12 hours. After completion of the reaction (monitored by TLC), the reaction mixture was concentrated under vacuum. The obtained residue was acidified with dilute HCl (1.5 N, 2 mL) and the aqueous part was extracted with EtOAc (2×15 mL). The combined organic layer was washed with water (15 mL), brine (15 mL) and dried over anhydrous $Na_2SO_4$. The organic part was concentrated under vacuum and the crude material was purified by Isolera column chromatography (eluent: 2-3% MeOH/DCM; silica gel: 230-400 mesh) to afford the title compound.

Yield: 60% (150 mg, off-white solid).

$^1$H NMR (400 MHz, DMSO-$d_6$): δ 12.29 (s, 1H), 7.73 (d, J=12.0 Hz, 1H), 7.65-7.64 (m, 1H), 7.37-7.34 (m, 2H), 7.28-7.25 (m, 2H), 7.09-7.05 (m, 2H), 5.39 (d, J=12.0 Hz, 1H), 3.88-3.73 (m, 2H), 3.46 (s, 2H), 1.52-1.34 (m, 4H), 1.08-0.98 (m, 4H), 0.72-0.69 (m, 6H). LCMS: (Method A) 296.0 (M+H), Rt. 2.86 min, 95.59% (Max). HPLC: (Method B) Rt. 6.03 min, 97.02% (Max).

Intermediate 3

7-Bromo-3,3-dibutyl-8-hydroxy-5-phenyl-2,3,4,5-tetrahydro-1,5-benzothiazepine 1,1-dioxide

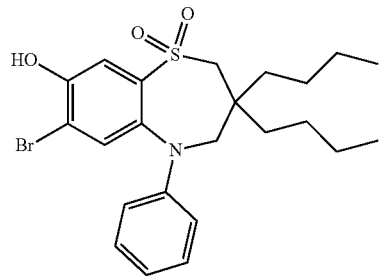 [SMILES: CCCCC1(CCCC)CN(c2ccccc2)c2cc(Br)c(O)cc2S(=O)(=O)C1]

To a stirred solution of 7-bromo-3,3-dibutyl-8-methoxy-5-phenyl-2,3,4,5-tetrahydro-1,5-benzothiazepine 1,1-dioxide (2.0 g, 4.04 mmol) in DCM (20 mL) at −10° C., BBr$_3$ (1M in DCM, 8.0 ml, 8.09 mmol) was added and the resulting mixture was stirred for 3 hours at room temperature. After completion of the reaction (monitored by TLC), the reaction mixture was quenched with methanol (5 mL) and concentrated under vacuum. The resulting crude material was purified by Isolera column chromatography (eluent: 10-15% EtOAc/PE; silica gel: 230-400 mesh) to afford the title compound.

Yield: 83% (1.6 g, off-white solid).

$^1$H NMR (400 MHz, DMSO-d$_6$): δ 10.84 (s, 1H), 7.47 (s, 1H), 7.24 (t, J=4.0 Hz, 2H), 7.08 (s, 1H), 7.01 (d, J=7.9 Hz, 2H), 6.89 (t, J=7.4 Hz, 1H), 3.68 (bs, 2H), 3.42 (s, 2H), 1.36-1.30 (m, 4H), 1.14-1.11 (m, 8H), 0.75 (t, J=8.00 Hz, 6H). LCMS: (Method C) 482.0 (M$^+$+2), Rt. 3.15 min, 91.28% (Max).

Intermediate 4

Ethyl 3-((3,3-dibutyl-7-bromo-1,1-dioxido-5-phenyl-2,3,4,5-tetrahydro-1,5-benzothiazepin-8-yl)oxy)propanoate

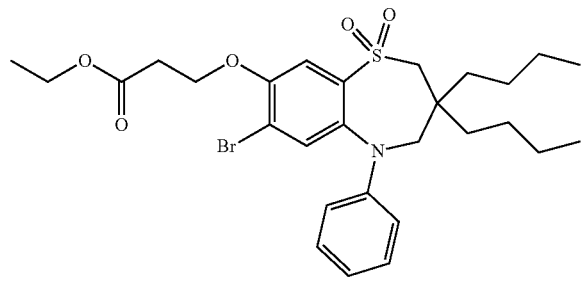 [SMILES: CCCCC1(CCCC)CN(c2ccccc2)c2cc(Br)c(OCCC(=O)OCC)cc2S(=O)(=O)C1]

To a stirred suspension of 7-bromo-3,3-dibutyl-8-hydroxy-5-phenyl-2,3,4,5-tetrahydro-1,5-benzothiazepine 1,1-dioxide (Intermediate 3; 1.5 g, 3.12 mmol) in ethyl acrylate (10 mL) at room temperature, DMAP (0.04 g 0.31 mmol) was added. The reaction mixture was heated in a sealed tube for 24 hours at 100° C. The progress of the reaction was monitored by TLC, which indicated the incomplete conversion (20%) of the starting material. The reaction mixture was then evaporated and dried under vacuum to afford the crude title compound, which was forwarded to the next step without any further purification. Yield: 1.5 g (crude, brown gum).

LCMS: (Method C) 583.2 (M$^+$+2), Rt. 3.59 min, 17.45% (Max).

Intermediate 5

5-Chloro-6-methoxybenzo[d]thiazol-2-amine

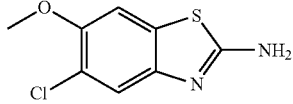

To a stirred solution of 3-chloro-4-methoxyaniline (10 g, 63.4 mmol) in acetic acid (100 mL) at room temperature was added ammonium thiocyanate (5.3 g, 69.8 mmol) and the mixture was then stirred for 30 minutes. Bromine (3.2 mL, 63.4 mmol) dissolved in acetic acid (20 mL) was added dropwise to the reaction mixture at 15° C. and the resulting mixture was stirred for 3 hours at room temperature. After completion of the reaction, the obtained solid was filtered off, washed with acetic acid (20 mL) and then dried under vacuum. The solid was then suspended in water (20 mL) and basified with 10% NaOH solution to about pH 10. The solid was filtered off, washed with water (3×25 mL) and then dried under vacuum to afford the title compound. Yield: 80% (11 g, off-white solid).

$^1$H NMR (400 MHz, DMSO-d$_6$): δ 7.53 (s, 1H), 7.41 (bs, 2H), 7.36 (s, 1H), 3.82 (s, 3H). LCMS: (Method A) 215.0 (M$^+$+H), Rt. 1.39 min, 97.22% (Max).

Intermediate 6

2-(((2-Amino-4-chloro-5-methoxyphenyl)thio)methyl)-2-ethylhexanoic acid

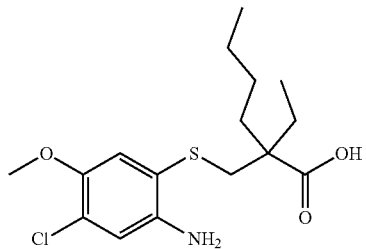 [SMILES: CCCCC(CC)(CSc1cc(OC)c(Cl)cc1N)C(=O)O]

To a stirred solution of 5-chloro-6-methoxybenzo[d]thiazol-2-amine (Intermediate 5; 8 g, 0.037 mol) in water (120 mL) was added KOH (34 g, 0.596 mol) and the reaction mixture was stirred for 16 hours at 120° C. After completion of the reaction (monitored by LCMS), the reaction mixture was cooled to room temperature. 2-(Bromomethyl)-2-ethylhexanoic acid (13.29 g, 0.0558 mol; dissolved in 40 mL of THF) was added dropwise and the mixture was then stirred for 16 hours at room temperature. After completion of the reaction (monitored by LCMS), the reaction mixture was cooled to 0° C. and acidified with concentrated HCl (pH 2). The reaction mixture was extracted with EtOAc (2×25 mL). The combined organic layer was then washed with water (30 mL) and brine (30 mL), dried over anhydrous Na$_2$SO$_4$ and concentrated under vacuum to obtain the crude material. The obtained crude material was forwarded as such to the next step without any further purification. Yield: 21 g (crude, brown gum).

UPLC: (Method A) 345.8 (M⁺+H), Rt. 1.58 min, 90.21% (Max).

Intermediate 7

3-Butyl-7-chloro-3-ethyl-8-methoxy-2,3-dihydro-1,5-benzothiazepin-4(5H)-one

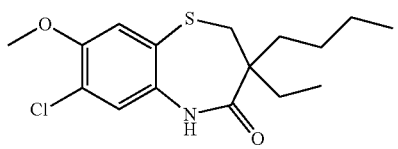 [SMILES: CCCCC1(CC)CSc2cc(OC)c(Cl)cc2NC1=O]

To a stirred solution of 2-(((2-amino-4-chloro-5-methoxyphenyl)thio)methyl)-2-ethylhexanoic acid (Intermediate 6; 21 g, 0.0607 mol) in EtOAc (130 mL) at 0° C., triethylamine (12.26 g, 0.1214 mol) and 1-propanephosphonic anhydride solution (50% EtOAc; 23.16 g, 0.073 mol) were added dropwise and the reaction mixture was stirred for 16 hours at room temperature. After completion of the reaction (monitored by UPLC), water (25 mL) was added to the reaction mixture and the aqueous layer was extracted with EtOAc (2×25 mL). The combined organic layer was washed with brine (25 mL), dried over anhydrous Na$_2$SO$_4$ and concentrated under vacuum. The crude material was purified by Isolera column chromatography (eluent: 10-12% EtOAc/PE; silica gel: 230-400 mesh) to afford the title compound. Yield: 55% (11 g, off-white solid).

$^1$H NMR (400 MHz, DMSO-d$_6$): δ 9.61 (s, 1H), 7.16 (d, J=14.8 Hz, 2H), 3.82 (s, 3H), 2.98 (s, 2H), 1.51-1.53 (m, 4H), 1.32-1.26 (m, 4H), 0.92-0.91 (m, 6H). LCMS: (Method A) 328.1 (M⁺+H), Rt. 2.60 min, 95.79% (Max). HPLC: (Method B) Rt. 5.51 min, 97.62% (Max).

Intermediate 8

3-Butyl-7-chloro-3-ethyl-8-methoxy-5-phenyl-2,3-dihydro-1,5-benzothiazepin-4(5H)-one

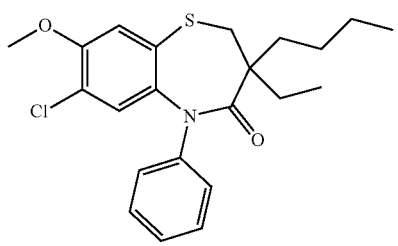 [SMILES: CCCCC1(CC)CSc2cc(OC)c(Cl)cc2N(c2ccccc2)C1=O]

To a stirred solution of 3-butyl-7-chloro-3-ethyl-8-methoxy-2,3-dihydro-1,5-benzothiazepin-4(5H)-one (Intermediate 7; 11 g, 0.034 mol) in iodobenzene (110 mL) were added copper (I) iodide (0.640 g, 0.0034 mol) and K$_2$CO$_3$ (9.25 g, 0.067 mol) and the solution was purged with nitrogen for 20 minutes for degasification. Tris[2-(2-methoxyethoxy)ethyl]amine (2.16 g, 0.0067 mol) was then added under nitrogen atmosphere and the resulting reaction mixture was heated for 40 h to 135° C. After completion of the reaction (monitored by UPLC), the reaction mixture was filtered through celite and the celite pad was washed with EtOAc (25 mL). The filtrate was concentrated under vacuum to obtain the crude material which was purified by Isolera column chromatography (eluent: 3-5% EtOAc/PE; silica gel: 230-400 mesh) to afford the title compound. Yield: 86% (11.7 g, pale brown solid).

$^1$H NMR (300 MHz, DMSO-d$_6$): δ 7.40-7.39 (m, 3H), 7.29 (d, J=7.2 Hz, 1H), 7.09 (d, J=6.9 Hz, 2H), 6.96 (s, 1H), 3.91 (s, 3H), 3.16 (s, 2H), 1.57-1.55 (m, 4H), 1.19 (d, J=6.9 Hz, 5H), 0.79 (t, J=6.3 Hz, 7H). LCMS: (Method A) 404.1 (M⁺+H), Rt. 3.19 min, 98.20% (Max).

Intermediate 9

3-Butyl-7-chloro-3-ethyl-8-methoxy-5-phenyl-2,3,4,5-tetrahydro-1,5-benzothiazepine

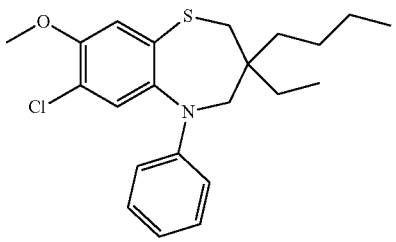 [SMILES: CCCCC1(CC)CSc2cc(OC)c(Cl)cc2N(c2ccccc2)C1]

To a stirred solution of 3-butyl-7-chloro-3-ethyl-8-methoxy-5-phenyl-2,3-dihydro-1,5-benzothiazepin-4(5H)-one (Intermediate 8; 11.7 g, 0.029 mol) in THF (110 mL) at 0° C. was dropwise added borane dimethylsulfide (2M in THF; 73 mL, 0.144 mol) and the reaction mixture was refluxed for 40 hours at 75° C. After completion of the reaction (monitored by UPLC), the reaction mixture was cooled to 0° C. and quenched with methanol (50 mL). The resulting solution was heated for 2 hours to 65° C., then cooled to RT and concentrated under vacuum. The obtained crude material was purified by Isolera column chromatography (eluent: 8-10% EtOAc/PE; silica gel: 230-400 mesh) to afford the title compound. Yield: 90% (10.2 g, colourless liquid).

$^1$H NMR (400 MHz, DMSO-d$_6$): δ 7.19 (t, J=7.2 Hz, 2H), 7.08 (s, 1H), 6.93 (s, 2H), 6.79 (d, J=4.0 Hz, 2H), 3.82 (s, 3H), 2.76 (s, 2H), 1.26-1.24 (m, 9H), 0.76-0.71 (m, 6H). LCMS: (Method A) 390.2 (M⁺+H), Rt. 3.01 min, 99.61% (Max).

Intermediate 10

3-Butyl-7-chloro-3-ethyl-8-methoxy-5-phenyl-2,3,4,5-tetrahydro-1,5-benzothiazepine 1,1-dioxide

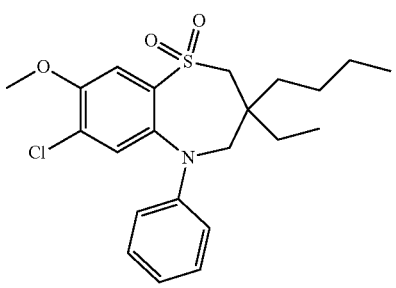 [SMILES: CCCCC1(CC)CN(c2ccccc2)c2cc(Cl)c(OC)cc2S(=O)(=O)C1]

To a stirred solution of 3-butyl-7-chloro-3-ethyl-8-methoxy-5-phenyl-2,3,4,5-tetrahydro-1,5-benzothiazepine (Intermediate 9; 10.2 g, 0.0261 mol) in 1,4-dioxane (100 mL) at room temperature were added water (100 mL) and oxone (81 g, 0.2615 mol) and the reaction mixture was stirred for 24 hours at room temperature. After completion of the reaction (monitored by TLC), the reaction mixture was filtered off through a Buchner funnel and the filtrate was extracted with EtOAc (2×25 mL). The combined organic layer was washed with water (25 mL) and brine (25 mL), dried over anhydrous $Na_2SO_4$ and concentrated under vacuum. The crude material was purified by Isolera column chromatography (eluent: 10-12% EtOAc/PE; silica gel: 230-400 mesh) to afford the title compound. Yield: 56% (6.2 g, yellowish solid).

$^1$H NMR (300 MHz, DMSO-$d_6$): δ 7.50 (s, 1H), 7.27 (t, J=7.8 Hz, 2H), 7.07-7.04 (m, 4H), 3.94 (s, 3H), 3.69 (s, 2H), 3.33 (s, 2H), 1.52-1.37 (m, 8H), 0.77-0.74 (m, 6H). LCMS: (Method A) 422.1 (M$^+$+H), Rt. 3.18 min, 98.51% (Max).

Intermediate 11

3-Butyl-7-chloro-3-ethyl-8-hydroxy-5-phenyl-2,3,4,5-tetrahydro-1,5-benzothiazepine 1,1-dioxide

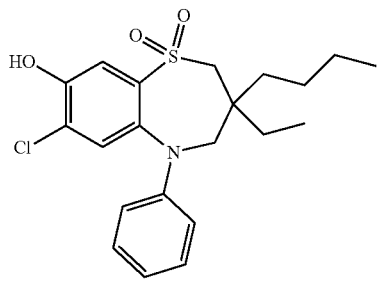 [SMILES: CCCCC1(CC)CN(c2ccccc2)c2cc(Cl)c(O)cc2S(=O)(=O)C1]

To a stirred solution of 3-butyl-7-chloro-3-ethyl-8-methoxy-5-phenyl-2,3,4,5-tetrahydro-1,5-benzothiazepine 1,1-dioxide (Intermediate 10; 1.1 g, 2.60 mmol) in DCM (11 mL) at 0° C. was added BBr$_3$ (1M in DCM, 13.03 mL, 13.03 mmol) and the solution was stirred for 1 hour at room temperature. After completion of the reaction (monitored by TLC), methanol was added dropwise at 0° C. until the effervescence ceased. The reaction mixture was diluted with DCM (20 mL) and washed with water (2×20 mL) and brine (20 mL). The organic part was dried over anhydrous $Na_2SO_4$ and concentrated under vacuum. The resulting crude material was purified by Isolera column chromatography (eluent: 30-32% EtOAc/PE; silica gel: 230-400 mesh) to afford the title compound.

Yield: 94% (1.0 g, off-white solid).

$^1$H NMR (400 MHz, DMSO-$d_6$): δ 10.83 (s, 1H), 7.50 (s, 1H), 7.23 (t, J=8.0 Hz, 2H), 6.99 (d, J=7.6 Hz, 2H), 6.97 (s, 1H), 6.88 (t, J=7.2 Hz, 1H), 3.64 (s, 2H), 3.28 (s, 2H), 1.51-1.34 (m, 4H), 1.12-1.02 (m, 4H), 0.77-0.72 (m, 6H). LCMS: (Method A) 408.2 (M$^+$+H), Rt. 2.87 min, 93.25% (Max).

Separation of Enantiomers (S)-3-butyl-7-chloro-3-ethyl-8-hydroxy-5-phenyl-2,3,4,5-tetrahydro-1,5-benzothiazepine 1,1-dioxide and (R)-3-butyl-7-chloro-3-ethyl-8-hydroxy-5-phenyl-2,3,4,5-tetrahydro-1,5-benzothiazepine 1,1-dioxide

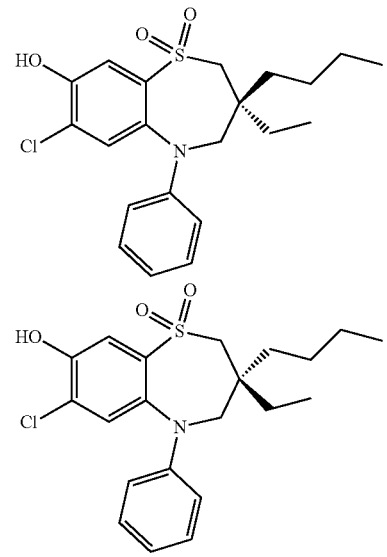

The two enantiomers of racemic 3-butyl-7-chloro-3-ethyl-8-hydroxy-5-phenyl-2,3,4,5-tetrahydro-1,5-benzothiazepine 1,1-dioxide (2.0 g, 4.9 mmol) were separated by chiral SFC (method F). The material was concentrated under vacuum at 40° C. The first eluting fraction corresponded to enantiomer 1 and the second eluting fraction corresponded to enantiomer 2. The absolute configuration of the two enantiomers is not known.

Enantiomer 1: Yield: 45% (900 mg, white solid). LCMS: (Method A) 408.1 (M$^+$+H), Rt. 2.86 min, 94.09% (Max). HPLC: (Method B) Rt. 5.93 min, 96.49% (Max). Chiral SFC: (Method H) Rt. 3.32 min, 95.52% (Max). (AR.NO: B601758)

Enantiomer 2: Yield: 45% (900 mg, white solid). LCMS: (Method A) 408.2 (M$^+$+H), Rt. 2.88 min, 94.34% (Max). HPLC: (Method B) Rt. 5.93 min, 94.42% (Max). Chiral Purity: (Method H) Rt. 4.32 min, 100% (Max).

Intermediate 12

Ethyl 3-((3-butyl-7-chloro-3-ethyl-1,1-dioxido-5-phenyl-2,3,4,5-tetrahydro-1,5-benzothiazepin-8-yl)oxy)propanoate

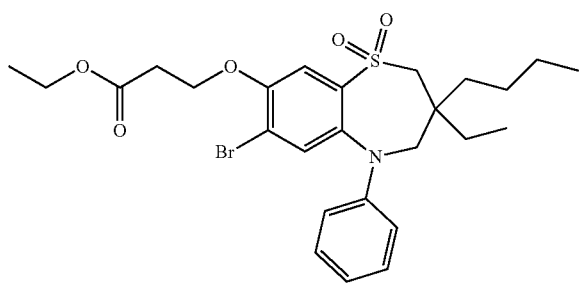 [SMILES: CCCCC1(CC)CN(c2ccccc2)c2cc(Br)c(OCCC(=O)OCC)cc2S(=O)(=O)C1]

To a stirred suspension of 3-butyl-7-chloro-3-ethyl-8-hydroxy-5-phenyl-2,3,4,5-tetrahydro-1,5-benzothiazepine 1,1-dioxide (Intermediate 11; 2.0 g, 4.91 mmol) in ethyl acrylate (10 mL) at room temperature, DMAP (0.06 g 0.49 mmol) was added. The reaction mixture was heated in a sealed tube for 24 hours at 100° C. The progress of the reaction was monitored by TLC, which indicated the incomplete conversion (25%) of the starting material. The reaction mixture was then evaporated and dried under vacuum to afford the crude title compound, which was forwarded to the next step without any further purification. Yield: 3.0 g (crude, brown gum).

LCMS: (Method C) 510.1 ($M^++2$), Rt. 3.23 min, 10% (Max).

Intermediate 13

2-(((2-Amino-4-chloro-5-methoxyphenyl)thio)methyl)-2-butylhexanoic acid

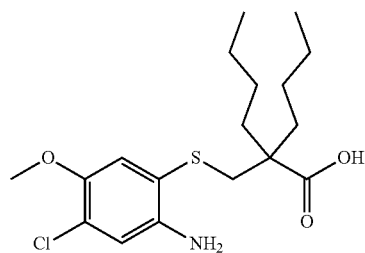 [SMILES: CCCCC(CCCC)(CSc1cc(OC)c(Cl)cc1N)C(=O)O]

To a stirred solution of 5-chloro-6-methoxybenzo[d]thiazol-2-amine (Intermediate 5; 10 g, 0.046 mol) in water (150 mL), KOH (40 g, 0.74 mol) was added and the reaction mixture was stirred for 16 hours at 120° C. After completion of the reaction (monitored by LCMS), the reaction mixture was cooled to room temperature. 2-(Bromomethyl)-2-butylhexanoic acid (12.33 g, 0.046 mol; dissolved in 50 mL of THF) was then added dropwise and the mixture was stirred for 16 hours at room temperature. After completion of the reaction (monitored by LCMS), the reaction mixture was cooled to 0° C. and acidified with concentrated HCl (pH 2). The reaction mixture was extracted with EtOAc (2×50 mL). The combined organic layer was then washed with water (50 mL) and brine (50 mL), dried over anhydrous $Na_2SO_4$ and concentrated under vacuum to obtain the crude material. The obtained crude material was forwarded as such to the next step without any further purification. Yield: 18.1 g (crude, brown gum).

UPLC: (Method A) 374.9 ($M^++H$), Rt. 1.74 min, 44.37% (Max).

Intermediate 14

3,3-Dibutyl-7-chloro-8-methoxy-2,3-dihydro-1,5-benzothiazepin-4(5H)-one

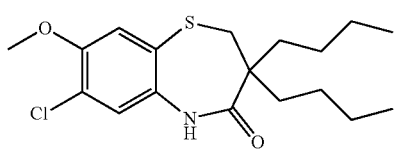 [SMILES: CCCCC1(CCCC)CSc2cc(OC)c(Cl)cc2NC1=O]

To a stirred solution of 2-(((2-amino-4-chloro-5-methoxyphenyl)thiomethyl)-2-butylhexanoic acid (Intermediate 13; 18.1 g, 0.048 mol) in EtOAc (110 mL) at 0° C., triethylamine (9.77 g, 0.096 mol) and 1-propanephosphonic anhydride solution (50% EtOAc) (18.47 g, 0.058 mol) were added dropwise and the reaction mixture was stirred for 16 hours at room temperature. After completion of the reaction (monitored by UPLC), water (25 mL) was added to the reaction mixture and the aqueous layer was extracted with EtOAc (2×25 mL). The combined organic layer was washed with brine (25 mL), dried over anhydrous $Na_2SO_4$ and concentrated under vacuum. The resulting crude material was purified by Isolera column chromatography (eluent: 10-12% EtOAc/PE; silica gel: 230-400 mesh) to afford the title compound. Yield: 28% (4.78 g, off-white solid).

$^1$H NMR (400 MHz, DMSO-$d_6$): δ 9.60 (s, 1H), 7.16 (t, J=11.6 Hz, 1H), 6.90 (s, 1H), 3.83 (s, 3H), 3.00 (s, 2H), 1.59-1.43 (m, 4H), 1.24-1.17 (m, 8H), 0.76 (t, J=4.0 Hz, 6H). LCMS: (Method A) 358.1 ($M^++2$), Rt. 3.10 min, 92.74% (Max).

Intermediate 15

3,3-Dibutyl-7-chloro-8-methoxy-5-phenyl-2,3-dihydro-1,5-benzothiazepin-4(5H)-one

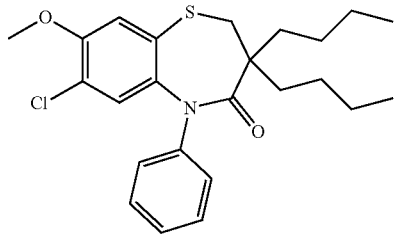 [SMILES: CCCCC1(CCCC)CSc2cc(OC)c(Cl)cc2N(c2ccccc2)C1=O]

To a stirred solution of 3,3-dibutyl-7-chloro-8-methoxy-2,3-dihydro-1,5-benzothiazepin-4(5H)-one (Intermediate 14; 4.78 g, 0.013 mol) in iodobenzene (40 mL) were added copper (I) iodide (0.25 g, 0.0013 mol) and $K_2CO_3$ (3.7 g, 0.026 mol) and the solution was purged with nitrogen for 20 minutes for degasification. Tris[2-(2-methoxyethoxy)ethyl] amine (0.86 g, 0.0026 mol) was then added under nitrogen atmosphere and the resulting reaction mixture was heated for 40 hours to 135° C. After completion of the reaction (monitored by UPLC), the reaction mixture was filtered through celite and the celite pad was washed with EtOAc (15 mL). The filtrate was concentrated under vacuum to obtain the crude material which was purified by Isolera column chromatography (eluent: 3-5% EtOAc/PE; silica gel: 230-400 mesh) to afford the title compound. Yield: 70.6% (4.1 g, pale brown solid).

LCMS: (Method C) 434.1 ($M^++2$), Rt. 3.55 min, 96.03% (Max).

Intermediate 16

3,3-Dibutyl-7-chloro-8-methoxy-5-phenyl-2,3,4,5-tetrahydro-1,5-benzothiazepine

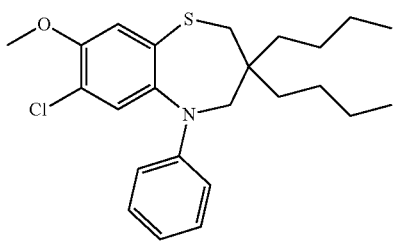 [SMILES: CCCCC1(CCCC)CSc2cc(OC)c(Cl)cc2N(c2ccccc2)C1]

To a stirred solution of 3,3-dibutyl-7-chloro-8-methoxy-5-phenyl-2,3-dihydro-1,5-benzothiazepin-4(5H)-one (Intermediate 15, 4.1 g, 0.009 mol) in THF (40 mL) at 0° C., borane dimethylsulfide (1M in THF, 47 mL, 0.047 mol) was added dropwise and the reaction mixture was refluxed for 40 hours at 75° C. After completion of the reaction (monitored by UPLC), the reaction mixture was cooled to 0° C. and quenched with methanol (50 mL). The resulting solution was heated for 2 hours to 65° C., then cooled to room temperature and concentrated under vacuum. The obtained crude material was purified by Isolera column chromatography (eluent: 8-10% EtOAc/PE; silica gel: 230-400 mesh) to afford the title compound. Yield: 84% (3.3 g, colourless liquid).

$^1$H NMR (400 MHz, DMSO-d$_6$): δ 7.21 (t, J=9.6 Hz, 2H), 7.06 (s, 1H), 6.95 (d, J=10.4 Hz, 2H), 6.83 (t, J=9.2 Hz, 2H), 6.77 (s, 1H), 3.82 (s, 3H), 3.57 (s, 2H), 3.32 (s, 2H), 1.30-1.20 (m, 4H), 1.10-1.00 (m, 8H), 0.76 (t, J=4.00 Hz, 6H).

Intermediate 17

3,3-Dibutyl-7-chloro-8-methoxy-5-phenyl-2,3,4,5-tetrahydro-1,5-benzothiazepine 1,1-dioxide

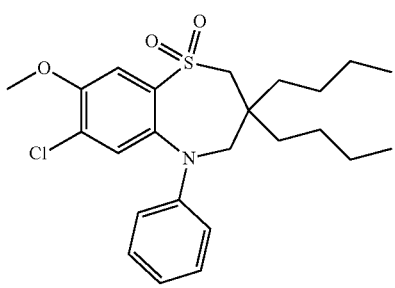 [SMILES: CCCCC1(CCCC)CN(c2ccccc2)c2cc(Cl)c(OC)cc2S(=O)(=O)C1]

To a stirred solution of 3,3-dibutyl-7-chloro-8-methoxy-5-phenyl-2,3,4,5-tetrahydro-1,5-benzothiazepine (Intermediate 16; 3.3 g, 0.008 mol) in 1,4-dioxane (42 mL) at room temperature were added water (16 mL) and oxone (24.26 g, 0.08 mol) and the reaction mixture was stirred for 24 hours at room temperature. After completion of the reaction (monitored by TLC), the reaction mixture was filtered off through a Buchner funnel and the filtrate was extracted with EtOAc (2×15 mL). The combined organic layer was washed with water (25 mL) and brine (25 mL), dried over anhydrous Na$_2$SO$_4$ and concentrated under vacuum. The crude material was purified by Isolera column chromatography (eluent: 10-12% EtOAc/PE; silica gel: 230-400 mesh) to afford the title compound. Yield: 68.7% (2.4 g, yellowish solid).

$^1$H NMR (400 MHz, DMSO-d$_6$): δ 7.49 (s, 1H), 7.27 (t, J=8.1 Hz, 2H), 7.08 (d, J=7.5 Hz, 2H), 6.98 (s, 1H), 6.95 (t, J=7.3 Hz, 1H), 3.93 (s, 3H), 3.70 (bs, 2H), 3.35 (s, 2H), 1.36-1.24 (m, 4H), 1.17-1.00 (m, 8H), 0.75 (t, J=4.00 Hz, 6H). LCMS: (Method C) 452.3 (M$^+$+2), Rt. 3.53 min, 96.85% (Max).

Intermediate 18

3,3-Dibutyl-7-chloro-8-hydroxy-5-phenyl-2,3,4,5-tetrahydro-1,5-benzothiazepine 1,1-dioxide

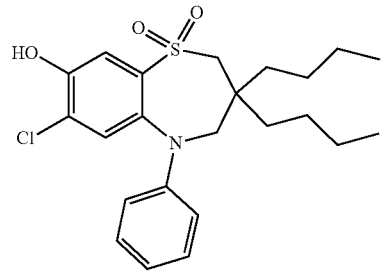 [SMILES: CCCCC1(CCCC)CN(c2ccccc2)c2cc(Cl)c(O)cc2S(=O)(=O)C1]

To a stirred solution of 3,3-dibutyl-7-chloro-8-methoxy-5-phenyl-2,3,4,5-tetrahydro-1,5-benzothiazepine 1,1-dioxide (Intermediate 17; 1.5 g, 3.33 mmol) in DCM (10 mL), BBr$_3$ (1M in DCM, 6.6 ml, 6.66 mmol) was added at −10° C. and the resulting mixture was stirred for 3 hours at room temperature. After completion of the reaction (monitored by TLC), the reaction mixture was quenched with methanol (5 mL) and the reaction mixture was concentrated under vacuum. The resulting crude material was purified by Isolera column chromatography (eluent: 10-15% EtOAc/PE; silica gel: 230-400 mesh) to afford the title compound. Yield: 83% (1.2 g, off-white solid).

$^1$H NMR (400 MHz, DMSO-d$_6$): δ 10.79 (s, 1H), 7.50 (s, 1H), 7.24 (t, J=8.2 Hz, 2H), 7.01 (d, J=7.8 Hz, 2H), 6.91 (t, J=9.0 Hz, 2H), 3.65 (bs, 2H), 3.29 (s, 2H), 1.40-1.30 (m, 5H), 1.20-1.12 (m, 7H), 0.74 (t, J=4.0 Hz, 6H). LCMS: (Method C) 438.1 (M$^+$+2), Rt. 3.1 min, 96.07% (Max).

Intermediate 19

Ethyl 3-((3,3-dibutyl-7-chloro-1,1-dioxido-5-phenyl-2,3,4,5-tetrahydro-1,5-benzothiazepin-8-yl)oxy)propanoate

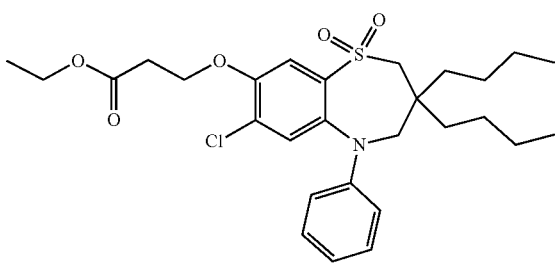 [SMILES: CCCCC1(CCCC)CN(c2ccccc2)c2cc(Cl)c(OCCC(=O)OCC)cc2S(=O)(=O)C1]

To a stirred suspension of 3,3-dibutyl-7-chloro-8-hydroxy-5-phenyl-2,3,4,5-tetrahydro-1,5-benzothiazepine 1,1-dioxide (Intermediate 18; 1.2 g, 2.75 mmol) in ethyl acrylate (5 mL) at room temperature, DMAP (30 mg, 0.27 mmol) was added. The reaction mixture was heated in a sealed tube for 24 hours at 100° C. The progress of the reaction was monitored by TLC, which indicated the incomplete conversion (20%) of the starting material. The reaction mixture was then concentrated under vacuum to afford the crude title compound, which was forwarded to the next step without any further purification. Yield: 1 g (crude, brown gum).

LCMS: (Method C) 537.3 (M$^+$+H), Rt. 3.55 min, 12.14% (Max).

Intermediate 20

Methyl 3-((3,3-dibutyl-7-(methylthio)-1,1-dioxido-5-phenyl-2,3,4,5-tetrahydro-1,5-benzothiazepin-8-yl)oxy)-2-hydroxypropanoate

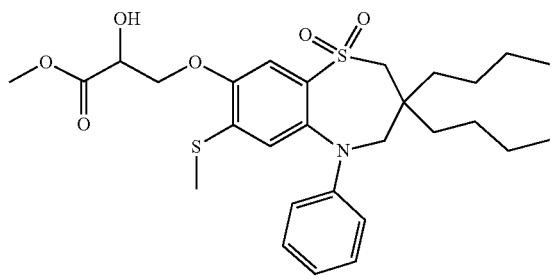 [SMILES: CCCCC1(CCCC)CN(c2ccccc2)c2cc(SC)c(OCC(O)C(=O)OC)cc2S(=O)(=O)C1]

To a stirred solution of 3,3-dibutyl-8-hydroxy-7-(methylthio)-5-phenyl-2,3,4,5-tetrahydro-1,5-benzothiazepine 1,1-dioxide (0.5 g, 0.001 mmol) in DMF (4 mL) at room temperature, Cs$_2$CO$_3$ (0.73 g, 0.002 mmol) and methyl oxirane-2-carboxylate (0.170 g, 0.002 mmol) were added and the reaction mixture was then stirred for 16 hours at 70° C. The progress of the reaction was monitored by TLC, which indicated the incomplete conversion of the starting material and formation of elimination product. The reaction mixture was concentrated under vacuum to afford the crude material which was purified by Isolera column chromatography (eluent: 25% EtOAc/PE; silica gel: 230-400 mesh) to furnish the title compound. Yield: 8% (50 mg, brown gum).

LCMS: (Method E) 550.2 (M$^+$+H), Rt. 2.79 min and 532.2 (M$^+$+H), Rt. 2.96 min, 88.39% (Max).

Intermediate 21

7-Bromo-3-butyl-3-ethyl-8-methoxy-5-phenyl-2,3,4,5-tetrahydro-1,5-benzothiazepine 1,1-dioxide

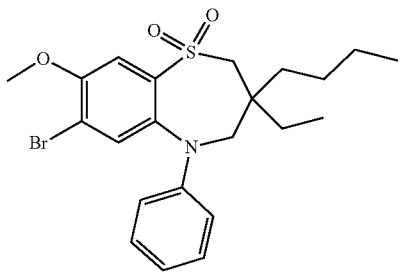 [SMILES: CCCCC1(CC)CN(c2ccccc2)c2cc(Br)c(OC)cc2S(=O)(=O)C1]

To a stirred solution of 7-bromo-3-butyl-3-ethyl-8-hydroxy-5-phenyl-2,3,4,5-tetrahydro-1,5-benzothiazepine 1,1-dioxide (1.0 g, 2 mmol) in dry DMF (15 mL) at 0° C., sodium hydride (60% in mineral oil) (0.09 mg, 2.40 mmol) was added and the reaction mixture was stirred for 10 min. Then methyl iodide (0.4 mL, 6 mmol) was added to the reaction mixture and the mixture was stirred at room temperature for 30 minutes. After completion of the reaction (monitored by TLC), the reaction mixture was quenched with ice cooled water (2 mL) and the aqueous layer was extracted with EtOAc (2×10 mL). The combined organic layer was washed with water (15 mL), brine (15 mL), dried over anhydrous Na$_2$SO$_4$ and concentrated under vacuum. The resulting crude material was forwarded to the next step without any further purification. Yield: 96% (900 mg, crude, brown gummy solid).

$^1$H NMR (400 MHz, DMSO-d$_6$): δ 7.45 (s, 1H), 7.26 (t, J=8.0 Hz, 2H), 7.18-7.16 (m, 1H), 7.06-7.04 (m, 2H), 6.93 (t, J=7.2 Hz, 1H), 3.93 (s, 3H), 3.70-3.61 (m, 2H), 3.10 (s, 2H), 1.51-0.90 (m, 8H), 0.80-0.72 (m, 6H). LCMS: (Method A) 468.1 (M+2), Rt. 3.21 min, 96.82% (Max).

Intermediate 22

3-Butyl-3-ethyl-8-hydroxy-7-(methylthio)-5-phenyl-2,3,4,5-tetrahydro-1,5-benzothiazepine 1,1-dioxide

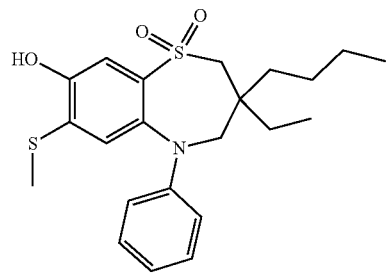 [SMILES: CCCCC1(CC)CN(c2ccccc2)c2cc(SC)c(O)cc2S(=O)(=O)C1]

To a stirred solution of 7-bromo-3-butyl-3-ethyl-8-methoxy-5-phenyl-2,3,4,5-tetrahydro-1,5-benzothiazepine 1,1-dioxide (Intermediate 21; 0.9 g, 1.90 mmol) in dry DMF (15 mL), sodium thiomethoxide (687 mg, 9.5 mmol) was added at room temperature and the reaction mixture was stirred at 60° C. for 16 hours. After completion of the reaction (monitored by LCMS), the reaction mixture was quenched with ice cold water (2 mL) and the aqueous layer was extracted with EtOAc (2×10 mL). The combined organic layer was washed with water (15 mL), brine (15 mL), dried over anhydrous Na$_2$SO$_4$ and concentrated under vacuum. The resulting crude material was purified by Isolera column chromatography (eluent: 10-15% EtOAc/PE; silica gel: 230-400 mesh) to afford the title compound. Yield: 93% (750 mg, pale brown solid).

$^1$H NMR (400 MHz, DMSO-d$_6$): δ 7.16-7.12 (m, 3H), 6.85-6.83 (m, 2H), 6.71 (t, J=7.2 Hz, 1H), 6.60 (s, 1H), 3.74-3.61 (m, 2H), 3.12 (s, 2H), 2.13 (s, 3H), 1.70-1.08 (m, 8H), 0.80-0.74 (m, 6H). UPLC: (Method A) 420.5 (M+H), Rt. 1.86 min, 91.84% (Max).

Intermediate 23

(S)-3-Butyl-3-ethyl-8-hydroxy-7-(methylthio)-5-phenyl-2,3,4,5-tetrahydro-1,5-benzothiazepine 1,1-dioxide and (R)-3-butyl-3-ethyl-8-hydroxy-7-(methylthio)-5-phenyl-2,3,4,5-tetrahydro-1,5-benzothiazepine 1,1-dioxide

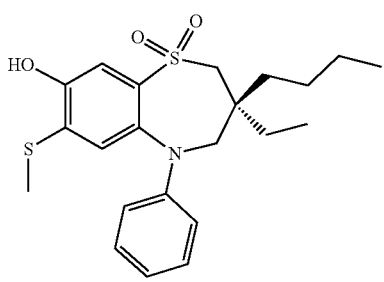

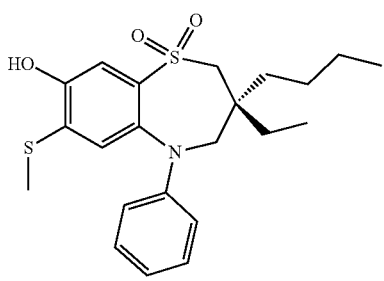

The two enantiomers of racemic 3-butyl-3-ethyl-8-hydroxy-7-(methylthio)-5-phenyl-2,3,4,5-tetrahydro-1,5-benzothiazepine 1,1-dioxide (Intermediate 22) were separated by chiral SFC (method F). The material was concentrated under vacuum at 40° C. The first eluting fraction corresponded to enantiomer 1 and the second eluting fraction corresponded to enantiomer 2. The absolute configuration of the two enantiomers is not known.

Enantiomer 1: Yield: 44% (3.1 g, pale brown solid). $^1$H NMR (400 MHz, DMSO-$d_6$): δ 10.54 (s, 1H), 7.30 (s, 1H), 7.21-7.17 (m, 2H), 6.91 (d, J=7.6 Hz, 2H), 6.80 (t, J=7.2 Hz, 1H), 6.69 (s, 1H), 3.65 (bs, 2H), 3.20 (s, 2H), 2.18 (s, 3H), 1.60-1.50 (m, 1H), 1.50-1.40 (m, 1H), 1.40-1.25 (m, 2H), 1.20-1.00 (m, 4H), 0.80-0.74 (m, 6H). LCMS: (Method E) 419.9 (M$^+$+H), Rt. 3.04 min, 95.84% (Max). HPLC: (Method B) Rt. 5.93 min, 96.07% (Max). Chiral SFC: (Method H) Rt. 3.58 min, 99.19% (Max).

Enantiomer 2: Yield: 42% (3.0 g, pale brown solid). $^1$H NMR (400 MHz, DMSO-$d_6$): δ 10.52 (s, 1H), 7.29 (s, 1H), 7.18 (t, J=11.2 Hz, 2H), 6.90 (d, J=10.4 Hz, 2H), 6.78 (t, J=9.6 Hz, 1H), 6.67 (s, 1H), 3.64 (bs, 2H), 3.19 (s, 2H), 2.16 (s, 3H), 1.51-1.49 (m, 1H), 1.50-1.20 (m, 3H), 1.20-0.95 (m, 4H), 0.85-0.65 (m, 6H). LCMS: (Method E) 419.9 (M$^+$+H), Rt. 3.04 min, 97.11% (Max). HPLC: (Method B) Rt. 5.93 min, 98.25% (Max). Chiral Purity: (Method H) Rt. 5.03 min, 98.68% (Max).

Intermediate 24

Ethyl 3-((3-butyl-3-ethyl-7-(methylthio)-1,1-dioxido-5-phenyl-2,3,4,5-tetrahydro-1,5-benzothiazepin-8-yl)oxy)propanoate

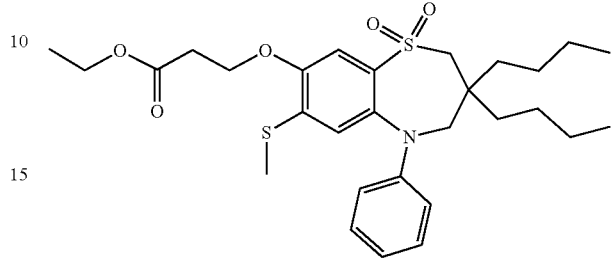

To a stirred suspension of 3-butyl-3-ethyl-8-hydroxy-7-(methylthio)-5-phenyl-2,3,4,5-tetrahydro-1,5-benzothiazepine 1,1-dioxide (Intermediate 22; 1.0 g, 2.38 mmol) in ethyl acrylate (5 mL) at room temperature, DMAP (30 mg, 0.23 mmol) was added. The reaction mixture was heated in a sealed tube for 24 hours at 100° C. The progress of the reaction was monitored by TLC, which indicated the incomplete conversion (30%) of the starting material. The reaction mixture was then evaporated and dried under vacuum to afford the crude title compound, which was forwarded to the next step without any further purification. Yield: 1.3 g (crude, brown gum).

LCMS: (Method E) 520.2 (M$^+$+H), Rt. 6.18 min, 29.31% (Max).

Intermediate 25

Ethyl (E)-3-((3,3-dibutyl-7-(methylthio)-1,1-dioxido-5-phenyl-2,3,4,5-tetrahydro-1,5-benzothiazepin-8-yl)oxy)acrylate and ethyl (Z)-3-((3,3-dibutyl-7-(methylthio)-1,1-dioxido-5-phenyl-2,3,4,5-tetrahydro-1,5-benzothiazepin-8-yl)oxy)acrylate

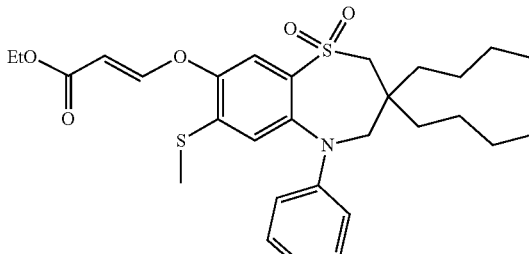

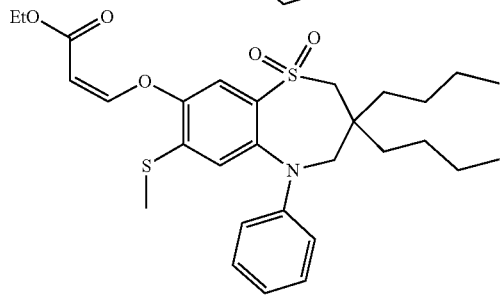

To a stirred solution of 3,3-dibutyl-8-hydroxy-7-(methylthio)-5-phenyl-2,3,4,5-tetrahydro-1,5-benzothiazepine 1,1-dioxide (4 g, 8.93 mmol) in dry DMF (50 mL), ethyl (E)-3-bromoacrylate (2.4 g, 13.4 mmol), potassium carbonate (2.46 g, 17.87 mmol) and tetra-butyl ammonium bromide (0.287 g, 0.89 mmol) were added at room temperature and the reaction mixture was heated at 90° C. for 12 hours. After completion of the reaction (monitored by TLC), the reaction mixture was poured into ice-cold water and extracted with EtOAc (3×25 mL). The combined organic layer was washed with brine (50 mL), dried over anhydrous $Na_2SO_4$ and concentrated under vacuum to afford the title compound as a mixture of the (E)- and (Z)-isomers (1.7:1 ratio). This mixture was separated by Prep-HPLC (method A) to afford the first eluting fraction corresponding to the (Z)-isomer and the second eluting fraction corresponding to the (E)-isomer, with overall 73% yield.

(E)-isomer: Yield: 39% (1.9 g, white solid). $^1$H NMR (400 MHz, DMSO-$d_6$): δ 7.72 (d, J=16.0 Hz, 1H), 7.48 (s, 1H), 7.32-7.27 (m, 2H), 7.19-7.16 (m, 2H), 7.02-6.97 (m, 1H), 6.63 (s, 1H), 5.48 (d, J=16.0 Hz, 1H), 4.14-4.07 (m, 2H), 3.75 (bs, 2H), 3.36 (s, 2H), 2.14 (s, 3H), 1.40-1.31 (m, 4H), 1.27-1.08 (m, 11H), 0.75-0.73 (m, 6H). LCMS: (Method C) 546.1 (M+H), Rt. 3.47 min, 97.89% (Max)

(Z)-isomer: Yield: 34% (1.65 g, white solid). $^1$H NMR (400 MHz, DMSO-$d_6$): δ 7.47 (s, 1H), 7.32-7.28 (m, 2H), 7.20-7.19 (m, 2H), 7.16-7.14 (m, 1H), 7.01-6.97 (m, 1H), 6.66 (s, 1H), 5.26 (d, J=8.0 Hz, 1H), 4.13-4.08 (m, 2H), 3.75 (bs, 2H), 3.33 (s, 2H), 2.18 (s, 3H), 1.43-1.36 (m, 2H), 1.33-1.30 (m, 2H), 1.22 (m, 3H), 1.10-0.98 (m, 8H), 0.76-0.73 (m, 6H). LCMS: (Method C) 546.1 (M+H), Rt. 3.34 min, 98.32% (Max).

Intermediate 26

Ethyl 3-((3,3-dibutyl-7-(methylthio)-1,1-dioxido-5-phenyl-2,3,4,5-tetrahydro-1,5-benzothiazepin-8-yl)oxy)propanoate

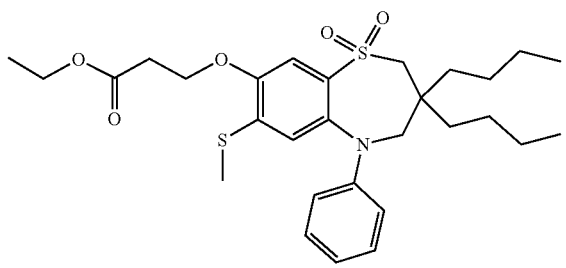 [SMILES: CCCCC1(CCCC)CN(c2ccccc2)c2cc(SC)c(OCCC(=O)OCC)cc2S(=O)(=O)C1]

To stirred solution of a mixture of ethyl (E)-3-((3,3-dibutyl-7-(methylthio)-1,1-dioxido-5-phenyl-2,3,4,5-tetrahydro-1,5-benzothiazepin-8-yl)oxy)acrylate and ethyl (Z)-3-((3,3-dibutyl-7-(methylthio)-1,1-dioxido-5-phenyl-2,3,4,5-tetrahydro-1,5-benzothiazepin-8-yl)oxy)acrylate (Intermediate 25; 2.8 g, 0.51 mmol) in EtOAc (15 mL), Pd/C (0.56 g, 52.6 mmol) and AcOH (0.1 mL) were added under nitrogen atmosphere and the mixture was stirred under hydrogen atmosphere in a tinyclave (under 2.5-3.0 kg pressure) for 12 hours at room temperature. After completion of the reaction (monitored by LCMS), the reaction mixture was filtered through celite and the celite pad was washed with EtOAc (2×15 mL). The combined filtrate was concentrated under vacuum to furnish the title compound.
Yield: 64% (1.8 g, off-white solid).

Intermediate 27

3-Butyl-7-(dimethylamino)-3-ethyl-8-methoxy-5-phenyl-2,3,4,5-tetrahydro-1,5-benzothiazepine 1,1-dioxide

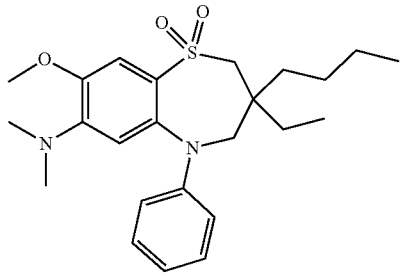 [SMILES: CCCCC1(CC)CN(c2ccccc2)c2cc(N(C)C)c(OC)cc2S(=O)(=O)C1]

To a stirred solution of 7-bromo-3-butyl-3-ethyl-8-methoxy-5-phenyl-2,3,4,5-tetrahydro-1,5-benzothiazepine 1,1-dioxide (Intermediate 21, 3 g, 6.43 mmol) in toluene (10 mL), $Cs_2CO_3$ (5.2 g, 16.1 mmol) was added and the reaction mixture was degassed for 10 minutes with $N_2$. Dimethylamine (2M in THF, 6.4 mL, 12.8 mmol), $Pd(OAc)_2$ (0.04 g, 0.16 mmol) followed by X-Phos (0.08 g, 0.16 mmol) were then added and the reaction mixture was heated for 16 hours at 90° C. After completion of the reaction (monitored by TLC), the reaction mixture was filtered through celite and the celite pad was washed with EtOAc (100 mL). The combined organic part was concentrated under vacuum and the resulting crude was purified by Isolera column chromatography (eluent: 13-15% EtOAc/PE, silica gel: 230-400 mesh) to afford the title compound. Yield: 26% (0.7 g, yellow gum).

$^1$H NMR (400 MHz, DMSO-$d_6$): δ 7.28 (s, 1H), 7.22-7.18 (m, 2H), 6.97 (d, J=8.0 Hz, 2H), 6.83 (t, J=7.2 Hz, 1H), 6.34 (s, 1H), 3.85 (s, 3H), 3.70 (bs, 2H), 3.29 (s, 2H), 2.66 (s, 6H), 1.54-1.41 (m, 2H), 1.35-1.24 (m, 2H), 1.20-1.12 (m, 4H), 0.85-0.75 (m, 6H). LCMS: (Method A) 431.2 (M$^+$+H), Rt. 3.19 min, 83.34% (Max).

Intermediate 28

3-butyl-7-(dimethylamino)-3-ethyl-8-hydroxy-5-phenyl-2,3,4,5-tetrahydro-1,5-benzothiazepine 1,1-dioxide

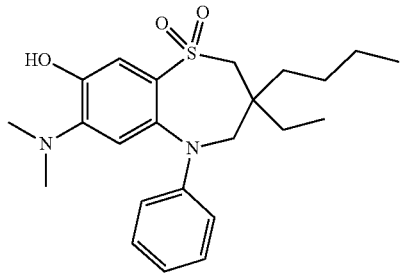 [SMILES: CCCCC1(CC)CN(c2ccccc2)c2cc(N(C)C)c(O)cc2S(=O)(=O)C1]

To a stirred solution of 3-butyl-7-(dimethylamino)-3-ethyl-8-methoxy-5-phenyl-2,3,4,5-tetrahydro-1,5-benzothiazepine 1,1-dioxide (Intermediate 27; 1.9 g, 4.41 mmol) in DMF (15 mL) at room temperature, sodium thiomethoxide (1.54 g, 22.06 mmol) was added and the reaction mixture was stirred for 12 hours at 80° C. After completion of the reaction (monitored by TLC), the reaction mixture was cooled to room temperature and quenched with water (15 mL). The aqueous layer was extracted with EtOAc (2×15 mL), and the combined organic layer was washed with water (20 mL) and brine (20 mL) and dried over anhydrous Na$_2$SO$_4$. The organic part was concentrated under vacuum to afford the crude compound which was forwarded as such to the next step without any further purification. Yield: 1.8 g (crude, brown gum).

LCMS: (Method E) 417.2 (M$^+$+H), Rt. 2.11 min, 55.04% (Max).

Intermediate 29

Methyl 3-((3,3-dibutyl-7-(methylthio)-1,1-dioxido-5-phenyl-2,3,4,5-tetrahydro-1,5-benzothiazepin-8-yl)oxy)-2-hydroxy-2-methylpropanoate

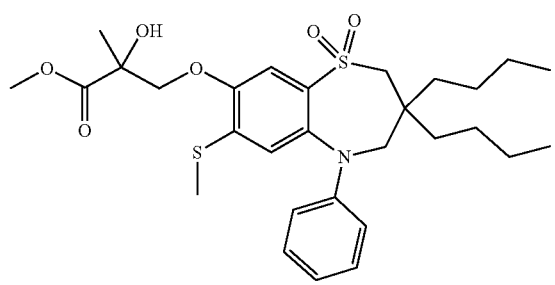 [SMILES: CCCCC1(CCCC)CN(c2ccccc2)c2cc(SC)c(OCC(C)(O)C(=O)OC)cc2S(=O)(=O)C1]

To a stirred solution of 3,3-dibutyl-8-hydroxy-7-(methylthio)-5-phenyl-2,3,4,5-tetrahydro-1,5-benzothiazepine 1,1-dioxide (500 mg, 1.11 mmol) in N-methyl-2-pyrrolidone (5 mL), Cs$_2$CO$_3$ (723 mg, 2.23 mmol) and methyl 2-methylglycidate (260 mg, 2.23 mmol) were added and the reaction mixture was heated for 16 hours at 80° C. After completion of the reaction (monitored by TLC), the reaction mixture was quenched with dilute HCl (1.5 N, 5 mL) and diluted with water (5 mL). The aqueous layer was extracted with EtOAc (2×10 mL), and the combined organic layer was washed with water (10 mL) and brine (10 mL). The organic part was dried over anhydrous Na$_2$SO$_4$, filtered and concentrated under vacuum. The resulting crude material was purified by Isolera column chromatography (eluent: 40% EtOAc/PE; silica gel: 230-400 mesh) to afford the title compound. Yield: 40% (250 mg, white gum).

$^1$H NMR (400 MHz, DMSO-d$_6$): δ 7.29 (s, 1H), 7.21 (t, J=7.6 Hz, 2H), 7.00 (d, J=7.2 Hz, 2H), 6.86 (t, J=7.2 Hz, 1H), 6.65 (s, 1H), 4.16-4.01 (m, 2H), 3.67-3.59 (m, 5H), 3.26 (s, 2H), 2.13 (s, 3H), 1.42-1.35 (m, 5H), 1.34-1.25 (m, 2H), 1.24-1.05 (m, 8H), 0.77-0.74 (m, 6H). LCMS: (Method A) 564.1 (M$^+$+H), Rt. 3.15 min, 99.13% (Max).

Intermediate 30

2-(((2-Amino-4-bromo-5-methoxyphenyl)thio)methyl)-2-methylhexanoic acid

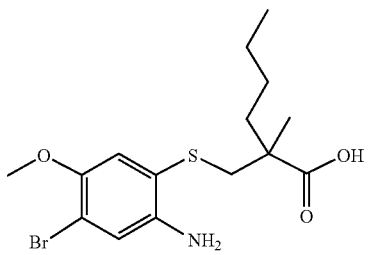 [SMILES: CCCCC(C)(CSc1cc(OC)c(Br)cc1N)C(=O)O]

To a stirred solution of 5-bromo-6-methoxybenzo[d]thiazol-2-amine (63 g, 0.243 mol) in water (630 mL), KOH (218.2 g, 3.89 mol) was added and the reaction mixture was stirred for 16 hours at 120° C. After completion of the reaction (monitored by LCMS), the reaction mixture was cooled to room temperature. A solution of 2-(bromomethyl)-2-methylhexanoic acid (70.5 g, 6.31 mol) in THF (210 mL) was then added dropwise and the reaction mixture was stirred for 16 hours at room temperature. After completion of the reaction (monitored by LCMS), the reaction mixture was cooled to 0° C. and acidified with conc. HCl (pH 2). The reaction mixture was extracted with EtOAc (2×350 mL) and the combined organic layer was washed with water (150 mL) and brine (150 mL). The organic part was dried over anhydrous Na$_2$SO$_4$ and concentrated under vacuum. The resulting crude was forwarded as such to the next step without any further purification. Yield: 75 g (crude, brown gum).

LCMS: (Method A) 376.1 (M$^+$), 378.0 (M$^+$+2), Rt. 2.44 min, 92.97% (Max).

Intermediate 31

7-Bromo-3-butyl-8-methoxy-3-methyl-2,3-dihydro-1,5-benzothiazepin-4(5H)-one

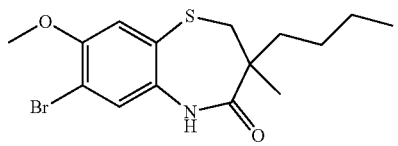 [SMILES: CCCCC1(C)CSc2cc(OC)c(Br)cc2NC1=O]

To a stirred solution of 2-(((2-amino-4-bromo-5-methoxyphenyl)thio)methyl)-2-methylhexanoic acid (Intermediate 30; 75.0 g, 0.199 mol) in EtOAc (750 mL) at 0° C., triethylamine (60.4 g, 0.59 mol) and 1-propanephosphonic anhydride solution (50% in EtOAc, 95.1 g, 0.29 mol) were added dropwise. The reaction mixture was stirred for 16 h at room temperature. After completion of the reaction (monitored by UPLC), the reaction mixture was quenched with water (150 mL) and the aqueous layer was extracted with EtOAc (2×200 mL). The combined organic layer was washed with brine (150 mL) and dried over anhydrous Na$_2$SO$_4$. The organic part was concentrated under vacuum and the resulting crude material was purified by Isolera column chromatography (eluent: 10-12% EtOAc/PE; silica gel: 230-400 mesh) to afford the title compound. Yield: 63% (45 g, off-white solid).

¹H NMR (400 MHz, DMSO-d$_6$): δ 9.62 (s, 1H), 7.33 (s, 1H), 7.13 (s, 1H), 3.83 (s, 3H), 3.17 (s, 2H), 1.46-1.44 (m, 2H), 1.22 (s, 3H), 1.17-1.14 (m, 4H), 0.79 (t, J=6.8 Hz, 3H). LCMS: (Method A) 360.0 (M$^+$+2), Rt. 2.64 min, 97.14% (Max).

Intermediate 32

7-Bromo-3-butyl-8-methoxy-3-methyl-5-phenyl-2,3-dihydro-1,5-benzothiazepin-4(5H)-one and 3-butyl-7-iodo-8-methoxy-3-methyl-5-phenyl-2,3-dihydro-1,5-benzothiazepin-4(5H)-one

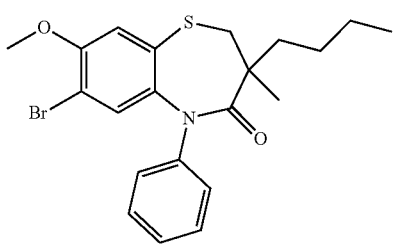

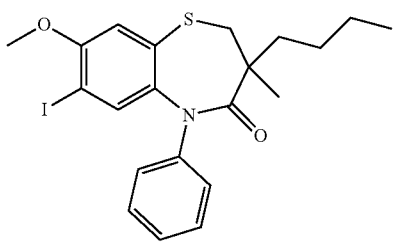

To a stirred solution of 7-bromo-3-butyl-8-methoxy-3-methyl-2,3-dihydro-1,5-benzothiazepin-4(5H)-one (Intermediate 31; 45 g, 0.12 mol) in iodobenzene (225 mL), copper (I) iodide (2.4 g, 0.012 mol) and K$_2$CO$_3$ (34.6 g, 0.251 mol) were added and the mixture was purged with nitrogen for 20 minutes for degasification. Tris[2-(2-methoxyethoxy)ethyl]amine (8.11 g, 0.025 mol) was then added under nitrogen atmosphere and the resulting reaction mixture was heated for 40 hours at 135° C. After completion of the reaction (monitored by UPLC), the reaction mixture was filtered through celite and the celite pad was washed with EtOAc (200 mL). The filtrate was concentrated under vacuum and the resulting crude material was purified by recrystallization with MeOH to afford the title compounds.

Yield: 88% (47.5 g, off-white solid).

LCMS: (Method E) 434.1 (M$^+$) for the 7-bromo substituted compound and 482.1 (M$^+$+H) for the 7-iodo substituted compound, Rt. 3.23 min, 99.31% (combined for the bromo- and iodo-substituted compounds) (Max).

Intermediate 33

7-Bromo-3-butyl-8-methoxy-3-methyl-5-phenyl-2,3,4,5-tetrahydro-1,5-benzothiazepine and 3-butyl-7-iodo-8-methoxy-3-methyl-5-phenyl-2,3,4,5-tetrahydro-1,5-benzothiazepine

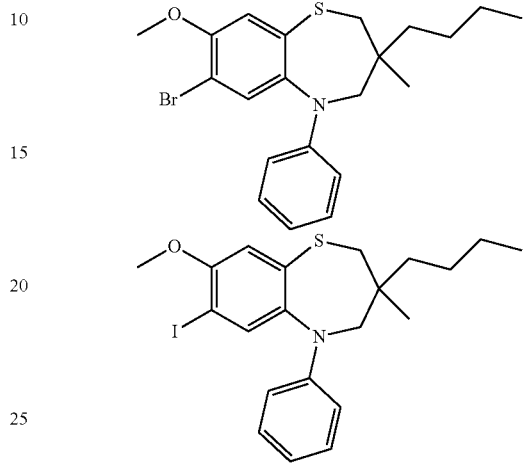

To a stirred solution of a mixture of 7-bromo-3-butyl-8-methoxy-3-methyl-5-phenyl-2,3-dihydro-1,5-benzothiazepin-4(5H)-one and 3-butyl-7-iodo-8-methoxy-3-methyl-5-phenyl-2,3-dihydro-1,5-benzothiazepin-4(5H)-one (Intermediate 32; 47.5 g, 0.109 mol) in THF (475 mL) at 0° C., borane dimethylsulfide (1M in THF, 82 mL, 0.16 mol) was added dropwise and the reaction mixture was refluxed for 40 hours at 75° C. After completion of the reaction (monitored by UPLC), the reaction mixture was cooled to 0° C. and quenched with methanol (475 mL). The resulting solution was heated for 2 hours at 65° C., and then cooled to room temperature and concentrated under vacuum. The resulting crude material was purified by Isolera column chromatography (eluent: 8-10% EtOAc/PE; silica gel: 230-400 mesh) to afford the title compound. Yield: 46 g (crude, colourless liquid).

LCMS: (Method E) 421.8 (M$^+$+2H), 467.8 (M$^+$+H) Rt. 3.62 min, 54.71% (Max).

Intermediate 34

7-Bromo-3-butyl-8-methoxy-3-methyl-5-phenyl-2,3,4,5-tetrahydro-1,5-benzothiazepine 1,1-dioxide and 3-butyl-7-iodo-8-methoxy-3-methyl-5-phenyl-2,3,4,5-tetrahydro-1,5-benzothiazepine 1,1-dioxide

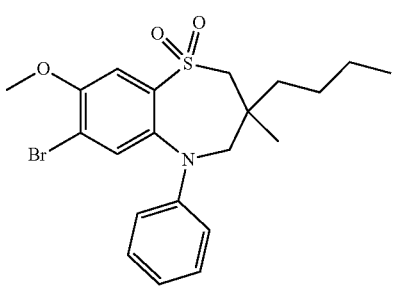

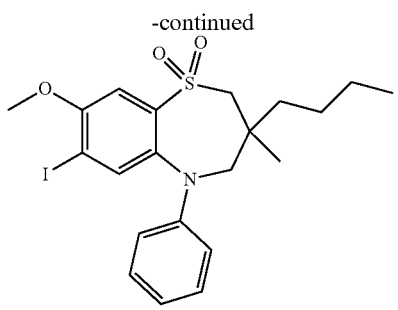

To a stirred solution of a mixture of 7-bromo-3-butyl-8-methoxy-3-methyl-5-phenyl-2,3,4,5-tetrahydro-1,5-benzothiazepine and 3-butyl-7-iodo-8-methoxy-3-methyl-5-phenyl-2,3,4,5-tetrahydro-1,5-benzothiazepine (Intermediate 33; 23 g, 0.05 mol) in acetic acid (230 mL) were added sodium tungstate (2.3 g, 10% wt/wt) and $H_2O_2$ (30% in water, 18.6 mL, 0.16 mol) and the reaction mixture was stirred for 5 hours at room temperature. After completion of the reaction (monitored by TLC), the reaction mixture was quenched with water (200 mL) and the aqueous layer was extracted with EtOAc (2×200 mL). The combined organic layer was washed with water (150 mL) and brine (150 mL), dried over anhydrous $Na_2SO_4$ and concentrated under vacuum. The resulting crude material was purified by Isolera column chromatography (eluent: 10-12% EtOAc/PE; silica gel: 230-400 mesh) to afford the title compound. Yield: 72% (18 g, yellowish solid).
$^1$H NMR (400 MHz, DMSO-$d_6$): δ 7.47 (s, 1H), 7.34 (s, 1H), 7.27-7.20 (m, 2H), 6.99-6.94 (m, 2H), 6.89-6.85 (m, 1H), 3.94 (s, 3H), 3.40-3.33 (m, 2H), 2.53 (s, 2H), 1.46-1.30 (m, 2H), 1.27-1.20 (m, 4H), 1.10-1.06 (m, 3H), 0.78 (t, J=6.80 Hz, 3H). LCMS: (Method E) 454.1 (M$^+$+2H) for the 7-bromo substituted compound and 500.1 (M$^+$+H) for 7-iodo substituted compound, Rt. 3.25 min, 92.56% (Max).

Intermediate 35

3-Butyl-8-hydroxy-3-methyl-7-(methylthio)-5-phenyl-2,3,4,5-tetrahydro-1,5-benzothiazepine 1,1-dioxide

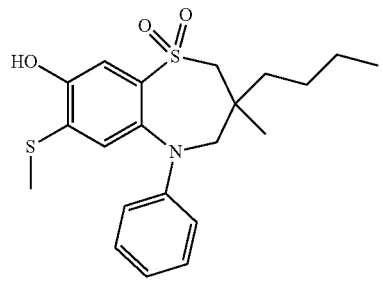 [SMILES: CCCCC1(C)CN(c2ccccc2)c2cc(SC)c(O)cc2S(=O)(=O)C1]

To a stirred solution of a mixture of 7-bromo-3-butyl-8-methoxy-3-methyl-5-phenyl-2,3,4,5-tetrahydro-1,5-benzothiazepine 1,1-dioxide and 3-butyl-7-iodo-8-methoxy-3-methyl-5-phenyl-2,3,4,5-tetrahydro-1,5-benzothiazepine 1,1-dioxide (Intermediate 34; 31 g, 0.07 mol) in DMF (310 mL), sodium thiomethoxide (24.01 g 0.34 mol) was added at room temperature and the resulting mixture was stirred overnight at 65° C. After completion of the reaction (monitored by TLC), the reaction mixture was quenched with water (150 mL) and the aqueous layer was extracted with EtOAc (2×300 mL). The combined organic layer was washed with brine (150 mL), dried over anhydrous $Na_2SO_4$ and concentrated under vacuum. The resulting crude material was purified by recrystallization with MeOH to afford the title compound. Yield: 83% (23 g, off-white solid).
$^1$H NMR (400 MHz, DMSO-$d_6$): δ 10.60 (s, 1H), 7.32 (s, 1H), 7.18-7.14 (m, 2H), 6.86 (d, J=7.6 Hz, 2H), 6.77 (s, 1H), 6.76-6.73 (m, 1H), 3.27-3.15 (m, 2H), 2.54 (s, 2H), 2.26 (s, 3H), 1.47-1.29 (m, 2H), 1.27-1.20 (m, 4H), 1.18-1.12 (m, 3H), 0.81 (t, J=7.2 Hz, 3H). LCMS: (Method E) 406.2 (M$^+$+H), Rt. 2.98 min, 95.07% (Max).

Separation of Enantiomers (S)-3-butyl-8-hydroxy-3-methyl-7-(methylthio)-5-phenyl-2,3,4,5-tetrahydro-1,5-benzothiazepine 1,1-dioxide and (R)-3-butyl-8-hydroxy-3-methyl-7-(methylthio)-5-phenyl-2,3,4,5-tetrahydro-1,5-benzothiazepine 1,1-dioxide

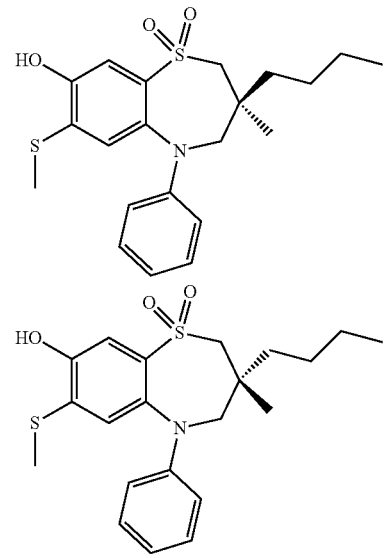

The two enantiomers of racemic 3-butyl-8-hydroxy-3-methyl-7-(methylthio)-5-phenyl-2,3,4,5-tetrahydro-1,5-benzothiazepine 1,1-dioxide (2.9 g, 0.01 mol) were separated by chiral SFC (method M). The material was concentrated under vacuum at 40° C. The first eluting fraction corresponded to enantiomer 1 and the second eluting fraction corresponded to enantiomer 2. The absolute configuration of the two enantiomers is not known.

Enantiomer 1: Yield: 41% (1.2 g, white solid). $^1$H NMR (400 MHz, DMSO-$d_6$): δ 10.51 (s, 1H), 7.31 (s, 1H), 7.18-7.14 (m, 2H), 6.85 (d, J=8.0 Hz, 2H), 6.77-6.73 (m, 2H), 3.27-3.15 (m, 2H), 2.53 (s, 2H), 2.21 (s, 3H), 1.46-1.31 (m, 2H), 1.29-1.12 (m, 4H), 1.06-1.01 (m, 3H), 0.81 (t, J=7.2 Hz, 3H). LCMS: (Method A) 406.1 (M$^+$+H), Rt. 2.72 min, 97.0% (Max). HPLC: (Method B) Rt. 5.61 min, 97.78% (Max). Chiral SFC: (Method M) Rt. 2.36 min, 98.75% (Max).

Enantiomer 2: Yield: 38% (1.1 g, white solid). $^1$H NMR (400 MHz, DMSO-$d_6$): δ 10.57 (s, 1H), 7.31 (s, 1H), 7.18-7.14 (m, 2H), 6.85 (d, J=7.6 Hz, 2H), 6.77-6.73 (m, 2H), 3.27-3.15 (m, 2H), 2.53 (s, 2H), 2.21 (s, 3H), 1.48-1.31

(m, 2H), 1.29-1.18 (m, 4H), 1.12-1.01 (m, 3H), 0.81 (t, J=7.2 Hz, 3H). LCMS: (Method A) 406.2 (M⁺+H), Rt. 2.85 min, 99.57% (Max). HPLC: (Method B) Rt. 5.61 min, 99.83% (Max).

Chiral SFC: (Method M) Rt. 3.58 min, 100% (Max).

Intermediate 36

7-bromo-3,3-dibutyl-5-(3,4-difluorophenyl)-8-methoxy-2,3-dihydro-1,5-benzothiazepin-4(5H)-one

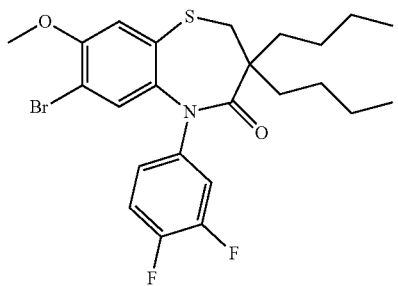 [SMILES: CCCCC1(CCCC)CSc2cc(OC)c(Br)cc2N(c2ccc(F)c(F)c2)C1=O]

To a stirred solution of 7-bromo-3,3-dibutyl-8-methoxy-2,3-dihydro-1,5-benzothiazepin-4(5H)-one (3.0 g, 0.007 mol) in 4-bromo-1,2-difluorobenzene (5 mL), copper (I) iodide (0.286 mg, 0.0015 mol) and K₂CO₃ (2.07 g, 0.015 mol) were added and the reaction mixture was purged with nitrogen 20 minutes for degasification. Tris[2-(2-methoxyethoxy)ethyl]amine (0.242 mL, 0.00075 mol) was then added under nitrogen atmosphere and the resulting reaction mixture was heated for 16 hours at 130° C. After completion of the reaction (monitored by UPLC), the reaction mixture was filtered through celite and the celite pad was washed with EtOAc (50 mL). The filtrate was washed with water (50 mL) and brine (50 mL) and dried over anhydrous Na₂SO₄. The organic part was concentrated under vacuum and the resulting crude material was purified by Isolera column chromatography (eluent: 8-10% EtOAc/PE; silica gel: 230-400 mesh) to afford the title compound. Yield: 74% (2.8 g, pale brown solid).

LCMS: (Method E) 512.1 (M⁺), Rt. 3.07 min, 85% (Max).

Intermediate 37

7-bromo-3,3-dibutyl-5-(3,4-difluorophenyl)-8-methoxy-2,3,4,5-tetrahydro-1,5-benzothiazepine

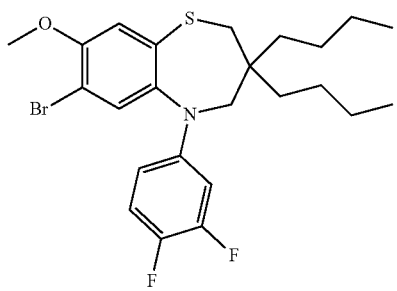 [SMILES: CCCCC1(CCCC)CSc2cc(OC)c(Br)cc2N(c2ccc(F)c(F)c2)C1]

To a stirred solution of 7-bromo-3,3-dibutyl-5-(3,4-difluorophenyl)-8-methoxy-2,3-dihydro-1,5-benzothiazepin-4(5H)-one (Intermediate 36; 2.8 g, 0.0054 mmol) in THF (15 mL) at 0° C., borane dimethylsulfide (2M in THF; 8 mL, 0.016 mmol) was added dropwise and the reaction mixture was refluxed for 3 hours at 60° C. After completion of the reaction (monitored by UPLC), the reaction mixture was cooled to 0° C., quenched with methanol (10 mL) and then heated for 2 hours to 60° C.

The resulting reaction mixture was then cooled to room temperature and concentrated under vacuum to afford the crude. The resulting crude was forwarded as such to the next step without any further purification. Yield: 1.49 g (crude, colourless liquid).

Intermediate 38

7-bromo-3,3-dibutyl-5-(3,4-difluorophenyl)-8-methoxy-2,3,4,5-tetrahydro-1,5-benzothiazepine 1,1-dioxide

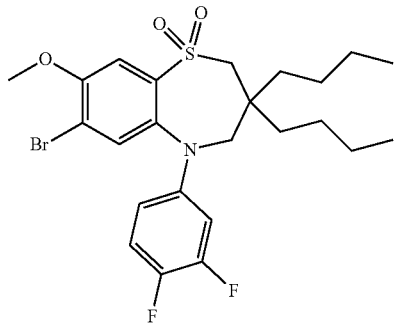 [SMILES: CCCCC1(CCCC)CN(c2ccc(F)c(F)c2)c2cc(Br)c(OC)cc2S(=O)(=O)C1]

To a stirred solution of 7-bromo-3,3-dibutyl-5-(3,4-difluorophenyl)-8-methoxy-2,3,4,5-tetrahydro-1,5-benzothiazepine (Intermediate 37; 1.49 g, 0.01 mmol) in THF (75 mL) and water (7.5 mL), oxone (38.3 g, 0.13 mmol) was added at room temperature and the reaction mixture was then stirred for 24 hours at that temperature. After completion of the reaction (monitored by TLC), the reaction mixture was filtered off through a Buchner funnel and the filtrate was extracted with EtOAc (2×25 mL). The combined organic layer was washed with water (25 mL) and brine (25 mL) and dried over anhydrous Na₂SO₄. The organic part was concentrated under vacuum and the resulting crude material was purified by Isolera column chromatography (eluent: 10-12% EtOAc/PE; silica gel: 230-400 mesh) to afford the title compound. Yield: 62% (1 g, off-white solid).

LCMS: (Method A) 532.0 (M⁺+2), Rt. 3.31 min, 93.84% (Max).

Intermediate 39

3,3-dibutyl-5-(3,4-difluorophenyl)-8-methoxy-7-(methylthio)-2,3,4,5-tetrahydro-1,5-benzothiazepine 1,1-dioxide

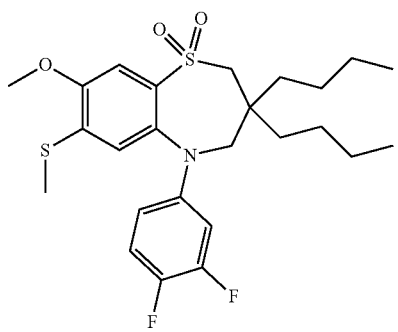 [SMILES: CCCCC1(CCCC)CN(c2ccc(F)c(F)c2)c2cc(SC)c(OC)cc2S(=O)(=O)C1]

To a stirred solution of 7-bromo-3,3-dibutyl-5-(3,4-difluorophenyl)-8-methoxy-2,3,4,5-tetrahydro-1,5-benzothiazepine 1,1-dioxide (Intermediate 38; 500 mg, 0.9757 mmol) in DMF (5 mL), sodium thiomethoxide (102 mg, 1.46 mmol) was added and the resulting reaction mixture was heated for 2 hours at 60° C. After completion of the reaction (monitored by TLC), water (10 mL) was added to the reaction mixture and the aqueous layer was extracted with EtOAc (2×20 mL). The combined organic layer was washed with brine (500 mL), dried over anhydrous $Na_2SO_4$ and concentrated under vacuum. The resulting crude material was purified by Isolera column chromatography (eluent: 18-20% EtOAc/PE; silica gel: 230-400 mesh) to afford the title compound. Yield: 82% (0.45 g, off-white solid).

LCMS: (Method E) 498.2 ($M^+$+H), Rt. 3.57 min, 90.72% (Max).

Intermediate 40

3,3-dibutyl-5-(3,4-difluorophenyl)-8-hydroxy-7-(methylthio)-2,3,4,5-tetrahydro-1,5-benzothiazepine 1,1-dioxide

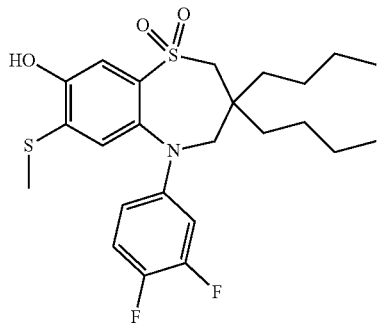 [SMILES: CCCCC1(CCCC)CN(c2ccc(F)c(F)c2)c2cc(SC)c(O)cc2S(=O)(=O)C1]

To a stirred solution of 3,3-dibutyl-5-(3,4-difluorophenyl)-8-methoxy-7-(methylthio)-2,3,4,5-tetrahydro-1,5-benzothiazepine 1,1-dioxide (Intermediate 39; 450 mg, 0.9042 mmol) in DCM (5 mL), $BBr_3$ (1M in DCM; 3 mL, 2.712 mmol) was added at 0° C. and the reaction mixture was stirred for 1 hour at room temperature. After completion of the reaction (monitored by TLC), methanol (10 mL) was added dropwise at 0° C. until the effervescence ceased. The reaction mixture was then diluted with DCM (10 mL), and the DCM layer was washed with water (2×10 mL) and brine (10 mL). The organic part was dried over anhydrous $Na_2SO_4$ and concentrated under vacuum. The resulting crude material was purified by Isolera column chromatography (eluent: 100% EtOAc; silica gel: 230-400 mesh) to afford the title compound. Yield: 91% (0.4 g, off-white solid).

$^1$H NMR (400 MHz, DMSO-$d_6$): δ 10.63 (s, 1H), 7.29 (s, 1H), 7.28-7.19 (m, 1H), 7.03-6.98 (m, 1H), 6.72 (s, 1H), 6.64-6.59 (m, 1H), 3.62 (bs, 2H), 3.22 (s, 2H), 2.22 (s, 3H), 1.40-1.34 (m, 4H), 1.15-1.05 (m, 8H), 0.79 (t, J=6.80 Hz, 6H). LCMS: (Method A) 484.2 ($M^+$+H), Rt. 2.97 min, 94% (Max).

Intermediate 41

7-bromo-3,3-dibutyl-5-(4-fluorophenyl)-8-methoxy-2,3-dihydro-1,5-benzothiazepin-4(5H)-one and 3,3-dibutyl-5-(4-fluorophenyl)-7-iodo-8-methoxy-2,3-dihydro-1,5-benzothiazepin-4(5H)-one

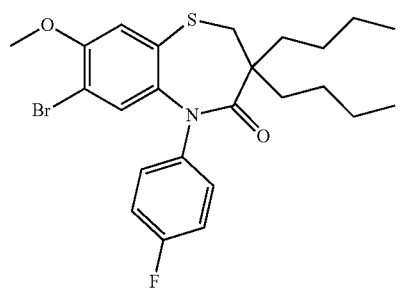

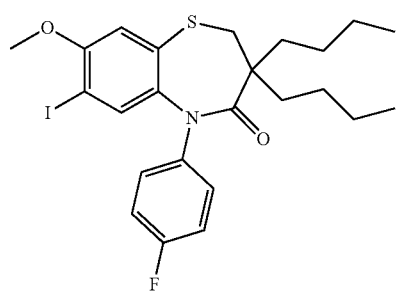

To a stirred solution of a mixture of 7-bromo-3,3-dibutyl-8-methoxy-2,3-dihydro-1,5-benzothiazepin-4(5H)-one (3 g, 7.49 mmol) in 4-fluoroiodobenzene (30 mL), copper (I) iodide (0.14 g, 0.74 mmol) and $K_2CO_3$ (2.07 g, 14.9 mmol) were added and the reaction mixture was purged with nitrogen for 20 minutes for degasification. Tris[2-(2-methoxyethoxy)ethyl]amine (0.49 g, 1.49 mmol) was then added under nitrogen atmosphere and the resulting reaction mixture was heated for 16 hours at 135° C.

After completion of the reaction (monitored by TLC), the reaction mixture was filtered through celite and the celite pad was washed with EtOAc (25 mL). The filtrate was washed with water (15 mL) and brine (15 mL) and dried over anhydrous $Na_2SO_4$. The resulting crude material was purified by Isolera column chromatography (eluent: 20% EtOAc/PE; silica gel: 230-400 mesh) to afford the title compound. Yield: 95% (3.5 g, pale yellow solid).

LCMS: (Method E) 494.0 ($M^+$) for the 7-bromo substituted compound and 541.9 ($M^+$+H) for the 7-iodo substituted compound, Rt. 3.50 min, 96.61% (Max).

Intermediate 42

7-bromo-3,3-dibutyl-5-(4-fluorophenyl)-8-methoxy-2,3,4,5-tetrahydro-1,5-benzothiazepine and 3,3-dibutyl-5-(4-fluorophenyl)-7-iodo-8-methoxy-2,3,4,5-tetrahydro-1,5-benzothiazepine

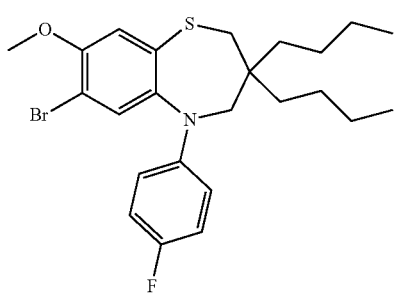

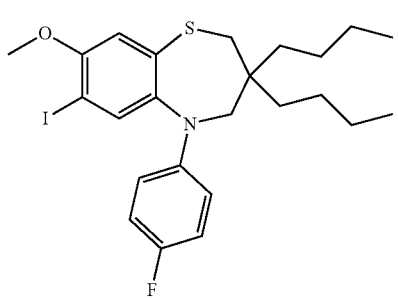

To a stirred solution of a mixture of 7-bromo-3,3-dibutyl-5-(4-fluorophenyl)-8-methoxy-2,3-dihydro-1,5-benzothiazepin-4(5H)-one and 3,3-dibutyl-5-(4-fluorophenyl)-7-iodo-8-methoxy-2,3-dihydro-1,5-benzothiazepin-4(5H)-one (Intermediate 41; 3.5 g, 7.07 mmol) in THF (35 mL) at 0° C., borane dimethylsulfide (2M in THF; 5.3 mL, 10.61 mmol) was added dropwise and the reaction mixture was refluxed for 16 hours at 65° C. After completion of the reaction (monitored by TLC), the reaction mixture was cooled to 0° C., quenched with methanol (10 mL) and heated for 2 hours at 65° C. The resulting reaction mixture was then cooled to room temperature, concentrated under vacuum and the residue was partitioned between water (50 mL) and EtOAc (50 mL). The aqueous layer was extracted with DCM (2×50 mL), and the combined organic layer was washed with water (25 mL) and brine (25 mL). The organic part was dried over anhydrous $Na_2SO_4$ and concentrated under vacuum to afford the crude. The resulting crude was forwarded as such to the next step without any further purification. Yield: 3.6 g (crude, pale yellow gum).

LCMS: (Method E) 482.0 ($M^+$+2H) for the 7-bromo substituted compound and 527.9 ($M^+$+H) for the 7-iodo substituted compound, Rt. 3.86 min, 81.04% (combined for the bromo and iodo substituted compounds) (Max).

Intermediate 43

7-bromo-3,3-dibutyl-5-(4-fluorophenyl)-8-methoxy-2,3,4,5-tetrahydro-1,5-benzothiazepine 1,1-dioxide and 3,3-dibutyl-5-(4-fluorophenyl)-7-iodo-8-methoxy-2,3,4,5-tetrahydro-1,5-benzothiazepine 1,1-dioxide

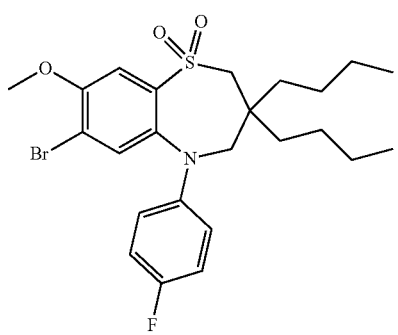

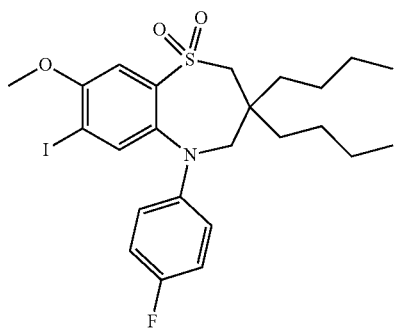

To a stirred solution of a mixture of 7-bromo-3,3-dibutyl-5-(4-fluorophenyl)-8-methoxy-2,3,4,5-tetrahydro-1,5-benzothiazepine and 3,3-dibutyl-5-(4-fluorophenyl)-7-iodo-8-methoxy-2,3,4,5-tetrahydro-1,5-benzothiazepine (Intermediate 42; 3.6 g, 7.49 mmol) in acetic acid (36 mL), sodium tungstate (360 mg, 0.01 mmol) and hydrogen peroxide (30% in $H_2O$; 2.6 mL, 22.47 mmol) were added at 0° C. and the resulting reaction mixture was stirred for 16 hours at room temperature. After completion of the reaction (monitored by TLC), the reaction mixture was filtered off through a Buchner funnel and the filtrate was extracted with EtOAc (2×50 mL). The combined organic layer was washed with water (25 mL) and brine (25 mL) and dried over anhydrous $Na_2SO_4$. The organic part was concentrated under vacuum and the resulting crude material was purified by Isolera column chromatography (eluent: 12% EtOAc/PE; silica gel: 230-400 mesh) to afford the title compound.

Yield: 79% (3.4 g, off-white solid).

LCMS: ((Method A) 512.2 ($M^+$+H) for the 7-bromo substituted compound and 560.2 ($M^+$+H) for the 7-iodo substituted compound; Rt. 3.40 min, 70.63% (Max).

Intermediate 44

3,3-dibutyl-5-(4-fluorophenyl)-8-hydroxy-7-(methylthio)-2,3,4,5-tetrahydro-1,5-benzothiazepine 1,1-dioxide

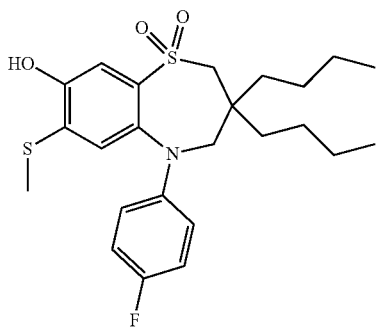 [SMILES: CCCCC1(CCCC)CN(c2ccc(F)cc2)c2cc(SC)c(O)cc2S(=O)(=O)C1]

To a stirred solution of a mixture of 7-bromo-3,3-dibutyl-5-(4-fluorophenyl)-8-methoxy-2,3,4,5-tetrahydro-1,5-benzothiazepine 1,1-dioxide and 3,3-dibutyl-5-(4-fluorophenyl)-7-iodo-8-methoxy-2,3,4,5-tetrahydro-1,5-benzothiazepine 1,1-dioxide (Intermediate 43; 1.6 g, 3.12 mmol) in DMF (16 mL), sodium thiomethoxide (1.09 g, 15.6 mmol) was added at room temperature and the reaction mixture was stirred for 16 hours at 65° C. After completion of the reaction (monitored by TLC), the reaction mixture was cooled to room temperature and quenched with water (15 mL). The aqueous layer was extracted with EtOAc (2×25 mL) and the combined organic layer was washed with brine (10 mL). The organic part was dried over anhydrous Na$_2$SO$_4$ and concentrated under vacuum. The resulting crude material was purified by Isolera column chromatography (eluent: 30% EtOAc/PE; silica gel: 230-400 mesh) to afford the title compound. Yield: 90% (1.3 g, off-white solid).

$^1$H NMR (400 MHz, DMSO-d$_6$): δ 10.48 (s, 1H), 7.28 (d, J=4.4 Hz, 1H), 7.08-7.01 (m, 4H), 6.59 (s, 1H), 3.80-3.67 (m, 2H), 3.22 (s, 2H), 2.16 (s, 3H), 1.36-1.33 (m, 4H), 1.12-1.03 (m, 8H), 0.79-0.77 (m, 6H).

LCMS: (Method E) 466.0 (M$^+$+H), Rt. 3.23 min, 88.86% (Max).

Intermediate 45

2-(((2-Amino-4-bromo-5-methoxyphenyl)thio)methyl)-2-ethylpentanoic acid

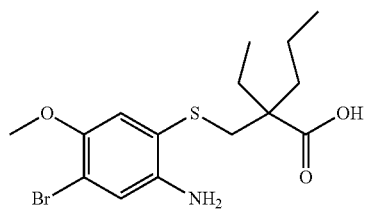 [SMILES: CCCC(CC)(CSc1cc(OC)c(Br)cc1N)C(=O)O]

To a solution of 5-bromo-6-methoxybenzo[d]thiazol-2-amine (20 g, 77.2 mmol) in water (200 mL) were added KOH (69.1 g, 123 mmol) and Na$_2$SO$_3$ (9.7 g, 77.2 mmol) and the reaction mixture was heated for 16 hours at 120° C. The reaction mixture was then cooled to 10° C. A solution of 2-(bromomethyl)-2-ethylpentanoic acid (26 g, 115 mmol) in THF (30 mL) was added dropwise and the reaction mixture was heated for 16 hours at 60° C. After completion of the reaction (monitored by TLC), the reaction mixture was quenched with conc. HCl, acidified and then extracted with EtOAc (2×150 mL). The combined organic layer was washed with ice-cold water (150 mL) and brine (150 mL) and dried over anhydrous Na$_2$SO$_4$. The organic part was filtered and concentrated to afford the title compound. Yield: 30 g (crude, purple liquid).

LCMS: (Method E) 377.8 (M$^+$+2), Rt. 2.60 min, 77.37% (Max).

Intermediate 46

7-Bromo-3-ethyl-8-methoxy-3-propyl-2,3-dihydro-1,5-benzothiazepin-4(5H)-one

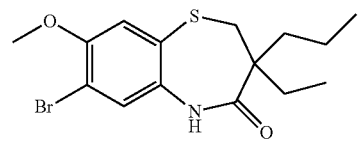 [SMILES: CCCC1(CC)CSc2cc(OC)c(Br)cc2NC1=O]

To a solution of 2-(((2-amino-4-bromo-5-methoxyphenyl)thio)methyl)-2-ethylpentanoic acid (Intermediate 45; 30 g, 80 mmol) in DCM (200 mL), triethylamine (21.5 mL, 159 mmol) was added and the reaction mixture was cooled to 0° C. 1-propanephosphonic anhydride solution (50% in EtOAc; 50.8 g, 159 mmol) was added dropwise and the reaction mixture was stirred for 16 hours at room temperature. After completion of the reaction (monitored by TLC), the reaction mixture was quenched with ice-cold water (25 mL) and the aqueous layer was extracted with EtOAc (2×100 mL). The combined organic layer was washed with ice-cold water (100 mL) and brine (100 mL) and dried over anhydrous Na$_2$SO$_4$. The organic part was filtered off, concentrated under vacuum and the obtained residue was triturated with cold methanol. The precipitated solid was filtered off and dried under vacuum to afford the title compound. Yield: 32% (9 g, grey solid).

$^1$H NMR (400 MHz, DMSO-d$_6$): δ 9.63 (s, 1H), 7.34 (s, 1H), 7.11 (s, 1H), 3.83 (s, 3H), 2.99 (s, 2H), 1.73-1.40 (m, 4H), 1.24-1.16 (m, 2H), 0.84-0.76 (m, 6H). LCMS: (Method E) 357.8 (M$^+$), Rt. 2.83 min, 99.18% (Max).

Intermediate 47

7-Bromo-3-ethyl-8-methoxy-5-phenyl-3-propyl-2,3-dihydro-1,5-benzothiazepin-4(5H)-one and 3-ethyl-7-iodo-8-methoxy-5-phenyl-3-propyl-2,3-dihydro-1,5-benzothiazepin-4(5H)-one

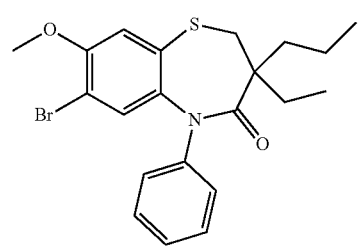

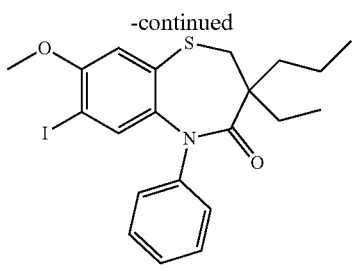

To a solution of 7-bromo-3-ethyl-8-methoxy-3-propyl-2,3-dihydro-1,5-benzothiazepin-4(5H)-one (Intermediate 46; 9 g, 25.1 mmol) in iodobenzene (90 mL), were added K$_2$CO$_3$ (3.81 g, 27.62 mmol), tris[2-(2-methoxyethoxy)ethyl]amine (1.62 g, 5.02 mmol) and CuI (0.48 g, 2.51 mmol) and the reaction mixture was heated for 16 hours at 135° C. After completion of the reaction (monitored by TLC), the reaction mixture was quenched with ice-cold water (25 mL) and the aqueous layer was extracted with EtOAc (2×100 mL). The combined organic layer was washed with ice-cold water (100 mL) and brine (100 mL) and dried over anhydrous Na$_2$SO$_4$. The organic part was filtered off and concentrated under vacuum. The resulting crude material was triturated with petroleum ether to afford the title compound. Yield: 64% (7 g, pale yellow solid).

LCMS: (Method B) 434.0 (M$^+$+H), for the 7-bromo substituted compound Rt. 14.82 min, 37.52% (Max) and 482.0 (M$^+$+H), for the 7-iodo substituted compound Rt. 15.04 min, 57.75% (Max).

Intermediate 48

7-Bromo-3-ethyl-8-methoxy-5-phenyl-3-propyl-2,3,4,5-tetrahydro-1,5-benzothiazepine and 3-ethyl-7-iodo-8-methoxy-5-phenyl-3-propyl-2,3,4,5-tetrahydro-1,5-benzothiazepine

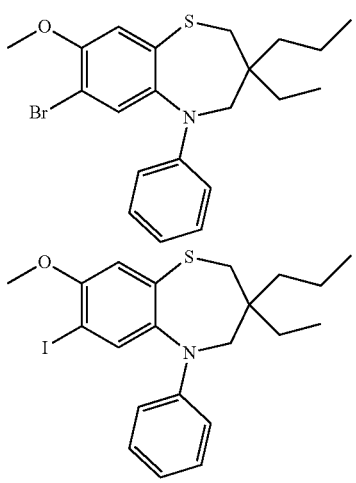

To a stirred solution of a mixture of 7-bromo-3-ethyl-8-methoxy-5-phenyl-3-propyl-2,3-dihydro-1,5-benzothiazepin-4(5H)-one and 3-ethyl-7-iodo-8-methoxy-5-phenyl-3-propyl-2,3-dihydro-1,5-benzothiazepin-4(5H)-one (Intermediate 47; 7.0 g, 16.12 mmol) in THF (70 mL) at 0° C., borane dimethylsulfide (1M in THF; 48.38 mL, 48.38 mmol) was added and the reaction mixture was heated for 16 hours at 70° C. After completion of the reaction (monitored by TLC), the reaction mixture was cooled to 0° C., methanol (150 mL) was added and the mixture was heated for 2 hours at 60° C. The reaction mixture was then cooled to room temperature and concentrated under vacuum. The obtained residue was partitioned between water (50 mL) and EtOAc (50 mL), and the aqueous layer was extracted with EtOAc (2×100 mL). The combined organic layer was washed with ice-cold water (100 mL) and brine (100 mL), dried over anhydrous Na$_2$SO$_4$ and concentrated under vacuum. The resulting crude material was forwarded as such to the next step without any further purification.

Yield: 7.5 g (crude, pale brown gum).

LCMS: (Method E) 419.8 (M$^+$+H) for the 7-bromo substituted compound & 467.8 (M$^+$+H) for the 7-iodo substituted compound; Rt. 3.77 min, 80.10% (Max).

Intermediate 49

7-Bromo-3-ethyl-8-methoxy-5-phenyl-3-propyl-2,3,4,5-tetrahydro-1,5-benzothiazepine 1,1-dioxide and 3-ethyl-7-iodo-8-methoxy-5-phenyl-3-propyl-2,3,4,5-tetrahydro-1,5-benzothiazepine 1,1-dioxide

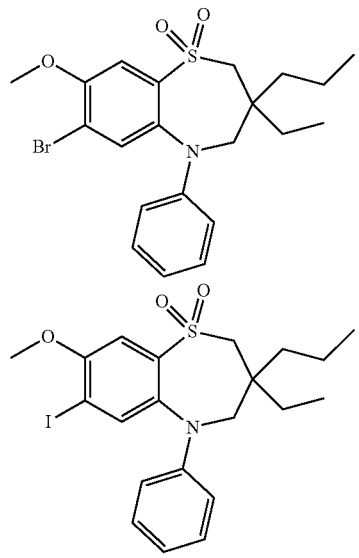

To a solution of a mixture of 7-bromo-3-ethyl-8-methoxy-5-phenyl-3-propyl-2,3,4,5-tetrahydro-1,5-benzothiazepine and 3-ethyl-7-iodo-8-methoxy-5-phenyl-3-propyl-2,3,4,5-tetrahydro-1,5-benzothiazepine (Intermediate 48; 7.5 g, 17.83 mmol) in THF (60 mL) and water (30 mL), oxone (27.4 g, 89.19 mmol) was added and the reaction mixture was stirred for 16 hours at room temperature.

After completion of the reaction (monitored by TLC), the aqueous layer was extracted with EtOAc (2×100 mL). The combined organic layer was washed with ice-cold water (100 mL) and brine (100 mL), dried over anhydrous Na$_2$SO$_4$ and concentrated under vacuum. The resulting crude material was purified by Isolera column chromatography (eluent: 13% EtOAc/PE; silica gel: 230-400 mesh) to afford the title compound. Yield: 62% (5 g, pale brown solid).

LCMS: (Method E) 452.9 (M$^+$+H) for the 7-bromo substituted compound and 499.7 (M$^+$+H) for the 7-iodo substituted compound, Rt. 3.24 min, 96.49% (Max).

Intermediate 50

3-Ethyl-8-hydroxy-7-(methylthio)-5-phenyl-3-propyl-2,3,4,5-tetrahydro-1,5-benzothiazepine 1,1-dioxide

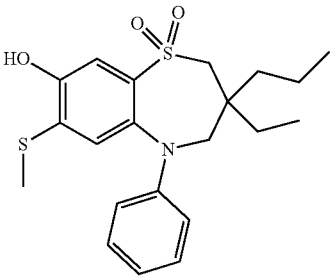 [SMILES: CCCC1(CC)CN(c2ccccc2)c2cc(SC)c(O)cc2S(=O)(=O)C1]

To a solution of a mixture of 7-bromo-3-ethyl-8-methoxy-5-phenyl-3-propyl-2,3,4,5-tetrahydro-1,5-benzothiazepine 1,1-dioxide and 3-ethyl-7-iodo-8-methoxy-5-phenyl-3-propyl-2,3,4,5-tetrahydro-1,5-benzothiazepine 1,1-dioxide (Intermediate 49; 1 g, 2.00 mmol) in DMF (5 mL), sodium thiomethoxide (0.78 g, 1.0 mmol) was added and the reaction mixture was stirred for 12 hours at 100° C. After completion of the reaction (monitored by TLC), the reaction mixture was quenched with ice-cold water (25 mL) and then extracted with EtOAc (2×20 mL). The combined organic layer was washed with ice-cold water (10 mL) and then brine (10 mL), dried over anhydrous $Na_2SO_4$ and concentrated under vacuum. The resulting crude material was purified by Isolera column chromatography (eluent: 30% EtOAc/PE; silica gel: 230-400 mesh) to afford the title compound.

Yield: 61% (0.49 g, off-white solid).

$^1$H NMR (400 MHz, DMSO-$d_6$): δ 10.54 (s, 1H), 7.31 (s, 1H), 7.19 (t, J=8.0 Hz, 2H), 6.91 (d, J=7.6 Hz, 2H), 6.80 (t, J=7.6 Hz, 1H), 6.69 (s, 1H), 3.64 (bs, 2H), 3.21 (s, 2H), 2.18 (s, 3H), 1.57-1.55 (m, 1H), 1.45-1.33 (m, 3H), 1.31-1.18 (m, 2H), 0.78-0.74 (m, 6H). LCMS: (Method E) 406.2 (M$^+$+H), Rt. 2.93 min, 95.46% (Max).

Intermediate 51

Methyl Tritylserinate

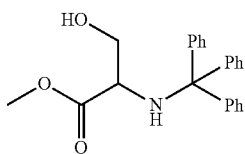 [SMILES: COC(=O)C(CO)NC(c1ccccc1)(c1ccccc1)c1ccccc1]

To a stirred solution of methyl serinate hydrochloride (0.65 g, 0.5 mmol) in DCM (10 mL), triethylamine (2 mL, 1.50 mmol) was added and the reaction mixture was cooled to 0° C. Then trityl chloride (1.67 g, 0.6 mmol) was added and the reaction mixture was stirred for 16 hours at room temperature. After completion of the reaction (monitored by TLC), the reaction mixture was quenched with water (10 mL) and the aqueous layer was extracted with DCM (2×10 mL). The combined organic layer was washed with water (10 mL) and brine (10 mL) and dried over anhydrous $Na_2SO_4$. The organic part was filtered and concentrated under vacuum. The resulting crude material was purified by Isolera column chromatography (eluent: 7% EtOAc/PE; silica gel: 230-400 mesh) to afford the title compound. Yield: 33% (0.7 g, white solid).

$^1$H NMR (400 MHz, CDCl$_3$): δ 7.54-7.50 (m, 6H), 7.32-7.27 (m, 6H), 7.24-7.20 (m, 3H), 3.74-3.72 (m, 1H), 3.62-3.51 (m, 2H), 3.33 (s, 3H), 3.00 (bs, 1H), 2.33 (bs, 1H).

Intermediate 52

Methyl O-(3-butyl-3-ethyl-7-(methylthio)-1,1-dioxido-5-phenyl-2,3,4,5-tetrahydro-1,5-benzothiazepin-8-yl)-N-tritylserinate

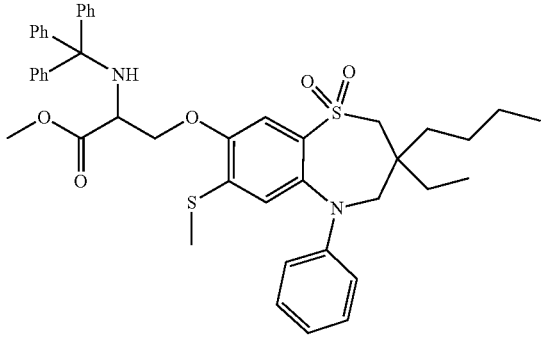 [SMILES: CCCCC1(CC)CN(c2ccccc2)c2cc(SC)c(OCC(NC(c3ccccc3)(c3ccccc3)c3ccccc3)C(=O)OC)cc2S(=O)(=O)C1]

To a stirred solution of 3-butyl-3-ethyl-8-hydroxy-7-(methylthio)-5-phenyl-2,3,4,5-tetrahydro-1,5-benzothiazepine 1,1-dioxide (Intermediate 22; 470 mg, 1.12 mmol) in toluene (10 mL) at 0° C., triphenylphosphine (653 mg, 2.24 mmol) and methyl tritylserinate (Intermediate 51; 504 mg, 2.24 mmol) were added and the reaction mixture was stirred for 5 minutes. Then diisopropyl azodicarboxylate (452 mg, 2.24 mmol) was added dropwise and the reaction mixture heated for 4 hours at 90° C. After completion of the reaction (monitored by TLC), the reaction mixture was concentrated under vacuum and the obtained residue was diluted with water (10 mL). The aqueous layer was extracted with EtOAc (2×10 mL) and the combined organic layer was washed with water (10 mL) and brine (10 mL) and dried over anhydrous $Na_2SO_4$. The organic part was filtered, concentrated under vacuum and the resulting crude material was purified by Isolera column chromatography (eluent: 8% EtOAc/PE; silica gel: 230-400 mesh) to afford the title compound. Yield: 41% (350 mg, pale yellow solid).

$^1$H NMR (400 MHz, DMSO-$d_6$): δ 7.48-7.45 (m, 6H), 7.33-7.29 (m, 7H), 7.23-7.20 (m, 5H), 6.98 (d, J=8.0 Hz, 2H), 6.86 (t, J=7.2 Hz, 1H), 6.69 (s, 1H), 4.26-4.22 (m, 1H), 4.09-4.05 (m, 1H), 3.81-3.55 (m, 3H), 3.27 (s, 2H), 3.21 (s, 3H), 2.14 (s, 3H), 1.62-1.53 (m, 1H), 1.52-1.41 (m, 1H), 1.41-1.36 (m, 2H), 1.23-0.95 (m, 4H), 0.84-0.73 (m, 6H).

Intermediate 53

Methyl O-(3-butyl-3-ethyl-7-(methylthio)-1,1-di-oxido-5-phenyl-2,3,4,5-tetrahydro-1,5-benzothiaz-epin-8-yl)serinate

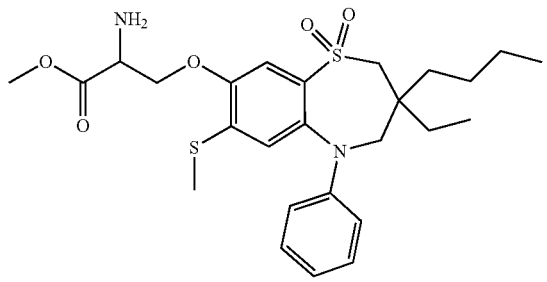 [SMILES: CCCCC1(CC)CN(c2ccccc2)c2cc(SC)c(OCC(N)C(=O)OC)cc2S(=O)(=O)C1]

To a stirred solution of methyl O-(3-butyl-3-ethyl-7-(methylthio)-1,1-dioxido-5-phenyl-2,3,4,5-tetrahydro-1,5-benzothiazepin-8-yl)-N-tritylserinate (Intermediate 52; 340 mg, 0.44 mmol) in DCM (10 mL) at 0° C., TFA (152 mg, 1.33 mmol) was added and the reaction mixture was stirred for 1 hour at room temperature. After completion of the reaction (monitored by TLC), the reaction mixture poured into ice-cold water (10 mL) and the aqueous layer was extracted with EtOAc (2×10 mL). The combined organic layer was washed with water (10 mL) and brine (10 mL) and dried over anhydrous $Na_2SO_4$. The organic part was filtered and concentrated under vacuum to afford the title compound. The resulting crude material was forwarded as such to the next step without any further purification.

Yield: 170 mg (crude, off-white solid).

LCMS: (Method E) 521.2 ($M^+$+H), Rt. 2.40 min, 37.79% (Max).

Intermediate 54

Methyl 3-((3-butyl-3-methyl-7-(methylthio)-1,1-dioxido-5-phenyl-2,3,4,5-tetrahydro-1,5-benzothiaz-epin-8-yl)oxy)-2-hydroxypropanoate

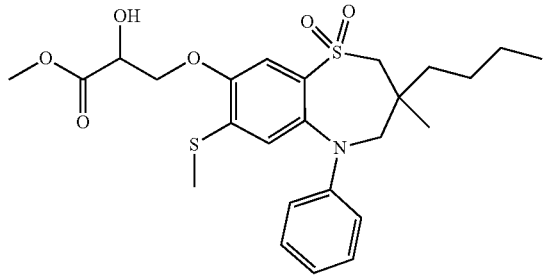 [SMILES: CCCCC1(C)CN(c2ccccc2)c2cc(SC)c(OCC(O)C(=O)OC)cc2S(=O)(=O)C1]

To a stirred solution of 3-butyl-8-hydroxy-3-methyl-7-(methylthio)-5-phenyl-2,3,4,5-tetrahydro-1,5-benzothiazepine 1,1-dioxide (Intermediate 35; 300 mg, 0.74 mmol) in DMF (5 mL), $Cs_2CO_3$ (482 mg, 1.47 mmol) and methyl 2-methylglycidate (227 mg, 2.21 mmol) were added and the reaction mixture was stirred for 72 hours at room temperature. After conversion of 70% of the starting material (monitored by TLC), the reaction mixture was quenched with dilute HCl (1.5 N, 5 mL) and diluted with water (5 mL). The aqueous layer was extracted with EtOAc (2×10 mL) and the combined organic layer was washed with water (10 mL) and brine (10 mL). The organic part was dried over anhydrous $Na_2SO_4$, filtered and concentrated under vacuum. The resulting crude material was purified by Isolera column chromatography (eluent: 40% EtOAc/PE; silica gel: 230-400 mesh) to afford the title compound. Yield: 45% (170 mg, pale yellow gum).

LCMS: (Method E) 508.0 ($M^+$+H), Rt. 2.91 min, 97.36% (Max).

Intermediate 55

Methyl 3-((3-butyl-3-methyl-7-(methylthio)-1,1-dioxido-5-phenyl-2,3,4,5-tetrahydro-1,5-benzothiaz-epin-8-yl)oxy)-2-hydroxypropanoate

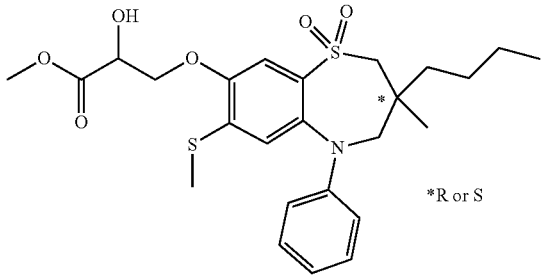 [SMILES: CCCCC1(C)CN(c2ccccc2)c2cc(SC)c(OCC(O)C(=O)OC)cc2S(=O)(=O)C1]

*R or S

To a stirred solution of enantiomer 1 of 3-butyl-8-hydroxy-3-methyl-7-(methylthio)-5-phenyl-2,3,4,5-tetrahydro-1,5-benzothiazepine 1,1-dioxide (Intermediate 35; 300 mg, 0.74 mmol) in DMF (5 mL), $Cs_2CO_3$ (482 mg, 1.47 mmol) and methyl-2-methyl glycidate (227 mg, 2.21 mmol) were added and the reaction mixture was stirred for 48 hours at room temperature. After completion of the reaction (monitored by TLC), the reaction mixture was quenched with dilute HCl (1.5 N, 5 mL) and diluted with water (5 mL). The aqueous layer was extracted with EtOAc (2×10 mL) and the combined organic layer was washed with water (10 mL) and brine (10 mL). The organic part was dried over anhydrous $Na_2SO_4$, filtered and concentrated under vacuum. The resulting crude material was purified by Isolera column chromatography (eluent: 40% EtOAc PE; silica gel: 230-400 mesh) to afford a mixture of diastereomers 1 and 2 of the title compound. Yield: 53% (200 mg, pale yellow gum).

LCMS: (Method E) 508.2 ($M^+$+H), Rt. 2.92 min, 97.98% (Max).

Intermediate 56

Methyl 3-((3-butyl-3-methyl-7-(methylthio)-1,1-dioxido-5-phenyl-2,3,4,5-tetrahydro-1,5-benzothiaz-epin-8-yl)oxy)-2-hydroxy-2-methylpropanoate (Individual Diastereomers)

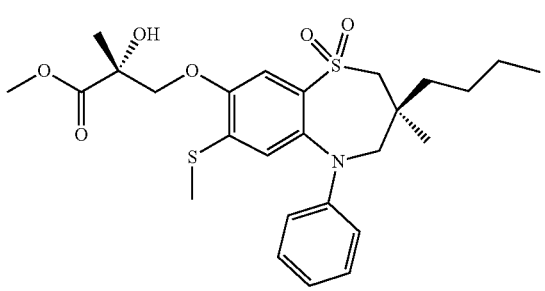

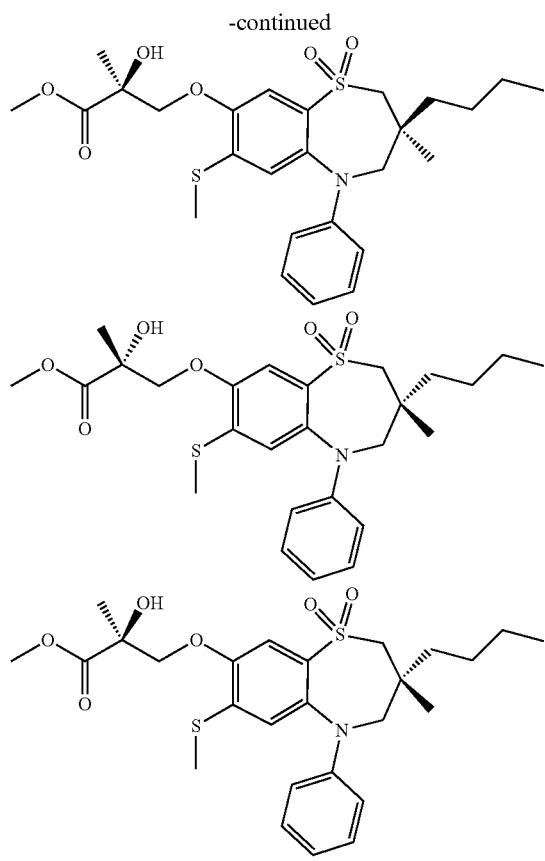

Diastereomers 1 and 2

To a stirred solution of enantiomer 1 of 3-butyl-8-hydroxy-3-methyl-7-(methylthio)-5-phenyl-2,3,4,5-tetrahydro-1,5-benzothiazepine 1,1-dioxide (Intermediate 35; 230 mg, 0.56 mmol) in DMF (2.5 mL), $Cs_2CO_3$ (0.37 g, 1.13 mmol) was added and the reaction mixture was stirred for 15 minutes at room temperature. Then methyl 2-methyloxirane-2-carboxylate (0.19 g, 1.70 mmol) was added and the reaction mixture was stirred for 48 hours at room temperature. After completion of the reaction (monitored by TLC), the reaction mixture was quenched with dilute HCl (1.5 N, 10 mL) and diluted with water (10 mL). The aqueous layer was extracted with EtOAc (2×15 mL), and the combined organic layer was washed with water (15 mL) and brine (15 mL). The organic part was dried over anhydrous $Na_2SO_4$, filtered and concentrated under vacuum. The resulting crude material was purified by Isolera column chromatography (eluent: 25% EtOAc/PE; silica gel: 230-400 mesh) to afford the title compound. Yield: 84% (250 mg, pink gum).

LCMS: (Method E) 522.2 ($M^++H$), Rt. 2.6 min, 95.83% (Max).

Diastereomers 3 and 4

To a stirred solution of enantiomer 2 of 3-butyl-8-hydroxy-3-methyl-7-(methylthio)-5-phenyl-2,3,4,5-tetrahydro-1,5-benzothiazepine 1,1-dioxide (Intermediate 35; 250 mg, 0.61 mmol) in DMF (2.5 mL), $Cs_2CO_3$ (0.4 g, 1.23 mmol) was added and the reaction mixture was stirred for 15 minutes at room temperature. Then methyl 2-methyloxirane-2-carboxylate (0.21 g, 1.84 mmol) was added and the reaction mixture was stirred for 48 hours at room temperature. After completion of the reaction (monitored by TLC), the reaction mixture was quenched with dilute HCl (1.5 N, 10 mL) and diluted with water (10 mL). The aqueous layer was extracted with EtOAc (2×15 mL), and the combined organic layer was washed with water (15 mL) and brine (15 mL). The organic part was dried over anhydrous $Na_2SO_4$, filtered and concentrated under vacuum. The resulting crude material was purified by Isolera column chromatography (eluent: 25% EtOAc/PE; silica gel: 230-400 mesh) to afford the title compound. Yield: 62% (200 mg, pink gum).

LCMS: (Method E) 522.2 ($M^++H$), Rt. 3.39 min, 97.06% (Max).

Diastereomers 3 and 4 of the title compound (200 mg, 0.38 mmol) were separated by chiral SFC (method F). The first eluting fraction corresponded to diastereomer 1 and the second eluting fraction corresponded to diastereomer 2. Each of the two fractions was then individually treated for further purification. The obtained residue was acidified with dilute HCl (1.5 N, pH4) and the aqueous layer extracted with EtOAc (3×10 mL). The combined organic layer was washed with water (10 mL) and brine (10 mL) and dried over anhydrous $Na_2SO_4$. The organic part was filtered and concentrated under vacuum at 40° C. to afford a purified diastereomer of the title compound.

Diastereomer 3: Yield: 25% (50 mg, off-white solid). $^1$H NMR (400 MHz, DMSO-$d_6$): δ 7.33 (s, 1H), 7.19 (t, J=8.4 Hz, 2H), 6.92 (d, J=7.6 Hz, 2H), 6.80 (t, J=7.2 Hz, 2H), 5.72 (s, 1H), 4.16-4.11 (m, 2H), 3.68 (s, 3H), 3.33-3.31 (m, 4H), 2.19 (s, 3H), 1.43 (s, 3H), 1.24-1.12 (m, 6H), 1.01 (s, 3H), 0.80 (t, J=7.20 Hz, 3H). LCMS: (Method E) 522.2 ($M^++H$), Rt. 2.61 min, 98.51% (Max). Chiral SFC: (Method G) Rt. 3.27 min, 100% (Max).

Diastereomer 4: Yield: 30% (60 mg, off-white solid). $^1$H NMR (400 MHz, DMSO-$d_6$): δ 7.32 (s, 1H), 7.19 (t, J=8.4 Hz, 2H), 6.92 (d, J=7.6 Hz, 2H), 6.80 (t, J=7.2 Hz, 2H), 5.73 (s, 1H), 4.20-4.17 (m, 1H), 4.12-4.10 (m, 1H), 3.68 (s, 3H), 3.34-3.26 (m, 4H), 2.19 (s, 3H), 1.43 (s, 3H), 1.31-1.24 (m, 6H), 1.01 (s, 3H), 0.80 (t, J=7.20 Hz, 3H). LCMS: (Method E) 522.2 ($M^++H$), Rt. 2.61 min, 96.58% (Max). Chiral SFC: (Method G) Rt. 5.59 min, 100% (Max).

The absolute configuration of the four diastereomers is not known.

Intermediate 57

Methyl 3-((3-butyl-3-ethyl-7-(methylthio)-1,1-dioxido-5-phenyl-2,3,4,5-tetrahydro-1,5-benzo-thiazepin-8-yl)oxy)-2-hydroxy-2-methylpropanoate

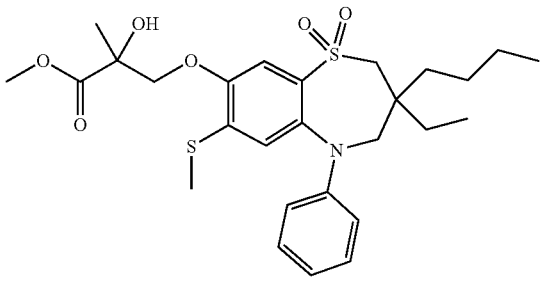 [SMILES: CCCCC1(CC)CN(c2ccccc2)c2cc(SC)c(OCC(C)(O)C(=O)OC)cc2S(=O)(=O)C1]

To a stirred solution of 3-butyl-3-ethyl-8-hydroxy-7-(methylthio)-5-phenyl-2,3,4,5-tetrahydro-1,5-benzothiazepine 1,1-dioxide (Intermediate 22; 500 mg, 1.19 mmol) in DMF (5 mL), $Cs_2CO_3$ (0.77 g, 2.38 mmol) was added and the reaction mixture was stirred for 15 minutes at room temperature. Methyl 2-methylglycidate (0.41 g, 3.57 mmol) was then added and the reaction mixture was stirred for 72 hours at room temperature. After completion of the reaction (monitored by TLC), the reaction mixture was quenched with dilute HCl (15 mL) and diluted with water (10 mL). The aqueous layer was extracted with EtOAc (2×15 mL) and the combined EtOAc layer was washed with water (15 mL) and brine (15 mL). The organic part was dried over anhydrous Na₂SO₄, filtered and concentrated under vacuum. The resulting crude material was purified by Isolera column chromatography (eluent: 10% EtOAc/PE; silica gel: 230-400 mesh) to afford the title compound. Yield: 24% (150 mg, colourless gum).

LCMS: (Method E) 536.2 (M⁺+H), Rt. 2.93 min, 83.35% (Max).

Intermediate 58

Methyl 3-((3-butyl-3-ethyl-7-(methylthio)-1,1-dioxido-5-phenyl-2,3,4,5-tetrahydro-1,5-benzo-thiazepin-8-yl)oxy)-2-hydroxy-2-methylpropanoate

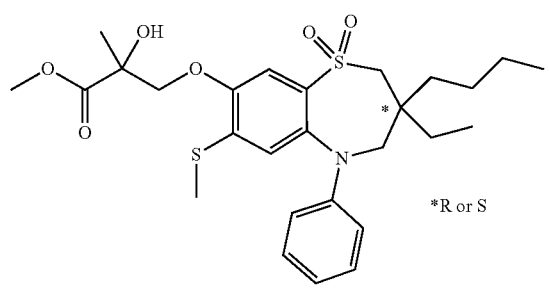 [SMILES: CCCCC1(CC)CN(c2ccccc2)c2cc(SC)c(OCC(C)(O)C(=O)OC)cc2S(=O)(=O)C1]

*R or S

To a stirred solution of enantiomer 2 of 3-butyl-3-ethyl-8-hydroxy-7-(methylthio)-5-phenyl-2,3,4,5-tetrahydro-1,5-benzothiazepine 1,1-dioxide (Intermediate 23; 780 mg, 1.85 mmol) in DMF (5 mL), Cs₂CO₃ (0.1.21 g, 3.71 mmol) was added and the reaction mixture was stirred for 15 minutes. Then methyl-2-methylglycidate (647 mg, 5.57 mmol) was added and the reaction mixture was stirred for 72 hours at room temperature. After completion of the reaction (monitored by TLC), the reaction mixture was quenched with dilute HCl (1.5 N, 15 mL) and diluted with water (10 mL). The aqueous layer was extracted with EtOAc (2×20 mL), and the combined organic layer was washed with water (25 mL) and brine (25 mL). The organic part was dried over anhydrous Na₂SO₄, filtered and concentrated under vacuum. The resulting crude material was purified by Isolera column chromatography (eluent: 40-50% EtOAc/PE; silica gel: 230-400 mesh) to afford the title compound.

Yield: 65% (650 mg, colourless gum).

LCMS: (Method E) 536.1 (M⁺+H), Rt. 3.07 min, 94.03% (Max).

Intermediate 59

Methyl 3-((3-butyl-3-ethyl-7-(methylthio)-1,1-dioxido-5-phenyl-2,3,4,5-tetrahydro-1,5-benzo-thiazepin-8-yl)oxy)-2-fluoro-2-methylpropanoate

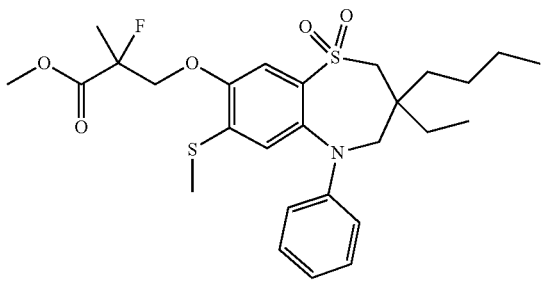 [SMILES: CCCCC1(CC)CN(c2ccccc2)c2cc(SC)c(OCC(C)(F)C(=O)OC)cc2S(=O)(=O)C1]

To a stirred solution of methyl 3-((3-butyl-3-ethyl-7-(methylthio)-1,1-dioxido-5-phenyl-2,3,4,5-tetrahydro-1,5-benzothiazepin-8-yl)oxy)-2-hydroxy-2-methylpropanoate (Intermediate 57; 130 mg, 0.24 mmol) in DCM (5 mL) at −10° C., diethylaminosulfur trifluoride (0.08 g, 0.48 mmol) was added and the reaction mixture was stirred for 2 hours. Methyl 2-methylglycidate (0.41 g, 3.57 mmol) was then added and the reaction mixture was stirred for 2 hours at room temperature. After completion of the reaction (monitored by TLC), the reaction mixture was quenched with water (5 mL) and the aqueous layer was extracted with EtOAc (2×5 mL). The combined organic layer was washed with water (5 mL) and brine (5 mL) and dried over anhydrous Na₂SO₄. The organic part was filtered and concentrated under vacuum. The resulting crude material was purified by Isolera column chromatography (eluent: 20% EtOAc/PE; silica gel: 230-400 mesh) to afford the title compound.

Yield: 30% (40 mg, colourless gum).

LCMS: (Method E) 538.2 (M⁺+H), Rt. 3.10 min, 74.80% (Max).

Intermediate 60

Methyl 3-((3-butyl-3-ethyl-7-(methylthio)-1,1-dioxido-5-phenyl-2,3,4,5-tetrahydro-1,5-benzo-thiazepin-8-yl)oxy)-2-fluoro-2-methylpropanoate (Individual Diastereomers)

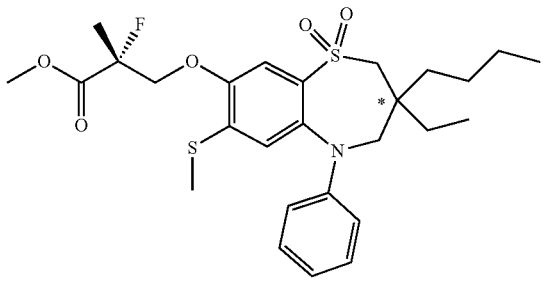

-continued

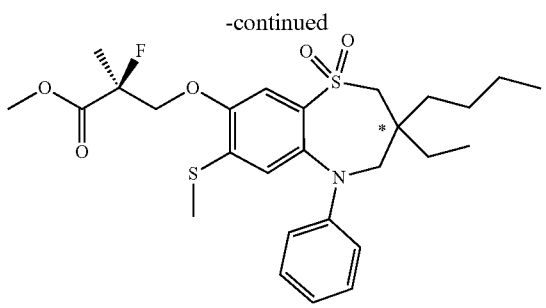

* the indicated carbons are each R or are each S

To a stirred solution of methyl 3-((3-butyl-3-ethyl-7-(methylthio)-1,1-dioxido-5-phenyl-2,3,4,5-tetrahydro-1,5-benzothiazepin-8-yl)oxy)-2-hydroxy-2-methylpropanoate (Intermediate 58; 650 mg, 1.21 mmol) in DCM (15 mL) at −10° C., diethylaminosulfur trifluoride (235 mg, 1.45 mmol) was added and the reaction mixture was stirred for 2 hours at 0 to 15° C. After completion of the reaction (monitored by TLC), the reaction mixture was quenched with ice-cold water (5 mL) at 0° C. and the aqueous layer was extracted with EtOAc (2×20 mL). The combined organic layer was washed with water (20 mL) and brine (20 mL) and dried over anhydrous $Na_2SO_4$. The organic part was filtered and concentrated under vacuum. The resulting crude material was purified by Isolera column chromatography (eluent: 20% EtOAc/PE; silica gel: 230-400 mesh) to afford the title compound.

Yield: 40% (160 mg, white gum).
$^1$H NMR (400 MHz, DMSO-$d_6$): δ 7.35 (s, 1H), 7.23 (t, J=7.2 Hz, 2H), 7.00 (d, J=8.0 Hz, 2H), 6.88 (t, J=7.2 Hz, 1H), 6.69 (s, 1H), 4.50-4.39 (m, 2H), 3.74 (bs, 3H), 3.69 (s, 2H), 3.28 (s, 2H), 2.18 (s, 3H), 1.71-1.62 (m, 1H), 1.51-1.49 (m, 3H), 1.48-1.41 (m, 1H), 1.39-1.25 (m, 2H), 1.24-0.92 (m, 4H), 0.85-0.71 (m, 6H). LCMS: (Method E) 537.9 (M$^+$+H), Rt. 3.24 min, 99.74% (Max), HPLC: (Method B) Rt. 6.27 min, 98.45% (Max).

Diastereomers 1 and 2 of the title compound (160 mg, 0.29 mmol) were separated by SFC (method F). The first eluting fraction corresponded to diastereomer 1 and the second eluting fraction corresponded to diastereomer 2. The material was concentrated under vacuum at 40° C. Each of the two fractions was then individually treated for further purification. The obtained residue was acidified with dilute HCl (1.5 N, pH4) and the aqueous layer extracted with EtOAc (3×5 mL). The combined organic layer was washed with water (10 mL) and brine (10 mL) and dried over anhydrous $Na_2SO_4$. The organic part was filtered and concentrated under vacuum at 40° C. to afford a purified diastereomer of the title compound.

Diastereomer 1: Yield: 63% (51 mg, pale yellow solid).
$^1$H NMR (400 MHz, DMSO-$d_6$): δ 7.35 (s, 1H), 7.23 (t, J=7.2 Hz, 2H), 7.00 (d, J=7.6 Hz, 2H), 6.87 (t, J=7.2 Hz, 1H), 6.69 (s, 1H), 4.53-4.39 (m, 2H), 3.76 (bs, 3H), 3.69 (s, 2H), 3.28 (s, 2H), 2.15 (s, 3H), 1.69-1.57 (m, 3H), 1.56-1.51 (m, 1H), 1.50-1.39 (m, 1H), 1.37-1.25 (m, 2H), 1.21-0.98 (m, 4H), 0.78-0.69 (m, 6H). LCMS: (Method E) 538.2 (M$^+$+H), Rt. 3.21 min, 99.68% (Max). Chiral SFC: (Method H) Rt. 2.21 min, 99.40% (Max).

Diastereomer 2: Yield: 68% (55 mg, pale yellow solid).
$^1$H NMR (400 MHz, DMSO-$d_6$): δ 7.35 (s, 1H), 7.23 (t, J=7.2 Hz, 2H), 7.00 (d, J=7.6 Hz, 2H), 6.87 (t, J=7.2 Hz, 1H), 6.69 (s, 1H), 4.53-4.39 (m, 2H), 3.76 (bs, 3H), 3.69 (s, 2H), 3.28 (s, 2H), 2.15 (s, 3H), 1.69-1.57 (m, 3H), 1.56-1.51 (m, 1H), 1.50-1.39 (m, 1H), 1.37-1.25 (m, 2H), 1.21-0.98 (m, 4H), 0.78-0.69 (m, 6H). LCMS: (Method E) 537.8 (M$^+$+H), Rt. 3.24 min, 99.72% (Max). Chiral SFC: (Method H) Rt. 2.78 min, 99.44% (Max).

The absolute configuration of the two diastereomers is not known.

Intermediate 61

Methyl Trityl-D-Serinate

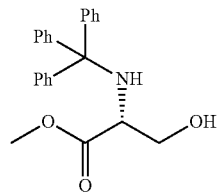 [SMILES: COC(=O)[C@@H](CO)NC(c1ccccc1)(c1ccccc1)c1ccccc1]

To a stirred solution of methyl-D-serinate hydrochloride (2 g, 12.8 mmol) in DCM (10 mL) at 0° C., triethylamine (6.1 mL, 45.9 mmol) was added. Trityl chloride (4.26 g, 15.3 mmol) was then added and the reaction mixture was stirred for 16 hours at room temperature. After completion of the reaction (monitored by TLC), the reaction mixture was quenched with water (20 mL) and the aqueous layer was extracted with DCM (2×30 mL). The combined organic layer was washed with water (30 mL) and brine (30 mL) and dried over anhydrous $Na_2SO_4$. The organic part was filtered and concentrated under vacuum. The resulting crude material was purified by Isolera column chromatography (eluent: 27% EtOAc/PE; silica gel: 230-400 mesh) to afford the title compound. Yield: 95% (2.5 g, white solid).
$^1$H NMR (400 MHz, DMSO-$d_6$): δ 7.43 (d, J=8.0 Hz, 6H), 7.29 (t, J=8.0 Hz, 6H), 7.20 (t, J=7.2 Hz, 3H), 4.95-4.92 (m, 1H), 3.63-3.51 (m, 1H), 3.46-3.40 (m, 1H), 3.24-3.18 (m, 1H), 3.13 (s, 3H), 2.82-2.71 (m, 1H).

Intermediate 62

Methyl O—((S)-3-butyl-3-ethyl-7-(methylthio)-1,1-dioxido-5-phenyl-2,3,4,5-tetrahydro-1,5-benzothiazepin-8-yl)-N-trityl-D-serinate and methyl O—((R)-3-butyl-3-ethyl-7-(methylthio)-1,1-dioxido-5-phenyl-2,3,4,5-tetrahydro-1,5-benzothiazepin-8-yl)-N-trityl-D-serinate

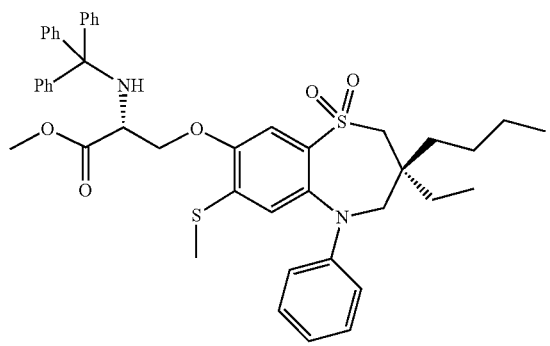

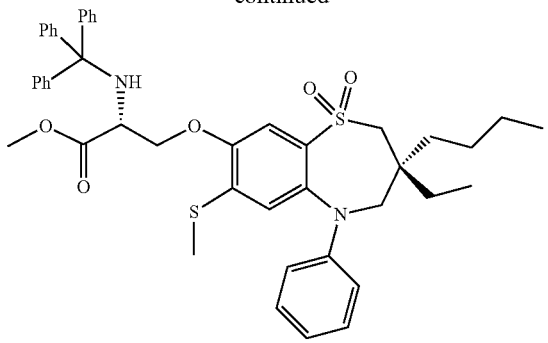

Diastereomer 1

To a stirred solution of enantiomer 1 of 3-butyl-3-ethyl-8-hydroxy-7-(methylthio)-5-phenyl-2,3,4,5-tetrahydro-1,5-benzothiazepine 1,1-dioxide (Intermediate 23; 400 mg, 0.95 mmol) in toluene (10 mL) at 0° C., triphenylphosphine (533 mg, 1.90 mmol) and methyl trityl-D-serinate (Intermediate 61; 460 mg, 1.14 mmol) were added and the reaction mixture was stirred for 5 minutes. Then DIAD (320 mg, 1.42 mmol) was added and the reaction mixture was heated for 4 hours at 90° C. After completion of the reaction (monitored by TLC), the reaction mixture was concentrated under vacuum and the obtained residue was diluted with water (10 mL). The aqueous layer was extracted with EtOAc (2×10 mL) The combined organic layer was washed with water (10 mL) and brine (10 mL) and dried over anhydrous $Na_2SO_4$. The organic part was filtered and concentrated under vacuum. The resulting crude material was purified by Isolera column chromatography (eluent: 20% EtOAc/PE; silica gel: 230-400 mesh) to afford the title compound. Yield: 98% (740 mg, off-white solid).

$^1$H NMR (400 MHz, DMSO-$d_6$): 7.47-7.42 (m, 6H), 7.33-7.27 (m, 7H), 7.24-7.20 (m, 6H), 6.98 (d, J=8.0 Hz, 2H), 6.86 (t, J=7.2 Hz, 1H), 6.69 (s, 1H), 4.33-4.19 (m, 1H), 4.01-4.07 (m, 1H), 3.74 (bs, 2H), 3.69-3.59 (m, 1H), 3.23 (s, 2H), 3.21 (s, 3H), 2.14 (s, 3H), 1.65-1.51 (m, 1H), 1.52-1.41 (m, 1H), 1.41-1.36 (m, 2H), 1.23-0.95 (m, 4H), 0.84-0.73 (m, 6H).

Diastereomer 2

To a stirred solution of enantiomer 2 of 3-butyl-3-ethyl-8-hydroxy-7-(methylthio)-5-phenyl-2,3,4,5-tetrahydro-1,5-benzothiazepine 1,1-dioxide (Intermediate 23; 400 mg, 0.95 mmol) in toluene (10 mL) at 0° C., triphenylphosphine (533 mg, 1.90 mmol) and methyl trityl-D-serinate (Intermediate 61; 460 mg, 1.14 mmol) were added and the reaction mixture was stirred for 5 minutes. Then DIAD (320 mg, 1.42 mmol) was added dropwise and the reaction mixture was heated for 4 hours at 90° C. After completion of the reaction (monitored by TLC), the reaction mixture was concentrated under vacuum and the obtained residue was partitioned between water (10 mL) and EtOAc (10 mL). The aqueous layer was extracted with EtOAc (2×10 mL), and the combined organic layer was washed with water (10 mL) and brine (10 mL). The organic part was dried over anhydrous $Na_2SO_4$, filtered and concentrated under vacuum. The resulting crude material was purified by Isolera column chromatography (eluent: 20% EtOAc/PE; silica gel: 230-400 mesh) to afford the title compound.

Yield: 82% (600 mg, off-white solid).

$^1$H NMR (400 MHz, DMSO-$d_6$): 7.47-7.42 (m, 6H), 7.33-7.27 (m, 7H), 7.24-7.20 (m, 6H), 6.98 (d, J=8.0 Hz, 2H), 6.86 (t, J=7.2 Hz, 1H), 6.69 (s, 1H), 4.33-4.19 (m, 1H), 4.01-4.07 (m, 1H), 3.74 (bs, 2H), 3.69-3.59 (m, 1H), 3.23 (s, 2H), 3.21 (s, 3H), 2.14 (s, 3H), 1.65-1.51 (m, 1H), 1.52-1.41 (m, 1H), 1.41-1.36 (m, 2H), 1.23-0.95 (m, 4H), 0.84-0.73 (m, 6H).

The absolute configuration of the two diastereomers is not known.

Intermediate 63

Methyl O—((S)-3-butyl-3-ethyl-7-(methylthio)-1,1-dioxido-5-phenyl-2,3,4,5-tetrahydro-1,5-benzothiazepin-8-yl)-D-serinate and methyl O—((R)-3-butyl-3-ethyl-7-(methylthio)-1,1-dioxido-5-phenyl-2,3,4,5-tetrahydro-1,5-benzothiazepin-8-yl)-D-serinate

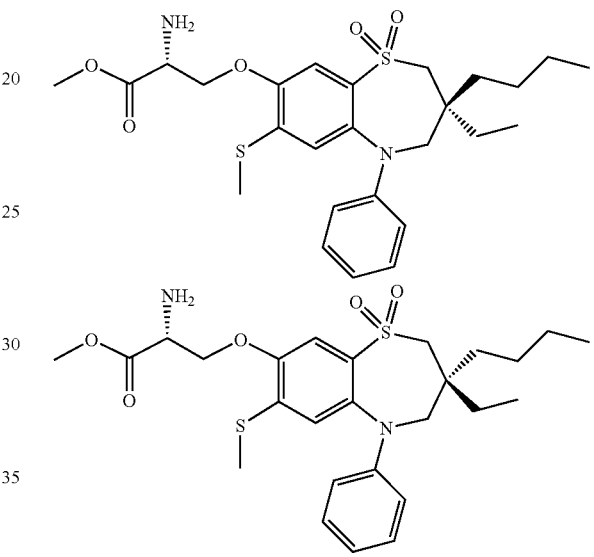

Diastereomer 1

To a stirred solution of diastereomer 1 of methyl O-(3-butyl-3-ethyl-7-(methylthio)-1,1-dioxido-5-phenyl-2,3,4,5-tetrahydro-1,5-benzothiazepin-8-yl)-N-trityl-D-serinate (Intermediate 62; 740 mg, 0.98 mmol) in DCM (10 mL) at 0° C., TFA (1 mL) was added and the reaction mixture was stirred for 1 hour at room temperature. After completion of the reaction (monitored by TLC), the reaction mixture was poured into ice-cold water (10 mL) and the aqueous layer was extracted with EtOAc (2×15 mL). The combined organic layer was washed with water (15 mL) and brine (15 mL) and dried over anhydrous $Na_2SO_4$. The organic part was filtered and concentrated under vacuum. The resulting crude material was purified by Isolera column chromatography (eluent: 5-10% MeOH/DCM; silica gel: 230-400 mesh) to afford the title compound. Yield: 79% (400 mg, off-white solid).

LCMS: (Method F) 521.2 (M$^+$+H), Rt. 0.21 min, 58.92% (Max).

Diastereomer 2

To a stirred solution of diastereomer 2 of methyl O-(3-butyl-3-ethyl-7-(methylthio)-1,1-dioxido-5-phenyl-2,3,4,5-tetrahydro-1,5-benzothiazepin-8-yl)-N-trityl-D-serinate (Intermediate 62; 600 mg, 0.78 mmol) in DCM (6 mL) at 0° C., TFA (1 mL) was added and the reaction mixture was stirred for 1 hour at room temperature. After completion of the reaction (monitored by TLC), the reaction mixture was poured into ice-cold water (10 mL) and the aqueous layer was extracted with EtOAc (2×15 mL). The combined organic layer was washed with water (15 mL) and brine (15 mL) and dried over anhydrous $Na_2SO_4$. The organic part was filtered and concentrated under vacuum. The resulting crude material was purified by Isolera column chromatography (eluent: 5-10% MeOH/DCM; silica gel: 230-400 mesh) to afford the title compound. Yield: 90% (370 mg, off-white solid).

LCMS: (Method E) 521.2 ($M^+$+H), Rt. 2.57 min, 59.57% (Max).

The absolute configuration of the two diastereomers is not known.

Intermediate 64

2-(((2-Amino-5-methoxyphenyl)thio)methyl)-2-ethylhexanoic acid

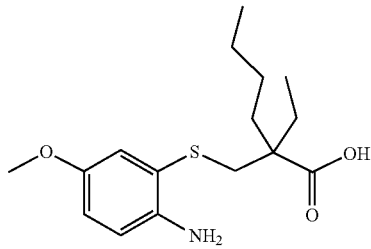 [SMILES: CCCCC(CC)(CSc1cc(OC)ccc1N)C(=O)O]

To a stirred solution of 6-methoxybenzo[d]thiazol-2-amine (270 g, 1.498 mol) in water (2700 mL), was added KOH (1345 g, 23.96 mol) and the reaction mixture was stirred for 16 hours at 120° C. After completion of the reaction (monitored by LCMS), the reaction mixture was cooled to room temperature. A solution of 2-(bromomethyl)-2-ethylhexanoic acid (533 g, 2.25 mol) in THF (1000 mL) was then added dropwise and the resulting reaction mixture was stirred for 16 hours at room temperature. After completion of the reaction (monitored by LCMS), the reaction mixture was cooled to 0° C. and acidified with concentrated HCl (pH 2). The reaction mixture was extracted with EtOAc (2×4000 mL) and the combined organic layer was washed with water (1000 mL) and brine (1000 mL). The organic part was then dried over anhydrous $Na_2SO_4$ and concentrated under vacuum to obtain the crude material, which was forwarded as such to the next step without any further purification. Yield: 590 g (crude, brown gum).

LCMS: (Method A) 312.1 ($M^+$+H), Rt. 2.24 min, 97.34% (Max).

Intermediate 65

3-Butyl-3-ethyl-8-methoxy-2,3-dihydro-1,5-benzothiazepin-4(5H)-one

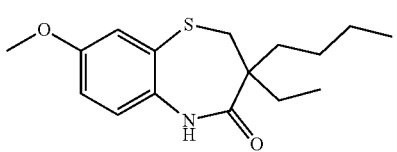 [SMILES: CCCCC1(CC)CSc2cc(OC)ccc2NC1=O]

To a stirred solution of 2-(((2-amino-5-methoxyphenyl)thio)methyl)-2-ethylhexanoic acid (Intermediate 64; 590 g, 1.89 mol) in EtOAc (2500 mL) at 0° C., triethyl amine (530 mL, 3.78 mol) and 1-propanephosphonic anhydride solution (50% in EtOAc; 785 g, 2.46 mol) were added dropwise and the reaction mixture was stirred for 16 hours at room temperature. After completion of the reaction (monitored by LCMS), water (2000 mL) was added to the reaction mixture and the aqueous layer was extracted with EtOAc (2×2000 mL). The combined organic layer was washed with brine (800 mL), dried over anhydrous $Na_2SO_4$ and concentrated under vacuum. The crude material was purified by washing with methanol to afford the title compound. Yield: 48% (265 g, off-white solid).

$^1$H NMR (300 MHz, DMSO-$d_6$): δ 9.53 (s, 1H), 7.04-7.01 (m, 2H), 6.87-6.86 (m, 1H), 3.72 (s, 3H), 2.50 (s, 2H), 1.68-1.66 (m, 4H), 1.50-1.48 (m, 4H), 0.79-0.72 (m, 6H). LCMS: (Method A) 294.3 ($M^+$+H), Rt. 2.68 min, 99.47% (Max).

Intermediate 66

7-Bromo-3-butyl-3-ethyl-8-methoxy-2,3-dihydro-1,5-benzothiazepin-4(5H)-one

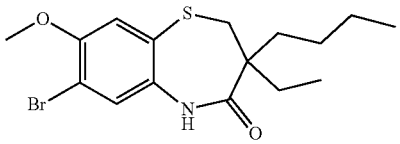 [SMILES: CCCCC1(CC)CSc2cc(OC)c(Br)cc2NC1=O]

To a stirred solution of 3-butyl-3-ethyl-8-methoxy-2,3-dihydro-1,5-benzothiazepin-4(5H)-one (Intermediate 65; 265 g, 0.903 mol) in a 1:1 mixture of DCM and acetonitrile (2650 mL), N-bromo succinimide (209 g, 1.17 mol) was added portionwise and the reaction mixture was stirred for 16 hours at room temperature. After completion of the reaction (monitored by TLC), the reaction mixture was concentrated. The obtained crude material was treated with cold acetonitrile and stirred for 30 minutes. The obtained precipitate was filtered off and wash with cold acetonitrile (2×100 mL) and dried under vacuum to afford the title compound. Yield: 179 g (79%, crude, brown solid).

$^1$H NMR (300 MHz, DMSO-$d_6$): δ 9.61 (s, 1H), 7.33 (s, 1H), 7.10 (s, 1H), 3.82 (s, 3H), 2.98 (s, 2H), 1.70-1.68 (m, 4H), 1.48-1.45 (m, 4H), 0.84-0.82 (m, 6H). LCMS: (Method A) 372.0 ($M^+$+H), Rt. 2.83 min, 99.20% (Max).

Intermediate 67

7-Bromo-3-butyl-3-ethyl-5-(4-fluorophenyl)-8-methoxy-2,3-dihydro-1,5-benzothiazepin-4(5H)-one and 3-butyl-3-ethyl-5-(4-fluorophenyl)-7-iodo-8-methoxy-2,3-dihydro-1,5-benzothiazepin-4(5H)-one

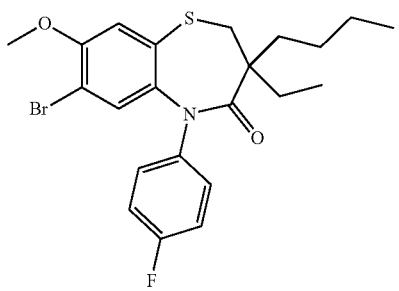

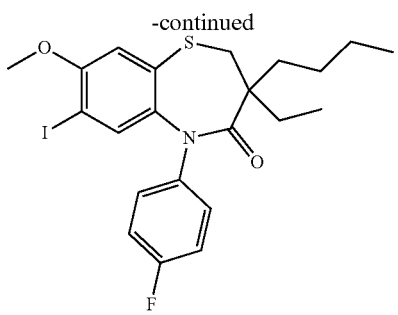

To a stirred solution of 7-bromo-3-butyl-3-ethyl-8-methoxy-2,3-dihydro-1,5-benzothiazepin-4(5H)-one (Intermediate 66; 15 g, 40.2 mmol) in 1-fluoro-4-iodobenzene (50 mL), copper (I) iodide (1.58 g, 0.8 mmol) and K$_2$CO$_3$ (11 g, 80.5 mmol) were added and the reaction mixture was purged with nitrogen for 20 minutes for degasification. Tris[2-(2-methoxyethoxy)ethyl]amine (1.3 mL, 4.0 mmol) was then added under nitrogen atmosphere and the resulting reaction mixture was heated for 16 hours at 135° C. After completion of the reaction (monitored by TLC), the reaction mixture was filtered through celite and the celite pad was washed with EtOAc (200 mL). The filtrate was washed with water (100 mL) and brine (75 mL) and dried over anhydrous Na$_2$SO$_4$. The resulting crude material was purified by Isolera column chromatography (eluent: 5% EtOAc/PE; silica gel: 230-400 mesh) to afford the title compound. Yield: 64% (12.2 g, off-white solid).

LCMS: (Method E) 467.1 (M$^+$+2) for the 7-bromo substituted compound and 514.1 (M$^+$+H) for the 7-iodo substituted compound), Rt. 3.33 min, 92.83% (Max).

Intermediate 68

7-Bromo-3-butyl-3-ethyl-5-(4-fluorophenyl)-8-methoxy-2,3,4,5-tetrahydro-1,5-benzothiazepine and 3-butyl-3-ethyl-5-(4-fluorophenyl)-7-iodo-8-methoxy-2,3,4,5-tetrahydro-1,5-benzothiazepine

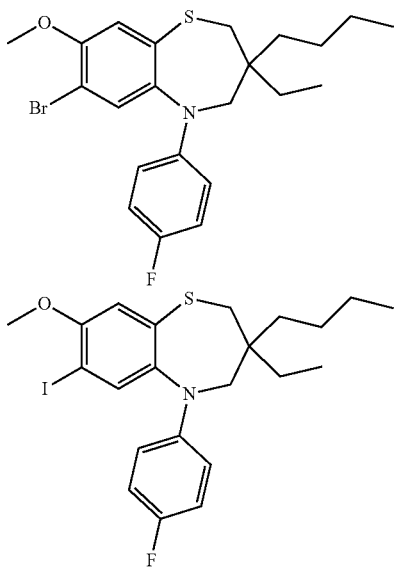

To a stirred solution of a mixture of 7-bromo-3-butyl-3-ethyl-5-(4-fluorophenyl)-8-methoxy-2,3-dihydro-1,5-benzothiazepin-4(5H)-one and 3-butyl-3-ethyl-5-(4-fluorophenyl)-7-iodo-8-methoxy-2,3-dihydro-1,5-benzothiazepin-4 (5H)-one (Intermediate 67; 12 g, 25.7 mmol) in THF (100 mL) at 0° C. was dropwise added borane dimethylsulfide (2M in THF; 38 mL, 77 mmol) and the reaction mixture was refluxed for 16 hours at 65° C. After completion of the reaction (monitored by TLC), the reaction mixture was cooled to 0° C., quenched with methanol (20 mL) and heated for 2 hours at 65° C. The resulting reaction mixture was then cooled to room temperature and concentrated under vacuum. The residue was diluted with water (100 mL) and the aqueous layer was extracted with DCM (2×100 mL). The combined organic layer was then washed with water (50 mL) and brine (50 mL) and dried over anhydrous Na$_2$SO$_4$. The organic part was concentrated under vacuum and the resulting crude was forwarded as such to the next step without any further purification. Yield: 10 g (crude, black gum).

LCMS: (Method E) 451.8 (M$^+$+H) for the 7-bromo substituted compound and 499.7 (M$^+$+H) for the 7-iodo substituted compound, Rt. 3.78 min, 75.13% (Max).

Intermediate 69

7-Bromo-3-butyl-3-ethyl-5-(4-fluorophenyl)-8-methoxy-2,3,4,5-tetrahydro-1,5-benzothiazepine 1,1-dioxide and 3-butyl-3-ethyl-5-(4-fluorophenyl)-7-iodo-8-methoxy-2,3,4,5-tetrahydro-1,5-benzothiazepine 1,1-dioxide

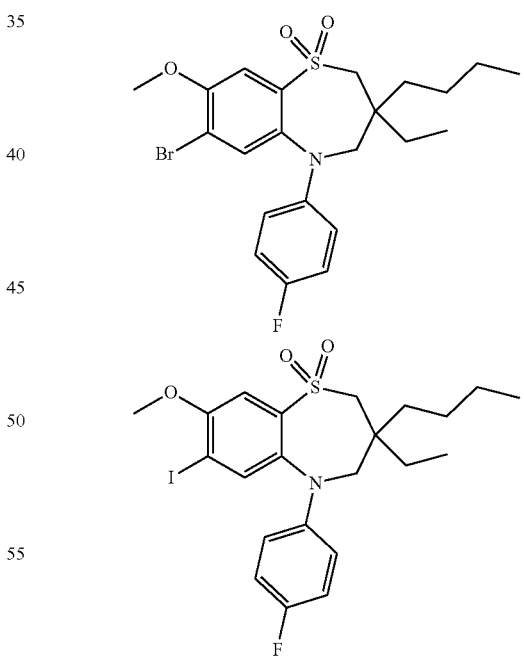

To a stirred solution of a mixture of 7-bromo-3-butyl-3-ethyl-5-(4-fluorophenyl)-8-methoxy-2,3,4,5-tetrahydro-1,5-benzothiazepine and 3-butyl-3-ethyl-5-(4-fluorophenyl)-7-iodo-8-methoxy-2,3,4,5-tetrahydro-1,5-benzothiazepine (Intermediate 68; 10 g, 26.6 mmol) in THF (100 mL) and water (60 mL), oxone (81 g, 26.6 mmol) was added at 0° C. The resulting reaction mixture was stirred for 16 hours at room temperature. After completion of the reaction (monitored by TLC), the reaction mixture was filtered off through a Buchner funnel and the filtrate was extracted with EtOAc (2×200 mL), The combined organic layer was washed with water (100 mL) and brine (100 mL), dried over anhydrous Na$_2$SO$_4$ and concentrated under vacuum. The resulting crude was purified by Isolera column chromatography (eluent: 15% EtOAc/PE; silica gel: 230-400 mesh) to afford the title compound. Yield: 54% (7 g, white solid).

LCMS: (Method E) 486.0 (M$^+$+2) for the 7-bromo substituted compound and 532.0 (M$^+$+H) for the 7-iodo substituted compound, Rt. 2.87 min, 91.53% (Max).

Intermediate 70

3-Butyl-3-ethyl-5-(4-fluorophenyl)-8-hydroxy-7-(methylthio)-2,3,4,5-tetrahydro-1,5-benzothiazepine 1,1-dioxide

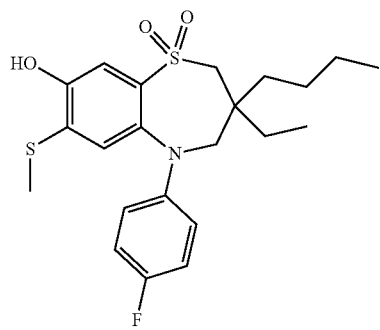

To a stirred solution of a mixture of 7-bromo-3-butyl-3-ethyl-5-(4-fluorophenyl)-8-methoxy-2,3,4,5-tetrahydro-1,5-benzothiazepine 1,1-dioxide and 3-butyl-3-ethyl-5-(4-fluorophenyl)-7-iodo-8-methoxy-2,3,4,5-tetrahydro-1,5-benzothiazepine 1,1-dioxide (Intermediate 69; 3 g, 6.2 mmol) in DMF (16 mL), sodium thiomethoxide (2.1 g, 31 mmol) was added at room temperature and the reaction mixture was stirred for 16 hours at 65° C. After completion of the reaction (monitored by TLC), the reaction mixture was cooled to room temperature and quenched with water (25 mL). The aqueous layer was extracted with EtOAc (2×50 mL). The combined organic layer was washed with brine (20 mL), dried over anhydrous Na$_2$SO$_4$ and concentrated under vacuum. The resulting crude was purified by Isolera column chromatography (eluent: 10% EtOAc/PE; silica gel: 230-400 mesh) to afford the title compound. Yield: 77% (2.13 g, brown solid).

$^1$H NMR (400 MHz, DMSO-d$_6$): δ 10.49 (s, 1H), 7.28 (s, 1H), 7.06-6.96 (m, 4H), 6.61 (s, 1H), 3.62 (bs, 2H), 3.21 (s, 2H), 2.17 (s, 3H), 1.61-1.25 (m, 4H), 1.20-1.01 (m, 4H), 0.81-0.74 (m, 6H). LCMS: (Method A) 438.1 (M$^+$+H), Rt. 2.78 min, 87.79% (Max).

Separation of Enantiomers (S)-3-butyl-3-ethyl-5-(4-fluorophenyl)-8-hydroxy-7-(methylthio)-2,3,4,5-tetrahydrobenzo-1,5-thiazepine 1,1-dioxide and (R)-3-butyl-3-ethyl-5-(4-fluorophenyl)-8-hydroxy-7-(methylthio)-2,3,4,5-tetrahydrobenzo-1,5-thiazepine 1,1-dioxide

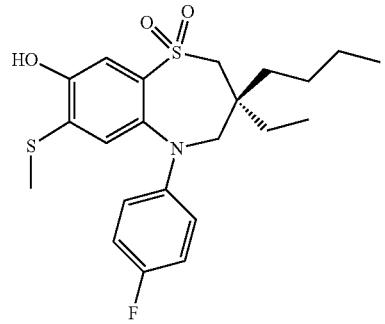

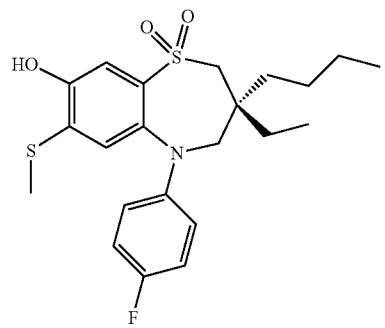

The two enantiomers of racemic 3-butyl-3-ethyl-5-(4-fluorophenyl)-8-hydroxy-7-(methylthio)-2,3,4,5-tetrahydro-1,5-benzothiazepine 1,1-dioxide (2.8 g, 0.01 mol) were separated by chiral SFC (Method H). The material was concentrated under vacuum at 40° C. The first eluting fraction corresponded to enantiomer 1 and the second eluting fraction corresponded to enantiomer 2. The absolute configuration of the two enantiomers is not known.

Enantiomer 1: Yield: 35.7% (1.0 g, white solid). $^1$H NMR (400 MHz, DMSO-d$_6$): δ 10.49 (s, 1H), 7.28 (s, 1H), 7.07-6.98 (m, 4H), 6.61 (s, 1H), 3.62 (s, 2H), 3.21 (s, 2H), 2.17 (s, 3H), 1.50-1.34 (m, 4H), 1.29-1.11 (m, 4H), 0.76-0.74 (m, 6H). LCMS: (Method E) 438.1 (M$^+$+H), Rt. 3.01 min, 96.38%. HPLC: (Method B) Rt. 5.80 min, 98.35% (Max). Chiral SFC: (Method H) Rt. 2.46 min, 100% (Max).

Enantiomer 2: Yield: 39.2% (1.1 g, white solid). LCMS: (Method E) 438.1 (M$^+$+H), Rt. 3.04 min, 96.52% (Max). Chiral SFC: (Method H) Rt. 3.17 min, 99.68% (Max).

Intermediate 71

Methyl 3-((3-butyl-3-ethyl-7-(methylthio)-1,1-di-oxido-5-phenyl-2,3,4,5-tetrahydro-1,5-benzothiazepin-8-yl)oxy)-2-hydroxypropanoate

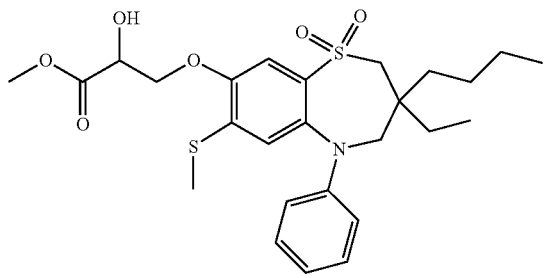 [SMILES: CCCCC1(CC)CN(c2ccccc2)c2cc(SC)c(OCC(O)C(=O)OC)cc2S(=O)(=O)C1]

To a stirred solution of 3-butyl-3-ethyl-8-hydroxy-7-(methylthio)-5-phenyl-2,3,4,5-tetrahydro-1,5-benzothiazepine 1,1-dioxide (Intermediate 22; 400 mg, 0.95 mmol) in DMF (4 mL), $Cs_2CO_3$ (621 mg, 1.90 mmol) and methyl-oxirane-2-carboxylate (291 mg, 2.85 mmol) were added. The reaction mixture was stirred for 16 hours at room temperature. After 70-80% conversion of starting material (monitored by TLC), the reaction mixture was quenched with dilute HCl (5 mL) and diluted with water (5 mL). The aqueous layer was extracted with EtOAc (2×10 mL), and the combined organic layer was washed with water (10 mL) and brine (10 mL). The organic part was dried over anhydrous $Na_2SO_4$, filtered and concentrated under vacuum. The resulting crude material was purified by Isolera column chromatography (eluent: 30% EtOAc/PE; silica gel: 230-400 mesh) to afford the title compound.

Yield: 60% (300 mg, yellow gum).

$^1$H NMR (400 MHz, DMSO-$d_6$): δ 7.34 (s, 1H), 7.22 (t, J=10.0 Hz, 2H), 6.98 (d, J=10.0 Hz, 2H), 6.86 (t, J=9.6 Hz, 1H), 6.69 (s, 1H), 5.89 (d, J=8.0 Hz, 1H), 4.47 (t, J=6.0 Hz, 1H), 4.27 (d, J=5.2 Hz, 2H), 3.68 (s, 3H), 3.60-3.55 (m, 2H), 3.27 (s, 2H), 2.15 (s, 3H), 1.81-1.70 (m, 1H), 1.60-1.25 (m, 3H), 1.22-0.95 (m, 4H), 0.85-0.65 (m, 6H). LCMS: (Method F) 522.3 (M$^+$+H), Rt. 2.76 min, 98.34% (Max).

Intermediate 72

Methyl 3-((3-butyl-3-ethyl-7-(methylthio)-1,1-di-oxido-5-phenyl-2,3,4,5-tetrahydro-1,5-benzothiazepin-8-yl)oxy)-2-hydroxypropanoate (Individual Diastereomers)

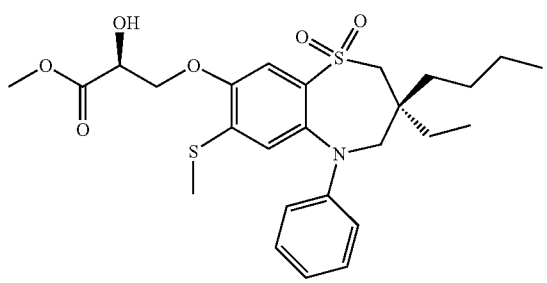

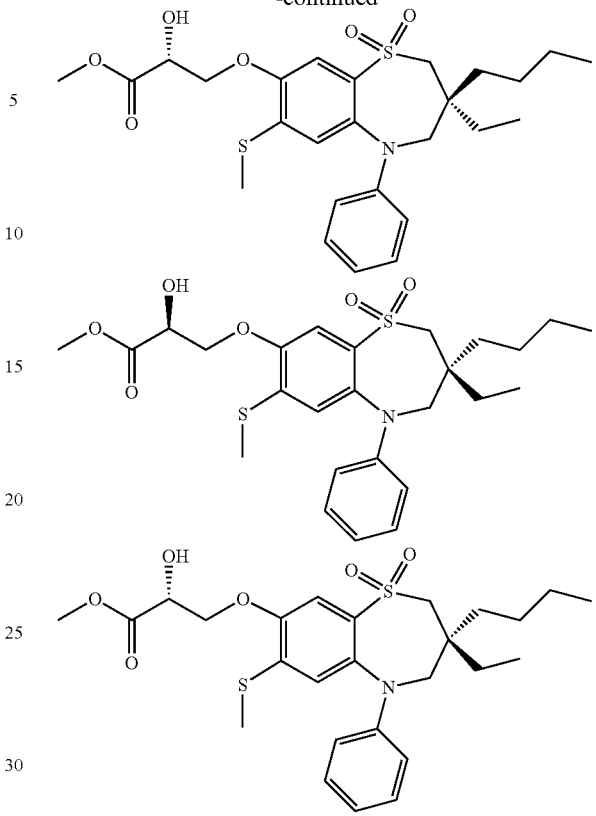

Diastereomers 1 and 2

To a stirred solution of enantiomer 1 of 3-butyl-3-ethyl-8-hydroxy-7-(methylthio)-5-phenyl-2,3,4,5-benzothiazepine 1,1-dioxide (Intermediate 23; 400 mg, 0.95 mmol) in DMF (4 mL) were added $Cs_2CO_3$ (621 mg, 1.90 mmol) and methyl-oxirane-2-carboxylate (291 mg, 2.85 mmol). The reaction mixture was stirred for 48 hours at room temperature. After 70-80% completion of the reaction (monitored by TLC), the reaction mixture was quenched with dilute HCl (5 mL) and diluted with water (5 mL). The aqueous layer was extracted with EtOAc (2×10 mL), then the combined organic layer was washed with water (10 mL) and brine (10 mL). The organic part was dried over anhydrous $Na_2SO_4$, filtered and concentrated under vacuum. The resulting crude material was purified by Isolera column chromatography (eluent: 30% EtOAc/PE; silica gel: 230-400 mesh) to afford the title compound. Yield: 60% (300 mg, brown gum). LCMS: (Method E) 522.1 (M$^+$+H), Rt. 3.03 min, 98.51% (Max).

The two diastereomers (290 mg, 0.55 mmol) were separated by chiral SFC Instrument (method N). The material was concentrated under vacuum at 40° C. The first eluting fraction corresponded to diastereomer 1 and the second eluting fraction corresponded to diastereomer 2.

Diastereomers 3 and 4

A mixture of diastereomers 3 and 4 of the title compound was obtained following the same procedure, starting from 400 mg of enantiomer 2 of Intermediate 23. Yield: 49% (280 mg, brown gum).

LCMS: (Method F) 522.2 (M$^+$+H), Rt. 2.759 min, 99.04% (Max). HPLC: (Method B) Rt. 5.681 min, 98.07% (Max).

The two diastereomers (270 mg, 0.52 mmol) were separated by chiral SFC Instrument (method G). The material was concentrated under vacuum at 40° C. The first eluting fraction corresponded to diastereomer 3 and the second eluting fraction corresponded to diastereomer 4.

Diastereomer 1: Yield: 37% (110 mg, light brown gum). $^1$H NMR (400 MHz, DMSO-$d_6$): δ 7.34 (s, 1H), 7.22 (t, J=8.4 Hz, 2H), 6.98 (d, J=7.6 Hz, 2H), 6.86 (t, J=7.2 Hz, 1H), 6.69 (s, 1H), 5.90 (d, J=6.0 Hz, 1H), 4.50-4.47 (m, 1H), 4.27 (t, J=2.4 Hz, 2H), 3.69 (s, 5H), 3.27 (s, 2H), 2.15 (s, 3H), 1.65-1.40 (m, 2H), 1.36-1.31 (m, 2H), 1.13-1.08 (m, 4H), 0.79-0.74 (m, 6H). LCMS: (Method E) 522.1 (M$^+$+H), Rt. 3.03 min, 96.69% (Max). HPLC: (Method B) Rt. 5.604 min, 97.44% (Max). Chiral SFC: (Method N) Rt. 2.93 min, 99.72% (Max).

Diastereomer 2: Yield: 37% (110 mg, light brown gum). $^1$H NMR (400 MHz, DMSO-$d_6$): δ 7.34 (s, 1H), 7.22 (t, J=10.4 Hz, 2H), 6.98 (d, J=10.4 Hz, 2H), 6.87 (d, J=10.0 Hz, 1H), 6.69 (s, 1H), 5.89 (d, J=8.0 Hz, 1H), 4.49-4.47 (m, 1H), 4.27-4.26 (m, 2H), 3.69 (s, 5H), 3.27 (s, 2H), 2.15 (s, 3H), 1.62-1.50 (m, 1H), 1.50-1.28 (m, 3H), 1.20-0.90 (m, 4H), 0.82-0.70 (m, 6H). LCMS: (Method E) 522.1 (M$^+$+H), Rt. 3.039 min, 97.48% (Max). HPLC: (Method B) Rt. 5.604 min, 99.06% (Max). Chiral SFC: (Method N) Rt. 3.76 min, 98.78% (Max).

Diastereomer 3: Yield: 37% (100 mg, white solid). $^1$H NMR (400 MHz, DMSO-$d_6$): δ 7.34 (s, 1H), 7.22 (t, J=10.0 Hz, 2H), 6.98 (d, J=10.8 Hz, 2H), 6.86 (t, J=9.2 Hz, 1H), 6.69 (s, 1H), 5.89 (d, J=7.6 Hz, 1H), 4.55-4.45 (m, 1H), 4.30-4.20 (m, 2H), 3.68 (s, 5H), 3.29-3.27 (m, 2H), 2.15 (s, 3H), 1.60-1.50 (m, 2H), 1.50-1.30 (m, 2H), 1.20-0.95 (m, 4H), 0.80-0.70 (m, 6H). LCMS: (Method E) 522.0 (M$^+$+H), Rt. 3.05 min, 95.91% (Max). HPLC: (Method B) Rt. 5.74 min, 99.94% (Max). Chiral SFC: (Method G) Rt. 3.09 min, 99.20% (Max).

Diastereomer 4: Yield: 37% (100 mg, off white solid). $^1$H NMR (400 MHz, DMSO-$d_6$): δ 7.34 (s, 1H), 7.22 (t, J=9.6 Hz, 2H), 6.99 (d, J=9.6 Hz, 2H), 6.87 (s, 1H), 6.69 (s, 1H), 5.90 (d, J=7.2 Hz, 1H), 4.48 (d, J=6.8 Hz, 1H), 4.27 (s, 2H), 3.69-3.67 (m, 5H), 3.27 (s, 2H), 2.15 (s, 3H), 1.60-1.50 (m, 2H), 1.45-1.30 (m, 2H), 1.20-1.00 (m, 4H), 0.79-0.73 (m, 6H). LCMS: (Method E) 522.0 (M$^+$+H), Rt. 3.06 min, 95.26% (Max). HPLC: (Method B) Rt. 5.74 min, 93.32% (Max). Chiral SFC: (Method G) Rt. 5.13 min, 99.07% (Max).

The absolute configuration of the four diastereomers is not known.

Intermediate 73

Methyl 3-((3-butyl-3-ethyl-5-(4-fluorophenyl)-7-(methylthio)-1,1-dioxido-2,3,4,5-tetrahydro-1,5-benzothiazepin-8-yl)oxy)-2-hydroxypropanoate

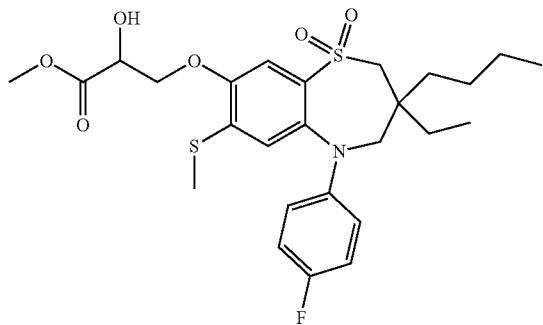 [SMILES: CCCCC1(CC)CN(c2ccc(F)cc2)c2cc(SC)c(OCC(O)C(=O)OC)cc2S(=O)(=O)C1]

To a stirred solution of 3-butyl-3-ethyl-5-(4-fluorophenyl)-8-hydroxy-7-(methylthio)-2,3,4,5-tetrahydro-1,5-benzothiazepine 1,1-dioxide (Intermediate 70; 100 mg, 0.22 mmol) in DMF (3 mL) were added Cs$_2$CO$_3$ (148 mg, 4.40 mmol) and methyl-oxirane-2-carboxylate (26 mg, 0.26 mmol). The reaction mixture was then stirred for 16 hours at room temperature. After 70% completion of the reaction (monitored by TLC), the reaction mixture was quenched with dilute HCl (1.5 N, 5 mL) and further diluted with water (5 mL). The aqueous layer was extracted with EtOAc (2×10 mL) and the combined organic layer was washed with water (10 mL) and brine (10 mL). The organic part was dried over anhydrous Na$_2$SO$_4$, filtered and concentrated under vacuum. The resulting crude material was purified by Isolera column chromatography (eluent: 45% EtOAc/PE; silica gel: 230-400 mesh) to afford the title compound. Yield: 82% (60 mg, brown solid).

$^1$H NMR (400 MHz, DMSO-$d_6$): δ 7.33 (s, 1H), 7.11-7.07 (m, 4H), 6.61 (s, 1H), 5.87-5.84 (m, 1H), 4.48 (d, J=5.6 Hz, 1H), 4.25 (t, J=2.8 Hz, 2H), 3.76 (s, 3H), 3.69-3.68 (m, 2H), 3.33-3.29 (m, 2H), 2.15 (s, 3H), 1.52-1.51 (m, 2H), 1.38-1.33 (m, 2H), 1.18-1.10 (m, 4H), 0.78-0.76 (m, 6H). LCMS: (Method E) 540.0 (M$^+$+H), Rt. 3.03 min, 76.03% (Max).

Intermediate 74

Methyl 3-((3-butyl-3-ethyl-5-(4-fluorophenyl)-7-(methylthio)-1,1-dioxido-2,3,4,5-tetrahydro-1,5-benzothiazepin-8-yl)oxy)-2-hydroxypropanoate (Individual Diastereomers)

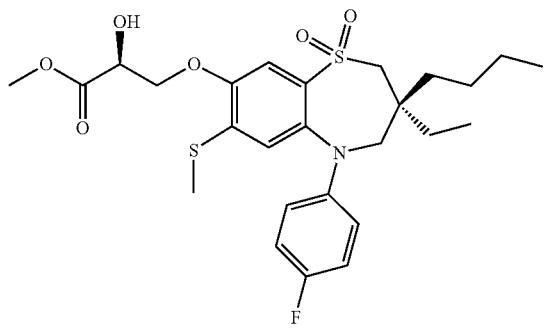

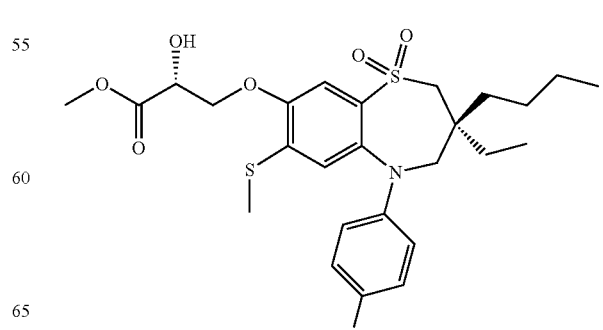

-continued

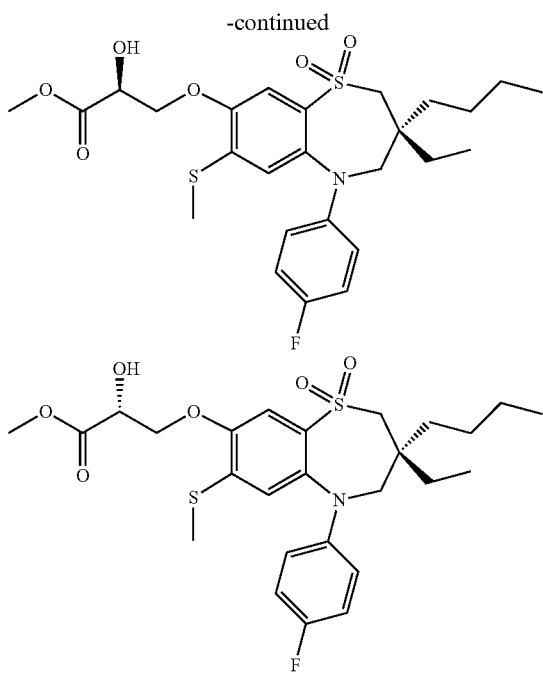

Diastereomers 1 and 2

To a stirred solution enantiomer 1 of 3-butyl-3-ethyl-5-(4-fluorophenyl)-8-hydroxy-7-(methylthio)-2,3,4,5-tetrahydro-1,5-benzothiazepine 1,1-dioxide (Intermediate 70; 160 mg, 0.36 mmol) in DMF (3 mL) were added $Cs_2CO_3$ (230 mg, 0.73 mmol) and methyl-oxirane-2-carboxylate (44 mg, 0.43 mmol). The reaction mixture was then stirred for 48 hours at room temperature. After 70-80% completion of the reaction (monitored by TLC), the reaction mixture was quenched with dilute HCl (1.5 N, 5 mL) and diluted with water (5 mL). The aqueous layer was extracted with EtOAc (2×10 mL) and the combined organic layer was washed with water (10 mL) and brine (10 mL), The organic part was dried over anhydrous $Na_2SO_4$, filtered and concentrated under vacuum. The resulting crude material was purified by Isolera column chromatography (eluent: 30-40% EtOAc/PE; silica gel: 230-400 mesh) to afford the title compound. Yield: 40% (80 mg, brown gum).
$^1$H NMR (400 MHz, $CDCl_3$): δ 7.41 (s, 1H), 7.08-7.04 (m, 2H), 7.03-7.06 (m, 2H), 6.55 (s, 1H), 4.57-4.56 (m, 1H), 4.46 (t, J=5.6 Hz, 2H), 3.87 (s, 3H), 3.75-3.65 (m, 2H), 3.19-3.17 (m, 2H), 2.17 (s, 3H), 1.79-1.61 (m, 2H), 1.49-1.42 (m, 2H), 1.28-1.20 (m, 2H), 1.18-1.10 (m, 2H), 0.85-0.79 (m, 6H). LCMS: (Method E) 540.1 ($M^++H$), Rt. 3.03 min, 95.30% (Max). HPLC: (Method B) Rt. 5.70 min, 93.00% (Max).

The two diastereomers were separated by chiral SFC Instrument (Method G). The material was concentrated under vacuum at 40° C. The first eluting fraction corresponded to diastereomer 1 and the second eluting fraction corresponded to diastereomer 2.

Diastereomers 3 and 4

A mixture of diastereomers 3 and 4 of the title compound was obtained following the same procedure, starting from 160 mg of enantiomer 2 of Intermediate 70. Yield: 40% (80 mg, brown gum). $^1$H NMR (400 MHz, $CDCl_3$): δ 7.41 (s, 1H), 7.29-6.97 (m, 4H), 6.55 (s, 1H), 4.57-4.55 (m, 1H), 4.39-4.38 (m, 2H), 3.80 (s, 3H), 3.78-3.60 (m, 2H), 3.19-3.15 (m, 2H), 2.17 (s, 3H), 1.49-1.40 (m, 4H), 1.27-1.20 (m, 2H), 1.18-1.10 (m, 2H), 0.80-0.78 (m, 6H). LCMS: (Method E) 540.0 ($M^++H$), Rt. 3.04 min, 95.89% (Max). HPLC: (Method B) Rt. 5.75 min, 93.07% (Max).

The two diastereomers were separated by chiral SFC Instrument (method G). The material was concentrated under vacuum at 40° C. The first eluting fraction corresponded to diastereomer 3 and the second eluting fraction corresponded to diastereomer 4.

Diastereomer 1: Yield: 37% (30 mg, brown solid). $^1$H NMR (400 MHz, DMSO-$d_6$): δ 7.33 (s, 1H), 7.09-7.07 (m, 4H), 6.61 (s, 1H), 5.89 (d, J=6.0 Hz, 1H), 4.48-4.48 (m, 1H), 4.28-4.26 (m, 2H), 3.68-3.51 (m, 5H), 3.37-3.35 (m, 2H), 2.15 (s, 3H), 1.61-1.52 (m, 1H), 1.38-1.31 (m, 3H), 1.24-1.01 (m, 4H), 0.78-0.72 (m, 6H). LCMS: (Method E) 540.0 ($M^++H$), Rt. 3.05 min, 99.79% (Max). HPLC: (Method B) Rt. 5.75 min, 99.24% (Max). Chiral SFC: (Method G) Rt. 1.4 min, 99.58% (Max).

Diastereomer 2: Yield: 37% (30 mg, brown solid). $^1$H NMR (400 MHz, DMSO-$d_6$): 7.33 (s, 1H), 7.09-7.07 (m, 4H), 6.61 (s, 1H), 5.89 (d, J=6.0 Hz, 1H), 4.49-4.48 (m, 1H), 4.26-4.26 (m, 2H), 3.68-3.51 (m, 5H), 3.37-3.35 (m, 2H), 2.15 (s, 3H), 1.50-1.41 (m, 1H), 1.38-1.31 (m, 3H), 1.24-1.01 (m, 4H), 0.78-0.75 (m, 6H). LCMS: (Method E) 540.0 ($M^++H$), Rt. 3.05 min, 99.10% (Max). HPLC: (Method B) Rt. 5.76 min, 97.56% (Max). Chiral SFC: (Method G) Rt. 2.16 min, 99.40% (Max).

Diastereomer 3: Yield: 12% (10 mg, brown solid). $^1$H NMR (400 MHz, DMSO-$d_6$): δ 7.33 (s, 1H), 7.09-7.07 (m, 4H), 6.61 (s, 1H), 5.88 (d, J=6.0 Hz, 1H), 4.48-4.47 (m, 1H), 4.26-4.24 (m, 2H), 3.69-3.68 (m, 5H), 3.33-3.21 (m, 2H), 2.15 (s, 3H), 1.68-1.50 (m, 1H), 1.42-1.38 (m, 3H), 1.35-1.01 (m, 4H), 0.76-0.72 (m, 6H). LCMS: (Method E) 540.0 ($M^++H$), Rt. 2.39 min, 99.79% (Max). HPLC: (Method B) Rt. 5.72 min, 99.52% (Max). Chiral SFC: (Method G) Rt. 2.01 min, 98.91% (Max).

Diastereomer 4: Yield: 12% (10 mg, brown solid). $^1$H NMR (400 MHz, DMSO-$d_6$): δ 7.33 (s, 1H), 7.09-7.07 (m, 4H), 6.61 (s, 1H), 5.88 (d, J=5.2 Hz, 1H), 4.49-4.45 (m, 1H), 4.27-4.24 (m, 2H), 3.69-3.68 (m, 5H), 3.33-3.21 (m, 2H), 2.15 (s, 3H), 1.68-1.50 (m, 1H), 1.42-1.38 (m, 3H), 1.34-1.01 (m, 4H), 0.78-0.74 (m, 6H). LCMS: (Method E) 540.0 (M+H), Rt. 3.04 min, 99.30% (Max). HPLC: (Method B) Rt.5.72 min, 98.98% (Max). Chiral SFC: (Method G) Rt. 3.78 min, 98.58% (Max).

The absolute configuration of the four diastereomers is not known.

Intermediate 75

3-Butyl-3-ethyl-8-hydroxy-7-methoxy-5-phenyl-2,3,4,5-tetrahydro-1,5-benzothiazepine 1,1-dioxide

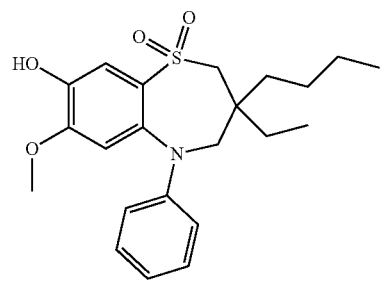 [SMILES: CCCCC1(CC)CN(c2ccccc2)c2cc(OC)c(O)cc2S(=O)(=O)C1]

To a stirred solution of 7-bromo-3-butyl-3-ethyl-8-hydroxy-5-phenyl-2,3,4,5-tetrahydro-1,5-benzothiazepine 1,1- dioxide (1 g, 2.21 mmol) in sodium methoxide (21%, 4.42 mL, 4.42 mmol), CuBr (0.1 g, 0.31 mmol) was added at room temperature and the resulting mixture was heated for 6 hours at 85° C. After completion of the reaction (monitored by TLC), the reaction mixture was concentrated under vacuum and the resulting crude mass was partitioned between EtOAc (25 mL) and water (25 mL). The aqueous layer was extracted with EtOAc (2×25 mL) and the combined organic layer was then washed with brine (25 mL) and dried over anhydrous $Na_2SO_4$. The organic part was concentrated under vacuum and the resulting crude was purified by Isolera column chromatography (eluent: 5% MeOH/DCM; silica gel: 230-400 mesh) to afford the title compound. Yield: 41% (0.36 g, pale pink solid).

$^1$H NMR (400 MHz, DMSO-$d_6$): δ 9.71 (s, 1H), 7.29 (s, 1H), 7.19 (t, J=7.6 Hz, 2H), 6.92 (d, J=8.0 Hz, 2H), 6.80 (t, J=7.6 Hz, 1H), 6.54 (s, 1H), 3.63 (s, 3H), 3.16 (s, 2H), 2.45 (s, 2H), 1.62-1.51 (m, 2H), 1.40-1.31 (m, 2H), 1.28-1.18 (m, 4H), 0.78-0.74 (m, 6H). LCMS: (Method A) 404.2 (M+H), Rt. 2.64 min, 94.56% (Max).

Intermediate 76

7-Bromo-3,3-dibutyl-8-hydroxy-5-phenyl-2,3,4,5-tetrahydro-1,5-benzothiazepine 1,1-dioxide

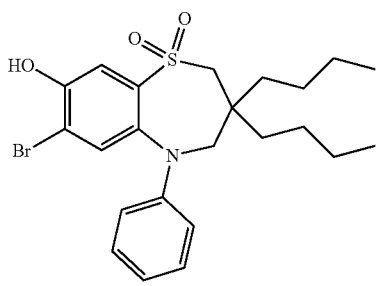 [SMILES: CCCCC1(CCCC)CN(c2ccccc2)c2cc(Br)c(O)cc2S(=O)(=O)C1]

To a stirred solution of 7-bromo-3,3-dibutyl-8-methoxy-5-phenyl-2,3,4,5-tetrahydro-1,5-benzothiazepine 1,1-dioxide (0.8 g, 1.62 mmol) in DCM (20 mL) at 0° C., BBr$_3$ (0.78 mL, 8.1 mmol) was added dropwise and the reaction mixture was stirred at room temperature for 1 hour. After completion of reaction (monitored by TLC), the reaction mixture was cooled to 0° C. EtOAc (10 mL) and ice-cold water (5 mL) were added dropwise and the mixture was stirred at room temperature for 1 hour. The reaction mixture was then partitioned between water (15 mL) and DCM (15 mL) and the aqueous layer was extracted with DCM (3×15 mL). The combined organic part was washed with brine (15 mL), dried over anhydrous $Na_2SO_4$ and concentrated under vacuum. The resulting crude material was forwarded to the next step as such without any further purification. Yield: 90% (700 mg, crude, off-white solid).

$^1$H NMR (400 MHz, DMSO-$d_6$): δ 10.83 (s, 1H), 7.46 (s, 1H), 7.23 (t, J=8.0 Hz, 2H), 7.07 (s, 1H), 6.99 (d, J=7.6 Hz, 2H), 6.88 (t, J=7.2 Hz, 1H), 3.80-3.72 (m, 2H), 3.27 (s, 2H), 1.34-1.31 (m, 4H), 1.13-0.99 (m, 8H), 0.75-0.72 (m, 6H). LCMS: (Method A) 480.1 (M$^+$), Rt. 3.19 min, 89.95% (Max).

Intermediate 77

3,3-Dibutyl-8-hydroxy-7-methoxy-5-phenyl-2,3,4,5-tetrahydro-1,5-benzothiazepine 1,1-dioxide

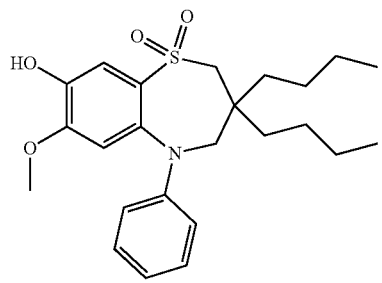 [SMILES: CCCCC1(CCCC)CN(c2ccccc2)c2cc(OC)c(O)cc2S(=O)(=O)C1]

To a stirred solution of 7-bromo-3,3-dibutyl-8-hydroxy-5-phenyl-2,3,4,5-tetrahydro-1,5-benzothiazepine 1,1-dioxide (Intermediate 76; 0.9 g, 1.87 mmol) in sodium methoxide (21%, 10 mL, 10.2 mmol), CuBr (0.15 g, 1.05 mmol) was added at room temperature and the resulting mixture was heated at 85° C. for 6 hours. After completion of the reaction (monitored by TLC), the reaction mixture was concentrated under vacuum and the resulting crude mass was partitioned between EtOAc (25 mL) and water (25 mL). The aqueous layer was extracted with EtOAc (2×25 mL) and the combined organic layer was washed with brine (25 mL) and dried over anhydrous $Na_2SO_4$. The organic part was concentrated under vacuum and the resulting crude was purified by Isolera column chromatography (eluent: 5% MeOH/DCM; silica gel: 230-400 mesh) to afford the title compound.

Yield: 78% (0.63 g, light pink gum).
UPLC: (Method A) 432.5 (M+H), Rt. 1.93 min, 90.07% (Max).

Intermediate 78

Methyl 3-((3,3-dibutyl-7-(methylthio)-1,1-dioxido-5-phenyl-2,3,4,5-tetrahydro-1,5-benzothiazepin-8-yl)oxy)-2-methoxypropanoate

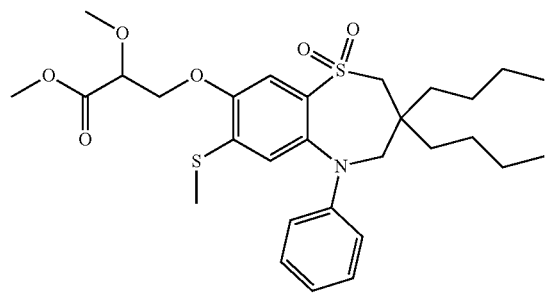 [SMILES: CCCCC1(CCCC)CN(c2ccccc2)c2cc(SC)c(OCC(OC)C(=O)OC)cc2S(=O)(=O)C1]

To a suspension of sodium hydride (60%, 7.2 mg, 0.18 mmol) in DMF (1 mL) at 0° C. was added a solution of methyl 3-((3,3-dibutyl-7-(methylthio)-1,1-dioxido-5-phenyl-2,3,4,5-tetrahydro-1,5-benzothiazepin-8-yl)oxy)-2-hydroxypropanoate (Intermediate 20; 200 mg, 0.36 mmol) in DMF (3 mL), and the reaction mixture was stirred for 15 minutes at room temperature. A solution of methyl iodide (0.12 mL, 2.3 mmol) in DMF (1 mL) was then added dropwise and the reaction mixture was stirred for 16 hours at room temperature. After completion of the reaction (monitored by TLC), the reaction mixture was quenched with dilute HCl (1.5 N, 1 mL) and further diluted with water (1 mL). The aqueous layer was extracted with EtOAc (2×10 mL) and the combined organic layer was washed with water (10 mL) and brine (10 mL). The organic part was dried over anhydrous $Na_2SO_4$, filtered and concentrated under vacuum. The resulting crude material was purified by Isolera column chromatography (eluent: 20-30% EtOAc/PE; silica gel: 230-400 mesh) to afford the title compound.

Yield: 48% (100 mg, brown solid).

$^1$H NMR (400 MHz, DMSO-$d_6$): δ 7.32 (s, 1H), 7.25-7.20 (m, 2H), 7.01 (d, J=8.0 Hz, 2H), 6.88 (t, J=9.6 Hz, 1H), 6.65 (s, 1H), 4.39-4.26 (m, 2H), 4.04-4.01 (m, 1H), 3.77 (s, 3H), 3.47-3.45 (m, 5H), 3.33-3.20 (m, 2H), 2.13 (s, 3H), 1.40-1.26 (m, 4H), 1.20-1.03 (m, 8H), 0.78-0.76 (m, 6H). LCMS: (Method E) 564.1 (M+H), Rt. 3.35 min, 95.11% (Max).

Intermediate 79

Methyl 3-((3-butyl-3-ethyl-7-(methylthio)-1,1-dioxido-5-phenyl-2,3,4,5-tetrahydro-1,5-benzothiazepin-8-yl)oxy)-2-hydroxy-2-methylpropanoate (Individual Diastereomers)

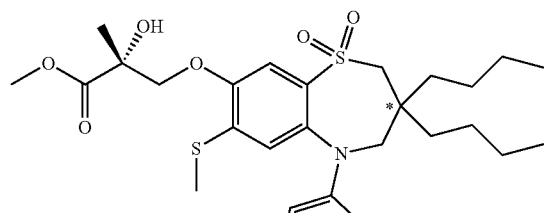

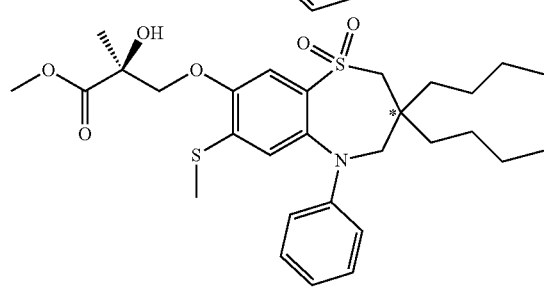

* the indicated carbons are each R or are each S

To a stirred solution enantiomer 2 of 3-butyl-3-ethyl-8-hydroxy-7-(methylthio)-5-phenyl-2,3,4,5-tetrahydro-1,5-benzothiazepine 1,1-dioxide (Intermediate 23, 250 mg, 0.59 mmol) in DMF (5 mL), $Cs_2CO_3$ (0.38 g, 1.19 mmol) was added and the reaction mixture was stirred for 15 minutes at room temperature. Methyl-2-methylglycidate (0.2 g, 1.78 mmol) was then added and the reaction mixture was stirred for 72 hours at room temperature. After completion of the reaction (monitored by TLC), the reaction mixture was quenched with dilute HCl (1.5 N, 5 mL) and diluted with water (5 mL). The aqueous layer was extracted with EtOAc (2×10 mL) and the combined organic layer was washed with water (10 mL) and brine (10 mL). The organic part was dried over anhydrous $Na_2SO_4$, filtered and concentrated under vacuum. The resulting crude material was purified by Isolera column chromatography (eluent: 15% EtOAc/PE; silica gel: 230-400 mesh) to afford the title compound.

Yield: 60% (150 mg, colourless gum).

$^1$H NMR (400 MHz, DMSO-$d_6$): δ 7.31 (s, 1H), 7.21-7.19 (m, 2H), 6.99-6.96 (m, 3H), 6.68 (s, 1H), 4.15-4.12 (m, 3H), 3.89-3.59 (m, 4H), 3.26 (s, 2H), 2.14 (s, 3H), 1.55-1.33 (m, 5H), 1.28-1.15 (m, 6H), 0.85-0.71 (m, 6H). LCMS: (Method E) 536.2 (M$^+$+H), Rt. 3.05 min, 99.11% (Max).

The two diastereomers enantiomers (150 mg, 0.28 mmol) were separated by SFC (method H). The first eluting fraction corresponded to diastereomer 1 and the second eluting fraction corresponded to diastereomer 2. The material was concentrated under vacuum at 40° C. Each of the two fractions was then individually treated for further purification. The obtained residue was acidified with dilute HCl (1.5 N, pH4) and the aqueous layer extracted with EtOAc (3×5 mL). The combined organic layer was washed with water (10 mL) and brine (10 mL) and dried over anhydrous $Na_2SO_4$. The organic part was filtered and concentrated under vacuum at 40° C. to afford a purified diastereomer of the title compound.

Diastereomer 1: Yield: 33% (50 mg, off-white solid). LCMS: (Method E) 535.8 (M$^+$+H), Rt. 2.69 min, 97.06% (Max). Chiral SFC: (Method F) Rt. 1.94 min, 100% (Max).

Diastereomer 2: Yield: 33% (50 mg, off-white solid). LCMS: (Method E) 535.8 (M$^+$+H), Rt. 2.69 min, 96.50% (Max). Chiral SFC: (Method F) Rt. 3.20 min, 100% (Max).

The absolute configuration of the two diastereomers is not known.

Intermediate 80

7-Bromo-3-butyl-5-(4-fluorophenyl)-8-methoxy-3-methyl-2,3-dihydro-1,5-benzothiazepin-4(5H)-one

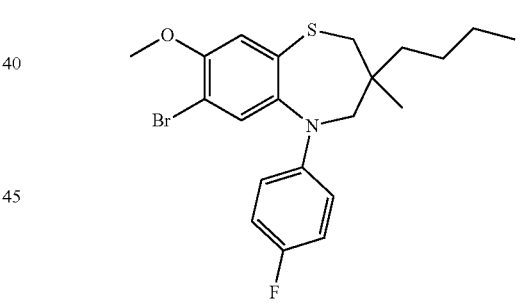

To a solution of 7-bromo-3-butyl-8-methoxy-3-methyl-2,3-dihydro-1,5-benzothiazepin-4(5H)-one (Intermediate 31; 5 g, 14 mmol) in 1-bromo-4-fluorobenzene (50 mL), dry $K_2CO_3$ (3.9 g, 28 mmol), CuI (0.26 g, 1.4 mmol) and tris[2-(2-methoxyethoxy)ethyl]amine (0.9 g, 2.8 mmol) were added and the reaction mixture was heated for 16 hours at 135° C. After completion of the reaction (monitored by TLC), the reaction mixture was concentrated under vacuum. The obtained residue was then partitioned between water (25 mL) and EtOAc (25 mL). The aqueous part was extracted with EtOAc (2×100 mL), and the combined organic layer was washed with ice-cold water (100 mL) and brine (100 mL). The organic part was dried over anhydrous $Na_2SO_4$, filtered and concentrated under vacuum. The obtained residue was triturated with petroleum ether. The obtained solid was then filtered off and dried to afford the title compound. Yield: 85% (5.5 g, pale brown solid).

LCMS: (Method E) 451.9 (M$^+$+H), Rt. 3.26 min, 81.86% (max).

Intermediate 81

7-Bromo-3-butyl-5-(4-fluorophenyl)-8-methoxy-3-methyl-2,3,4,5-tetrahydro-1,5-benzothiazepine

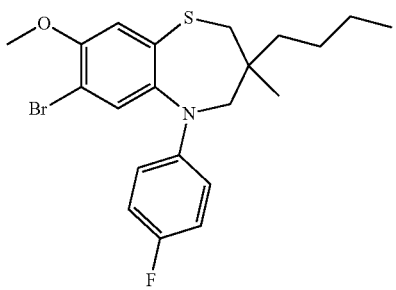 [SMILES: CCCCC1(C)CSc2cc(OC)c(Br)cc2N(c2ccc(F)cc2)C1]

To a solution of 7-bromo-3-butyl-5-(4-fluorophenyl)-8-methoxy-3-methyl-2,3-dihydro-1,5-benzothiazepin-4(5H)-one (Intermediate 80; 5.2 g, 11.5 mmol) in THF (50 mL) at 0° C., borane dimethylsulfide (1M in THF, 58 mL, 58 mmol) was added and the reaction mixture was heated for 16 hours at 75° C. After completion of the reaction (monitored by TLC), the reaction mixture was cooled to 0° C., methanol (60 mL) was added and the reaction mixture was heated for 2 hours at 60° C. The reaction mixture was then cooled to room temperature, concentrated under vacuum and the obtained residue was partitioned between water (50 mL) and EtOAc (50 mL). The aqueous layer was extracted with EtOAc (2×100 mL), and the combined organic layer was washed with ice-cold water (100 mL) and brine (100 mL). The organic part was dried over anhydrous Na$_2$SO$_4$, filtered and concentrated under vacuum to afford the title compound. Yield: 5.3 g (crude, colourless gum).

LCMS: (Method E) 439.9 (M$^+$+H), Rt. 3.55 min, 87.61% (max).

Intermediate 82

7-Bromo-3-butyl-5-(4-fluorophenyl)-8-methoxy-3-methyl-2,3,4,5-tetrahydro-1,5-benzothiazepine 1,1-dioxide

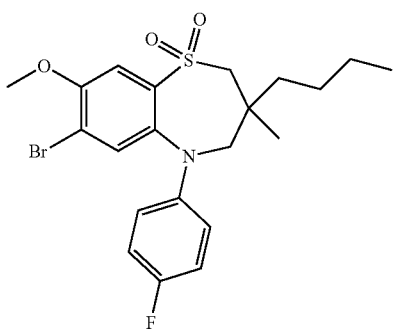 [SMILES: CCCCC1(C)CN(c2ccc(F)cc2)c2cc(Br)c(OC)cc2S(=O)(=O)C1]

To a solution of 7-bromo-3-butyl-5-(4-fluorophenyl)-8-methoxy-3-methyl-2,3,4,5-tetrahydro-1,5-benzothiazepine (Intermediate 81; 5.3 g, 12.1 mmol) in a mixture of THF and water (8:2, 55 mL), oxone (37.16 g, 120.8 mmol) was added and the reaction mixture was stirred for 16 hours at room temperature. After completion of the reaction (monitored by TLC), the aqueous layer was extracted with EtOAc (2×100 mL), and the combined organic layer was washed with ice-cold water (100 mL) and brine (100 mL). The organic part was dried over anhydrous Na$_2$SO$_4$ and concentrated under vacuum. The resulting crude material was purified by Isolera column chromatography (eluent: 15% EtOAc/PE; silica gel: 230-400 mesh) to afford the title compound. Yield: 75% (4.3 g, white solid).

$^1$H NMR (400 MHz, DMSO-d$_6$): δ 7.45 (s, 1H), 7.21 (s, 1H), 7.12-7.05 (m, 4H), 3.93 (s, 3H), 3.85-3.61 (m, 2H), 3.29 (s, 2H), 1.52-1.39 (m, 1H), 1.37-1.26 (m, 1H), 1.25-1.03 (m, 4H), 0.98 (s, 3H), 0.81-0.74 (m, 3H). LCMS: (Method E) 470.1 (M$^+$), Rt. 3.21 min, 98.04% (max).

Intermediate 83

3-Butyl-5-(4-fluorophenyl)-8-hydroxy-3-methyl-7-(methylthio)-2,3,4,5-tetrahydro-1,5-benzothiazepine 1,1-dioxide

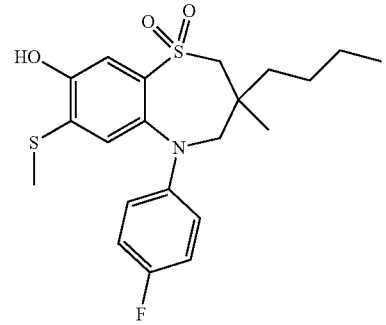 [SMILES: CCCCC1(C)CN(c2ccc(F)cc2)c2cc(SC)c(O)cc2S(=O)(=O)C1]

To a solution of 7-bromo-3-butyl-5-(4-fluorophenyl)-8-methoxy-3-methyl-2,3,4,5-tetrahydro-1,5-benzothiazepine 1,1-dioxide (Intermediate 82; 4.3 g, 9.14 mmol) in DMF (43 mL), sodium thiomethoxide (3.2 g, 45.7 mmol) was added and the reaction mixture was stirred for 12 hours at 80° C. After completion of the reaction (monitored by TLC), the reaction mixture was quenched with ice-cold water (25 mL) and the aqueous layer was extracted with EtOAc (2×50 mL). The combined organic layer was washed with ice-cold water (50 mL) and brine (50 mL) and dried over anhydrous Na$_2$SO$_4$. The organic part was concentrated under vacuum and the resulting crude material was purified by Isolera column chromatography (eluent: 30% EtOAc/PE; silica gel: 230-400 mesh) to afford the title compound. Yield: 90% (3.5 g, off-white solid).

$^1$H NMR (400 MHz, DMSO-d$_6$): δ 10.57 (s, 1H), 7.31 (s, 1H), 7.04-6.98 (m, 2H), 6.92-6.88 (m, 2H), 6.71 (s, 1H), 3.81-3.65 (m, 2H), 3.34-3.20 (m, 2H), 2.20 (s, 3H), 1.55-1.39 (m, 1H), 1.38-1.05 (m, 5H), 0.99 (s, 3H), 0.81-0.77 (m, 3H). LCMS: (Method E) 424.2 (M$^+$+H), Rt. 2.78 min, 98.08% (max).

Intermediate 84

Methyl 3-((3-butyl-5-(4-fluorophenyl)-3-methyl-7-(methylthio)-1,1-dioxido-2,3,4,5-tetrahydro-1,5-benzothiazepin-8-yl)oxy)-2-hydroxypropanoate

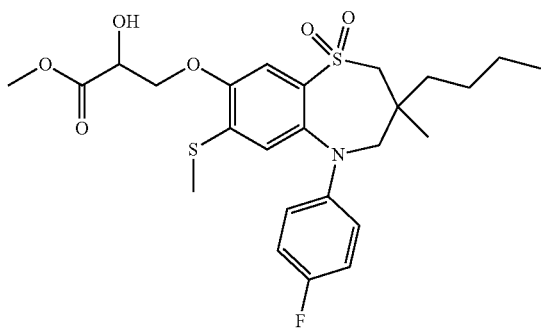 [SMILES: CCCCC1(C)CN(c2ccc(F)cc2)c2cc(SC)c(OCC(O)C(=O)OC)cc2S(=O)(=O)C1]

To a stirred solution of 3-butyl-5-(4-fluorophenyl)-8-hydroxy-3-methyl-7-(methylthio)-2,3,4,5-tetrahydro-1,5-benzothiazepine 1,1-dioxide (Intermediate 83; 200 mg, 0.47 mmol) in DMF (3 mL), $Cs_2CO_3$ (300 mg, 0.94 mmol) was added and the reaction mixture was stirred for 15 minutes at 0° C. Then β-propiolactone (144 mg, 1.41 mmol) was added and the reaction mixture was stirred for 16 hours at room temperature. After completion of the reaction (monitored by TLC), the reaction mixture was quenched with dilute HCl (1.5 N, 2 mL) and diluted with water (2 mL). The aqueous layer was extracted with EtOAc (2×10 mL) and the combined organic layer was washed with water (10 mL) and brine (10 mL). The organic part was dried over anhydrous $Na_2SO_4$, filtered and concentrated under vacuum. The resulting crude material was purified by Isolera column chromatography (eluent: 25-30% EtOAc/PE; silica gel: 230-400 mesh). Yield: 64% (160 mg, brown gum).

LCMS: (Method E) 526.0 ($M^++H$), Rt. 2.94 min, 99.11% (Max).

Intermediate 85

3-Butyl-7-(dimethylamino)-8-methoxy-3-methyl-5-phenyl-2,3,4,5-tetrahydro-1,5-benzothiazepine 1,1-dioxide

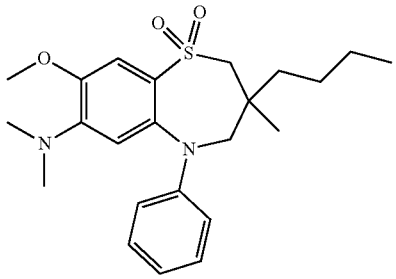 [SMILES: CCCCC1(C)CN(c2ccccc2)c2cc(N(C)C)c(OC)cc2S(=O)(=O)C1]

To a degassed solution of 7-bromo-3-butyl-8-methoxy-3-methyl-5-phenyl-2,3,4,5-tetrahydro-1,5-benzothiazepine 1,1-dioxide (Intermediate 34; 1 g, 2.2 mmol) in 1,4-dioxane (8 mL) in an autoclave, sodium tert-butoxide (570 mg, 4.4 mmol), xantphos (127 mg, 0.22 mmol) and dimethylamine (2 M solution in THF, 10 mL, 10 vol) were added, and the reaction mixture was further degasified for another 15 minutes. Then $pd_2(dba)_3$ (101 mg, 0.11 mmol) was added and the reaction mixture was heated for 16 hours at 100° C. After completion of the reaction (monitored by TLC), the reaction mixture was filtered through celite and the celite pad was washed with EtOAc (25 mL). The filtrate part was concentrated under vacuum and the resulting crude was purified by Isolera column chromatography (eluent: 0-24% EtOAc/PE; silica gel: 230-400 mesh) to afford the title compound.

Yield: 76% (0.7 g, brown solid).

$^1H$ NMR (400 MHz, DMSO-$d_6$): δ 7.29 (s, 1H), 7.17 (t, J=8.0 Hz, 2H), 6.91 (d, J=8.0 Hz, 2H), 6.77 (s, 1H), 6.43 (s, 1H), 3.86 (s, 3H), 3.81-3.72 (m, 2H), 3.25-3.14 (m, 2H), 2.69 (s, 6H), 1.55-1.43 (m, 1H), 1.33-1.11 (m, 5H), 1.00 (s, 3H), 0.82-0.78 (m, 3H). LCMS: (Method E) 417.2 ($M^++H$), Rt. 2.21 min, 97.88% (max).

Intermediate 86

3-Butyl-7-(dimethylamino)-8-hydroxy-3-methyl-5-phenyl-2,3,4,5-tetrahydro-1,5-benzothiazepine 1,1-dioxide

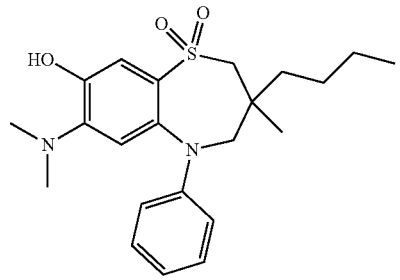 [SMILES: CCCCC1(C)CN(c2ccccc2)c2cc(N(C)C)c(O)cc2S(=O)(=O)C1]

To a solution of 3-butyl-7-(dimethylamino)-8-methoxy-3-methyl-5-phenyl-2,3,4,5-tetrahydro-1,5-benzothiazepine 1,1-dioxide (Intermediate 85; 0.7 g, 1.68 mmol) in DMF (7 mL), sodium thiomethoxide (0.65 g, 8.40 mmol) was added and the reaction mixture was stirred for 12 hours at 100° C. After completion of the reaction (monitored by TLC), the reaction mixture was quenched with ice-cold water (15 mL) and the aqueous layer was extracted with EtOAc (2×15 mL). The combined organic layer was washed with ice-cold water (15 mL) and brine (15 mL) and dried over anhydrous $Na_2SO_4$. The organic part was concentrated under vacuum to afford the title compound. Yield: 600 mg (crude, brown gum).

LCMS: (Method E) 403.2 ($M^++H$), Rt. 2.01 min, 96.67% (max).

Intermediate 87

3-Butyl-3-ethyl-8-hydroxy-7-(methylamino)-5-phenyl-2,3,4,5-tetrahydro-1,5-benzothiazepine 1,1-dioxide

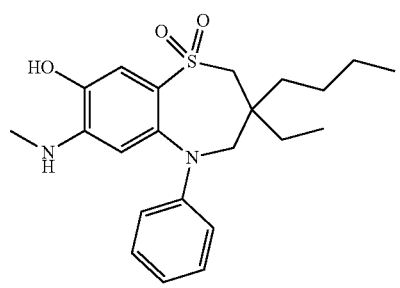 [SMILES: CCCCC1(CC)CN(c2ccccc2)c2cc(NC)c(O)cc2S(=O)(=O)C1]

To a stirred solution of 3-butyl-3-ethyl-8-methoxy-7-(methylamino)-5-phenyl-2,3,4,5-tetrahydro-1,5-benzothiazepine 1,1-dioxide (200 mg, 0.48 mmol) in DMF (6 mL), sodium thiomethoxide (52 mg, 0.96 mmol) was added and the reaction mixture was heated for 12 hours at 90° C. After completion of the reaction (monitored by TLC), the reaction mixture was quenched with water (10 mL) and the aqueous layer was extracted with EtOAc (2×10 mL). The combined organic layer was washed with water (2×10 mL) and brine (10 mL) and dried over anhydrous $Na_2SO_4$. The organic part was filtered and concentrated under vacuum to afford the title compound. Yield: 95% (180 mg, pink solid).

$^1$H NMR (400 MHz, DMSO-$d_6$): δ 9.88 (s, 1H), 7.17-7.13 (m, 3H), 6.89 (d, J=7.6 Hz, 2H), 6.74 (t, J=7.6 Hz, 1H), 5.96 (s, 1H), 5.71-5.68 (m, 1H), 3.65 (s, 2H), 3.06 (s, 2H), 2.54 (s, 3H), 1.63-1.49 (m, 2H), 1.47-1.28 (m, 2H), 1.17-1.01 (m, 4H), 0.80-0.71 (m, 6H). LCMS: (Method A) 403.0 (M$^+$+H), Rt. 3.00 min, 99.35% (Max). HPLC: (Method B) Rt. 5.47 min, 97.83% (Max).

Example 1

3-((7-Bromo-3-butyl-3-ethyl-1,1-dioxido-5-phenyl-2,3,4,5-tetrahydro-1,5-benzothiazepin-8-yl)oxy)propanoic acid

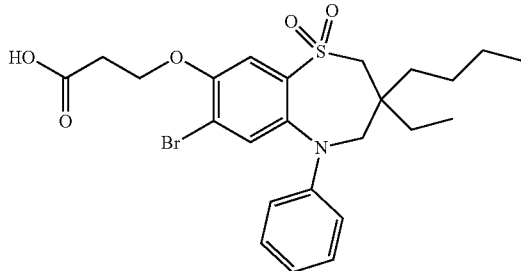

To stirred solution of (E)-3-((7-bromo-3-butyl-3-ethyl-1,1-dioxido-5-phenyl-2,3,4,5-tetrahydro-1,5-benzothiazepin-8-yl)oxy)acrylic acid (Intermediate 2; 0.5 g, 0.95 mmol) in ethanol (8 mL), $PtO_2$ (0.021 g, 0.095 mmol) was added under nitrogen atmosphere and the reaction mixture was stirred under hydrogen atmosphere in a tinyclave (under 2 kg pressure) for 1 hour at room temperature. After completion of the reaction (monitored by LCMS), the reaction mixture was filtered through celite and the celite pad was washed with EtOAc (2×15 mL). The combined filtrate was concentrated under vacuum to afford the crude material which was purified by Prep-HPLC (Method A) to furnish the title compound. Yield: 16% (80 mg, off-white solid).

$^1$H NMR (400 MHz, DMSO-$d_6$): δ 12.46 (bs, 1H), 7.45 (s, 1H), 7.26 (t, J=7.6 Hz, 2H), 7.13 (s, 1H), 7.05 (d, J=7.6 Hz, 2H), 6.93 (t, J=7.2 Hz, 1H), 4.29 (t, J=5.6 Hz, 2H), 3.75 (bs, 2H), 3.47 (s, 2H), 2.75 (t, J=6.0 Hz, 2H), 1.37-1.30 (m, 4H), 1.17-1.12 (m, 4H), 0.73 (t, J=6.40 Hz, 6H). LCMS: (Method D) 525.2 (M$^+$+H), Rt. 2.76 min, 99.55% (Max). HPLC: (Method B) Rt. 10.41 min, 99.39% (Max).

Examples 2 and 3

(S)-3-((7-bromo-3-butyl-3-ethyl-1,1-dioxido-5-phenyl-2,3,4,5-tetrahydro-1,5-benzothiazepin-8-yl)oxy)propanoic acid and (R)-3-((7-bromo-3-butyl-3-ethyl-1,1-dioxido-5-phenyl-2,3,4,5-tetrahydro-1,5-benzothiazepin-8-yl)oxy)propanoic acid

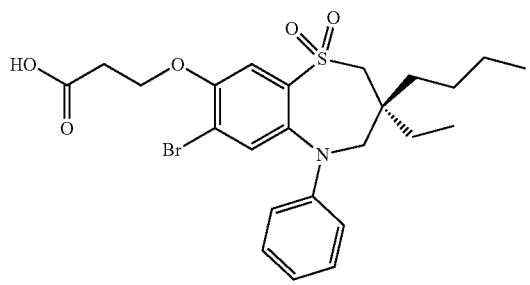 [SMILES: CCCCC1(CC)CN(c2ccccc2)c2cc(Br)c(OCCC(=O)O)cc2S(=O)(=O)C1]

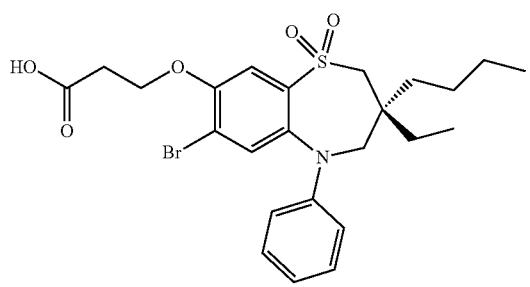

The two enantiomers of racemic 3-((7-bromo-3-butyl-3-ethyl-1,1-dioxido-5-phenyl-2,3,4,5-tetrahydro-1,5-benzothiazepin-8-yl)oxy)propanoic acid (Example 1; 80 mg, 0.15 mmol) were separated by chiral preparative SFC (Method E); mobile phase: $CO_2$: MeOH (60:40); wave length: 210 nm; cycle time: 4 min; back pressure: 100 bar. The material was concentrated under vacuum at 40° C. The first eluting fraction corresponded to enantiomer 1 and the second eluting fraction corresponded to enantiomer 2. The absolute configuration of the two enantiomers is not known.

Enantiomer 1: Yield: 29% (23 mg, white solid). $^1$H NMR (400 MHz, DMSO-$d_6$): δ 12.45 (bs, 1H), δ 7.45 (s, 1H), 7.26 (t, J=8.0 Hz, 2H), 7.14 (s, 1H), 7.05 (d, J=7.6 Hz, 2H), 6.92 (t, J=7.2 Hz, 2H), 4.29 (t, J=6.0 Hz, 2H), 3.69 (bs, 2H), 3.34 (s, 2H), 2.72 (t, J=6.0 Hz, 2H), 1.51-1.32 (m, 4H), 1.16-1.12 (m, 4H), 0.74 (t, J=8.00 Hz, 6H). LCMS: (Method C) 525.1 (M$^+$+H), Rt. 2.82 min, 99.36% (Max). HPLC: (Method B) Rt. 5.91 min, 99.39% (Max). Chiral SFC: (Method D) Rt. 2.46 min, 100% (Max).

Enantiomer 2: Yield: 37% (30 mg, white solid). $^1$H NMR (400 MHz, DMSO-$d_6$): δ 12.45 (bs, 1H), 7.45 (s, 1H), 7.26 (t, J=8.0 Hz, 2H), 7.14 (s, 1H), 7.05 (d, J=8.0 Hz, 2H), 6.92 (t, J=7.2 Hz, 1H), 4.28 (t, J=6.0 Hz, 2H), 3.69 (bs, 2H), 3.34 (s, 2H), 2.68 (t, J=6.4 Hz, 2H), 1.50-1.32 (m, 4H), 1.23-0.99 (m, 4H), 0.74 (t, J=4.00 Hz, 6H). LCMS: (Method C) 526.1 (M$^+$+2), Rt. 2.61 min, 97.99% (Max). HPLC: (Method B) Rt. 5.91 min, 99.31% (Max). Chiral SFC: (Method D) Rt. 3.89 min, 99.04% (Max).

Example 4

3-((7-Bromo-3,3-dibutyl-1,1-dioxido-5-phenyl-2,3,4,5-tetrahydro-1,5-benzothiazepin-8-yl)oxy)propanoic acid

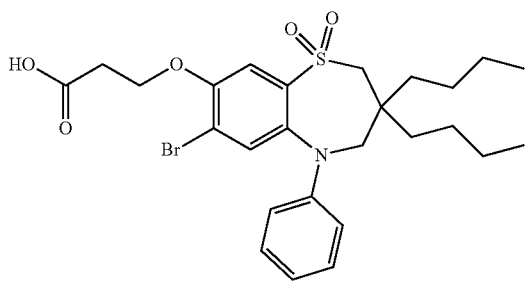 [SMILES: CCCCC1(CCCC)CN(c2ccccc2)c2cc(Br)c(OCCC(=O)O)cc2S(=O)(=O)C1]

To a stirred solution of ethyl 3-((3,3-dibutyl-7-bromo-1,1-dioxido-5-phenyl-2,3,4,5-tetrahydro-1,5-benzothiazepin-8-yl)oxy)propanoate (Intermediate 4; 1.5 g, 2.58 mmol) in 1,4-dioxane (5 mL), HCl (6N, 20 mL) was added dropwise at RT and the reaction mixture was heated 16 h at 100° C. After completion of the reaction (confirmed by LCMS), the reaction mixture was diluted with ice cold water (10 mL) and the aqueous layer was extracted with EtOAc (2×20 mL). The organic part was dried over anhydrous $Na_2SO_4$ and evaporated under vacuum. The crude material was purified by Isolera column chromatography (eluent: 35-40% EtOAc/PE; silica gel: 230-400 mesh) to afford the title compound. Yield: 59% (150 mg, off white solid). $^1$H NMR (400 MHz, DMSO-$d_6$): δ 7.45 (s, 1H), 7.27 (t, J=7.6 Hz, 2H), 7.11 (s, 1H), 7.08 (d, J=8.0 Hz, 2H), 6.95 (t, J=7.2 Hz, 1H), 4.29 (t, J=5.6 Hz, 2H), 3.70 (bs, 2H), 3.36 (s, 2H), 2.74 (t, J=5.6 Hz, 2H), 1.36-1.30 (m, 4H), 1.16-1.00 (m, 8H), 0.75 (t, J=6.40 Hz, 6H).

LCMS: (Method C) 554.2 ($M^+$+2), Rt. 3.08 min, 94.37% (Max). HPLC: (Method B) Rt. 6.43 min, 95.0% (Max).

Example 5

3-((3-Butyl-7-chloro-3-ethyl-1,1-dioxido-5-phenyl-2,3,4,5-tetrahydro-1,5-benzothiazepin-8-yl)oxy)propanoic acid

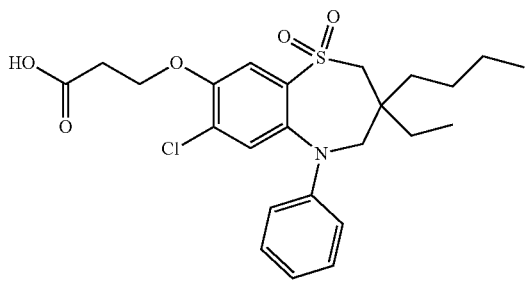 [SMILES: CCCCC1(CC)CN(c2ccccc2)c2cc(Cl)c(OCCC(=O)O)cc2S(=O)(=O)C1]

To a stirred solution of ethyl 3-((3-butyl-7-chloro-3-ethyl-1,1-dioxido-5-phenyl-2,3,4,5-tetrahydro-1,5-benzothiazepin-8-yl)oxy)propanoate (Intermediate 12; 3.0 g 5.9 mmol) in 1,4-dioxane (200 mL) at room temperature, HCl (6N, 30 mL) was added dropwise and the reaction mixture was heated for 16 hours at 100° C. After completion of the reaction (monitored by LCMS), the reaction mixture was diluted with ice cold water (30 mL) and the aqueous layer was extracted with EtOAc (2×50 mL). The organic part was dried over anhydrous $Na_2SO_4$ and evaporated under vacuum. The crude material was purified by Isolera column chromatography (eluent: 5-10% MeOH/DCM; silica gel: 230-400 mesh) to afford the title compound. Yield: 73% (205 mg, off-white solid).

$^1$H NMR (400 MHz, DMSO-$d_6$): δ 12.46 (bs, 1H), 7.50 (d, J=2.0 Hz, 1H), 7.26 (t, J=8.4 Hz, 2H), 7.06 (d, J=7.2 Hz, 2H), 7.00 (s, 1H), 6.94 (t, J=6.8 Hz, 1H), 4.31 (t, J=5.6 Hz, 2H), 3.67 (bs, 2H), 3.36 (s, 2H), 2.75 (t, J=6.0 Hz, 2H), 1.51-1.32 (m, 4H), 1.24-0.99 (m, 4H), 0.75 (t, J=6.80 Hz, 6H). LCMS: (Method C) 482.2 ($M^+$+2), Rt. 2.78 min, 96.49% (Max). HPLC: (Method B) Rt. 5.83 min, 97.44% (Max).

Examples 6 and 7

(S)-3-((3-Butyl-7-chloro-3-ethyl-1,1-dioxido-5-phenyl-2,3,4,5-tetrahydro-1,5-benzothiazepin-8-yl)oxy)propanoic acid and (R)-3-((3-butyl-7-chloro-3-ethyl-1,1-dioxido-5-phenyl-2,3,4,5-tetrahydro-1,5-benzothiazepin-8-yl)oxy)propanoic acid

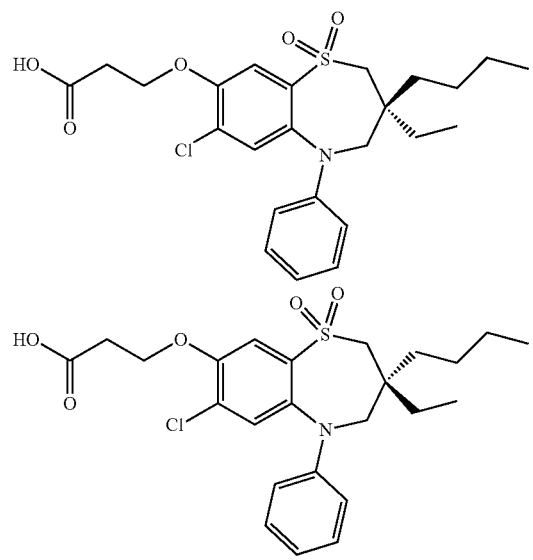

The two enantiomers of racemic 3-((3-butyl-7-chloro-3-ethyl-1,1-dioxido-5-phenyl-2,3,4,5-tetrahydro-1,5-benzothiazepin-8-yl)oxy)propanoic acid (Example 5; 100 mg, 0.20 mmol) were separated by chiral preparative SFC (Method E); mobile phase: $CO_2$: MeOH (60:40); wave length: 210 nm; cycle time: 5 min; back pressure: 100 bar. The material was concentrated under vacuum at 40° C. The first eluting fraction corresponded to enantiomer 1 and the second eluting fraction corresponded to enantiomer 2. The absolute configuration of the two enantiomers is not known.

Enantiomer 1: Yield: 25% (25 mg, white solid). $^1$H NMR (400 MHz, DMSO-$d_6$): δ 12.49 (s, 1H), 7.50 (s, 1H), 7.26 (t, J=8.0 Hz, 2H), 7.05 (d, J=7.6 Hz, 2H), 6.99 (s, 1H), 6.93 (t, J=7.2 Hz, 1H), 4.30 (t, J=5.6 Hz, 2H), 3.70 (s, 2H), 3.40 (s, 2H), 2.74 (t, J=5.6 Hz, 2H), 1.50-1.33 (m, 4H), 1.15-0.98 (m, 4H), 0.74 (t, J=4.40 Hz, 6H). LCMS: (Method C) 482.1 ($M^+$+2), Rt. 2.81 min, 95.89% (Max). HPLC: (Method B) Rt. 5.87 min, 98.01% (Max). Chiral SFC: (Method D) Rt. 2.71 min, 98.45% (Max).

Enantiomer 2: Yield: 15% (15 mg, white solid). ¹H NMR (400 MHz, DMSO-$d_6$): δ 12.37 (bs, 1H), 7.50 (s, 1H), 7.26 (t, J=8.0 Hz, 2H), 7.05 (d, J=8.0 Hz, 2H), 6.99 (s, 1H), 6.93 (t, J=7.2 Hz, 1H), 4.30 (t, J=5.6 Hz, 2H), 3.70 b (s, 2H), 3.41 (s, 2H), 2.73 (t, J=5.6 Hz, 2H), 1.50-1.30 (m, 4H), 1.15-0.99 (m, 4H), 0.74 (t, J=4.40 Hz, 6H). LCMS: (Method C) 482.1 (M⁺+2), Rt. 2.81 min, 96.76% (Max). HPLC: (Method B) Rt. 5.87 min, 99.5% (Max). Chiral SFC: (Method D) Rt. 4.33 min, 100% (Max).

Example 8

3-((3,3-Dibutyl-7-chloro-1,1-dioxido-5-phenyl-2,3,4,5-tetrahydro-1,5-benzothiazepin-8-yl)oxy)propanoic acid

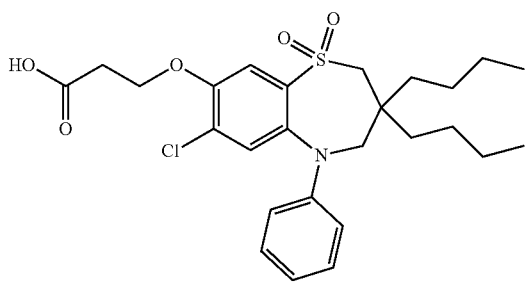 [SMILES: CCCCC1(CCCC)CN(c2ccccc2)c2cc(Cl)c(OCCC(=O)O)cc2S(=O)(=O)C1]

To a stirred solution of ethyl 3-((3,3-dibutyl-7-chloro-1,1-dioxido-5-phenyl-2,3,4,5-tetrahydro-1,5-benzothiazepin-8-yl)oxy)propanoate (Intermediate 19; 1.0 g, 1.86 mmol) in 1,4-dioxane (2 mL) at room temperature, HCl (6N, 10 mL) was added dropwise and the reaction mixture was heated for 12 hours at 100° C. After completion of the reaction (monitored by TLC), the reaction mixture was diluted with ice cold water (10 mL) and the aqueous layer was extracted with EtOAc (2×20 mL). The organic part was dried over anhydrous $Na_2SO_4$ and evaporated under vacuum. The resulting crude material was purified by Isolera column chromatography (eluent: 35-40% EtOAc/PE; silica gel: 230-400 mesh) to afford the title compound. Yield: 89% (100 mg, off-white solid).

¹H NMR (400 MHz, DMSO-$d_6$): δ 7.49 (s, 1H), 7.26 (t, J=8.0 Hz, 2H), 7.08 (d, J=7.6 Hz, 2H), 6.94 (t, J=4.8 Hz, 2H), 4.29 (t, J=5.6 Hz, 2H), 3.70 (bs, 2H), 3.32 (s, 2H), 2.71 (t, J=4.4 Hz, 2H), 1.40-1.29 (m, 5H), 1.13-0.99 (m, 7H), 0.75 (t, J=4.40 Hz, 6H). LCMS: (Method E) 509.1 (M⁺+H), Rt. 2.80 min, 91.44% (Max). HPLC: (Method B) Rt. 6.36 min, 96.12% (Max)

Example 9

3-((3,3-Dibutyl-7-(methylthio)-1,1-dioxido-5-phenyl-2,3,4,5-tetrahydro-1,5-benzothiazepin-8-yl)oxy)-2-hydroxypropanoic acid

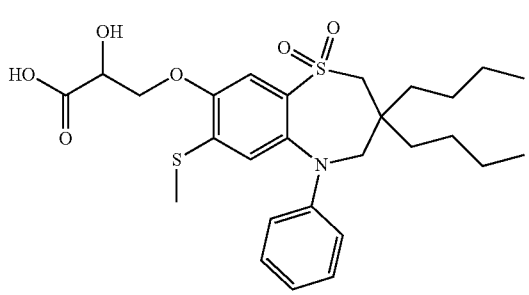 [SMILES: CCCCC1(CCCC)CN(c2ccccc2)c2cc(SC)c(OCC(O)C(=O)O)cc2S(=O)(=O)C1]

To a stirred solution of methyl 3-((3,3-dibutyl-7-(methylthio)-1,1-dioxido-5-phenyl-2,3,4,5-tetrahydro-1,5-benzothiazepin-8-yl)oxy)-2-hydroxypropanoate (Intermediate 20; 50 mg, 0.00009 mmol) in 1,4-dioxane (2 mL) at room temperature, HCl (6N, 1 mL) was added dropwise and the reaction mixture was stirred for 1 hour at 80° C. After completion of the reaction (monitored by TLC), the reaction mixture was diluted with ice cold water (5 mL) and the aqueous layer was extracted with EtOAc (2×20 mL). The combined organic layer was washed with brine (10 mL), dried over anhydrous $Na_2SO_4$ and concentrated under vacuum. The resulting crude material was purified by Prep-HPLC (Method A) to afford the title compound. Yield: 23% (11 mg, white solid).

¹H-NMR (400 MHz, DMSO-$d_6$): δ 7.33 (s, 1H), 7.21 (t, J=8.0 Hz, 2H), 6.99 (d, J=7.6 Hz, 2H), 6.86 (t, J=7.2 Hz, 1H), 6.67 (s, 1H), 4.31 (d, J=5.6 Hz, 1H), 4.06 (s, 2H), 3.50 (bs, 2H), 3.26 (s, 2H), 2.15 (s, 3H), 1.51-1.29 (m, 4H), 1.23-1.02 (m, 8H), 0.85-0.75 (m, 6H). LCMS: (Method A) 536.2 (M⁺+H), Rt. 2.84 min, 97.46% (Max). HPLC: (Method B) Rt. 5.94 min, 98.00% (Max).

Examples 10 and 11

(S)-3-((3,3-dibutyl-7-(methylthio)-1,1-dioxido-5-phenyl-2,3,4,5-tetrahydro-1,5-benzothiazepin-8-yl)oxy)-2-hydroxypropanoic acid and (R)-3-((3,3-dibutyl-7-(methylthio)-1,1-dioxido-5-phenyl-2,3,4,5-tetrahydro-1,5-benzothiazepin-8-yl)oxy)-2-hydroxypropanoic acid

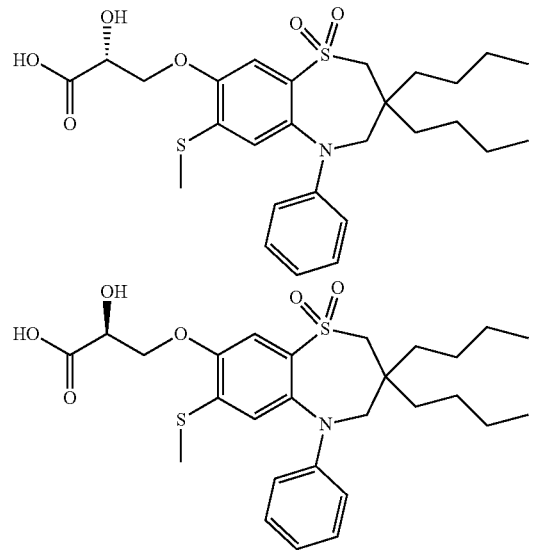

The two enantiomers of racemic 3-((3,3-dibutyl-7-(methylthio)-1,1-dioxido-5-phenyl-2,3,4,5-tetrahydro-1,5-benzothiazepin-8-yl)oxy)-2-hydroxypropanoic acid (Example 9; 2.9 g, 5.41 mmol) were separated by chiral SFC (method G). The material was concentrated under vacuum at 40° C. The first eluting fraction corresponded to enantiomer 1 and the second eluting fraction corresponded to enantiomer 2. The absolute configuration of the two enantiomers is not known.

Enantiomer 1: Yield: 7.8% (7.3 mg, white solid). ¹H NMR (400 MHz, DMSO-$d_6$): δ 7.35 (s, 1H), 7.22 (t, J=7.6 Hz, 2H), 7.01 (d, J=7.6 Hz, 2H), 6.87 (t, J=7.2 Hz, 1H), 6.67 (s, 1H), 4.33-4.15 (m, 3H), 3.78 (s, 2H), 3.27 (s, 2H), 2.15 (s, 3H), 1.51-1.25 (m, 4H), 1.24-0.93 (m, 8H), 0.77 (t, J=6.4 Hz, 6H). LCMS: (Method A) 536.3 (M⁺+H), Rt. 2.82 min, 95.59% (Max). HPLC: (Method B) Rt. 5.77 min, 99.06% (Max). Chiral SFC: (Method G) Rt. 2.47 min, 99.16% (Max).

Enantiomer 2: Yield: 8% (7.7 mg, white solid). ¹H NMR (400 MHz, DMSO-d₆): δ 7.34 (s, 1H), 7.22 (t, J=7.6 Hz, 2H), 7.01 (d, J=7.2 Hz, 2H), 6.87 (t, J=7.2 Hz, 1H), 6.67 (s, 1H), 4.33-4.15 (m, 3H), 3.78 (s, 2H), 3.27 (s, 2H), 2.15 (s, 3H), 1.49-1.25 (m, 4H), 1.24-0.93 (m, 8H), 0.77 (t, J=6.4 Hz, 6H). LCMS: (Method A) 536.2 (M⁺+H), Rt. 2.82 min, 94.18% (Max). HPLC: (Method B) Rt. 5.78 min, 96.55% (Max). Chiral SFC: (Method G) Rt. 3.24 min, 91.11% (Max).

Example 12

3-((3-Butyl-3-ethyl-7-(methylthio)-1,1-dioxido-5-phenyl-2,3,4,5-tetrahydro-1,5-benzothiazepin-8-yl)oxy)propanoic acid

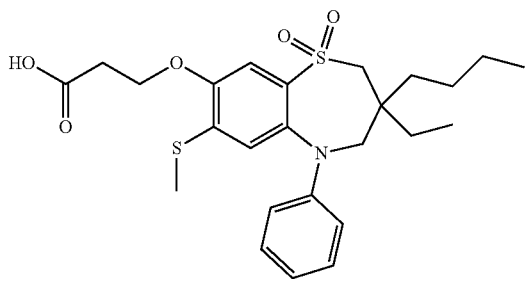 [SMILES: CCCCC1(CC)CN(c2ccccc2)c2cc(SC)c(OCCC(=O)O)cc2S(=O)(=O)C1]

To a stirred solution of ethyl 3-((3-butyl-3-ethyl-7-(methylthio)-1,1-dioxido-5-phenyl-2,3,4,5-tetrahydro-1,5-benzothiazepin-8-yl)oxy)propanoate (Intermediate 24; 1.3 g 2.5 mmol) in 1,4-dioxane (3 mL) at room temperature, HCl (6N, 13 mL) was added dropwise and the reaction mixture was heated for 12 hours at 100° C. After completion of the reaction (monitored by TLC), the reaction mixture was diluted with ice cold water (10 mL) and the aqueous layer was extracted with EtOAc (2×20 mL). The organic part was dried over anhydrous Na₂SO₄ and concentrated under vacuum. The resulting crude material was purified by Prep-HPLC (Method A) to afford the title compound. Yield: 83% (235 mg, off-white solid).

¹H NMR (400 MHz, DMSO-d₆): δ 7.32 (s, 1H), 7.22 (t, J=8.0 Hz, 2H), 6.98 (d, J=7.6 Hz, 2H), 6.85 (t, J=7.6 Hz, 1H), 6.70 (s, 1H), 4.27 (t, J=6.0 Hz, 2H), 3.68 (bs, 2H), 3.27 (s, 2H), 2.68 (t, J=6.0 Hz, 2H), 2.15 (s, 3H), 1.56-1.31 (m, 4H), 1.20-1.10 (m, 4H), 0.76 (t, J=5.20 Hz, 6H). LCMS: (Method C) 492.1 (M⁺+H), Rt. 2.82 min, 98.71% (Max). HPLC: (Method B) Rt. 5.76 min, 99.16% (Max).

Examples 13 and 14

(S)-3-((3-Butyl-3-ethyl-7-(methylthio)-1,1-dioxido-5-phenyl-2,3,4,5-tetrahydro-1,5-benzothiazepin-8-yl)oxy)propanoic acid and (R)-3-((3-butyl-3-ethyl-7-(methylthio)-1,1-dioxido-5-phenyl-2,3,4,5-tetrahydro-1,5-benzothiazepin-8-yl)oxy)propanoic acid

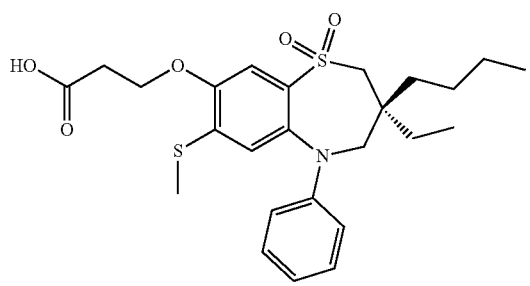

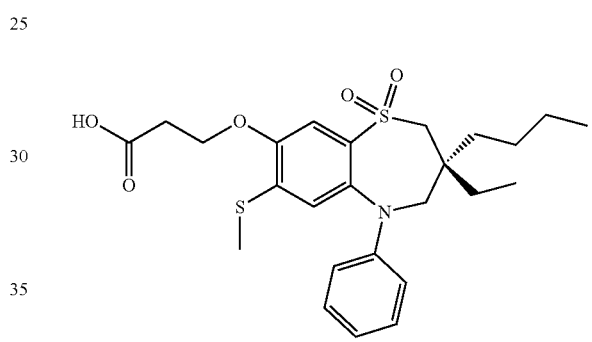

The two enantiomers of racemic 3-((3-butyl-3-ethyl-7-(methylthio)-1,1-dioxido-5-phenyl-2,3,4,5-tetrahydro-1,5-benzothiazepin-8-yl)oxy)propanoic acid (Example 10; 140 mg, 0.28 mmol) were separated by chiral preparative SFC (Method D); mobile phase: CO₂: MeOH (60:40); wave length: 210 nm; cycle time: 3 min; back pressure: 100 bar. The material was concentrated under vacuum at 40° C. The first eluting fraction corresponded to enantiomer 1 and the second eluting fraction corresponded to enantiomer 2. The absolute configuration of the two enantiomers is not known.

Enantiomer 1: Yield: 38% (53 mg, white solid). ¹H NMR (400 MHz, DMSO-d₆): δ 7.31 (s, 1H), 7.21 (t, J=7.6 Hz, 2H), 6.97 (d, J=7.6 Hz, 2H), 6.84 (t, J=7.2 Hz, 1H), 6.70 (s, 1H), 4.24 (t, J=6.4 Hz, 2H), 3.65 (bs, 2H), 3.17 (s, 2H), 2.58 (t, J=5.6 Hz, 2H), 2.15 (s, 3H), 1.54-1.31 (m, 4H), 1.14-1.04 (m, 4H), 0.77 (t, J=6.40 Hz, 6H). LCMS: (Method C) 492.1 (M⁺+H), Rt. 2.74 min, 98.94% (Max). HPLC: (Method B) Rt. 5.76 min, 97.76% (Max). Chiral SFC: (Method B) Rt. 2.34 min, 100% (Max).

Enantiomer 2: Yield: 10% (14 mg, white solid). ¹H NMR (400 MHz, DMSO-d₆): δ 7.31 (s, 1H), 7.21 (t, J=7.6 Hz, 2H), 6.97 (d, J=6.8 Hz, 2H), 6.84 (t, J=6.8 Hz, 1H), 6.70 (s, 1H), 4.24 (t, J=5.6 Hz, 2H), 3.67 (bs, 2H), 3.17 (s, 2H), 2.55 (t, J=5.6 Hz, 2H), 2.15 (s, 3H), 1.37-1.31 (m, 2H), 1.24-1.10 (m, 2H), 1.09-1.04 (m, 4H), 0.77 (t, J=6.40 Hz, 6H). LCMS: (Method C) 492.1 (M⁺+H), Rt. 2.74 min, 99.69% (Max). HPLC: (Method B) Rt. 5.87 min, 99.5% (Max). Chiral SFC: (Method B) Rt. 2.78 min, 99.24% (Max).

Example 15

3-((3,3-dibutyl-7-(methylthio)-1,1-dioxido-5-phenyl-2,3,4,5-tetrahydro-1,5-benzothiazepin-8-yl)oxy)propanoic acid

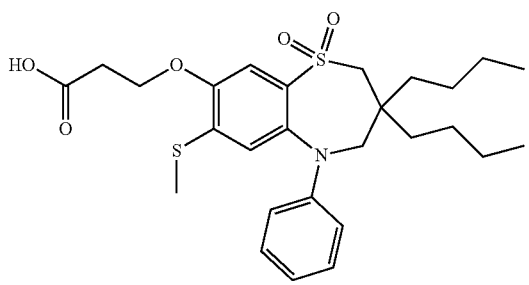 [SMILES: CCCCC1(CCCC)CN(c2ccccc2)c2cc(SC)c(OCCC(=O)O)cc2S(=O)(=O)C1]

To a stirred solution of ethyl 3-((3,3-dibutyl-7-(methylthio)-1,1-dioxido-5-phenyl-2,3,4,5-tetrahydro-1,5-benzothiazepin-8-yl)oxy)propanoate (Intermediate 26; 200 mg, 0.37 mmol) in 1,4-dioxane (20 mL), HCl (10%, 20 mL) was added dropwise at room temperature and the reaction mixture was heated for 12 hours at 80° C. After completion of the reaction (monitored by TLC), the reaction mixture was concentrated under vacuum to obtain the crude mass. The crude mass was extracted with EtOAc (2×500 mL). The organic part was dried over anhydrous Na$_2$SO$_4$ and evaporated under vacuum. The resulting crude material was purified by flash column chromatography to afford the title compound. Yield: 22% (0.04 g, colourless liquid).

$^1$H NMR (400 MHz, DMSO-d$_6$): δ 12.46 (bs, 1H), 7.31 (s, 1H), 7.22 (t, J=7.6 Hz, 2H), 7.01 (d, J=7.6 Hz, 2H), 6.87 (t, J=7.2 Hz, 1H), 6.68 (s, 1H), 4.27 (t, J=6.0 Hz, 2H), 3.67 (bs, 2H), 3.36 (s, 2H), 2.73 (t, J=5.6 Hz, 2H), 2.14 (s, 3H), 1.43-1.30 (m, 4H), 1.18-1.02 (m, 8H), 0.77 (t, J=8.00 Hz, 6H). LCMS: (Method E) 520.2 (M$^+$+H), Rt. 3.00 min, 92.89% (Max). HPLC: (Method B) Rt. 6.24 min, 92.03% (Max).

Example 16

3-((3-Butyl-7-(dimethylamino)-3-ethyl-1,1-dioxido-5-phenyl-2,3,4,5-tetrahydro-1,5-benzothiazepin-8-yl)oxy)propanoic acid

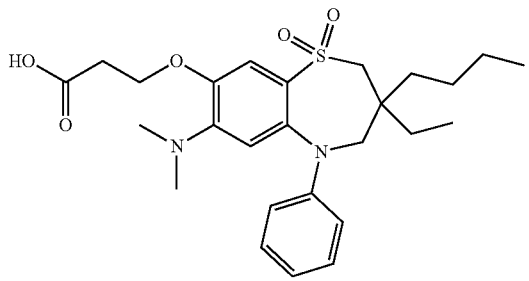 [SMILES: CCCCC1(CC)CN(c2ccccc2)c2cc(N(C)C)c(OCCC(=O)O)cc2S(=O)(=O)C1]

To a stirred solution of 3-butyl-7-(dimethylamino)-3-ethyl-8-hydroxy-5-phenyl-2,3,4,5-tetrahydro-1,5-benzothiazepine 1,1-dioxide (Intermediate 28; 100 mg, 0.24 mmol) in THF (3 mL) at 0° C., potassium tert-butoxide (27 mg, 0.24 mmol) was added and the reaction mixture was stirred for 15 minutes. Then 3-propiolactone (19 mg, 0.26 mmol) in THF (1 mL) was added dropwise and the reaction mixture was stirred for 3 hours at room temperature. After completion of the reaction (monitored by TLC), the reaction mixture was quenched with dilute HCl (2 mL) and diluted with water (2 mL). The aqueous layer was extracted with EtOAc (2×5 mL), and the combined organic layer was washed with water (5 mL) and brine (5 mL). The organic part was dried over anhydrous Na$_2$SO$_4$, filtered and concentrated under vacuum. The resulting crude material was purified by Isolera column chromatography (eluent: 3% MeOH/DCM; silica gel: 230-400 mesh) to afford the title compound.

Yield: 15% (18 mg, white solid).

$^1$H NMR (400 MHz, DMSO-d$_6$): δ 12.45 (s, 1H), 7.27 (s, 1H), 7.20 (t, J=7.6 Hz, 2H), 6.97 (d, J=8.0 Hz, 2H), 6.83 (t, J=7.6 Hz, 1H), 6.33 (s, 1H), 4.20 (t, J=5.6 Hz, 2H), 3.78 (s, 2H), 3.20 (s, 2H), 2.75 (t, J=5.6 Hz, 2H), 2.65 (s, 6H), 1.55-1.39 (m, 2H), 1.38-1.27 (m, 2H), 1.25-0.95 (m, 4H), 0.85-0.67 (m, 6H).

LCMS: (Method A) 489.3 (M$^+$+H), Rt. 2.70 min, 97.55% (Max). HPLC: (Method B) Rt. 4.65 min, 97.46% (Max).

Examples 17 and 18

(S)-3-((3-butyl-7-(dimethylamino)-3-ethyl-1,1-dioxido-5-phenyl-2,3,4,5-tetrahydro-1,5-benzothiazepin-8-yl)oxy)propanoic acid and (R)-3-((3-butyl-7-(dimethylamino)-3-ethyl-1,1-dioxido-5-phenyl-2,3,4,5-tetrahydro-1,5-benzothiazepin-8-yl)oxy)propanoic acid

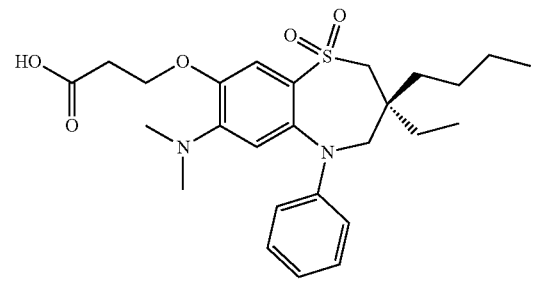

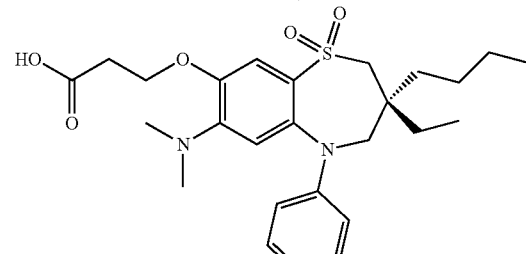

The two enantiomers of racemic 3-((3-butyl-7-(dimethylamino)-3-ethyl-1,1-dioxido-5-phenyl-2,3,4,5-tetrahydro-1,5-benzothiazepin-8-yl)oxy)propanoic acid (Example 16; 86 mg, 0.17 mmol) were separated by chiral SFC (method H). The material was concentrated under vacuum at 40° C. The first eluting fraction corresponded to enantiomer 1 and the second eluting fraction corresponded to enantiomer 2. The absolute configuration of the two enantiomers is not known.

Enantiomer 1: Yield: 25% (22 mg, white solid). $^1$H NMR (400 MHz, DMSO-d$_6$): δ 12.41 (s, 1H), 7.27 (s, 1H), 7.20 (t, J=8.0 Hz, 2H), 6.97 (d, J=7.6 Hz, 2H), 6.82 (t, J=7.2 Hz, 1H), 6.32 (s, 1H), 4.19 (t, J=5.6 Hz, 2H), 3.78 (s, 2H), 3.20 (s, 2H), 2.76-2.73 (m, 2H), 2.65 (s, 6H), 1.60-1.18 (m, 4H), 1.19-0.92 (m, 4H), 0.78-0.73 (m, 6H). LCMS: (Method A) 489.1 (M⁺+H), Rt. 2.75 min, 98.71% (Max). HPLC: (Method B) Rt. 4.63 min, 98.12% (Max). Chiral SFC: (Method H) Rt. 2.37 min, 100% (Max).

Enantiomer 2: Yield: 21% (18.5 mg, white solid). ¹H NMR (400 MHz, DMSO-d₆): δ 12.41 (s, 1H), 7.26 (s, 1H), 7.20 (t, J=7.6 Hz, 2H), 6.96 (d, J=7.6 Hz, 2H), 6.82 (t, J=7.2 Hz, 1H), 6.32 (s, 1H), 4.19 (t, J=5.6 Hz, 2H), 3.65 (s, 2H), 3.19 (s, 2H), 2.76-2.73 (m, 2H), 2.65 (s, 6H), 1.65-0.92 (m, 8H), 0.78-0.73 (m, 6H). LCMS: (Method A) 489.2 (M⁺+H), Rt. 2.74 min, 99.41% (Max). HPLC: (Method B) Rt. 4.64 min, 98.06% (Max). Chiral HPLC: (Method H) Rt. 3.06 min, 99.50% (Max).

Example 19

3-((3,3-Dibutyl-7-(methylthio)-1,1-dioxido-5-phenyl-2,3,4,5-tetrahydro-1,5-benzothiazepin-8-yl)oxy)-2-hydroxy-2-methylpropanoic acid

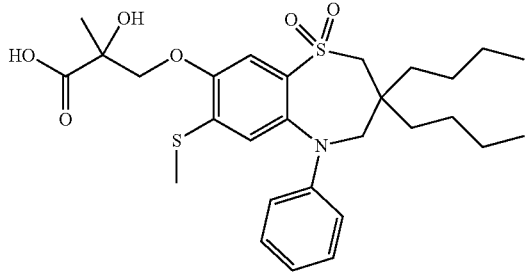 [SMILES: CCCCC1(CCCC)CN(c2ccccc2)c2cc(SC)c(OCC(C)(O)C(=O)O)cc2S(=O)(=O)C1]

To a stirred solution of methyl 3-((3,3-dibutyl-7-(methylthio)-1,1-dioxido-5-phenyl-2,3,4,5-tetrahydro-1,5-benzothiazepin-8-yl)oxy)-2-hydroxy-2-methylpropanoate (Intermediate 29; 150 mg, 0.26 mmol) in a mixture of 1,4-dioxane and water (4:1, 5 mL), lithium hydroxide (33 mg, 0.76 mmol) was added and the reaction mixture was stirred for 2 hours at room temperature. After completion of the reaction (monitored by TLC), the reaction mixture was acidified with dilute HCl (1.5 N, pH4) and then diluted with ice-cold water (2 mL). The aqueous layer was extracted with EtOAc (2×10 mL), and the combined organic layer was washed with water (10 mL) and brine (10 mL). The organic part was dried over anhydrous Na₂SO₄, filtered and concentrated under vacuum. The resulting crude material was purified by Isolera column chromatography (eluent: 8% MeOH/DCM; silica gel: 230-400 mesh) to afford the title compound. Yield: 70% (100 mg, white solid).

¹H NMR (400 MHz, DMSO-d₆): 7.31 (s, 1H), 7.22 (t, J=7.2 Hz, 2H), 7.00 (d, J=7.6 Hz, 2H), 6.87 (t, J=7.2 Hz, 1H), 6.67 (s, 1H), 4.11 (s, 2H), 3.69 (s, 2H), 3.27 (s, 2H), 2.15 (s, 3H), 1.44-1.27 (m, 7H), 1.20-1.02 (m, 8H), 0.77 (t, J=6.8 Hz, 6H). LCMS: (Method E) 550.0 (M⁺+H), Rt. 3.11 min, 98.54% (Max).

HPLC: (Method B) Rt. 6.10 min, 99.14% (Max).

Examples 20 and 21

(S)-3-((3,3-dibutyl-7-(methylthio)-1,1-dioxido-5-phenyl-2,3,4,5-tetrahydro-1,5-benzothiazepin-8-yl)oxy)-2-hydroxy-2-methylpropanoic acid and (R)-3-((3,3-dibutyl-7-(methylthio)-1,1-dioxido-5-phenyl-2,3,4,5-tetrahydro-1,5-benzothiazepin-8-yl)oxy)-2-hydroxy-2-methylpropanoic acid

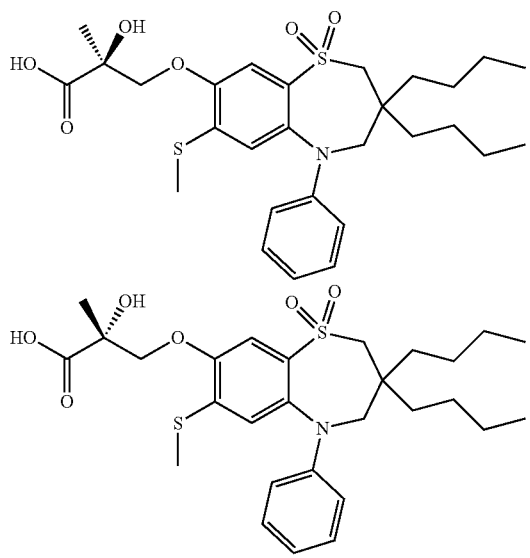

The two enantiomers of racemic 3-((3,3-dibutyl-7-(methylthio)-1,1-dioxido-5-phenyl-2,3,4,5-tetrahydro-1,5-benzothiazepin-8-yl)oxy)-2-hydroxy-2-methylpropanoic acid (Example 19; 75 mg, 0.13 mmol) were separated by chiral SFC (method H). The material was concentrated under vacuum at 40° C. The first eluting fraction corresponded to enantiomer 1 and the second eluting fraction corresponded to enantiomer 2. The absolute configuration of the two enantiomers is not known.

Each of the two fractions was then individually treated for further purification. The obtained residue was acidified with dilute HCl (1.5 N, pH4) and the aqueous layer extracted with EtOAc (3×5 mL). The combined organic layer was washed with water (5 mL) and brine (5 mL) and dried over anhydrous Na₂SO₄. The organic part was filtered and concentrated under vacuum at 40° C. to afford a purified enantiomer of the title compound.

Enantiomer 1: Yield: 26% (10 mg, off-white solid). ¹H NMR (400 MHz, DMSO-d₆): δ 12.71 (s, 1H), 7.31 (s, 1H), 7.23 (t, J=7.6 Hz, 2H), 7.01 (d, J=7.6 Hz, 2H), 6.87 (t, J=7.6 Hz, 1H), 6.67 (s, 1H), 4.11 (s, 2H), 3.69 (s, 2H), 3.27 (s, 2H), 2.15 (s, 3H), 1.51-1.25 (m, 8H), 1.24-0.95 (m, 8H), 0.77 (t, J=6.4 Hz, 6H).

LCMS: (Method E) 550.1 (M⁺+H), Rt. 3.15 min, 92.15% (Max). HPLC: (Method B) Rt. 6.05 min, 96.01% (Max). Chiral SFC: (Method H) Rt. 2.61 min, 95.05% (Max).

Enantiomer 2: Yield: 26% (10 mg, off-white solid). ¹H NMR (400 MHz, DMSO-d₆): δ 12.66 (s, 1H), 7.31 (s, 1H), 7.23 (t, J=7.6 Hz, 2H), 7.01 (d, J=7.6 Hz, 2H), 6.87 (t, J=7.2 Hz, 1H), 6.67 (s, 1H), 4.11 (s, 2H), 3.69 (s, 2H), 3.27 (s, 2H), 2.15 (s, 3H), 1.51-1.27 (m, 8H), 1.24-0.95 (m, 8H), 0.77 (t, J=6.4 Hz, 6H).

LCMS: (Method E) 550.0 (M⁺+H), Rt. 3.15 min, 94.83% (Max). HPLC: (Method B) Rt. 6.05 min, 96.40% (Max). Chiral SFC: (Method H) Rt. 4.62 min, 97.50% (Max).

Example 22

3-((3-butyl-3-methyl-7-(methylthio)-1,1-dioxido-5-phenyl-2,3,4,5-tetrahydro-1,5-benzothiazepin-8-yl)oxy)propanoic acid

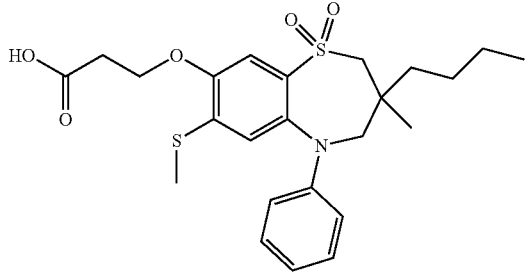 [SMILES: CCCCC1(C)CN(c2ccccc2)c2cc(SC)c(OCCC(=O)O)cc2S(=O)(=O)C1]

To a stirred solution of 3-butyl-8-hydroxy-3-methyl-7-(methylthio)-5-phenyl-2,3,4,5-tetrahydro-1,5-benzothiazepine 1,1-dioxide (Intermediate 35; 300 mg, 0.74 mmol) in THF (3 mL) at 0° C., potassium tert-butoxide (91 mg, 0.81 mmol) was added and the reaction mixture was stirred for 15 minutes. A solution of β-propiolactone (58.6 mg, 0.81 mmol) in THF (1 mL) was then added dropwise and the reaction mixture was stirred for 16 hours at room temperature. After completion of the reaction (monitored by TLC), the reaction mixture was quenched with dilute HCl (1.5 N, 3 mL) and diluted with water (2 mL). The aqueous layer was extracted with EtOAc (2×10 mL), and the combined organic layer was washed with water (10 mL) and brine (10 mL). The organic part was dried over anhydrous Na₂SO₄, filtered and concentrated under vacuum. The resulting crude material was purified by Isolera column chromatography (eluent: 3% MeOH/DCM; silica gel: 230-400 mesh) to afford the title compound. Yield: 17% (60 mg, off-white solid).

¹H NMR (400 MHz, DMSO-d₆): δ 12.44 (s, 1H), 7.33 (s, 1H), 7.18 (t, J=7.6 Hz, 2H), 6.91 (d, J=7.6 Hz, 2H), 6.81-6.77 (m, 2H), 4.29 (t, J=6.0 Hz, 2H), 3.78 (m, 2H), 3.30-3.26 (m, 2H), 2.74 (t, J=6.0 Hz, 2H), 2.19 (s, 3H), 1.58-1.45 (m, 1H), 1.35-1.10 (m, 5H), 1.01 (s, 3H), 0.80 (t, J=7.2 Hz, 3H). LCMS: (Method E) 478.0 (M⁺+H), Rt. 2.88 min, 97.42% (Max). HPLC: (Method B) Rt. 5.50 min, 97.96% (Max).

Examples 23 and 24

(S)-3-((3-butyl-3-methyl-7-(methylthio)-1,1-dioxido-5-phenyl-2,3,4,5-tetrahydro-1,5-benzothiazepin-8-yl)oxy)propanoic acid and (R)-3-((3-butyl-3-methyl-7-(methylthio)-1,1-dioxido-5-phenyl-2,3,4,5-tetrahydro-1,5-benzothiazepin-8-yl)oxy)propanoic acid

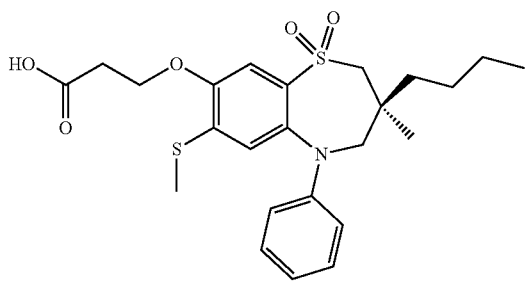

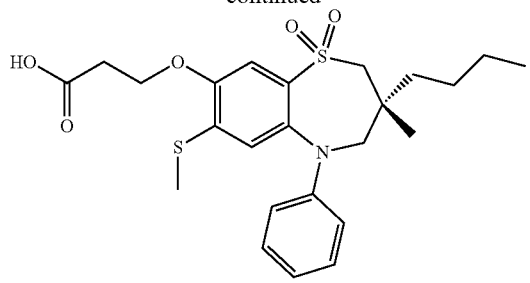

The two enantiomers of racemic 3-((3-butyl-3-methyl-7-(methylthio)-1,1-dioxido-5-phenyl-2,3,4,5-tetrahydro-1,5-benzothiazepin-8-yl)oxy)propanoic acid (Example 22; 60 mg, 0.12 mmol) were separated by chiral SFC (method H). The material was concentrated under vacuum at 40° C. The first eluting fraction corresponded to enantiomer 1 and the second eluting fraction corresponded to enantiomer 2. The absolute configuration of the two enantiomers is not known.

Each of the two fractions was then individually treated for further purification. The obtained residue was acidified with dilute HCl (1.5 N, pH4) and the aqueous layer extracted with EtOAc (3×5 mL). The combined organic layer was washed with water (5 mL) and brine (5 mL) and dried over anhydrous Na₂SO₄. The organic part was filtered and concentrated under vacuum at 40° C. to afford a purified enantiomer of the title compound.

Enantiomer 1: Yield: 30% (18 mg, off-white solid). ¹H NMR (400 MHz, DMSO-d₆): δ 7.33 (s, 1H), 7.18 (t, J=7.6 Hz, 2H), 6.91 (d, J=7.6 Hz, 2H), 6.81-6.77 (m, 2H), 4.28 (t, J=6.0 Hz, 2H), 3.78-3.74 (m, 1H), 3.29-3.21 (m, 1H), 2.75-2.65 (m, 2H), 2.57-2.45 (m, 2H), 2.19 (s, 3H), 1.58-1.42 (m, 1H), 1.33-1.12 (m, 5H), 1.01 (s, 3H), 0.80 (t, J=6.8 Hz, 3H). LCMS: (Method E) 478.2 (M⁺+H), Rt. 2.89 min, 98.93% (Max). HPLC: (Method B) Rt. 5.50 min, 98.36% (Max). Chiral SFC: (Method K) Rt. 8.44 min, 99.61% (Max).

Enantiomer 2: Yield: 13% (8.2 mg, off-white solid). ¹H NMR (400 MHz, DMSO-d₆): δ 7.33 (s, 1H), 7.18 (t, J=7.6 Hz, 2H), 6.91 (d, J=7.6 Hz, 2H), 6.81-6.77 (m, 2H), 4.28 (t, J=6.0 Hz, 2H), 3.75-3.78 (m, 1H), 3.29-3.21 (m, 1H), 2.75-2.65 (m, 2H), 2.57-2.45 (m, 2H), 2.19 (s, 3H), 1.58-1.42 (m, 1H), 1.33-1.12 (m, 5H), 1.01 (s, 3H), 0.80 (t, J=6.8 Hz, 3H). LCMS: (Method E) 478.2 (M⁺+H), Rt. 2.89 min, 97.83% (Max).

HPLC: (Method B) Rt. 5.50 min, 96.14% (Max). Chiral SFC: (Method K) Rt. 9.49 min, 98.42% (Max).

Example 25

3-((3,3-dibutyl-5-(3,4-difluorophenyl)-7-(methylthio)-1,1-dioxido-2,3,4,5-tetrahydro-1,5-benzothiazepin-8-yl)oxy)propanoic acid

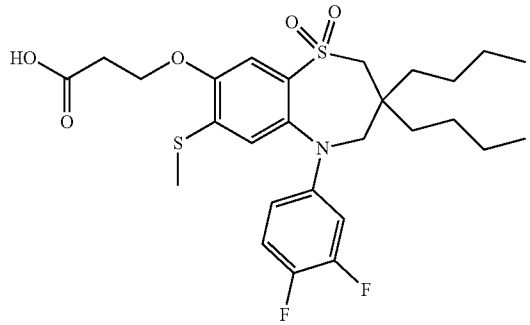 [SMILES: CCCCC1(CCCC)CN(c2ccc(F)c(F)c2)c2cc(SC)c(OCCC(=O)O)cc2S(=O)(=O)C1]

To a stirred solution of 3,3-dibutyl-5-(3,4-difluorophenyl)-8-hydroxy-7-(methylthio)-2,3,4,5-tetrahydro-1,5-benzothiazepine 1,1-dioxide (Intermediate 40; 100 mg, 0.21 mmol) in THF (1 mL) at 0° C., potassium tert-butoxide (26 mg, 0.23 mmol) was added and the reaction mixture was stirred for 15 minutes. A solution of β-propiolactone (15 mg, 0.21 mmol) in THF (1 mL) was then added dropwise and the reaction mixture was stirred for 2 hours at room temperature. After completion of the reaction (monitored by TLC), the reaction mixture was quenched with dilute HCl (1.5 N, 3 mL) and diluted with water (2 mL). The aqueous layer was extracted with EtOAc (2×4 mL), and the combined organic layer was washed with water (5 mL) and brine (5 mL). The organic part was dried over anhydrous $Na_2SO_4$, filtered and concentrated under vacuum. The resulting crude material was purified by Prep HPLC (Method A) to afford the title compound. Yield: 17% (19.5 mg, off-white solid).

$^1$H NMR (400 MHz, DMSO-$d_6$): δ 12.47 (s, 1H), 7.31 (s, 1H), 7.27-7.20 (m, 1H), 7.77-7.05 (m, 1H), 6.76 (s, 1H), 6.71-6.64 (m, 1H), 4.28 (t, J=6.0 Hz, 2H), 3.69 (bs, 2H), 3.29 (s, 2H), 2.72-2.68 (m, 2H), 2.22 (s, 3H), 1.45-1.25 (m, 4H), 1.20-1.05 (m, 8H), 0.86-0.81 (m, 6H). LCMS: (Method E) 556.0 (M$^+$+H), Rt. 3.19 min, 97.95% (Max). HPLC: (Method B) Rt. 6.25 min, 97.84% (Max).

Example 26

3-((3,3-dibutyl-5-(4-fluorophenyl)-7-(methylthio)-1,1-dioxido-2,3,4,5-tetrahydro-1,5-benzothiazepin-8-yl)oxy)propanoic acid

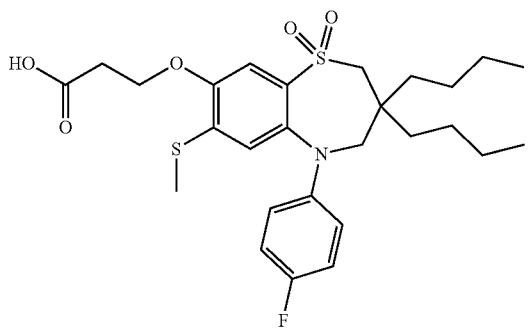 [SMILES: CCCCC1(CCCC)CN(c2ccc(F)cc2)c2cc(SC)c(OCCC(=O)O)cc2S(=O)(=O)C1]

To a stirred solution of 3,3-dibutyl-5-(4-fluorophenyl)-8-hydroxy-7-(methylthio)-2,3,4,5-tetrahydro-1,5-benzothiazepine 1,1-dioxide (Intermediate 44; 100 mg, 0.21 mmol) in THF (1 mL) at 0° C., potassium tert-butoxide (26 mg, 0.23 mmol) was added and the reaction mixture was stirred for 15 minutes. A solution of β-propiolactone (17 mg, 0.23 mmol) in THF (1 mL) was then added dropwise and the reaction mixture was stirred for 16 hours at room temperature. After completion of the reaction (monitored by TLC), the reaction mixture was quenched with dilute HCl (1.5 N, 3 mL) and diluted with water (2 mL). The aqueous layer was extracted with EtOAc (2×4 mL) and the combined organic layer was washed with water (5 mL) and brine (5 mL). The organic part was dried over anhydrous $Na_2SO_4$, filtered and concentrated under vacuum. The resulting crude material was purified by Isolera column chromatography (eluent: 40% EtOAc/PE; silica gel: 230-400 mesh) to afford the title compound. Yield: 60% (70 mg, off-white solid).

$^1$H NMR (400 MHz, DMSO-$d_6$): δ 12.41 (s, 1H), 7.30 (s, 1H), 7.09 (d, J=6.4 Hz, 4H), 6.60 (s, 1H), 4.26 (t, J=5.6 Hz, 2H), 3.78 (s, 2H), 3.30 (s, 2H), 2.71 (t, J=6.0 Hz, 2H), 2.14 (s, 3H), 1.49-1.37 (m, 4H), 1.20-0.97 (m, 8H), 0.78-0.75 (m, 6H). LCMS: (Method E) 537.8 (M$^+$+H), Rt. 3.19 min, 95.96% (Max).

HPLC: (Method B) Rt. 6.22 min, 95.82% (Max).

Example 27

3-((3-ethyl-7-(methylthio)-1,1-dioxido-5-phenyl-3-propyl-2,3,4,5-tetrahydro-1,5-benzothiazepin-8-yl)oxy)propanoic acid

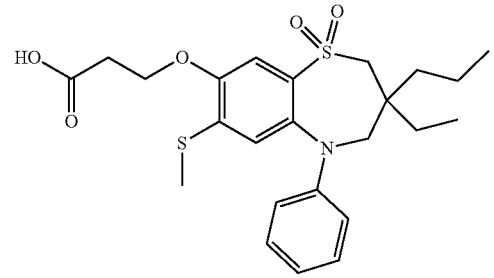 [SMILES: CCCC1(CC)CN(c2ccccc2)c2cc(SC)c(OCCC(=O)O)cc2S(=O)(=O)C1]

To a stirred solution of 3-ethyl-8-hydroxy-7-(methylthio)-5-phenyl-3-propyl-2,3,4,5-tetrahydro-1,5-benzothiazepine 1,1-dioxide (Intermediate 50; 300 mg, 0.74 mmol) in THF (5 mL) at 0° C., potassium tert-butoxide (92 mg, 0.81 mmol) was added and the reaction mixture was stirred for 5 minutes. A solution of β-propiolactone (53 mg, 0.74 mmol) in THF (2 mL) was then added dropwise and the reaction mixture was stirred for 4 hours at room temperature. After completion of the reaction (monitored by TLC), the reaction mixture was quenched with dilute HCl (1.5 N, 3 mL) and diluted with water (5 mL). The aqueous layer was extracted with EtOAc (2×10 mL) and the combined organic layer was washed with water (10 mL) and brine (10 mL). The organic part was dried over anhydrous $Na_2SO_4$, filtered and concentrated under vacuum. The resulting crude material was purified by Isolera column chromatography (eluent: 6% MeOH/DCM; silica gel: 230-400 mesh) to afford the title compound. Yield: 5% (12 mg, pale brown solid).

$^1$H NMR (400 MHz, DMSO-$d_6$): δ 12.47 (s, 1H), 7.32 (s, 1H), 7.22 (t, J=7.6 Hz, 2H), 6.97 (d, J=7.6 Hz, 2H), 6.85 (t, J=7.2 Hz, 1H), 6.71 (s, 1H), 4.28 (t, J=6.0 Hz, 2H), 3.69 (s, 2H), 3.28 (s, 2H), 2.72 (t, J=6.0 Hz, 2H), 2.16 (s, 3H), 1.65-1.50 (m, 1H), 1.43-1.30 (m, 3H), 1.24-1.19 (m, 2H), 0.81-0.55 (m, 6H).

LCMS: (Method E) 478.2 (M$^+$+H), Rt. 2.88 min, 94.89% (Max). HPLC: (Method B) Rt. 5.37 min, 95.20% (Max).

Example 28

O-(3-butyl-3-ethyl-7-(methylthio)-1,1-dioxido-5-phenyl-2,3,4,5-tetrahydro-1,5-benzothiazepin-8-yl)serine

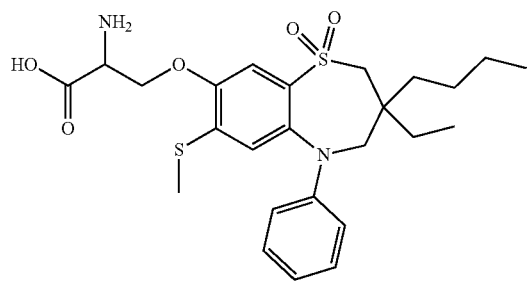 [SMILES: CCCCC1(CC)CN(c2ccccc2)c2cc(SC)c(OCC(N)C(=O)O)cc2S(=O)(=O)C1]

To a stirred solution of methyl O-(3-butyl-3-ethyl-7-(methylthio)-1,1-dioxido-5-phenyl-2,3,4,5-tetrahydro-1,5-benzothiazepin-8-yl)serinate (Intermediate 53; 170 mg, 0.33 mmol) in 1,4-dioxane (2 mL), lithium hydroxide (28 mg, 0.65 mmol) was added and the reaction mixture was stirred for 2 hours at room temperature. After completion of the reaction (monitored by TLC), the reaction mixture was diluted with water (2 mL) and the aqueous layer was extracted with EtOAc (2×5 mL). The combined organic layer was washed with water (5 mL) and brine (5 mL) and dried over anhydrous $Na_2SO_4$. The organic part was filtered, concentrated under vacuum and the resulting crude material was purified by Isolera column chromatography (eluent: 24% MeOH/DCM; silica gel: 230-400 mesh). The obtained residue was re-purified by prep HPLC (method A) to afford the title compound. Yield: 58% (95 mg, white solid).

$^1$H NMR (400 MHz, DMSO-$d_6$): 7.91-7.61 (m, 2H), 7.39 (s, 1H), 7.23 (t, J=7.6 Hz, 2H), 7.01 (d, J=8.0 Hz, 2H), 6.88 (t, J=7.2 Hz, 1H), 6.70 (s, 1H), 4.43-4.40 (m, 1H), 4.27-4.22 (m, 1H), 3.69 (s, 2H), 3.59-3.57 (m, 1H), 2.68 (s, 2H), 2.17 (s, 3H), 1.61-1.41 (m, 2H), 1.38-1.29 (m, 2H), 1.29-0.97 (m, 4H), 0.81-0.71 (m, 6H). LCMS: (Method E) 507.2 (M$^+$+H), Rt. 2.26 min, 99.37% (Max). HPLC: (Method B) Rt. 4.46 min, 99.16% (Max).

Example 29

3-((3-butyl-7-(dimethylamino)-3-methyl-1,1-dioxido-5-phenyl-2,3,4,5-tetrahydro-1,5-benzothiazepin-8-yl)oxy)propanoic acid

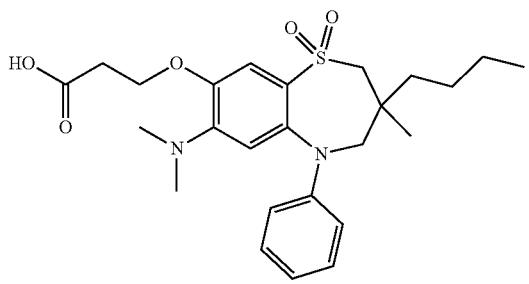 [SMILES: CCCCC1(C)CN(c2ccccc2)c2cc(N(C)C)c(OCCC(=O)O)cc2S(=O)(=O)C1]

To a stirred solution of 3-butyl-7-(dimethylamino)-8-hydroxy-3-methyl-5-phenyl-2,3,4,5-tetrahydro-1,5-benzothiazepine 1,1-dioxide (Intermediate 86; 600 mg, 1.40 mmol) in THF (3 mL) at 0° C., potassium tert-butoxide (167 mg, 1.4 mmol) was added and the reaction mixture was stirred for 15 minutes. A solution of (3-propiolactone (118 mg, 1.6 mmol) in THF (1 mL) was then added dropwise and the reaction mixture was stirred for 4 hours at room temperature. After completion of the reaction (monitored by TLC), the reaction mixture was quenched with dilute HCl (1.5 N, 5 mL) and diluted with water (5 mL). The aqueous layer was extracted with EtOAc (2×15 mL) and the combined organic layer was washed with water (15 mL) and brine (15 mL). The organic part was dried over anhydrous $Na_2SO_4$, filtered and concentrated under vacuum. The resulting crude material was purified by Isolera column chromatography (eluent: 3% MeOH/DCM; silica gel: 230-400 mesh) and again re-purified by prep HPLC (Method A) to afford the title compound.

LCMS: (Method E) 474.8 (M$^+$+H), Rt. 2.12 min, 98.47% (Max). HPLC: (Method B) Rt. 4.43 min, 99.05% (Max).

Separation of Enantiomers (S)-3-((3-butyl-7-(dimethylamino)-3-methyl-1,1-dioxido-5-phenyl-2,3,4,5-tetrahydro-1,5-benzo-thiazepin-8-yl)oxy)propanoic acid and (R)-3-((3-butyl-7-(dimethylamino)-3-methyl-1,1-dioxido-5-phenyl-2,3,4,5-tetrahydro-1,5-benzothiazepin-8-yl)oxy) propanoic acid

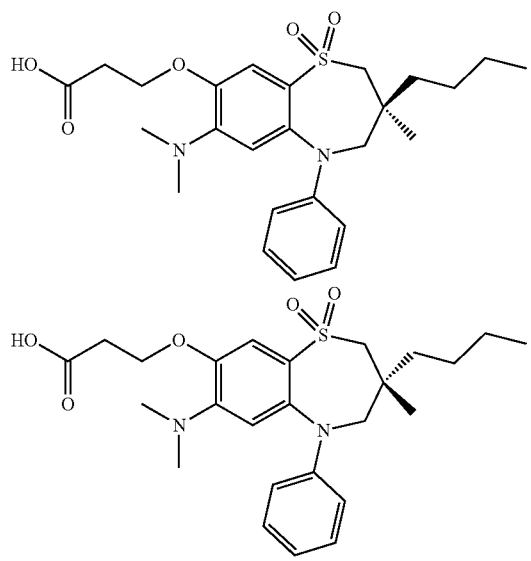

The two enantiomers of racemic 3-((3-butyl-7-(dimethylamino)-3-methyl-1,1-dioxido-5-phenyl-2,3,4,5-tetrahydro-1,5-benzothiazepin-8-yl)oxy)propanoic acid (140 mg, 0.29 mmol) were separated by chiral SFC (method F). The material was concentrated under vacuum at 40° C. The first eluting fraction corresponded to enantiomer 1 and the second eluting fraction corresponded to enantiomer 2. The absolute configuration of the two enantiomers is not known.

Each of the two fractions was then individually treated for further purification. The obtained residue was acidified with dilute HCl (1.5 N, pH4) and the aqueous layer extracted with EtOAc (3×5 mL). The combined organic layer was washed with water (5 mL) and brine (5 mL) and dried over anhydrous $Na_2SO_4$. The organic part was filtered and concentrated under vacuum at 40° C. to afford a purified enantiomer of the title compound.

Enantiomer 1: Yield: 30% (42 mg, off-white solid). $^1$H NMR (400 MHz, DMSO-$d_6$): δ 12.42 (s, 1H), 7.29 (s, 1H), 7.17 (t, J=7.6 Hz, 2H), 6.91 (d, J=7.6 Hz, 2H), 6.77 (t, J=7.2 Hz, 1H), 6.42 (s, 1H), 4.21 (t, J=6.0 Hz, 2H), 3.91-3.32 (m, 2H), 3.26-3.15 (m, 2H), 2.77 (t, J=5.6 Hz, 2H), 2.68 (s, 6H), 1.58-1.48 (m, 1H), 1.47-1.18 (m, 3H), 1.17-1.05 (m, 2H), 1.00 (s, 3H), 0.85-0.78 (m, 3H). LCMS: (Method E) 475.1 (M$^+$+H), Rt. 2.08 min, 99.82% (Max). HPLC: (Method B) Rt. 4.44 min, 99.39% (Max). Chiral SFC: (Method H) Rt. 2.2 min, 100% (Max).

Enantiomer 2: Yield: 35% (50 mg, off white solid). $^1$H NMR (400 MHz, DMSO-$d_6$): δ 12.41 (s, 1H), 7.29 (s, 1H), 7.17 (t, J=7.6 Hz, 2H), 6.91 (d, J=7.6 Hz, 2H), 6.77 (t, J=7.2 Hz, 1H), 6.42 (s, 1H), 4.21 (t, J=6.0 Hz, 2H), 3.89-3.31 (m, 2H), 3.26-3.15 (m, 2H), 2.77 (t, J=5.6 Hz, 2H), 2.68 (s, 6H), 1.55-1.44 (m, 1H), 1.47-1.18 (m, 3H), 1.17-1.05 (m, 2H), 1.02 (s, 3H), 0.85-0.78 (m, 3H). LCMS: (Method A) 475.2

(M++H), Rt. 2.60 min, 98.32% (Max). HPLC: (Method B) Rt. 4.43 min, 99.79% (Max). Chiral HPLC: (Method H) Rt. 2.82 min, 93.27% (Max).

Example 30

3-((3-butyl-7-chloro-3-ethyl-1,1-dioxido-5-phenyl-2,3,4,5-tetrahydro-1,5-benzothiazepin-8-yl)oxy)butanoic Acid (Individual Diastereomers)

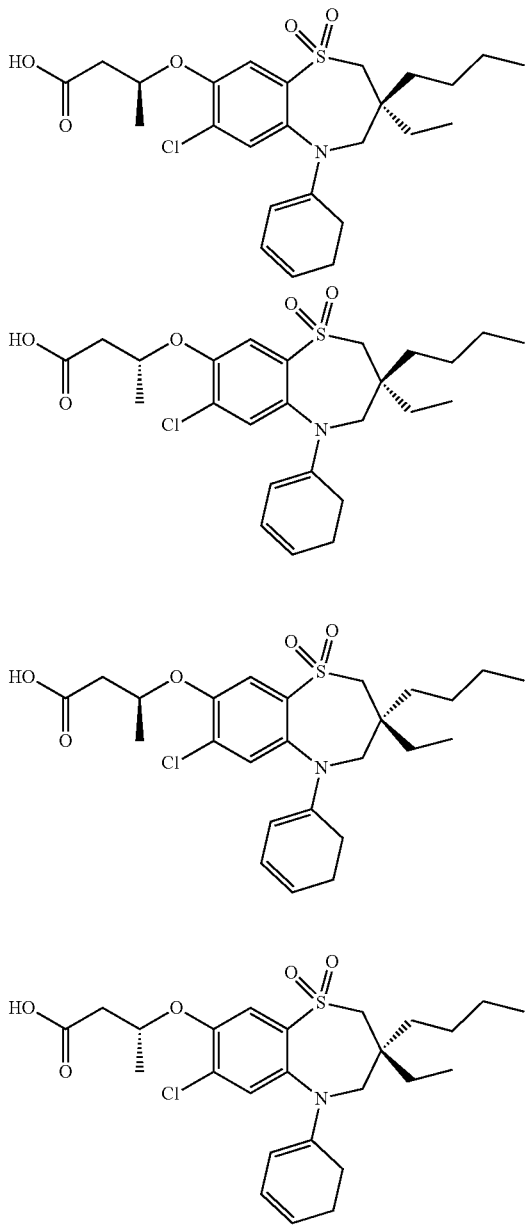

Diastereomers 1 and 2

To a stirred solution of enantiomer 2 of 3-butyl-7-chloro-3-ethyl-8-hydroxy-5-phenyl-2,3,4,5-tetrahydro-1,5-benzothiazepine 1,1-dioxide (Intermediate 11; 0.22 g, 0.52 mmol) in dry THF (5 mL), potassium tert-butoxide (0.06 g, 0.52 mmol) was added at 0° C. and the reaction mixture was stirred for 15 minutes. A solution of 4-methyloxetan-2-one (0.05 g, 0.58 mmol) in THF (1 mL) was then added slowly to the reaction mixture at 0° C. and the reaction mixture was stirred for 12 hours at 60° C. After completion of the reaction (monitored by TLC), the reaction mixture was quenched with dilute HCl (1.5 N, 1 mL) and the aqueous layer was extracted with EtOAc (2×10 mL). The combined organic layer was washed with water (10 mL) and brine (10 mL), dried over anhydrous $Na_2SO_4$ and concentrated under vacuum at 50° C. The resulting crude material was purified by Isolera column chromatography (eluent: 30-40% EtOAc/PE; silica gel: 230-400 mesh) to afford a mixture of diastereomers 1 and 2 of the title compound.

Diastereomers 1 and 2: Yield: 27% (0.07 g, of-white solid). $^1$H NMR (400 MHz, DMSO-$d_6$): δ 7.55 (s, 1H), 7.26 (t, J=8.0 Hz, 2H), 7.07 (d, J=7.6 Hz, 2H), 6.94 (t, J=7.6 Hz, 2H), 4.81 (q, J=6.4 Hz, 1H), 3.71 (bs, 2H), 3.36-3.33 (m, 2H), 2.67-2.62 (m, 2H), 1.51-1.48 (m, 1H), 1.37-1.31 (m, 6H), 1.23-1.09 (m, 4H), 0.72 (t, J=5.6 Hz, 6H). LCMS: (Method E) 494.1 (M++H), Rt. 2.73 min, 98.62% (Max). HPLC: (Method B) Rt. 6.06 min, 98.06% (Max).

The two diastereomers (60 mg, 0.12 mmol) were separated by SFC (method J). The material was concentrated under vacuum at 40° C. The first eluting fraction corresponded to diastereomer 1 and the second first eluting fraction corresponded to diastereomer 2.

Diastereomer 1: Yield: 23% (14 mg, white solid). $^1$H NMR (400 MHz, DMSO-$d_6$): δ 7.55 (s, 1H), 7.26 (t, J=8.0 Hz, 2H), 7.07 (d, J=7.6 Hz, 2H), 6.93 (t, J=8.0 Hz, 2H), 4.81 (q, J=6.0 Hz, 1H), 3.72 (bs, 2H), 3.31 (s, 2H), 2.61-2.59 (m, 2H), 1.49-1.35 (m, 1H), 1.33-1.23 (m, 6H), 1.09-1.06 (m, 4H), 0.73 (t, J=7.20 Hz, 6H). LCMS: (Method E) 494.1 (M++H), Rt. 2.74 min, 99.57% (Max). HPLC: (Method B) Rt. 6.06 min, 99.49% (Max). Chiral SFC: (Method L) Rt. 2.37 min, 99.7% (Max).

Diastereomer 2: Yield: 24% (14.5 mg, white solid). $^1$H NMR (400 MHz, DMSO-$d_6$): δ 7.55 (s, 1H), 7.26 (t, J=8.0 Hz, 2H), 7.07 (d, J=7.2 Hz, 2H), 6.93 (t, J=8.4 Hz, 2H), 4.82-4.80 (m, 1H), 3.72 (bs, 2H), 3.32 (s, 2H), 2.62-2.60 (m, 2H), 1.51-1.36 (m, 1H), 1.32-1.26 (m, 6H), 1.10-1.02 (m, 4H), 0.72 (t, J=7.2 Hz, 6H). LCMS: (Method E) 494.1 (M++H), Rt. 2.73 min, 98.95% (Max). HPLC: (Method B) Rt. 6.05 min, 99.36% (Max). Chiral SFC: (Method L) Rt. 2.97 min, 98.74% (Max).

Diastereomers 3 and 4

A mixture of diastereomers 3 and 4 of the title compound was obtained following the same procedure as above, starting from 0.20 g of enantiomer 1 of Intermediate 11. After purification by Isolera column chromatography, the obtained residue was re-purified by prep-HPLC (method A) to afford the title compound. The two diastereomers were not further separated.

Diastereomers 3 and 4: Yield: 29% (0.07 g, off-white solid). $^1$H NMR (400 MHz, DMSO-$d_6$): δ 12.45 (s, 1H), 7.56 (s, 1H), 7.27 (t, J=8.3 Hz, 2H), 7.08 (d, J=7.8 Hz, 2H), 6.95 (t, J=6.6 Hz, 2H), 4.83 (q, J=6.2 Hz, 1H), 3.85 (bs, 2H), 3.31 (s, 2H), 2.72-2.70 (m, 2H), 1.51-1.47 (m, 1H), 1.48-1.32 (m, 6H), 1.18-0.98 (m, 4H), 0.76-0.70 (m, 6H). LCMS: (Method E) 493.1 (M+) Rt. 2.72 min, 99.30% (Max). HPLC: (Method B) Rt. 6.05 min, 97.83% (Max).

The absolute configuration of the four diastereomers is not known.

Example 31

3-((3-butyl-3-methyl-7-(methylthio)-1,1-dioxido-5-phenyl-2,3,4,5-tetrahydro-1,5-benzothiazepin-8-yl)oxy)-2-hydroxypropanoic acid

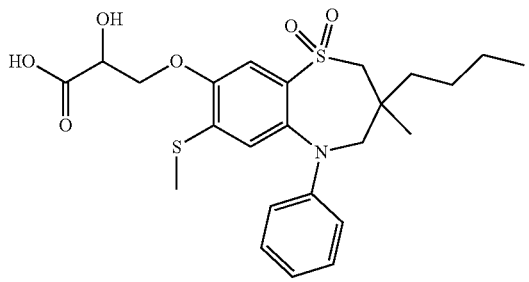 [SMILES: CCCCC1(C)CN(c2ccccc2)c2cc(SC)c(OCC(O)C(=O)O)cc2S(=O)(=O)C1]

To a stirred solution of methyl 3-((3-butyl-3-methyl-7-(methylthio)-1,1-dioxido-5-phenyl-2,3,4,5-benzothiazepin-8-yl)oxy)-2-hydroxypropanoate (Intermediate 54; 170 mg, 0.33 mmol) in 1,4-dioxane (2 mL), dilute HCl (7N, 1.7 mL) was added and the reaction mixture was heated for 3 hours at 65° C. After completion of the reaction (monitored by TLC), the reaction mixture was quenched with ice-cold water (2 mL) and the aqueous layer was extracted with EtOAc (2×10 mL). The combined organic layer was washed with water (10 mL) and brine (10 mL) and dried over anhydrous $Na_2SO_4$. The organic part was filtered and concentrated under vacuum. The resulting crude material was purified by Isolera column chromatography (eluent: 8% MeOH/DCM; silica gel: 230-400 mesh) to afford the title compound. Yield: 61% (80 mg, off-white solid).

$^1$H NMR (400 MHz, CDCl$_3$): 7.47 (s, 1H), 7.27-7.24 (m, 2H), 7.02 (d, J=4.8 Hz, 2H), 6.96-6.92 (m, 1H), 6.74-6.72 (m, 1H), 4.61-4.59 (m, 1H), 4.48-4.45 (m, 2H), 3.95-3.75 (m, 1H), 3.74-3.41 (m, 1H), 3.18-3.13 (m, 2H), 2.20 (s, 3H), 1.55-1.48 (m, 1H), (1.35-1.22 (m, 5H), 1.14-1.13 (m, 3H), 0.86-0.84 (m, 3H).

LCMS: (Method E) 494.0 (M$^+$+H), Rt. 2.72 min, 98.87% (Max). HPLC: (Method B) Rt. 5.12 min, 99.06% (Max).

Example 32

3-((3-butyl-3-methyl-7-(methylthio)-1,1-dioxido-5-phenyl-2,3,4,5-tetrahydro-1,5-benzothiazepin-8-yl)oxy)-2-hydroxypropanoic Acid (Individual Diastereomers)

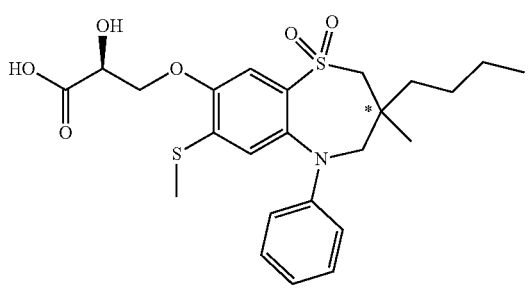

-continued

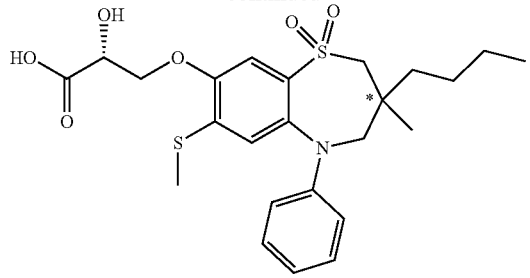

* the indicated carbons are each R or are each S

To a stirred solution of methyl 3-((3-butyl-3-methyl-7-(methylthio)-1,1-dioxido-5-phenyl-2,3,4,5-tetrahydro-1,5-benzothiazepin-8-yl)oxy)-2-hydroxypropanoate (Intermediate 55; 200 mg, 0.39 mmol) in 1,4-dioxane (2 mL), dilute HCl (7 N, 1 mL) was added and the reaction mixture was heated for 3 hours at 65° C. After completion of the reaction (monitored by TLC), the reaction mixture was diluted with ice-cold water (2 mL) and the aqueous layer was extracted with EtOAc (2×10 mL). The combined EtOAc layer was washed with water (10 mL) and brine (10 mL) and dried over anhydrous $Na_2SO_4$. The organic part was filtered and concentrated under vacuum. The resulting crude material was purified by Isolera column chromatography (eluent: 8% MeOH/DCM; silica gel: 230-400 mesh) to afford the title compound. Yield: 61% (120 mg, off-white solid).

$^1$H NMR (400 MHz, DMSO-d$_6$): 7.37 (s, 1H), 7.18 (t, J=7.6 Hz, 2H), 6.91 (d, J=7.2 Hz, 2H), 6.81-6.77 (m, 2H), 4.37-4.34 (m, 1H), 4.06-4.01 (m, 2H), 3.79-3.74 (m, 1H), 3.61-3.45 (m, 1H), 3.30-3.22 (m, 2H), 2.20 (s, 3H), 1.52-1.46 (m, 1H), 1.36-1.11 (m, 5H), 1.01 (s, 3H), 0.80 (t, J=7.2 Hz, 3H). LCMS: (Method E) 493.9 (M$^+$+H), Rt. 2.40 min, 93.95% (Max). HPLC: (Method B) Rt. 5.08 min, 93.40% (Max).

The two diastereomers were separated by SFC (method H). The material was concentrated under vacuum at 40° C. The first eluting fraction corresponded to diastereomer 1 and the second eluting fraction corresponded to diastereomer 2. Each of the two fractions was then individually treated for further purification. The obtained residue was acidified with dilute HCl (1.5 N, pH4) and the aqueous layer extracted with EtOAc (3×5 mL). The combined organic layer was washed with water (5 mL) and brine (5 mL) and dried over anhydrous $Na_2SO_4$. The organic part was filtered and concentrated under vacuum at 40° C. to afford a purified diastereomer of the title compound.

Diastereomer 1: Yield: 36% (22 mg, off-white solid). $^1$H NMR (400 MHz, DMSO-d$_6$): δ 7.37 (s, 1H), 7.18 (t, J=7.6 Hz, 2H), 6.91 (d, J=8.0 Hz, 2H), 6.81-6.77 (m, 2H), 4.38-4.36 (m, 1H), 4.11-4.08 (m, 2H), 3.79-3.74 (m, 1H), 3.61-3.45 (m, 1H), 3.30-3.19 (m, 2H), 2.21 (s, 3H), 1.56-1.39 (m, 1H), 1.36-1.11 (m, 5H), 1.01 (s, 3H), 0.80 (t, J=7.2 Hz, 3H). LCMS: (Method E) 493.9 (M$^+$+H), Rt. 2.39 min, 98.39% (Max). HPLC: (Method B) Rt. 5.11 min, 99.74% (Max). Chiral SFC: (Method H) Rt. 3.36 min, 100% (Max).

Diastereomer 2: Yield: 41% (25 mg, off-white solid). $^1$H NMR (400 MHz, DMSO-d$_6$): δ 7.37 (s, 1H), 7.18 (t, J=7.6 Hz, 2H), 6.91 (d, J=6.4 Hz, 2H), 6.81-6.77 (m, 2H), 4.37-4.35 (m, 1H), 4.11-4.08 (m, 2H), 3.79-3.74 (m, 1H), 3.61-3.45 (m, 1H), 3.30-3.19 (m, 2H), 2.21 (s, 3H), 1.56-1.39 (m, 1H), 1.36-1.11 (m, 5H), 1.01 (s, 3H), 0.80 (t, J=7.2 Hz, 3H). LCMS: (Method E) 493.9 (M$^+$+H), Rt. 2.39 min, 97.50%

(Max). HPLC: (Method B) Rt. 5.08 min, 98.48% (Max). Chiral SFC: (Method H) Rt. 4.39 min, 98.97% (Max).

The absolute configuration of the two diastereomers is not known.

Example 33

3-((3-butyl-3-methyl-7-(methylthio)-1,1-dioxido-5-phenyl-2,3,4,5-tetrahydro-1,5-benzothiazepin-8-yl)oxy)-2-hydroxy-2-methylpropanoic Acid (Individual Diastereomers)

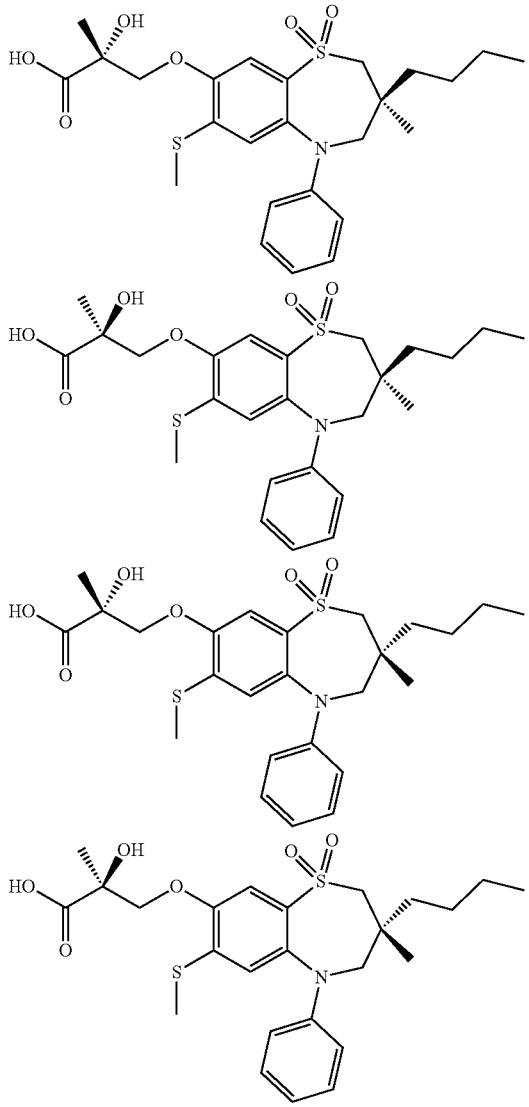

Diastereomers 1 and 2

To a stirred solution of diastereomers 1 and 2 of methyl 3-((3-butyl-3-methyl-7-(methylthio)-1,1-dioxido-5-phenyl-2,3,4,5-tetrahydro-1,5-benzothiazepin-8-yl)oxy)-2-hydroxy-2-methylpropanoate (Intermediate 56; 250 mg, 0.48 mmol) in 1,4-dioxane (2 mL), dilute HCl (6 N, 5 mL) was added and the reaction mixture was stirred for 4 hours at 80° C. After completion of the reaction (monitored by TLC), the reaction mixture was diluted with ice-cold water (5 mL) and the aqueous layer was extracted with EtOAc (2×20 mL). The combined organic layer was washed with water (15 mL) and brine (15 mL) and dried over anhydrous $Na_2SO_4$. The organic part was filtered, concentrated under vacuum and the resulting crude material was purified by Isolera column chromatography (eluent: 50-60% EtOAc/PE; silica gel: 230-400 mesh). The obtained residue was re-purified by prep HPLC (Method A) to afford the title compound. Yield: 25% (60 mg, white solid).

LCMS: (Method E) 507.8 (M$^+$+H), Rt. 1.44 min, 99.07% (Max). HPLC: (Method B) Rt. 5.18 min, 99.82% (Max).

The two diastereomers (60 mg, 0.11 mmol) were separated by chiral SFC (method F). The first eluting fraction corresponded to diastereomer 1 and the second eluting fraction corresponded to diastereomer 2. Each of the two fractions was then individually treated for further purification. The obtained residue was acidified with dilute HCl (1.5 N, pH4) and the aqueous layer extracted with EtOAc (3×5 mL). The combined organic layer was washed with water (5 mL) and brine (5 mL) and dried over anhydrous $Na_2SO_4$. The organic part was filtered and concentrated under vacuum at 40° C. to afford a purified diastereomer of the title compound.

Diastereomer 1: Yield: 27% (16 mg, off-white solid). $^1$H NMR (400 MHz, DMSO-d$_6$): δ 12.75 (s, 1H), 7.33 (s, 1H), 7.18 (t, J=7.6 Hz, 2H), 6.91 (d, J=7.2 Hz, 2H), 6.79 (s, 2H), 5.65-5.11 (m, 1H), 4.12 (s, 2H), 3.78 (bs, 2H), 3.29-3.24 (m, 2H), 2.20 (s, 3H), 1.40 (s, 3H), 1.39-1.15 (m, 6H), 1.01 (s, 3H), 0.81-0.78 (m, 3H). LCMS: (Method E) 508.1 (M$^+$+H), Rt. 2.44 min, 98.51% (Max). HPLC: (Method B) Rt. 5.23 min, 97.95% (Max). Chiral SFC: (Method H) Rt. 3.12 min, 100% (Max).

Diastereomer 2: Yield: 27% (16 mg, off-white solid). $^1$H NMR (400 MHz, DMSO-d$_6$): δ 12.77 (s, 1H), 7.33 (s, 1H), 7.19 (t, J=8.0 Hz, 2H), 6.92 (d, J=6.4 Hz, 2H), 6.79 (s, 2H), 5.65-5.11 (m, 1H), 4.13 (s, 2H), 3.78 (bs, 2H), 3.29-3.24 (m, 2H), 2.20 (s, 3H), 1.40 (s, 3H), 1.39-1.15 (m, 6H), 1.01 (s, 3H), 0.87-0.80 (m, 3H). LCMS: (Method E) 508.1 (M$^+$+H), Rt. 2.45 min, 98.38% (Max). HPLC: (Method B) Rt. 5.24 min, 98.70% (Max). Chiral SFC: (Method H) Rt. 3.99 min, 98.85% (Max)

Diastereomer 3

To a stirred solution of diastereomer 3 of methyl 3-((3-butyl-3-methyl-7-(methylthio)-1,1-dioxido-5-phenyl-2,3,4,5-tetrahydro-1,5-benzothiazepin-8-yl)oxy)-2-hydroxy-2-methylpropanoate (Intermediate 56; 50 mg, 0.09 mmol) in 1,4-dioxane (2 mL), dilute HCl (6 N, 3 mL) was added and the reaction mixture was stirred for 4 hours at 80° C. After completion of the reaction (monitored by TLC), the reaction mixture was diluted with ice-cold water (5 mL), and the aqueous layer was extracted with EtOAc (2×10 mL). The combined organic layer was washed with water (10 mL) and brine (10 mL) and dried over anhydrous $Na_2SO_4$. The organic part was filtered and concentrated under vacuum. The resulting crude material was purified by Isolera column chromatography (eluent: 50-60% EtOAc/PE; silica gel: 230-400 mesh) to afford the title compound. Yield: 54% (26 mg, white solid).

$^1$H NMR (400 MHz, DMSO-d$_6$): δ 12.77 (s, 1H), 7.34 (s, 1H), 7.19 (t, J=8.0 Hz, 2H), 6.91 (d, J=7.6 Hz, 2H), 6.80 (t, J=8.0 Hz, 2H), 5.40 (s, 1H), 4.13 (s, 2H), 3.37 (bs, 2H), 3.33-3.21 (m, 2H), 2.20 (s, 3H), 1.48 (s, 3H), 1.40-1.20 (m, 6H), 1.01 (s, 3H), 0.85-0.75 (m, 3H). LCMS: (Method A) 508.1 (M$^+$+H), Rt. 2.50 min, 96.08% (Max). HPLC: (Method B) Rt. 5.19 min, 97.64% (Max). Chiral SFC: (Method G) Rt. 1.69 min, 100% (Max)

Diastereomer 4

To a stirred solution of diastereomer 4 of methyl 3-((3-butyl-3-methyl-7-(methylthio)-1,1-dioxido-5-phenyl-2,3,4,5-tetrahydro-1,5-benzothiazepin-8-yl)oxy)-2-hydroxy-2-methylpropanoate (Intermediate 56; 60 mg, 0.11 mmol) in 1,4-dioxane (2 mL), dilute HCl (6 N, 3 mL) was added and the reaction mixture was stirred for 4 hours at 80° C. After completion of the reaction (monitored by TLC), the reaction mixture was diluted with ice-cold water (5 mL) and the aqueous layer was extracted with EtOAc (2×10 mL). The combined organic layer was washed with water (10 mL) and brine (10 mL) and dried over anhydrous $Na_2SO_4$. The organic part was filtered and concentrated under vacuum. The resulting crude material was purified by Isolera column chromatography (eluent: 50-60% EtOAc/PE; silica gel: 230-400 mesh) to afford the title compound. Yield: 33% (25 mg, white solid).

$^1$H NMR (400 MHz, DMSO-$d_6$): δ 12.80 (s, 1H), 7.34 (s, 1H), 7.19 (t, J=7.6 Hz, 2H), 6.92 (d, J=7.6 Hz, 2H), 6.80 (t, J=7.6 Hz, 2H), 5.40 (s, 1H), 4.16-4.11 (m, 2H), 3.79 (bs, 2H), 3.34-3.18 (m, 2H), 2.20 (s, 3H), 1.48 (s, 3H), 1.43-1.25 (m, 6H), 1.01 (s, 3H), 0.86-0.82 (m, 3H). LCMS: (Method A) 508.1 (M$^+$+H), Rt. 2.49 min, 94.27% (Max). HPLC: (Method B) Rt. 5.18 min, 96.78% (Max). Chiral SFC: (Method G) Rt. 2.75 min, 97.3% (Max).

The absolute configuration of the four diastereomers is not known.

Example 34

3-((3-butyl-3-ethyl-7-(methylthio)-1,1-dioxido-5-phenyl-2,3,4,5-tetrahydro-1,5-benzothiazepin-8-yl)oxy)-2-fluoro-2-methylpropanoic acid

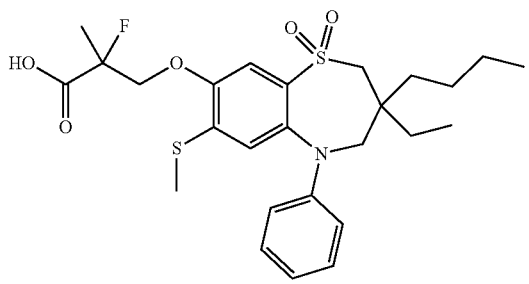 [SMILES: CCCCC1(CC)CN(c2ccccc2)c2cc(SC)c(OCC(C)(F)C(=O)O)cc2S(=O)(=O)C1]

To a stirred solution of methyl 3-((3-butyl-3-ethyl-7-(methylthio)-1,1-dioxido-5-phenyl-2,3,4,5-tetrahydro-1,5-benzothiazepin-8-yl)oxy)-2-fluoro-2-methylpropanoate (Intermediate 59; 40 mg, 0.07 mmol) in a mixture of 1,4-dioxane and water (7:3, 10 mL), lithium hydroxide (6.5 mg, 0.14 mmol) was added and the reaction mixture was stirred for 1 hour at room temperature. After completion of the reaction (monitored by TLC), the reaction mixture was acidified with dilute HCl (1.5 N, pH4) and diluted with ice-cold water (2 mL). The aqueous layer was extracted with EtOAc (2×5 mL) and the combined organic layer was washed with water (5 mL) and brine (5 mL). The organic part was dried over anhydrous $Na_2SO_4$, filtered and concentrated under vacuum. The resulting crude material was purified by Isolera column chromatography (eluent: 9% MeOH/DCM; silica gel: 230-400 mesh) and the obtained residue was re-purified by prep HPLC (Method A) to afford the title compound. Yield: 13% (5 mg, white solid).

$^1$H NMR (400 MHz, DMSO-$d_6$): 7.35 (s, 1H), 7.22 (t, J=8.4 Hz, 2H), 6.99 (d, J=7.2 Hz, 2H), 6.86 (t, J=7.6 Hz, 1H), 6.70 (s, 1H), 4.48-4.37 (m, 2H), 3.70 (s, 2H), 3.27 (s, 2H), 2.16 (s, 3H), 1.65-1.54 (m, 3H), 1.50-1.35 (m, 2H), 1.34-1.29 (m, 2H), 1.27-0.98 (m, 4H), 0.81-0.71 (m, 6H). LCMS: (Method E) 524.2 (M$^+$+H), Rt. 2.85 min, 97.85% (Max). HPLC: (Method B) Rt. 5.77 min, 98.44% (Max).

Example 35

3-((3-butyl-3-ethyl-7-(methylthio)-1,1-dioxido-5-phenyl-2,3,4,5-tetrahydro-1,5-benzothiazepin-8-yl)oxy)-2-fluoro-2-methylpropanoic Acid (Individual Diastereomers)

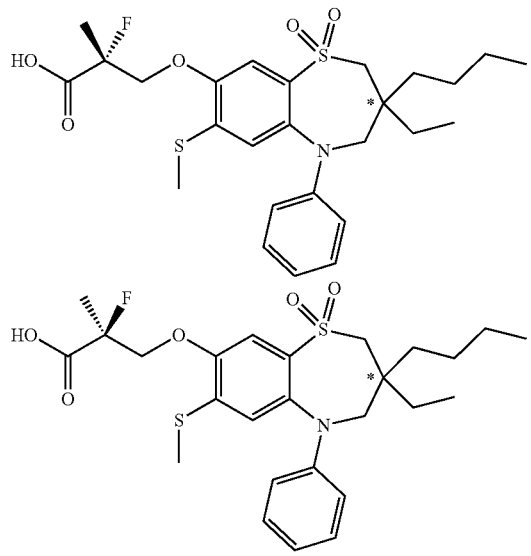

\* the indicated carbons are each R or are each S

Diastereomer 1

To a stirred solution of diastereomer 1 of methyl 3-((3-butyl-3-ethyl-7-(methylthio)-1,1-dioxido-5-phenyl-2,3,4,5-tetrahydro-1,5-benzothiazepin-8-yl)oxy)-2-fluoro-2-methylpropanoate (Intermediate 60; 50 mg, 0.09 mmol) in a mixture of 1,4-dioxane and water (7:3, 10 mL), lithium hydroxide (7.8 mg, 0.18 mmol) was added and the reaction mixture was stirred for 1 hour at room temperature. After completion of the reaction (monitored by TLC), the reaction mixture was quenched with dilute HCl (1.5 N, 1 mL) and diluted with water (2 mL). The aqueous layer was extracted with EtOAc (2×4 mL) and the combined organic layer was washed with water (5 mL) and brine (5 mL). The organic part was dried over anhydrous $Na_2SO_4$, filtered and concentrated under vacuum to afford the title compound. Yield: 68% (33 mg, off-white solid).

$^1$H NMR (400 MHz, DMSO-$d_6$): δ 13.51 (bs, 1H), 7.39 (s, 1H), 7.23 (t, J=7.6 Hz, 2H), 6.99 (d, J=7.6 Hz, 2H), 6.87 (t, J=7.2 Hz, 1H), 6.70 (s, 1H), 4.49-4.37 (m, 2H), 3.69 (bs, 2H), 3.27 (s, 2H), 2.16 (s, 3H), 1.61-1.54 (m, 4H), 1.48-1.41 (m, 1H), 1.39-1.28 (m, 2H), 1.23-0.97 (m, 4H), 0.81-0.71 (m, 6H). LCMS: (Method E) 523.8 (M$^+$+H), Rt. 3.02 min, 99.25% (Max). HPLC: (Method B) Rt. 5.80 min, 99.45% (Max). Chiral SFC: (Method H) Rt. 4.84 min, 99.18% (Max).

Diastereomer 2

To a stirred solution of diastereomer 2 methyl 3-((3-butyl-3-ethyl-7-(methylthio)-1,1-dioxido-5-phenyl-2,3,4,5-tetrahydro-1,5-benzothiazepin-8-yl)oxy)-2-fluoro-2-methylpropanoate (Intermediate 60; 55 mg, 0.10 mmol) in a mixture of 1,4-dioxane and water (7:3, 10 mL), lithium hydroxide (8.6 mg, 0.18 mmol) was added and the reaction mixture was stirred for 1 hour at room temperature. After completion of the reaction (monitored by TLC), the reaction mixture was quenched with dilute HCl (1.5 N, 1 mL) and diluted with water (2 mL). The aqueous layer was extracted with EtOAc (2×4 mL).

The combined organic layer was washed with water (5 mL) and brine (5 mL) and dried over anhydrous $Na_2SO_4$. The organic part was filtered and concentrated under vacuum to afford the title compound. Yield: 62% (33 mg, off-white solid). $^1$H NMR (400 MHz, DMSO-$d_6$): δ 13.52 (s, 1H), 7.35 (s, 1H), 7.22 (t, J=8.0 Hz, 2H), 6.99 (d, J=7.6 Hz, 2H), 6.88 (t, J=7.2 Hz, 1H), 6.70 (s, 1H), 4.48-4.34 (m, 2H), 3.71 (bs, 2H), 3.27 (s, 2H), 2.16 (s, 3H), 1.62-1.57 (m, 4H), 1.37-1.24 (m, 3H), 1.18-0.95 (m, 4H), 0.79-0.72 (m, 6H). LCMS: (Method E) 523.8 (M$^+$+H), Rt. 3.02 min, 99.47% (Max). HPLC: (Method B) Rt. 5.80 min, 99.60% (Max). Chiral SFC: (Method H) Rt. 5.52 min, 98.89% (Max).

The absolute configuration of the two diastereomers is not known.

Example 36

O—((S)-3-butyl-3-ethyl-7-(methylthio)-1,1-dioxido-5-phenyl-2,3,4,5-tetrahydro-1,5-benzothiazepin-8-yl)-D-serine and O—((R)-3-butyl-3-ethyl-7-(methylthio)-1,1-dioxido-5-phenyl-2,3,4,5-tetrahydro-1,5-benzothiazepin-8-yl)-D-serine

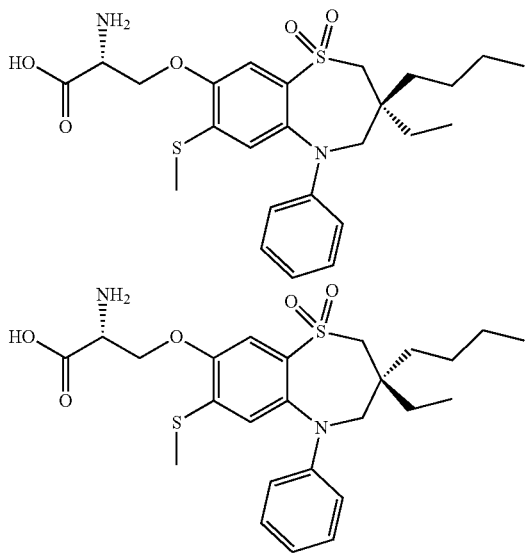

Diastereomer 1

To a stirred solution of diastereomer 1 of methyl O-(3-butyl-3-ethyl-7-(methylthio)-1,1-dioxido-5-phenyl-2,3,4,5-tetrahydro-1,5-benzothiazepin-8-yl)-D-serinate (Intermediate 63; 400 mg, 0.77 mmol) in a mixture of 1,4-dioxane and water (7:3, 10 mL), lithium hydroxide (64 mg, 1.53 mmol) was added and the reaction mixture was stirred for 2 hours at room temperature. After completion of the reaction (monitored by TLC), the reaction mixture was diluted with water (5 mL) and the aqueous layer was extracted with DCM (2×15 mL). The combined organic layer was washed with water (15 mL) and brine (15 mL) and dried over anhydrous $Na_2SO_4$. The organic part was filtered and concentrated under vacuum. The resulting crude material was purified by Isolera column chromatography (eluent: 24% MeOH/DCM; silica gel: 230-400 mesh). The obtained residue was re-purified by prep HPLC using (Method A) to afford the title compound. Yield: 10% (38 mg, white solid).

$^1$H NMR (400 MHz, DMSO-$d_6$): 7.89-7.77 (m, 2H), 7.36 (s, 1H), 7.23 (t, J=7.2 Hz, 2H), 7.00 (d, J=7.2 Hz, 2H), 6.87 (t, J=7.2 Hz, 1H), 6.70 (s, 1H), 4.44-4.41 (m, 1H), 4.27-4.22 (m, 1H), 3.76 (s, 2H), 3.61-3.51 (m, 1H), 3.28 (s, 2H), 2.17 (s, 3H), 1.64-1.31 (m, 4H), 1.21-0.95 (m, 4H), 0.88-0.68 (m, 6H). LCMS: (Method F) 507.1 (M$^+$+H), Rt. 2.60 min, 93.95% (Max). HPLC: (Method B) Rt. 4.55 min, 96.16% (Max).

Diastereomer 2

To a stirred solution of diastereomer 2 of methyl O-(3-butyl-3-ethyl-7-(methylthio)-1,1-dioxido-5-phenyl-2,3,4,5-tetrahydro-1,5-benzothiazepin-8-yl)-D-serinate (Intermediate 63; 370 mg, 0.71 mmol) in a mixture of 1,4-dioxane and water (7:3, 10 mL), lithium hydroxide (59 mg, 1.42 mmol) was added and the reaction mixture was stirred for 2 hours at room temperature. After completion of the reaction (monitored by TLC), the reaction mixture was diluted with water (5 mL) and the aqueous layer was extracted with DCM (2×15 mL). The combined organic layer was washed with water (15 mL) and brine (15 mL) and dried over anhydrous $Na_2SO_4$. The organic part was filtered and concentrated under vacuum. The resulting crude material was purified by Isolera column chromatography (eluent: 24% MeOH/DCM; silica gel: 230-400 mesh) to afford the title compound. Yield: 14% (53 mg, white solid).

$^1$H NMR (400 MHz, DMSO-$d_6$): 7.35 (s, 1H), 7.22 (t, J=7.6 Hz, 2H), 7.00 (d, J=7.6 Hz, 2H), 6.87 (t, J=7.2 Hz, 1H), 6.71 (s, 1H), 4.44-4.41 (m, 1H), 4.27-4.22 (m, 1H), 3.75 (s, 2H), 3.61-3.48 (m, 1H), 3.28 (s, 2H), 2.17 (s, 3H), 1.64-1.31 (m, 4H), 1.21-0.95 (m, 4H), 0.88-0.68 (m, 6H). LCMS: (Method F) 507.2 (M$^+$+H), Rt. 2.34 min, 96.63% (Max). HPLC: (Method B) Rt. 4.55 min, 94.35% (Max).

The absolute configuration of the two diastereomers is not known.

Example 37

3-((3-butyl-3-ethyl-5-(4-fluorophenyl)-7-(methylthio)-1,1-dioxido-2,3,4,5-tetrahydro-1,5-benzothiazepin-8-yl)oxy)propanoic acid

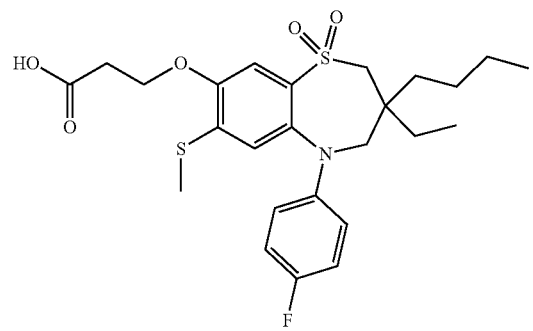 [SMILES: CCCCC1(CC)CN(c2ccc(F)cc2)c2cc(SC)c(OCCC(=O)O)cc2S(=O)(=O)C1]

To a stirred solution of 3-butyl-3-ethyl-5-(4-fluorophenyl)-8-hydroxy-7-(methylthio)-2,3,4,5-tetrahydro-1,5-benzothiazepine 1,1-dioxide (Intermediate 70; 100 mg, 0.22 mmol) in THF (3 mL) at 0° C., potassium tert-butoxide (25 mg, 0.22 mmol) was added and the reaction mixture was stirred for 15 minutes. A solution of β-propiolactone (15 mg, 0.22 mmol) in THF (1 mL) was then added dropwise and the reaction mixture was stirred for 16 hours at room temperature. After completion of the reaction (monitored by TLC), the reaction mixture was quenched with dilute HCl (1.5 N, 1 mL) and diluted with water (1 mL). The aqueous layer was extracted with EtOAc (2×5 mL). The combined organic layer was washed with water (5 mL) and brine (5 mL) and dried over anhydrous Na$_2$SO$_4$. The organic part was filtered, concentrated under vacuum and the resulting crude material was purified by Prep HPLC (Method A). The purified fractions were concentrated under vacuum and the obtained residue was dissolved in EtOAc (10 mL). The EtOAc layer was washed with water (5 mL) and brine (5 mL) and dried over anhydrous Na$_2$SO$_4$. The organic part was filtered and concentrated under vacuum to afford the title compound. Yield: 22% (25 mg, white solid).

$^1$H NMR (400 MHz, DMSO-d$_6$): δ 12.42 (s, 1H), 7.30 (s, 1H), 7.08-7.05 (m, 4H), 6.62 (s, 1H), 4.26 (t, J=5.6 Hz, 2H), 3.73-3.62 (m, 2H), 3.30-3.26 (m, 2H), 2.73-2.60 (m, 2H), 2.15 (s, 3H), 1.38-1.37 (m, 2H), 1.35-1.33 (m, 2H), 1.24-1.12 (m, 4H), 0.78-0.72 (m, 6H). LCMS: (Method E) 510.0 (M$^+$+H), Rt. 3.00 min, 98.19% (Max). HPLC: (Method B) Rt. 5.66 min, 98.97% (Max).

Example 38

(S)-3-((3-butyl-3-ethyl-5-(4-fluorophenyl)-7-(methylthio)-1,1-dioxido-2,3,4,5-tetrahydro-1,5-benzothiazepin-8-yl)oxy)propanoic acid and (R)-3-((3-butyl-3-ethyl-5-(4-fluorophenyl)-7-(methylthio)-1,1-dioxido-2,3,4,5-tetrahydro-1,5-benzothiazepin-8-yl)oxy)propanoic acid

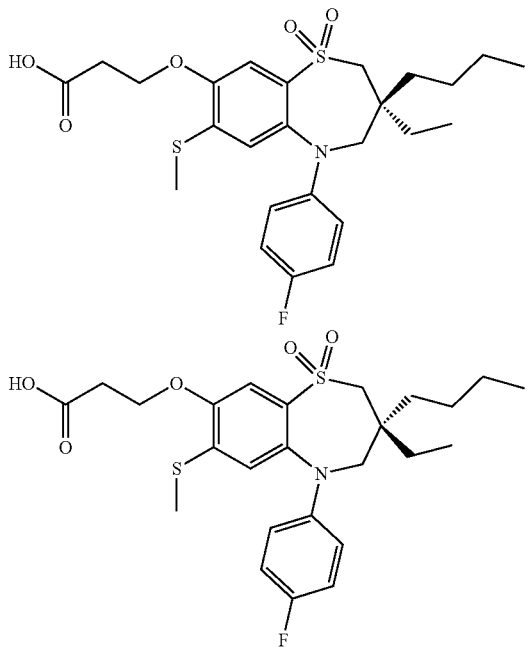

Enantiomer 1

To a stirred solution of enantiomer 1 of 3-butyl-3-ethyl-5-(4-fluorophenyl)-8-hydroxy-7-(methylthio)-2,3,4,5-tetrahydro-1,5-benzothiazepine 1,1-dioxide (Intermediate 70; 100 mg, 0.22 mmol) in THF (3 mL) at 0° C., potassium tert-butoxide (25 mg, 0.22 mmol) was added and the reaction mixture was stirred for 15 minutes. A solution of β-propiolactone (15 mg, 0.22 mmol) in THF (1 mL) was then added dropwise and the reaction mixture was stirred for 16 hours at room temperature. After completion of the reaction (monitored by TLC), the reaction mixture was quenched with dilute HCl (1.5 N, 1 mL) and diluted with water (1 mL). The aqueous layer was extracted with EtOAc (2×5 mL), and the combined organic layer was washed with water (5 mL) and brine (5 mL). The organic part was dried over anhydrous Na$_2$SO$_4$, filtered and concentrated under vacuum. The resulting crude material was purified by Isolera column chromatography (eluent: 40% EtOAc/PE; silica gel: 230-400 mesh) to afford the title compound. Yield: 26% (30 mg, off-white solid).

$^1$H NMR (400 MHz, DMSO-d$_6$): δ 12.45 (s, 1H), 7.31 (s, 1H), 7.08-7.06 (m, 4H), 6.62 (s, 1H), 4.27 (t, J=6.0 Hz, 2H), 3.82-3.67 (m, 2H), 3.26-3.29 (m, 2H), 2.72 (t, J=6.0 Hz, 2H), 2.15 (s, 3H), 1.60-1.50 (m, 2H), 1.38-1.31 (m, 2H), 1.16-1.16 (m, 4H), 0.78-0.76 (m, 6H). LCMS: (Method E) 510.0 (M$^+$+H), Rt. 3.01 min, 95.68% (Max). HPLC: (Method B) Rt. 6.02 min, 97.25% (Max). Chiral HPLC: (Method H) Rt. 2.98 min, 99.49% (Max).

Enantiomer 2

To a stirred solution of enantiomer 2 of 3-butyl-3-ethyl-5-(4-fluorophenyl)-8-hydroxy-7-(methylthio)-2,3,4,5-tetrahydro-1,5-benzothiazepine 1,1-dioxide (Intermediate 70; 100 mg, 0.22 mmol) in THF (3 mL) at 0° C., potassium tert-butoxide (25 mg, 0.22 mmol) was added and the reaction mixture was stirred for 15 minutes. A solution of β-propiolactone (15 mg, 0.22 mmol) in THF (1 mL) was then added dropwise and the reaction mixture was stirred for 16 hours at room temperature. After completion of the reaction (monitored by TLC), the reaction mixture was quenched with dilute HCl (1.5 N, 1 mL) and diluted with water (1 mL). The aqueous layer was extracted with EtOAc (2×5 mL), and the combined organic layer was washed with water (5 mL) and brine (5 mL). The organic part was dried over anhydrous Na$_2$SO$_4$, filtered and concentrated under vacuum. The resulting crude material was purified by Isolera column chromatography (eluent: 40% EtOAc/PE; silica gel: 230-400 mesh) to afford the title compound. Yield: 9% (10 mg, off-white solid).

$^1$H NMR (400 MHz, DMSO-d$_6$): δ 12.45 (s, 1H), 7.30 (s, 1H), 7.08-7.06 (m, 4H), 6.62 (s, 1H), 4.26 (t, J=5.6 Hz, 2H), 3.82-3.67 (m, 2H), 3.26-3.29 (m, 2H), 2.72 (t, J=7.6 Hz, 2H), 2.15 (s, 3H), 1.52-1.51 (m, 2H), 1.38-1.31 (m, 2H), 1.24-1.11 (m, 4H), 0.78-0.76 (m, 6H). LCMS: (Method E) 510.0 (M$^+$+H), Rt. 3.01 min, 91.43% (Max). HPLC: (Method B) Rt. 6.02 min, 93.54% (Max). Chiral HPLC: (Method H) Rt. 3.32 min, 98.84% (Max).

The absolute configuration of the two enantiomers is not known.

Example 39

3-((3-butyl-3-ethyl-7-(methylthio)-1,1-dioxido-5-phenyl-2,3,4,5-tetrahydro-1,5-benzothiazepin-8-yl)oxy)-2-hydroxypropanoic acid

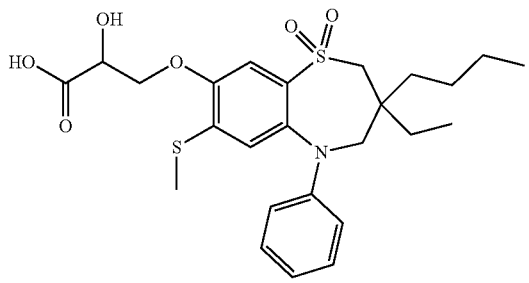

To a solution of methyl 3-((3-butyl-3-ethyl-7-(methylthio)-1,1-dioxido-5-phenyl-2,3,4,5-tetrahydro-1,5-benzothiazepin-8-yl)oxy)-2-hydroxypropanoate (Intermediate 71; 300 mg, 0.57 mmol) in 1,4-dioxane (5 mL), dilute HCl (6N, 9 mL) was added dropwise and the reaction mixture was heated for 4 hours at 80° C. After completion of the reaction (monitored by TLC), the reaction mixture was extracted with EtOAc (2×10 mL) and the combined organic layer was washed with water (10 mL) and brine (10 mL). The organic part was dried over anhydrous $Na_2SO_4$, filtered and concentrated under vacuum. The resulting crude material was purified by Isolera column chromatography (eluent: 8-10% MeOH/DCM; silica gel: 230-400 mesh) and the obtained material was re-purified by Prep HPLC (Method A). The purified fractions were concentrated under vacuum and the obtained residue was dissolved in EtOAc (10 mL). The organic layer was washed with water (5 mL) and brine (5 mL) and dried over anhydrous $Na_2SO_4$. The organic part was filtered and concentrated under vacuum to afford the title compound. Yield: 37% (110 mg, white solid).

$^1$H NMR (400 MHz, DMSO-$d_6$): δ 7.35 (s, 1H), 7.21 (t, J=8.0 Hz, 2H), 6.97 (d, J=7.2 Hz, 2H), 6.85 (t, J=7.2 Hz, 1H), 6.70 (s, 1H), 4.31 (s, 1H), 4.12 (s, 2H), 3.95-3.55 (m, 2H), 3.26 (s, 2H), 2.16 (s, 3H), 1.65-1.45 (m, 1H), 1.50-1.35 (m, 1H), 1.40-1.30 (m, 2H), 1.22-1.03 (m, 4H), 0.79-0.74 (m, 6H). LCMS: (Method F) 508.2 (M$^+$+H), Rt. 2.57 min, 98.77% (Max). HPLC: (Method B) Rt. 5.28 min, 98.17% (Max).

Example 40

3-((3-butyl-3-ethyl-7-(methylthio)-1,1-dioxido-5-phenyl-2,3,4,5-tetrahydro-1,5-benzothiazepin-8-yl)oxy)-2-hydroxypropanoic Acid (Individual Diastereomers)

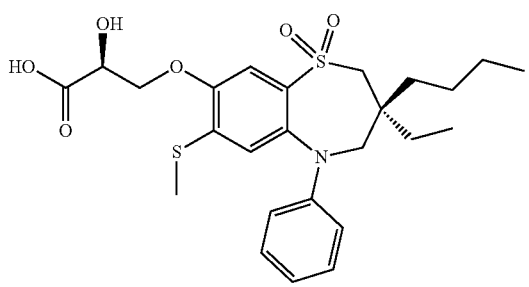

-continued

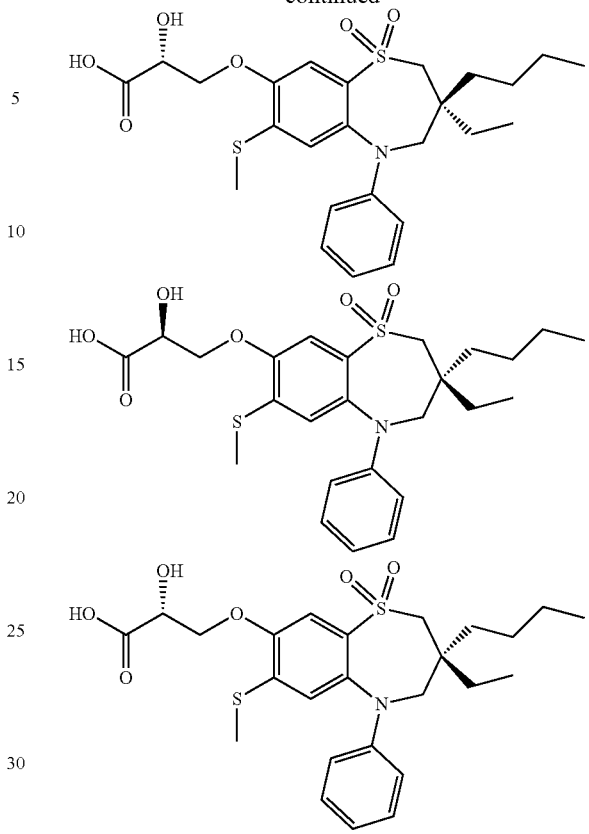

Diastereomer 1

To a solution of diastereomer 1 of methyl 3-((3-butyl-3-ethyl-7-(methylthio)-1,1-dioxido-5-phenyl-2,3,4,5-tetrahydro-1,5-benzothiazepin-8-yl)oxy)-2-hydroxypropanoate (Intermediate 72; 100 mg, 0.19 mmol) in 1,4-dioxane (1 mL), dilute HCl (6N, 2 mL) was added dropwise and the reaction mixture was heated for 16 hours at 80° C. After completion of the reaction (monitored by TLC), the reaction mixture was diluted with water (2 mL) and the aqueous layer was extracted with EtOAc (2×5 mL).

The combined organic layer was washed with water (5 mL) and brine (5 mL) and dried over anhydrous $Na_2SO_4$. The organic part was filtered and concentrated under vacuum. The resulting crude material was purified by Isolera column chromatography (eluent: 5-10% MeOH/DCM; silica gel: 230-400 mesh) to afford the title compound.

Diastereomers 2, 3 and 4 of the title compound were obtained following the same procedure, starting from 100 mg of diastereomers 2, 3 and 4 of Intermediate 72, respectively.

Diastereomer 1: Yield: 56% (55 mg, white solid). $^1$H NMR (400 MHz, DMSO-$d_6$): δ 7.36 (s, 1H), 7.22 (t, J=8.4 Hz, 2H), 6.98 (d, J=8.0 Hz, 2H), 6.85 (t, J=7.2 Hz, 1H), 6.70 (s, 1H), 4.31 (t, J=7.6 Hz, 1H), 4.22-4.14 (m, 2H), 3.68 (s, 2H), 3.26 (s, 2H), 2.16 (s, 3H), 1.62-1.50 (m, 2H), 1.40-1.25 (m, 2H), 1.18-1.03 (m, 4H), 0.85-0.65 (m, 6H). LCMS: (Method E) 508.0 (M$^+$+H), Rt. 2.89 min, 97.46% (Max). HPLC: (Method B) Rt. 5.34 min, 99.12% (Max). Chiral SFC: (Method I) Rt. 1.67 min, 97.58% (Max).

Diastereomer 2: Yield: 61% (60 mg, white solid). $^1$H NMR (400 MHz, DMSO-$d_6$): δ 7.35 (s, 1H), 7.22 (t, J=8.0 Hz, 2H), 6.98 (d, J=8.0 Hz, 2H), 6.86 (t, J=7.2 Hz, 1H), 6.70 (s, 1H), 4.33 (d, J=8.0 Hz, 1H), 4.20-4.10 (m, 2H), 3.70 (s, 2H), 3.26 (s, 2H), 2.16 (s, 3H), 1.65-1.40 (m, 2H), 1.40-1.28 (m, 2H), 1.20-0.97 (m, 4H), 0.80-0.65 (m, 6H). LCMS: (Method E) 508.0 (M⁺+H), Rt. 2.89 min, 97.42% (Max). HPLC: (Method B) Rt. 5.34 min, 99.94% (Max). Chiral SFC: (Method I) Rt. 2.49 min, 99.18% (Max).

Diastereomer 3: Yield: 56% (55 mg, white solid). ¹H NMR (400 MHz, DMSO-d₆): δ 7.36 (s, 1H), 7.22 (t, J=8.4 Hz, 2H), 6.98 (d, J=7.6 Hz, 2H), 6.85 (t, J=7.2 Hz, 1H), 6.70 (s, 1H), 4.31 (t, J=7.6 Hz, 1H), 4.21-4.13 (m, 2H), 3.68 (s, 2H), 3.27 (s, 2H), 2.16 (s, 3H), 1.65-1.40 (m, 2H), 1.39-1.28 (m, 2H), 1.20-1.03 (m, 4H), 0.79-0.74 (m, 6H). LCMS: (Method E) 508.1 (M⁺+H), Rt. 2.88 min, 99.97% (Max). HPLC: (Method B) Rt. 5.34 min, 98.37% (Max). Chiral SFC: (Method H) Rt. 2.05 min, 99.25% (Max).

Diastereomer 4: Yield: 56% (55 mg, white solid). ¹H NMR (400 MHz, DMSO-d₆): δ 7.36 (s, 1H), 7.22 (t, J=8.0 Hz, 2H), 6.98 (d, J=8.0 Hz, 2H), 6.86 (t, J=7.2 Hz, 1H), 6.70 (s, 1H), 4.31 (q, J=2.4 Hz, 1H), 4.24-4.14 (m, 2H), 3.70 (s, 2H), 3.27 (s, 2H), 2.16 (s, 3H), 1.62-1.40 (m, 2H), 1.40-1.28 (m, 2H), 1.20-0.95 (m, 4H), 0.79-0.74 (m, 6H). LCMS: (Method E) 508.0 (M⁺+H), Rt. 2.87 min, 96.68% (Max). HPLC: (Method B) Rt. 5.29 min, 98.11% (Max). Chiral SFC: (Method H) Rt. 3.10 min, 99.51% (Max).

The absolute configuration of the four diastereomers is not known.

Example 41

3-((3-Butyl-3-ethyl-5-(4-fluorophenyl)-7-(methylthio)-1,1-dioxido-2,3,4,5-tetrahydro-1,5-benzothiazepin-8-yl)oxy)-2-hydroxypropanoic acid

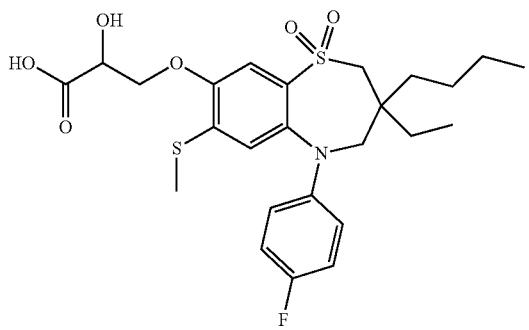 [SMILES: CCCCC1(CC)CN(c2ccc(F)cc2)c2cc(SC)c(OCC(O)C(=O)O)cc2S(=O)(=O)C1]

To a solution of methyl 3-((3-butyl-3-ethyl-5-(4-fluorophenyl)-7-(methylthio)-1,1-dioxido-2,3,4,5-tetrahydro-1,5-benzothiazepin-8-yl)oxy)-2-hydroxypropanoate (Intermediate 73; 60 mg, 0.11 mmol) in 1,4-dioxane (1 mL), dilute HCl (6 N, 2 mL) was added and the reaction mixture was heated for 2 hours at 80° C. After completion of the reaction (monitored by TLC), the reaction mixture was extracted with EtOAc (2×4 mL) and the combined organic layer was washed with water (4 mL) and brine (4 mL). The organic part was dried over anhydrous Na₂SO₄, filtered and concentrated under vacuum. The resulting crude material was triturated with hexane to afford the title compound. Yield: 86% (30 mg, brown solid).

¹H NMR (400 MHz, DMSO-d₆): δ 12.87 (s, 1H), 7.34 (s, 1H), 7.08-7.06 (m, 4H), 5.60 (s, 1H), 4.36-4.27 (m, 1H), 4.24 (t, J=3.6 Hz, 2H), 3.75-3.68 (m, 2H), 3.33-3.29 (m, 2H), 2.16 (s, 3H), 1.58-1.51 (m, 2H), 1.36-1.35 (m, 2H), 1.10-1.08 (m, 4H), 0.78-0.76 (m, 6H). LCMS: (Method E) 526.0 (M⁺+H), Rt. 2.88 min, 94.37% (Max). HPLC: (Method B) Rt. 5.31 min, 92.62% (Max).

Example 42

3-((3-Butyl-3-ethyl-5-(4-fluorophenyl)-7-(methylthio)-1,1-dioxido-2,3,4,5-tetrahydro-1,5-benzothiazepin-8-yl)oxy)-2-hydroxypropanoic Acid (Individual Diastereomers)

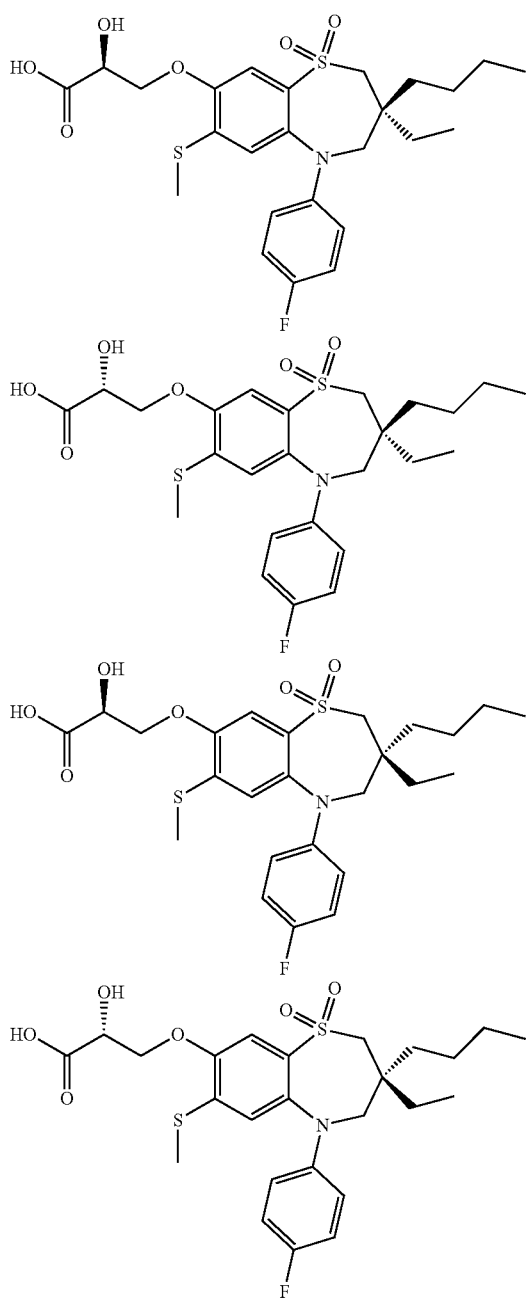

To a solution of diastereomer 1 of methyl 3-((3-butyl-3-ethyl-5-(4-fluorophenyl)-7-(methylthio)-1,1-dioxido-2,3,4,5-tetrahydro-1,5-benzothiazepin-8-yl)oxy)-2-hydroxypropanoate (Intermediate 74; 30 mg, 0.05 mmol) in 1,4-dioxane (1 mL), dilute HCl (6 N, 2 mL) was added and the reaction mixture was heated for 2 hours at 60° C. After completion of the reaction (monitored by TLC), the reaction mixture was extracted with EtOAc (2×4 mL). The combined organic layer was washed with water (4 mL) and brine (4 mL) and dried over anhydrous Na$_2$SO$_4$. The organic part was filtered and concentrated under vacuum. The resulting crude material was triturated with hexane, filtered and dried under vacuum to afford the title compound.

Diastereomers 2, 3 and 4 of the title compound were obtained following the same procedure, starting from 30, 10 and 10 mg of diastereomers 2, 3 and 4 of Intermediate 74, respectively.

Diastereomer 1: Yield: 10% (3 mg, white solid). $^1$H NMR (400 MHz, CDCl$_3$): δ 7.45 (s, 1H), 7.30-7.27 (m, 4H), 6.55 (s, 1H), 4.69-4.58 (m, 1H), 4.51-4.40 (m, 2H), 3.70-3.65 (m, 2H), 3.21-3.17 (m, 2H), 2.17 (s, 3H), 1.61-1.44 (m, 4H), 1.36-1.31 (m, 2H), 1.30-1.21 (m, 2H), 0.85-0.79 (m, 6H). LCMS: (Method E) 526.0 (M$^+$+H), Rt. 2.88 min, 92.83% (Max). HPLC: (Method B) Rt. 5.37 min, 96.85% (Max), Chiral SFC: (Method G) Rt. 11.85 min, 100% (Max).

Diastereomer 2: Yield: 17% (5 mg, white solid). $^1$H NMR (400 MHz, DMSO-d$_6$): δ 7.34 (s, 1H), 7.08-7.06 (m, 4H), 6.62 (s, 1H), 4.28-4.27 (m, 3H), 3.68-3.50 (m, 2H), 3.33-3.28 (m, 2H), 2.15 (s, 3H), 1.50-1.38 (m, 2H), 1.36-1.31 (m, 2H), 1.23-1.02 (m, 4H), 0.77-0.74 (m, 6H). LCMS: (Method E) 526.0 (M$^+$+H), Rt. 2.87 min, 88.49% (Max). HPLC: (Method B) Rt. 5.37 min, 90.21% (Max), Chiral SFC: (Method G) Rt. 14.73 min, 93.17% (Max).

Diastereomer 3: Yield: 42% (4 mg, white solid). $^1$H NMR (400 MHz, CDCl$_3$): δ 7.44 (s, 1H), 7.08-6.98 (m, 4H), 6.55 (s, 1H), 4.62-4.60 (m, 1H), 4.46-4.43 (m, 2H), 3.78-3.68 (m, 2H), 3.18-3.10 (m, 2H), 2.17 (s, 3H), 1.88-1.61 (m, 2H), 1.50-1.42 (m, 2H), 1.22-1.11 (m, 4H), 0.84-0.83 (m, 6H). LCMS: (Method E) 526.0 (M$^+$+H), Rt. 2.88 min, 95.50% (Max). HPLC: (Method B) Rt. 5.29 min, 93.24% (Max). Chiral SFC: (Method G) Rt. 4.02 min, 76.11% (Max).

Diastereomer 4: Yield: 40% (5 mg, white solid). $^1$H NMR (400 MHz, DMSO-d$_6$): δ 7.34 (s, 1H), 7.08-7.06 (m, 4H), 6.62 (s, 1H), 4.34-4.30 (m, 1H), 4.28-4.21 (m, 2H), 3.68-3.50 (m, 2H), 3.33-3.31 (m, 2H), 2.15 (s, 3H), 1.60-1.51 (m, 2H), 1.38-1.32 (m, 2H), 1.14-1.01 (m, 4H), 0.77-0.72 (m, 6H). LCMS: (Method E) 526.2 (M$^+$+H), Rt. 5.05 min, 90.29% (Max). HPLC: (Method B) Rt. 5.37 min, 91.88% (Max), Chiral SFC: (Method G) Rt. 5.31 min, 94.4% (Max).

The absolute configuration of the four diastereomers is not known.

Example 43

3-((3-butyl-3-ethyl-7-methoxy-1,1-dioxido-5-phenyl-2,3,4,5-tetrahydro-1,5-benzothiazepin-8-yl)oxy)propanoic acid

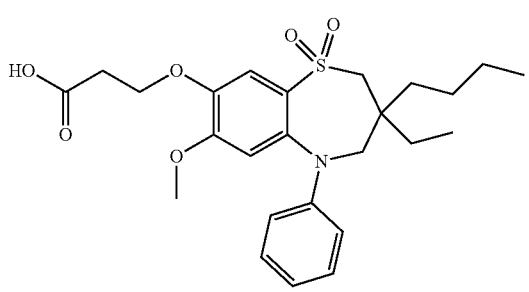 [SMILES: CCCCC1(CC)CN(c2ccccc2)c2cc(OC)c(OCCC(=O)O)cc2S(=O)(=O)C1]

To a stirred solution of 3-butyl-3-ethyl-8-hydroxy-7-methoxy-5-phenyl-2,3,4,5-tetrahydro-1,5-benzothiazepine 1,1-dioxide (Intermediate 75; 200 mg, 0.49 mmol) in THF (3 mL) at 0° C., potassium tert-butoxide (62 mg, 0.54 mmol) was added and the reaction mixture was stirred for 15 minutes. A solution of β-propiolactone (35 mg, 0.49 mmol) in THF (1 mL) was then added dropwise and the reaction mixture was stirred for 16 hours at room temperature. After completion of the reaction (monitored by TLC), the reaction mixture was quenched with dilute HCl (1.5 N, 1 mL) and diluted with water (1 mL). The aqueous layer was extracted with EtOAc (2×5 mL) and the combined organic layer was washed with water (5 mL) and brine (5 mL). The organic part was dried over anhydrous Na$_2$SO$_4$, filtered and concentrated under vacuum. The resulting crude material was purified by Isolera column chromatography (eluent: 70% EtOAc/PE; silica gel: 230-400 mesh) to afford the title compound.

Yield: 8% (12 mg, off-white solid).

$^1$H NMR (400 MHz, DMSO-d$_6$): δ 7.33 (s, 1H), 7.21 (t, J=8.4 Hz, 2H), 6.98 (d, J=7.6 Hz, 2H), 6.84 (t, J=7.2 Hz, 1H), 6.54 (s, 1H), 4.17 (t, J=6.4 Hz, 2H), 3.72-3.61 (m, 5H), 3.23 (s, 2H), 2.60 (s, 2H), 1.54-1.30 (m, 4H), 1.24-1.14 (m, 4H), 1.10-1.03 (m, 6H). LCMS: (Method E) 476.0 (M$^+$+H), Rt. 2.91 min, 95.24% (Max). HPLC: (Method B) Rt. 5.32 min, 94.80% (Max).

Example 44

(S)-3-((3-Butyl-3-ethyl-7-methoxy-1,1-dioxido-5-phenyl-2,3,4,5-tetrahydro-1,5-benzothiazepin-8-yl)oxy)propanoic acid and (R)-3-((3-butyl-3-ethyl-7-methoxy-1,1-dioxido-5-phenyl-2,3,4,5-tetrahydro-1,5-benzothiazepin-8-yl)oxy)propanoic acid

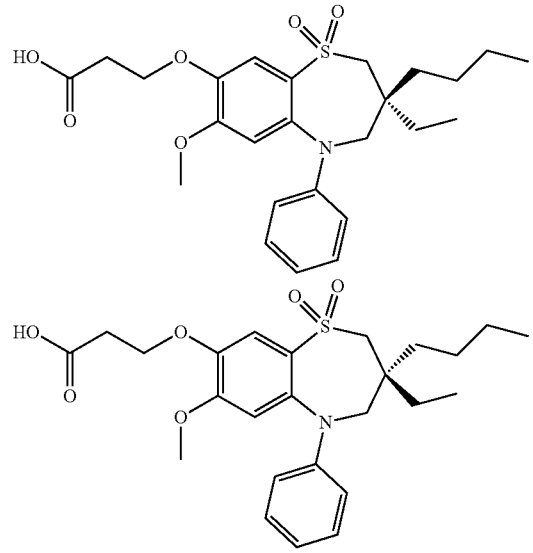

The two enantiomers of racemic 3-((3-butyl-3-ethyl-7-methoxy-1,1-dioxido-5-phenyl-2,3,4,5-tetrahydro-1,5-benzothiazepin-8-yl)oxy)propanoic acid (Example 43; 75 mg, 0.55 mmol) were separated by chiral SFC Instrument (method I). The material was concentrated under vacuum at 40° C. The first eluting fraction corresponded to enantiomer 1 and the second eluting fraction corresponded to enantiomer 2. The absolute configuration of the two enantiomers is not known.

Enantiomer 1: Yield: 6% (4 mg, off-white solid). $^1$H NMR (400 MHz, DMSO-$d_6$): δ 7.34 (s, 1H), 7.22 (t, J=8.4 Hz, 2H), 6.99 (d, J=8.0 Hz, 2H), 6.85 (t, J=7.2 Hz, 1H), 6.54 (s, 1H), 4.28-4.20 (m, 2H), 3.89-3.58 (m, 5H), 3.22 (s, 2H), 2.52-2.51 (m, 2H), 1.55-1.41 (m, 3H), 1.36-1.24 (m, 2H), 1.15-1.14 (m, 3H), 0.79-0.74 (m, 6H). LCMS: (Method E) 476.0 (M$^+$+H), Rt. 2.89 min, 97.91% (Max). HPLC: (Method D) Rt. 5.15 min, 98.48% (Max). Chiral SFC: (Method I) Rt. 3.85 min, 96.61% (Max).

Enantiomer 2: Yield: 4% (3 mg, off-white solid). $^1$H NMR (400 MHz, DMSO-$d_6$): δ 7.34 (s, 1H), 7.21 (t, J=8.0 Hz, 2H), 6.98 (d, J=7.2 Hz, 2H), 6.84 (t, J=7.6 Hz, 1H), 6.54 (s, 1H), 4.13-4.16 (m, 2H), 3.84-3.61 (m, 5H), 3.23 (s, 2H), 2.61-2.59 (m, 2H), 1.54-1.42 (m, 3H), 1.36-1.31 (m, 2H), 1.14-1.01 (m, 3H), 0.79-0.74 (m, 6H). LCMS: (Method E) 476.1 (M$^+$+H), Rt. 2.89 min, 93.86% (Max). HPLC: (Method B) Rt. 5.33 min, 99.15% (Max). Chiral SFC: (Method I) Rt. 4.64 min, 92.11% (Max).

Example 45

3-((3,3-Dibutyl-7-methoxy-1,1-dioxido-5-phenyl-2,3,4,5-tetrahydro-1,5-benzothiazepin-8-yl)oxy)propanoic acid

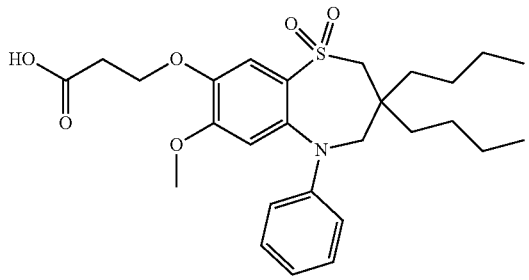 [SMILES: CCCCC1(CCCC)CN(c2ccccc2)c2cc(OC)c(OCCC(=O)O)cc2S(=O)(=O)C1]

To a stirred solution of 3,3-dibutyl-8-hydroxy-7-methoxy-5-phenyl-2,3,4,5-tetrahydro-1,5-benzothiazepine 1,1-dioxide (Intermediate 77; 230 mg, 0.53 mmol) in THF (3 mL) at 0° C., potassium tert-butoxide (65 mg, 0.58 mmol) was added and the reaction mixture was stirred for 15 minutes. A solution of 3-propiolactone (38 mg, 0.53 mmol) in THF (1 mL) was then added dropwise and the reaction mixture was stirred for 16 hours at room temperature. After completion of the reaction (monitored by TLC), the reaction mixture was quenched with dilute HCl (1.5 N, 1 mL) and then diluted with water (1 mL). The aqueous layer was extracted with EtOAc (2×5 mL) and the combined organic layer was washed with water (5 mL) and brine (5 mL). The organic part was dried over anhydrous Na$_2$SO$_4$, filtered and concentrated under vacuum. The resulting crude material was purified by Isolera column chromatography (eluent: 40% EtOAc/PE; silica gel: 230-400 mesh) to afford the title compound. Yield: 2% (5 mg, off-white solid).

$^1$H NMR (400 MHz, DMSO-$d_6$): δ 7.34 (s, 1H), 7.23 (t, J=8.4 Hz, 2H), 7.01 (d, J=7.6 Hz, 2H), 6.87 (t, J=7.6 Hz, 1H), 6.52 (s, 1H), 4.20 (t, J=6.0 Hz, 2H), 3.81-3.60 (m, 5H), 3.24 (s, 2H), 2.72 (t, J=5.6 Hz, 2H), 1.42-1.30 (m, 4H), 1.14-1.03 (m, 8H), 0.79-0.75 (m, 6H). LCMS: (Method E) 504.3 (M$^+$+H), Rt. 2.92 min, 96.63% (Max). HPLC: (Method D) Rt. 5.66 min, 96.82% (Max).

Example 46

3-((3,3-Dibutyl-7-(methylthio)-1,1-dioxido-5-phenyl-2,3,4,5-tetrahydro-1,5-benzothiazepin-8-yl)oxy)-2-methoxypropanoic acid

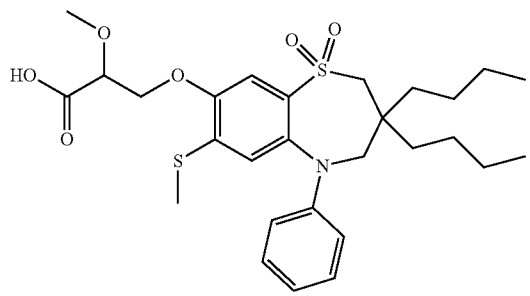

To a stirred solution of methyl 3-((3,3-dibutyl-7-(methylthio)-1,1-dioxido-5-phenyl-2,3,4,5-tetrahydro-1,5-benzothiazepin-8-yl)oxy)-2-methoxypropanoate (Intermediate 78; 30 mg, 0.053 mmol) in a mixture of 1,4-dioxane and water (1:1, 2 mL), lithium hydroxide (3 mg, 0.08 mmol) was added and the reaction mixture was stirred for 1 hour at room temperature. After completion of the reaction (monitored by TLC), the reaction mixture was quenched with dilute HCl (1.5 N, 1 mL) and diluted with water (1 mL). The aqueous layer was extracted with EtOAc (2×5 mL), and the combined organic layer was washed with water (5 mL) and brine (5 mL). The organic layer was then dried over anhydrous Na$_2$SO$_4$, filtered and concentrated under vacuum to afford the title compound. Yield: 69% (20 mg, white solid).

$^1$H NMR (400 MHz, DMSO-$d_6$): δ 12.90 (s, 1H), 7.34-7.29 (m, 1H), 7.23 (t, J=8.0 Hz, 2H), 7.01 (d, J=8.0 Hz, 2H), 6.88 (t, J=7.2 Hz, 1H), 6.67 (s, 1H), 4.37-4.35 (m, 1H), 4.30-4.26 (m, 1H), 4.18-4.16 (m, 1H), 3.78-3.60 (m, 2H), 3.41 (s, 3H), 3.33-3.27 (m, 2H), 2.15 (s, 3H), 1.50-1.43 (m, 2H), 1.35-1.32 (m, 2H), 1.17-1.02 (m, 8H), 0.78-0.75 (m, 6H). LCMS: (Method E) 550.1 (M$^+$+H), Rt. 3.17 min, 91.21% (Max). HPLC: (Method B) Rt. 6.13 min, 92.03% (Max).

Example 47

(R)-3-((3,3-dibutyl-7-(methylthio)-1,1-dioxido-5-phenyl-2,3,4,5-tetrahydro-1,5-benzothiazepin-8-yl)oxy)-2-methoxypropanoic acid and (S)-3-((3,3-dibutyl-7-(methylthio)-1,1-dioxido-5-phenyl-2,3,4,5-tetrahydro-1,5-benzothiazepin-8-yl)oxy)-2-methoxypropanoic acid

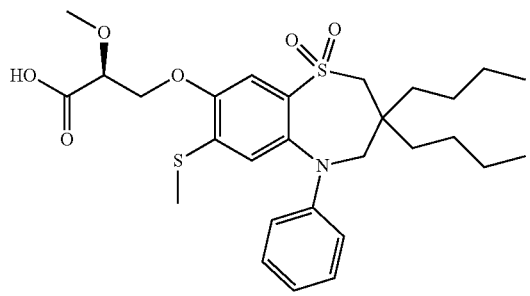

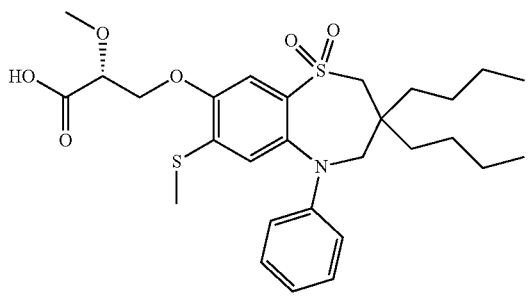 [SMILES: CCCCC1(CCCC)CN(c2ccccc2)c2cc(SC)c(OCC(OC)C(=O)O)cc2S(=O)(=O)C1]

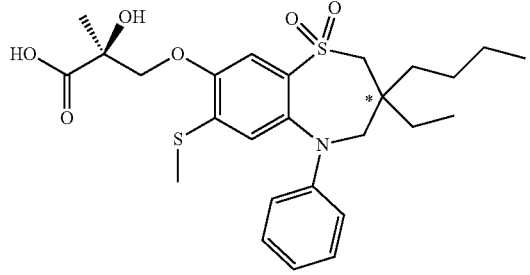

* the indicated carbons are each R or are each S

The two enantiomers of racemic 3-((3,3-dibutyl-7-(methylthio)-1,1-dioxido-5-phenyl-2,3,4,5-tetrahydro-1,5-benzothiazepin-8-yl)oxy)-2-methoxypropanoic acid (Example 46; 40 mg, 0.072 mmol) were separated by chiral SFC (method H). The material was concentrated under vacuum at 40° C. The first eluting fraction corresponded to enantiomer 1 and the second eluting fraction corresponded to enantiomer 2. The absolute configuration of the two enantiomers is not known.

Enantiomer 1: Yield: 7.5% (3 mg, grey solid). $^1$H NMR (400 MHz, CDCl$_3$): δ 7.54 (s, 1H), 7.41 (s, 1H), 7.28 (s, 1H), 7.07-6.98 (m, 3H), 6.63 (s, 1H), 4.53 (d, J=8.0 Hz, 1H), 4.38 (s, 1H), 4.26 (s, 1H), 3.68 (s, 1H), 3.61 (s, 3H), 3.59 (s, 1H), 3.18 (s, 2H), 2.16 (s, 3H), 1.54-1.40 (m, 4H), 1.35-1.30 (m, 2H), 1.27-1.15 (m, 4H), 1.12-1.11 (m, 2H), 0.83-0.81 (m, 6H). LCMS: (Method G) 550.3 (M$^+$+H), Rt. 2.55 min, 96.05% (Max). HPLC: (Method B) Rt. 6.21 min, 93.44% (Max). Chiral SFC: (Method H) Rt. 4.0 min, 98.66% (Max).

Enantiomer 2: Yield: 20% (8 mg, light brown solid). $^1$H NMR (400 MHz, DMSO-d$_6$): δ 7.33 (s, 1H), 7.22 (t, =8.4 Hz, 2H), 7.01 (d, J=8.0 Hz, 2H), 6.87 (t, J=7.2 Hz, 1H), 6.67 (s, 1H), 4.35 (s, 1H), 4.17 (d, =6.4 Hz, 1H), 3.94 (s, 1H), 3.67-3.64 (m, 2H), 3.45-3.41 (m, 2H), 3.29-3.25 (m, 3H), 2.19-2.13 (m, 3H), 1.42-1.30 (m, 4H), 1.14-1.04 (m, 8H), 0.79-0.75 (m, 6H). LCMS: (Method E) 550.3 (M$^+$+H), Rt. 3.21 min, 93.47% (Max). HPLC: (Method B) Rt. 6.21 min, 93.11% (Max). Chiral SFC: (Method H) Rt. 4.95 min, 98.08% (Max).

Example 48

3-((3-Butyl-3-ethyl-7-(methylthio)-1,1-dioxido-5-phenyl-2,3,4,5-tetrahydro-1,5-benzothiazepin-8-yl)oxy)-hydroxy-2-methylpropanoic Acid (Individual Diastereomers)

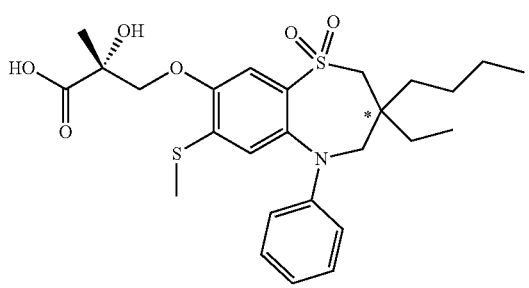

To a solution of diastereomer 1 of methyl 3-((3-butyl-3-ethyl-7-(methylthio)-1,1-dioxido-5-phenyl-2,3,4,5-tetrahydro-1,5-benzothiazepin-8-yl)oxy)-2-hydroxy-2-methylpropanoate (Intermediate 79; 50 mg, 0.09 mmol) in 1,4-dioxane (3 mL), dilute HCl (6 N, 3 mL) was added and the reaction mixture was heated for 3 hours at 80° C. After completion of the reaction (monitored by TLC), the reaction mixture was diluted with ice-cold water (2 mL) and the aqueous layer was extracted with EtOAc (2×5 mL). The combined organic layer was washed with water (5 mL) and brine (5 mL) and dried over anhydrous Na$_2$SO$_4$. The organic part was filtered, concentrated under vacuum and the resulting crude material was purified by Isolera column chromatography (eluent: 8% MeOH/DCM; silica gel: 230-400 mesh). The obtained material was re-purified by prep HPLC (Method A) to afford the title compound.

Diastereomers 2 of the title compound was obtained following the same procedure, starting from 50 mg of diastereomers 2 of Intermediate 79.

Diastereomer 1: Yield: 30% (15 mg, off-white solid). $^1$H NMR (400 MHz, DMSO-d$_6$): δ 7.32 (s, 1H), 7.22 (t, J=8.0 Hz, 2H), 6.98 (d, J=7.6 Hz, 2H), 6.86 (t, J=7.6 Hz, 1H), 6.70 (s, 1H), 4.12 (s, 2H), 3.78 (s, 2H), 3.27 (s, 2H), 2.16 (s, 3H), 1.62-1.54 (m, 1H), 1.42-1.38 (m, 3H), 1.35-1.32 (m, 3H), 1.16-0.93 (m, 4H), 0.81-0.71 (m, 6H). LCMS: (Method E) 522.2 (M$^+$+H), Rt. 2.84 min, 99.07% (Max). HPLC: (Method B) Rt. 5.45 min, 99.39% (Max). Chiral SFC: (Method H) Rt. 2.08 min, 100% (Max).

Diastereomer 2: Yield: 30% (13 mg, off-white solid). $^1$H NMR (400 MHz, DMSO-d$_6$): δ 12.70 (bs, 1H), 7.32 (s, 1H), 7.22 (t, J=8.0 Hz, 2H), 6.98 (d, J=7.6 Hz, 2H), 6.86 (t, J=7.6 Hz, 1H), 6.70 (s, 1H), 5.39 (bs, 1H), 4.12 (s, 2H), 3.78 (bs, 2H), 3.27 (s, 2H), 2.16 (s, 3H), 1.62-1.54 (m, 1H), 1.39 (s, 3H), 1.36-1.31 (m, 3H), 1.18-1.03 (m, 4H), 0.81-0.71 (m, 6H). LCMS: (Method E) 522.2 (M$^+$+H), Rt. 2.84 min, 99.52% (Max). HPLC: (Method B) Rt. 5.45 min, 99.03% (Max). Chiral SFC: (Method H) Rt. 3.47 min, 99.81% (Max).

The absolute configuration of the two diastereomers is not known.

Example 49

3-((3-Butyl-5-(4-fluorophenyl)-3-methyl-7-(methylthio)-1,1-dioxido-2,3,4,5-tetrahydro-1,5-benzothiazepin-8-yl)oxy)propanoic acid

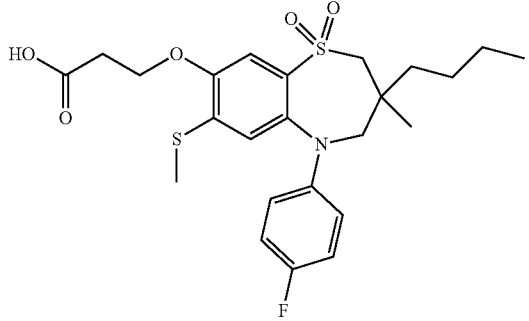 [SMILES: CCCCC1(C)CN(c2ccc(F)cc2)c2cc(SC)c(OCCC(=O)O)cc2S(=O)(=O)C1]

To a stirred solution of 3-butyl-5-(4-fluorophenyl)-8-hydroxy-3-methyl-7-(methylthio)-2,3,4,5-tetrahydro-1,5-benzothiazepine 1,1-dioxide (Intermediate 83; 150 mg, 0.35 mmol) in acetonitrile (5 mL), K₂CO₃ (219 mg, 1.5 mmol), 3-chloropropionic acid (80 mg, 0.74 mmol) and potassium iodide (23 mg, 0.14 mmol) were added. The reaction mixture was heated for 16 hours at 80° C. and the progress of the reaction was monitored by TLC. After completion of the reaction, the reaction mixture was quenched with dilute HCl (1.5 N, 2 mL) and diluted with water (2 mL). The aqueous layer was extracted with EtOAc (2×5 mL) and the combined organic layer was washed with water (5 mL) and brine (5 mL). The organic part was dried over anhydrous Na₂SO₄, filtered and concentrated under vacuum. The resulting crude material was purified by Isolera column chromatography (eluent: 100% EtOAc/PE; silica gel: 230-400 mesh). The obtained compound was purified by prep HPLC (method B) to afford the title compound. Yield: 51% (90 mg, white solid).
¹H NMR (400 MHz, CDCl₃): δ 7.45 (s, 1H), 7.00-6.97 (m, 4H), 6.65 (s, 1H), 4.40 (t, J=6.0 Hz, 2H), 3.75-3.72 (m, 1H), 3.55-3.51 (m, 1H), 3.18-3.09 (m, 2H), 2.94 (s, 2H), 2.20 (s, 3H), 1.59-1.47 (m, 1H), 1.35-1.28 (m, 5H), 1.12 (s, 3H), 0.86 (t, J=6.8 Hz, 3H). LCMS: (Method E) 496.2 (M⁺+H), Rt. 2.74 min, 98.94% (Max). HPLC: (Method B) Rt. 5.48 min, 99.70% (Max).

Example 50

(S)-3-((3-butyl-5-(4-fluorophenyl)-3-methyl-7-(methylthio)-1,1-dioxido-2,3,4,5-tetrahydro-1,5-benzothiazepin-8-yl)oxy)propanoic acid and (R)-3-((3-butyl-5-(4-fluorophenyl)-3-methyl-7-(methylthio)-1,1-dioxido-2,3,4,5-tetrahydro-1,5-benzothiazepin-8-yl)oxy)propanoic acid

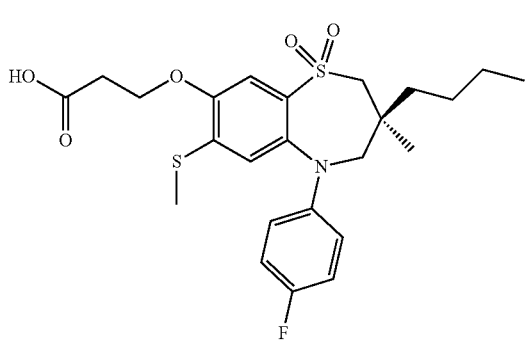

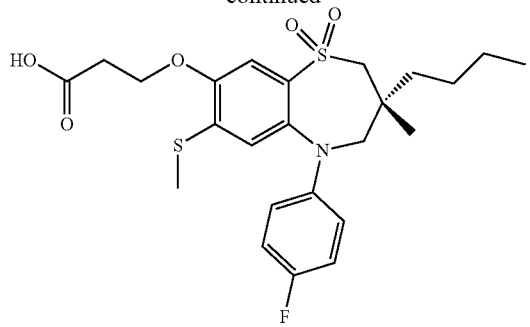

The two enantiomers of racemic 3-((3-butyl-5-(4-fluorophenyl)-3-methyl-7-(methylthio)-1,1-dioxido-2,3,4,5-tetrahydro-1,5-benzothiazepin-8-yl)oxy)propanoic acid (Example 49; 78 mg, 0.15 mmol) were separated by chiral SFC (method H). The material was concentrated under vacuum at 40° C. The first eluting fraction corresponded to enantiomer 1 and the second eluting fraction corresponded to enantiomer 2. The absolute configuration of the two enantiomers is not known.

Enantiomer 1: Yield: 25% (20 mg, off-white solid). ¹H NMR (400 MHz, CDCl₃): δ 7.45 (s, 1H), 6.99-6.97 (m, 4H), 6.65 (s, 1H), 4.40 (t, J=6.4 Hz, 2H), 3.81-3.69 (m, 1H), 3.55-3.51 (m, 1H), 3.18-3.09 (m, 2H), 2.93 (t, J=6.0 Hz, 2H), 2.20 (s, 3H), 1.60-1.45 (m, 1H), 1.36-1.22 (m, 5H), 1.12 (s, 3H), 0.9-0.84 (m, 3H). LCMS: (Method G) 496.2 (M⁺+H), Rt. 2.30 min, 99.12% (Max). HPLC: (Method B) Rt. 5.45 min, 97.07% (Max). Chiral SFC: (Method H) Rt. 4.85 min, 99.04% (Max).

Enantiomer 2: Yield: 25% (20 mg, off-white solid). ¹H NMR (400 MHz, CDCl₃): δ 7.45 (s, 1H), 7.03-6.95 (m, 4H), 6.65 (s, 1H), 4.40 (t, J=6.0 Hz, 2H), 3.81-3.68 (m, 1H), 3.59-3.53 (m, 1H), 3.22-3.05 (m, 2H), 2.93 (t, J=6.4 Hz, 2H), 2.20 (s, 3H), 1.60-1.45 (m, 1H), 1.33-1.20 (m, 5H), 1.12 (s, 3H), 0.87-0.84 (m, 3H). LCMS: (Method G) 496.2 (M⁺+H), Rt. 2.30 min, 96.29% (Max). HPLC: (Method B) Rt. 5.44 min, 93.92% (Max). Chiral SFC: (Method H) Rt. 6.01 min, 98.11% (Max).

Example 51

3-((3-Butyl-5-(4-fluorophenyl)-3-methyl-7-(methylthio)-1,1-dioxido-2,3,4,5-tetrahydro-1,5-benzothiazepin-8-yl)oxy)-2-hydroxypropanoic acid

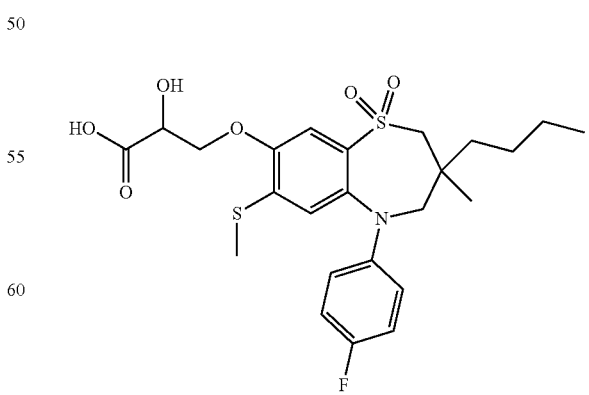

To a solution of methyl 3-((3-butyl-5-(4-fluorophenyl)-3-methyl-7-(methylthio)-1,1-dioxido-2,3,4,5-tetrahydro-1,5- benzothiazepin-8-yl)oxy)-2-hydroxypropanoate (Intermediate 84; 160 mg, 0.3 mmol) in 1,4-dioxane (1 mL), aq. HCl (6 N, 2 mL) was added and the reaction mixture was heated for 16 hours at 80° C. After completion of the reaction (monitored by TLC), the reaction mixture was extracted with EtOAc (2×5 mL). The combined organic layer was washed with water (5 mL) and brine (5 mL) and dried over anhydrous $Na_2SO_4$. The organic part was filtered and concentrated under vacuum. The resulting crude material was purified by Isolera column chromatography (eluent: 4% MeOH/DCM; silica gel: 230-400 mesh) to afford the title compound. Yield: 32% (50 mg, white solid).

$^1$H NMR (400 MHz, $CDCl_3$): δ 7.46 (s, 1H), 7.00-6.96 (m, 4H), 6.63 (s, 1H), 4.63 (s, 1H), 4.46 (s, 2H), 3.76-3.73 (m, 1H), 3.60-3.41 (m, 1H), 3.16 (s, 2H), 2.19 (s, 3H), 1.61-1.45 (m, 1H), 1.35-1.25 (m, 5H), 1.11 (s, 3H), 0.88-0.82 (m, 3H). LCMS: (Method E) 512.0 ($M^++H$), Rt. 2.80 min, 95.41% (Max). HPLC: (Method B) Rt. 5.09 min, 95.85% (Max).

Example 52

3-((3-butyl-3-ethyl-7-(methylamino)-1,1-dioxido-5-phenyl-2,3,4,5-tetrahydro-1,5-benzothiazepin-8-yl)oxy)propanoic acid

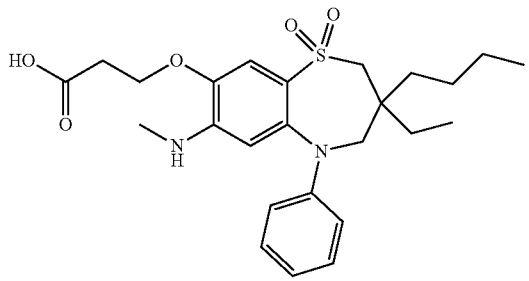 [SMILES: CCCCC1(CC)CN(c2ccccc2)c2cc(NC)c(OCCC(=O)O)cc2S(=O)(=O)C1]

To a stirred solution of 3-butyl-3-ethyl-8-hydroxy-7-(methylamino)-5-phenyl-2,3,4,5-tetrahydro-1,5-benzothiazepine 1,1-dioxide (Intermediate 87; 100 mg, 0.24 mmol) in THF (3 mL), potassium tert-butoxide (22.3 mg, 0.19 mmol) was added at 0° C. and the reaction mixture was stirred for 15 minutes. A solution of β-propiolactone (10.6 mg, 0.15 mmol) in THF (1 mL) was then added dropwise and the reaction mixture was stirred for 8 hours at room temperature. After completion of the reaction (monitored by TLC), the reaction mixture was quenched with dilute HCl (1.5 N, 2 mL) and diluted with water (2 mL). The aqueous layer was extracted with EtOAc (2×5 mL) and the combined organic layer was washed with water (5 mL) and brine (5 mL). The organic part was dried over anhydrous $Na_2SO_4$, filtered and concentrated under vacuum. The resulting crude material was purified by Isolera column chromatography (eluent: 8-15% MeOH/DCM; silica gel: 230-400 mesh) and the obtained material was re-purified by prep HPLC (method A) to afford the title compound.

Yield: 5% (6 mg, pale brown solid).

$^1$H NMR (400 MHz, DMSO-$d_6$): δ 12.43 (s, 1H), 7.20-7.16 (m, 3H), 6.95 (d, J=8.0 Hz, 2H), 6.79 (t, J=7.2 Hz, 1H), 5.98 (s, 1H), 5.86 (q, J=5.2 Hz, 1H), 4.18 (t, J=6.0 Hz, 2H), 3.75 (bs, 2H), 3.13 (s, 2H), 2.77 (t, J=6.0 Hz, 2H), 2.55 (s, 3H), 1.62-1.49 (m, 2H), 1.48-1.26 (m, 2H), 1.25-0.95 (m, 4H), 0.79-0.73 (m, 6H). LCMS: (Method A) 475.0 ($M^++H$), Rt. 2.95 min, 98.63% (Max). HPLC: (Method B) Rt. 5.47 min, 97.83% (Max).

Biological Assays

IBAT (h/m) Assay Protocol 10,000 cells (Human or Mouse IBAT-overexpressing cells) were seeded in 96-wells plate (Corning CLS3809) in 200 µL MEM-alpha medium (Gibco 12571-063) supplemented with 10% FBS (Gibco 10438026) containing Puromycin (Gibco A1113803) (10 µg/mL) and incubated at 37° C. in 5% $CO_2$ for 48 hours. After incubation, media was decanted from the wells and cells were washed two times with 300 µL of basal MEM-alpha medium (FBS-free). After decanting basal MEM-alpha medium each time, plates were tapped against paper towel to ensure maximum removal of residual media. Test inhibitor dilutions (highest test concentration being 10 µM, 3-fold serial dilution, 10 points) prepared in DMSO (Sigma D2650) were added in incubation mix (maintaining 0.2% final DMSO concentration) containing 0.25 µM 3H-taurocholic acid (ARC ART-1368) and 5 µM of cold taurocholic acid (Sigma T4009). 50 µL of incubation mix containing test inhibitors was then added to the wells (in duplicate) and the plates were incubated for 20 minutes in a $CO_2$ incubator at 37° C. After incubation, the reaction was stopped by keeping the plates on ice water mix for 2-3 minutes and then the incubation mix was aspirated completely from the wells. The wells were washed two times with 250 µL of chilled unlabeled 1 mM taurocholic acid dissolved in HEPES (Gibco 15630080)-buffered (10 mM) HBSS (Gibco 14175079) (pH 7.4). The plates were tapped against a paper towel after every wash to ensure maximum removal of blocking buffer. 100 µL of MicroScint-20 (PerkinElmer 6013621) was added to the wells and kept overnight at room temperature before reading the plates in TopCount NXT™ Microplate Scintillation and Luminescence Counter from PerkinElmer under 3H Test protocol (set at 120 seconds reading time per well).

LBAT (h/m) Assay Protocol 20,000 cells (Human or Mouse LBAT-overexpressing cells) were seeded in 96-wells plate (Corning CLS3809) in 100 µL MEM-alpha medium (Gibco 12571-063) supplemented with 10% FBS (Gibco 10438026) containing Geneticin (Gibco 10131-027) (1 mg/mL) and incubated at 37° C. in 5% $CO_2$ for 24 hours. After incubation, media was decanted from the wells and cells were washed two times with 300 µL of basal MEM-alpha medium (FBS-free). After decanting basal MEM-alpha medium each time, plates were tapped against paper towel to ensure maximum removal of residual media. For human LBAT, incubation mix was prepared by adding test inhibitor dilutions (3-fold serial dilution in DMSO (Sigma D2650), 10 points) in MEM-alpha (without FBS) containing 0.3 µM 3H-taurocholic acid (ARC ART-1368) and 7.5 µM cold taurocholic acid (Sigma T4009) (maintaining 0.2% final DMSO concentration). For mouse LBAT, incubation mix was prepared by adding test inhibitor dilutions (3-fold serial dilution in DMSO, 10 points) in MEM-alpha (without FBS) containing 0.3 µM 3H-taurocholic acid and 25 µM cold taurocholic acid maintaining 0.2% final DMSO concentration). 50 µL of incubation mix containing test inhibitors was then added to the wells (in duplicate) and the plates were incubated for 20 minutes in a $CO_2$ incubator at 37° C. After incubation, the reaction was stopped by keeping the plates on ice water mix for 2-3 minutes and then the incubation mix was aspirated completely from the wells. The wells were washed two times with 250 µL of chilled unlabeled 1 mM taurocholic acid dissolved in HEPES (Gibco 15630080)-buffered (10 mM) HBSS (Gibco 14175079) (pH 7.4). The plates were tapped against a paper towel after every wash to ensure maximum removal of blocking buffer. 100 µL of MicroScint-20 (PerkinElmer 6013621) was added to the wells and kept overnight at room temperature before reading the plates in TopCount NXT™ Microplate Scintillation and Luminescence Counter from PerkinElmer under 3H Test protocol (set at 120 seconds reading time per well, with normal plate orientation).

Bidirectional Permeability Assay (Caco-2 Cells)

Caco-2 cells (Evotec) were seeded at a density of 70,000 cells/well in Millicell® 24-well cell culture insert plates and maintained in an incubator (37° C., 5% $CO_2$, 95% RH) for 21 days with media change on alternate days.

Stock solutions (10 mM) of the test compounds, atenolol (low permeability marker), propranolol (high permeability marker) and digoxin (substrate for P-gp transport pathway) were prepared in dimethylsulfoxide (DMSO). An intermediate stock solution (1 mM) was prepared by diluting 10 µL of 10 mM master stock solution with 90 µL of neat DMSO. A working stock solution (10 µM) was prepared by diluting 50 µL of 1 mM with 4950 µL of FaSSIF buffer. Post addition of compounds to the FaSSIF, samples were subjected to sonication for 2 hours, and centrifuged at 4000 RPM for 30 minutes at 37° C. The 4 mL of resultant supernatant was directly used in the assay. The final DMSO concentration in the transport experiments was 1%.

On the day of assay, Caco-2 monolayers were washed twice with transport buffer (HBSS, pH 7.4) and pre-incubated for 30 min (37° C., 5% $CO_2$, 95% RH) in an incubator. The electrical resistance of the monolayers was measured with a Millicell®—ERS system. Monolayers with transepithelial electrical resistance (TEER) values greater than 350 ohm·cm$^2$ were selected for the assay.

The assay was conducted in absorptive direction (A2B) and secretory (B2A) directions. Transport experiments were initiated by addition of transport assay buffer (FaSSIF buffer prepared in HBSS) consisting of compounds to the donor compartment (apical chamber A-B; basolateral chamber B-A) in duplicate (n=2) wells. Drug free HBSS buffer (pH 7.4) containing 1% bovine serum albumin (BSA) was introduced to the receiver (A-B-basolateral; B-A-Apical) compartments. The volumes of apical and basolateral compartments were 0.4 and 0.8 mL, respectively. After adding dosing solution, plates were incubated in an incubator for 120 minutes at 37° C. After 120 minutes, donor and receiver samples were collected and matrix matched (1:1, 30 µL study sample+30 µL blank buffer) with the opposite buffer. Dosing samples matrix matched (1:1, 30 µL study sample+30 µL blank buffer) with the opposite buffer. Samples were processed by adding acetonitrile containing internal standard (60 µL study sample+200 µL acetonitrile containing internal standard-Tolbutamide, 500 ng/mL). Samples were vortexed and centrifuged at 4000 rpm for 10 minutes. The obtained supernatant (100 µL) was diluted with 100 µL of water and transferred to fresh 96 well plates. The concentration of compounds in the samples was analyzed by liquid chromatography tandem mass spectrometry (LCMS/MS) method using discovery grade bio-analytical method, as applicable.

The mean apparent permeability ($P_{app}$, ×10$^{-6}$ cm/sec) of the test compounds, atenolol, propranolol and digoxin were calculated as follows:

$$Papp = \frac{dq}{dt} \times \frac{1}{Co} \times \frac{1}{A}$$

where dq/dt=rate of transport (rate of transport of compound in the receiver compartment), $C_0$=initial concentration in the donor compartment, A=surface area of the effective filter membrane.

HepaRG-Based Assay Protocol

A cryopreserved vial of differentiated HepaRG cells (Biopredic International HPR116080) is thawed in HepaRG Thawing/Plating/General Purpose Medium (Biopredic International ADD670C) supplemented with 200 mM Glutamax (Gibco 35050061) following the protocol provided by Biopredic International. 70,000 cells per well are seeded in 96-wells plate (Corning CLS3809) in 100 µL of HepaRG Thawing/Plating/General Purpose Medium supplemented with 200 mM Glutamax and incubated at 37° C. in 5% $CO_2$ for 24 hours. Post incubation, the seeding media is replaced by HepaRG Maintenance/Metabolism Medium (Biopredic International ADD620C) and incubated for 6 days, with fresh HepaRG Maintenance/Metabolism Medium replenishment every 48 hours. After 7 days incubation post seeding, incubation media is decanted from the wells and cells are washed two times with 250 µL of William's E Basal Media (Gibco 12551032). After decanting William's E Basal Media each time, plates are tapped against paper towel to ensure maximum removal of residual media. Incubation mix is prepared by adding test inhibitor dilutions (3-fold serial dilution in DMSO (Sigma D2650)) in William's E media (basal) containing 0.3 µM 3H-taurocholic acid (ARC ART-1368) and 7.5 µM cold taurocholic acid (Sigma T4009) (maintaining 0.2% final DMSO concentration). 50 µl of incubation mix containing test inhibitors is then added to the wells (in duplicate) and the plates are incubated for 30 minutes in 5% $CO_2$ incubator at 37° C. After incubation, the reaction is stopped by keeping the plates on ice water mix for 2-3 minutes and the incubation mix is then aspirated completely from the wells. The wells are washed two times with 250 µL of chilled unlabeled 1 mM taurocholic acid dissolved in HEPES (Gibco 15630080)-buffered (10 mM) HBSS (Gibco 14175079) (pH 7.4). The plates are tapped against a paper towel after every wash to ensure maximum removal of blocking buffer.

100 µL of MicroScint-20 (PerkinElmer 6013621) is added to the wells and kept overnight at room temperature before reading the plates in TopCount NXT™ Microplate Scintillation and Luminescence Counter from PerkinElmer under 3H Test protocol (set at 120 seconds reading time per well, with normal plate orientation).

Preparation of Test Compound Dilutions

All test compounds were provided in powder form at room temperature. 10 mM DMSO stocks of the test compounds were prepared, aliquoted and stored at −20° C. From the 10 mM DMSO stock of the compounds, a 3-fold serial dilution in DMSO was prepared to get a total of 10 dilutions of the test compounds. 0.5 µL of this dilution in DMSO was added to 250 µL of FBS-free basal media containing 3H-taurocholic acid and cold taurocholic acid to prepare the incubation mixture.

Bioavailability Studies

Male mice (C57BL/6 or CD1) or Wistar rats of 8-9 weeks old were used. For each test compound, two groups of 3 animals each were used. One group was administered a single intravenous dose of 1 mg/kg (vehicle 100% DMSO) through the tail vein and the other group was administered a single oral dose of 10 mg/kg through gavage needle. The group that was administered an oral dose was fasted overnight. Blood samples were collected after 0.083, 0.25, 0.5, 1, 2, 4, 6, 8 and 24 hours following intravenous administration, and after 0.25, 0.5, 1, 2, 4, 6, 8 and 24 hours following oral administration. Blood samples were taken from saphenous vein. 0.2% EDTA was used as the anticoagulant. The samples were analyzed by a discovery grade bioanalytical method developed for the estimation of test compound in plasma, using an LC-MS/MS system.

Results

Biological data for the compounds of the examples is shown in Table 8 below.

TABLE 8

| Example | hLBAT IC$_{50}$ (nM) | hIBAT IC$_{50}$ (nM) | Permeability (Caco-2) P$_{app}$ A2B ($\times 10^{-6}$ cm/sec) | ER | Bioavailability (%) |
|---|---|---|---|---|---|
| 1 | 2174 | 18 | 13.4 | 0.9 | |
| 2 | 375 | 6 | 3.4 | 3.8 | 104 (C57BL/6) |
| 3 | 837 | 241 | | | |
| 4 | 375 | 26 | 2.2 | 2.3 | |
| 5 | 791 | 35 | | | |
| 6 | 410 | 17 | 13.6 | 1.4 | |
| 7 | 969 | 418 | | | |
| 8 | 376 | 74 | | | |
| 9 | 396 | 3 | 1.6 | 2.8 | |
| 10 | 379 | 1 | 2.1 | 1.6 | 13 (C57BL/6) |
| 11 | 613 | 4 | 1.5 | 1.4 | |
| 12 | 669 | 4 | | | |
| 13 | 489 | 4 | 10.3 | 2.0 | 102 (CD1) |
| 14 | 764 | 58 | | | |
| 15 | 1929 | 32 | 9.7 | 0.9 | |
| 16 | | 3 | 17.6 | 1.0 | |
| 17 | | 2 | 16.5 | 0.6 | |
| 18 | | 52 | | | |
| 19 | 601 | 39 | | | |
| 20 | 1395 | 42 | | | |
| 21 | 608 | 19 | | | |
| 22 | 543 | 10 | | | |
| 23 | 182 | 334 | | | |
| 24 | 596 | 7 | 22.5 | 0.6 | |
| 25 | 922 | 18 | | | |
| 26 | 1541 | 10 | | | |
| 27 | | 62 | | | |
| 28 | | 45 | 0.0 | | |
| 29, enantiomer 1 | 2587 | 5 | 20.5 | 0.7 | |
| 29, enantiomer 2 | 3308 | 57 | | | |
| 30, diastereomers 1 and 2 | 247 | 36 | | | |
| 30, diastereomers 3 and 4 | 818 | 263 | | | |
| 30, diastereomer 1 | 283 | 22 | 9.0 | 0.7 | |
| 30, diastereomer 2 | 322 | 52 | | | |
| 31 | 359 | 10 | | | |
| 32 | 2258 | 8 | | | |
| 32, diastereomer 1 | 2948 | 3 | 3.3 | 2.0 | |
| 32, diastereomer 2 | 4084 | 35 | | | |
| 33, diastereomer 1 | 5936 | 123 | | | |
| 33, diastereomer 2 | 1412 | 45 | | | |
| 33, diastereomer 3 | | | | | |
| 33, diastereomer 4 | 575 | | | | |
| 34 | 28 | 12 | 5.4 | 0.9 | |
| 35, diastereomer 1 | 48 | 4 | 4.0 | 2.0 | 8 (CD1) |
| 35, diastereomer 2 | 138 | 13 | | | |
| 36, diastereomer 1 | | 76 | | | |
| 36, diastereomer 2 | | 5 | 0.0 | 28.0 | |
| 37 | 297 | 3 | | | |
| 38, enantiomer 1 | 289 | 24 | | | |
| 38, enantiomer 2 | 439 | 0.8 | | | |
| 39 | 613 | 4 | | | |
| 40, diastereomer 1 | 1372 | 241 | | | |
| 40, diastereomer 2 | 513 | 24 | | | |
| 40, diastereomer 3 | 665 | 2 | | | |
| 40, diastereomer 4 | 389 | 10 | | | |
| 41 | 495 | 3 | | | |
| 42, diastereomer 1 | 1288 | 19 | | | |
| 42, diastereomer 2 | 2313 | 36 | | | |
| 42, diastereomer 3 | 892 | 0.5 | | | |
| 42, diastereomer 4 | 689 | 1 | | | |
| 43 | >20000 | 44 | | | |
| 44, enantiomer 1 | >20000 | 46 | | | |
| 44, enantiomer 2 | >23000 | 392 | | | |
| 45 | >6666 | 11 | | | |
| 46 | 1484 | 26 | | | |
| 48, diastereomer 1 | 1188 | 56 | | | |

TABLE 8-continued

| Example | hLBAT IC$_{50}$ (nM) | hIBAT IC$_{50}$ (nM) | P$_{app}$ A2B (×10$^{-6}$ cm/sec) | ER | Bioavailability (%) |
|---|---|---|---|---|---|
| 48, diastereomer 2 | 155 | 16 | 3.2 | 2.5 | |
| 49 | | 10 | | | |
| 51 | | 5 | | | |

PD Model: Evaluation of Test Compound on Total Bile Acids Levels in Male C57BL/6 Mice.

C57BL/6N Tac mice of 8-9 weeks old are used to study the effect of bile acid modulators on bile acid levels. After completion of quarantine and acclimatization period, animals are randomized based on bodyweight into x experimental groups: (i) vehicle control, and (ii) test compound y mg/kg po once daily. Animals are treated with test compound for 7 days. On day 5 of the study, animals are individually housed in fresh cages. On day 7, feces are collected from each cage, followed by blood withdrawal from each animal through retro-orbital route. Animals are euthanized to collect liver and terminal ileum from each animal for further analysis. Bodyweight and food consumption are measured twice weekly. Serum lipid profiles are analyzed in serum samples of day 7. Total bile acids in serum is measured in the serum samples of day 7. Fecal bile excretion is measured in the fecal sample of day 7. Hepatic expression of CYP7A1 and SHP are quantified in the liver samples of day 7. Liver triglycerides and total cholesterol are analyzed in the liver samples of day 7.

Urine Bile Acid Model: Evaluation of Test Compounds on Urine Bile Acid Levels in Male C57BL/6 Mice.

C57BL/6N Tac mice of 8-9 weeks old are used to study the effect of bile acid modulators on bile acid levels. After completion of quarantine and acclimatization period, animals are randomized based on bodyweight into x experimental groups: (i) vehicle control, and (ii) test compound y mg/kg po once daily. Animals are treated with test compound for 7 days. On day 6 of the study, animals are transferred to a metabolic cage. On day 7, feces and urine are collected from each metabolic cage, followed by blood withdrawal from each animal through retro-orbital route. Animals are euthanized to collect kidney from each animal for further analysis. Bodyweight is measured twice weekly. Total bile acids in serum is measured in serum samples of day 7. Fecal bile acid excretion is measured in the fecal sample of day 7. Urine excretion of bile acids is measured in the sample of day 7. Kidney expression of ASBT, OSTa, OSTAb and MRP2 is quantified in the samples of day 7.

The invention claimed is:

1. A compound of formula (I)

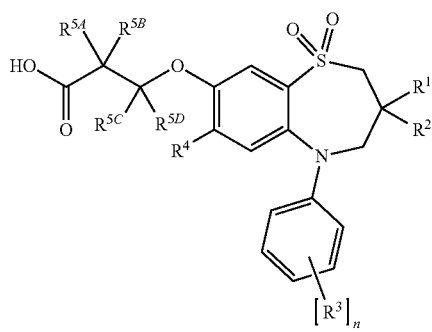

wherein $R^1$ and $R^2$ are each independently $C_{1-4}$ alkyl;

$R^3$ is independently selected from the group consisting of hydrogen, halogen, hydroxy, $C_{1-4}$ alkyl, $C_{1-4}$ haloalkyl, $C_{1-4}$ alkoxy, $C_{1-4}$ haloalkoxy, cyano, nitro, amino, N—($C_{1-4}$ alkyl)amino, N,N-di($C_{1-4}$ alkyl)amino and N-(aryl-$C_{1-4}$ alkyl)amino;

n is an integer 1, 2 or 3;

$R^4$ is selected from the group consisting of hydrogen, halogen, hydroxy, cyano, $C_{1-4}$ alkyl, $C_{3-6}$ cycloalkyl, $C_{1-4}$ alkoxy, $C_{3-6}$ cycloalkyloxy, $C_{1-4}$ alkylthio, $C_{3-6}$ cycloalkylthio, amino, N—($C_{1-4}$ alkyl)amino and N,N-di($C_{1-4}$ alkyl)amino; and $R^{5A}$, $R^{5B}$, $R^{5C}$ and $R^{5D}$ are each independently selected from the group consisting of hydrogen, halogen, hydroxy, amino, $C_{1-4}$ alkyl and $C_{1-4}$ alkoxy;

or a pharmaceutically acceptable salt thereof;

with the proviso that the compound is not racemic 3-((7-bromo-3-butyl-3-ethyl-1,1-dioxido-5-phenyl-2,3,4,5-tetrahydro-1,5-benzothiazepin-8-yl)oxy)propanoic acid.

2. A compound according to claim 1, wherein $R^1$ is n-butyl.

3. A compound according to claim 1, wherein $R^2$ is n-butyl.

4. A compound according to claim 1, wherein $R^2$ is ethyl.

5. A compound according to claim 1, wherein $R^3$ is independently selected from the group consisting of hydrogen, halogen, hydroxy, amino, cyano, $C_{1-4}$ haloalkyl, $C_{1-4}$ alkoxy and $C_{1-4}$ haloalkoxy.

6. A compound according to claim 1, wherein $R^4$ is selected from the group consisting of halogen, hydroxy, cyano, $C_{1-4}$ alkyl, $C_{1-4}$ alkoxy, $C_{1-4}$ alkylthio, amino, N—($C_{1-4}$ alkyl)amino and N,N-di($C_{1-4}$ alkyl)amino.

7. A compound according to claim 1, wherein $R^{5A}$ and $R^{5B}$ are each independently selected from the group consisting of hydrogen, halogen, hydroxy, amino, methyl and methoxy.

8. A compound according to claim 1, selected from the group consisting of:

(S)-3-((7-bromo-3-butyl-3-ethyl-1,1-dioxido-5-phenyl-2,3,4,5-tetrahydro-1,5-benzothiazepin-8-yl)oxy)propanoic acid;

(R)-3-((7-bromo-3-butyl-3-ethyl-1,1-dioxido-5-phenyl-2,3,4,5-tetrahydro-1,5-benzothiazepin-8-yl)oxy)propanoic acid;

3-((7-bromo-3,3-dibutyl-1,1-dioxido-5-phenyl-2,3,4,5-tetrahydro-1,5-benzothiazepin-8-yl)oxy)propanoic acid;

3-((3-butyl-7-chloro-3-ethyl-1,1-dioxido-5-phenyl-2,3,4,5-tetrahydro-1,5-benzothiazepin-8-yl)oxy)propanoic acid;
(S)-3-((3-butyl-7-chloro-3-ethyl-1,1-dioxido-5-phenyl-2,3,4,5-tetrahydro-1,5-benzothiazepin-8-yl)oxy)propanoic acid;
(R)-3-((3-butyl-7-chloro-3-ethyl-1,1-dioxido-5-phenyl-2,3,4,5-tetrahydro-1,5-benzothiazepin-8-yl)oxy)propanoic acid;
3-((3,3-dibutyl-7-chloro-1,1-dioxido-5-phenyl-2,3,4,5-tetrahydro-1,5-benzothiazepin-8-yl)oxy)propanoic acid;
3-((3,3-dibutyl-7-(methylthio)-1,1-dioxido-5-phenyl-2,3,4,5-tetrahydro-1,5-benzothiazepin-8-yl)oxy)-2-hydroxypropanoic acid;
(S)-3-((3,3-dibutyl-7-(methylthio)-1,1-dioxido-5-phenyl-2,3,4,5-tetrahydro-1,5-benzothiazepin-8-yl)oxy)-2-hydroxypropanoic acid;
(R)-3-((3,3-dibutyl-7-(methylthio)-1,1-dioxido-5-phenyl-2,3,4,5-tetrahydro-1,5-benzothiazepin-8-yl)oxy)-2-hydroxypropanoic acid;
3-((3-butyl-3-ethyl-7-(methylthio)-1,1-dioxido-5-phenyl-2,3,4,5-tetrahydro-1,5-benzothiazepin-8-yl)oxy)propanoic acid;
(S)-3-((3-butyl-3-ethyl-7-(methylthio)-1,1-dioxido-5-phenyl-2,3,4,5-tetrahydro-1,5-benzothiazepin-8-yl)oxy)propanoic acid;
(R)-3-((3-butyl-3-ethyl-7-(methylthio)-1,1-dioxido-5-phenyl-2,3,4,5-tetrahydro-1,5-benzothiazepin-8-yl)oxy)propanoic acid;
3-((3,3-dibutyl-7-(methylthio)-1,1-dioxido-5-phenyl-2,3,4,5-tetrahydro-1,5-benzothiazepin-8-yl)oxy)propanoic acid;
3-((3-butyl-7-(dimethylamino)-3-ethyl-1,1-dioxido-5-phenyl-2,3,4,5-tetrahydro-1,5-benzothiazepin-8-yl)oxy)propanoic acid;
(S)-3-((3-butyl-7-(dimethylamino)-3-ethyl-1,1-dioxido-5-phenyl-2,3,4,5-tetrahydro-1,5-benzothiazepin-8-yl)oxy)propanoic acid;
(R)-3-((3-butyl-7-(dimethylamino)-3-ethyl-1,1-dioxido-5-phenyl-2,3,4,5-tetrahydro-1,5-benzothiazepin-8-yl)oxy)propanoic acid;
3-((3,3-dibutyl-7-(methylthio)-1,1-dioxido-5-phenyl-2,3,4,5-tetrahydro-1,5-benzothiazepin-8-yl)oxy)-2-hydroxy-2-methylpropanoic acid;
(S)-3-((3,3-dibutyl-7-(methylthio)-1,1-dioxido-5-phenyl-2,3,4,5-tetrahydro-1,5-benzothiazepin-8-yl)oxy)-2-hydroxy-2-methylpropanoic acid;
(R)-3-((3,3-dibutyl-7-(methylthio)-1,1-dioxido-5-phenyl-2,3,4,5-tetrahydro-1,5-benzothiazepin-8-yl)oxy)-2-hydroxy-2-methylpropanoic acid;
3-((3-butyl-3-methyl-7-(methylthio)-1,1-dioxido-5-phenyl-2,3,4,5-tetrahydro-1,5-benzothiazepin-8-yl)oxy)propanoic acid;
(S)-3-((3-butyl-3-methyl-7-(methylthio)-1,1-dioxido-5-phenyl-2,3,4,5-tetrahydro-1,5-benzothiazepin-8-yl)oxy)propanoic acid;
(R)-3-((3-butyl-3-methyl-7-(methylthio)-1,1-dioxido-5-phenyl-2,3,4,5-tetrahydro-1,5-benzothiazepin-8-yl)oxy)propanoic acid;
3-((3,3-dibutyl-5-(3,4-difluorophenyl)-7-(methylthio)-1,1-dioxido-2,3,4,5-tetrahydro-1,5-benzothiazepin-8-yl)oxy)propanoic acid;
3-((3,3-dibutyl-5-(4-fluorophenyl)-7-(methylthio)-1,1-dioxido-2,3,4,5-tetrahydro-1,5-benzothiazepin-8-yl)oxy)propanoic acid;
3-((3-ethyl-7-(methylthio)-1,1-dioxido-5-phenyl-3-propyl-2,3,4,5-tetrahydro-1,5-benzothiazepin-8-yl)oxy)propanoic acid;
O-(3-butyl-3-ethyl-7-(methylthio)-1,1-dioxido-5-phenyl-2,3,4,5-tetrahydro-1,5-benzothiazepin-8-yl)serine;
3-((3-butyl-7-(dimethylamino)-3-methyl-1,1-dioxido-5-phenyl-2,3,4,5-tetrahydro-1,5-benzothiazepin-8-yl)oxy)propanoic acid;
(S)-3-((3-butyl-7-(dimethylamino)-3-methyl-1,1-dioxido-5-phenyl-2,3,4,5-tetrahydro-1,5-benzothiazepin-8-yl)oxy)propanoic acid;
(R)-3-((3-butyl-7-(dimethylamino)-3-methyl-1,1-dioxido-5-phenyl-2,3,4,5-tetrahydro-1,5-benzothiazepin-8-yl)oxy)propanoic acid;
3-((3-butyl-7-chloro-3-ethyl-1,1-dioxido-5-phenyl-2,3,4,5-tetrahydro-1,5-benzothiazepin-8-yl)oxy)butanoic acid;
(S)-3-(((R)-3-butyl-7-chloro-3-ethyl-1,1-dioxido-5-phenyl-2,3,4,5-tetrahydro-1,5-benzothiazepin-8-yl)oxy)butanoic acid;
(R)-3-(((R)-3-butyl-7-chloro-3-ethyl-1,1-dioxido-5-phenyl-2,3,4,5-tetrahydro-1,5-benzothiazepin-8-yl)oxy)butanoic acid;
(S)-3-(((S)-3-butyl-7-chloro-3-ethyl-1,1-dioxido-5-phenyl-2,3,4,5-tetrahydro-1,5-benzothiazepin-8-yl)oxy)butanoic acid;
(R)-3-(((S)-3-butyl-7-chloro-3-ethyl-1,1-dioxido-5-phenyl-2,3,4,5-tetrahydro-1,5-benzothiazepin-8-yl)oxy)butanoic acid;
3-((3-butyl-3-methyl-7-(methylthio)-1,1-dioxido-5-phenyl-2,3,4,5-tetrahydro-1,5-benzothiazepin-8-yl)oxy)-2-hydroxypropanoic acid;
(S)-3-(((R)-3-butyl-3-methyl-7-(methylthio)-1,1-dioxido-5-phenyl-2,3,4,5-tetrahydro-1,5-benzothiazepin-8-yl)oxy)-2-hydroxypropanoic acid;
(R)-3-(((R)-3-butyl-3-methyl-7-(methylthio)-1,1-dioxido-5-phenyl-2,3,4,5-tetrahydro-1,5-benzothiazepin-8-yl)oxy)-2-hydroxypropanoic acid;
(S)-3-(((S)-3-butyl-3-methyl-7-(methylthio)-1,1-dioxido-5-phenyl-2,3,4,5-tetrahydro-1,5-benzothiazepin-8-yl)oxy)-2-hydroxypropanoic acid;
(R)-3-(((S)-3-butyl-3-methyl-7-(methylthio)-1,1-dioxido-5-phenyl-2,3,4,5-tetrahydro-1,5-benzothiazepin-8-yl)oxy)-2-hydroxypropanoic acid;
3-((3-butyl-3-methyl-7-(methylthio)-1,1-dioxido-5-phenyl-2,3,4,5-tetrahydro-1,5-benzothiazepin-8-yl)oxy)-2-hydroxy-2-methylpropanoic acid;
(S)-3-(((R)-3-butyl-3-methyl-7-(methylthio)-1,1-dioxido-5-phenyl-2,3,4,5-tetrahydro-1,5-benzothiazepin-8-yl)oxy)-2-hydroxy-2-methylpropanoic acid;
(R)-3-(((R)-3-butyl-3-methyl-7-(methylthio)-1,1-dioxido-5-phenyl-2,3,4,5-tetrahydro-1,5-benzothiazepin-8-yl)oxy)-2-hydroxy-2-methylpropanoic acid;
(S)-3-(((S)-3-butyl-3-methyl-7-(methylthio)-1,1-dioxido-5-phenyl-2,3,4,5-tetrahydro-1,5-benzothiazepin-8-yl)oxy)-2-hydroxy-2-methylpropanoic acid;
(R)-3-(((S)-3-butyl-3-methyl-7-(methylthio)-1,1-dioxido-5-phenyl-2,3,4,5-tetrahydro-1,5-benzothiazepin-8-yl)oxy)-2-hydroxy-2-methylpropanoic acid;
3-((3-butyl-3-ethyl-7-(methylthio)-1,1-dioxido-5-phenyl-2,3,4,5-tetrahydro-1,5-benzothiazepin-8-yl)oxy)-2-fluoro-2-methylpropanoic acid;
(S)-3-(((R)-3-butyl-3-ethyl-7-(methylthio)-1,1-dioxido-5-phenyl-2,3,4,5-tetrahydro-1,5-benzothiazepin-8-yl)oxy)-2-fluoro-2-methylpropanoic acid;

(R)-3-(((R)-3-butyl-3-ethyl-7-(methylthio)-1,1-dioxido-5-phenyl-2,3,4,5-tetrahydro-1,5-benzothiazepin-8-yl)oxy)-2-fluoro-2-methylpropanoic acid;
(S)-3-(((S)-3-butyl-3-ethyl-7-(methylthio)-1,1-dioxido-5-phenyl-2,3,4,5-tetrahydro-1,5-benzothiazepin-8-yl)oxy)-2-fluoro-2-methylpropanoic acid;
(R)-3-(((S)-3-butyl-3-ethyl-7-(methylthio)-1,1-dioxido-5-phenyl-2,3,4,5-tetrahydro-1,5-benzothiazepin-8-yl)oxy)-2-fluoro-2-methylpropanoic acid;
O—((S)-3-butyl-3-ethyl-7-(methylthio)-1,1-dioxido-5-phenyl-2,3,4,5-tetrahydro-1,5-benzothiazepin-8-yl)-D-serine;
O—((R)-3-butyl-3-ethyl-7-(methylthio)-1,1-dioxido-5-phenyl-2,3,4,5-tetrahydro-1,5-benzothiazepin-8-yl)-D-serine;
3-((3-butyl-3-ethyl-5-(4-fluorophenyl)-7-(methylthio)-1,1-dioxido-2,3,4,5-tetrahydro-1,5-benzothiazepin-8-yl)oxy)propanoic acid;
(S)-3-((3-butyl-3-ethyl-5-(4-fluorophenyl)-7-(methylthio)-1,1-dioxido-2,3,4,5-tetrahydro-1,5-benzothiazepin-8-yl)oxy)propanoic acid;
(R)-3-((3-butyl-3-ethyl-5-(4-fluorophenyl)-7-(methylthio)-1,1-dioxido-2,3,4,5-tetrahydro-1,5-benzothiazepin-8-yl)oxy)propanoic acid;
3-((3-butyl-3-ethyl-7-(methylthio)-1,1-dioxido-5-phenyl-2,3,4,5-tetrahydro-1,5-benzothiazepin-8-yl)oxy)-2-hydroxypropanoic acid;
(S)-3-(((R)-3-butyl-3-ethyl-7-(methylthio)-1,1-dioxido-5-phenyl-2,3,4,5-tetrahydro-1,5-benzothiazepin-8-yl)oxy)-2-hydroxypropanoic acid;
(R)-3-(((R)-3-butyl-3-ethyl-7-(methylthio)-1,1-dioxido-5-phenyl-2,3,4,5-tetrahydro-1,5-benzothiazepin-8-yl)oxy)-2-hydroxypropanoic acid;
(S)-3-(((S)-3-butyl-3-ethyl-7-(methylthio)-1,1-dioxido-5-phenyl-2,3,4,5-tetrahydro-1,5-benzothiazepin-8-yl)oxy)-2-hydroxypropanoic acid;
(R)-3-(((S)-3-butyl-3-ethyl-7-(methylthio)-1,1-dioxido-5-phenyl-2,3,4,5-tetrahydro-1,5-benzothiazepin-8-yl)oxy)-2-hydroxypropanoic acid;
3-((3-butyl-3-ethyl-5-(4-fluorophenyl)-7-(methylthio)-1,1-dioxido-2,3,4,5-tetrahydro-1,5-benzothiazepin-8-yl)oxy)-2-hydroxypropanoic acid;
(S)-3-(((R)-3-butyl-3-ethyl-5-(4-fluorophenyl)-7-(methylthio)-1,1-dioxido-2,3,4,5-tetrahydro-1,5-benzothiazepin-8-yl)oxy)-2-hydroxypropanoic acid;
(R)-3-(((R)-3-butyl-3-ethyl-5-(4-fluorophenyl)-7-(methylthio)-1,1-dioxido-2,3,4,5-tetrahydro-1,5-benzothiazepin-8-yl)oxy)-2-hydroxypropanoic acid;
(S)-3-(((S)-3-butyl-3-ethyl-5-(4-fluorophenyl)-7-(methylthio)-1,1-dioxido-2,3,4,5-tetrahydro-1,5-benzothiazepin-8-yl)oxy)-2-hydroxypropanoic acid;
(R)-3-(((S)-3-butyl-3-ethyl-5-(4-fluorophenyl)-7-(methylthio)-1,1-dioxido-2,3,4,5-tetrahydro-1,5-benzothiazepin-8-yl)oxy)-2-hydroxypropanoic acid;
3-((3-butyl-3-ethyl-7-methoxy-1,1-dioxido-5-phenyl-2,3,4,5-tetrahydro-1,5-benzothiazepin-8-yl)oxy)propanoic acid;
(S)-3-((3-butyl-3-ethyl-7-methoxy-1,1-dioxido-5-phenyl-2,3,4,5-tetrahydro-1,5-benzothiazepin-8-yl)oxy)propanoic acid;
(R)-3-((3-butyl-3-ethyl-7-methoxy-1,1-dioxido-5-phenyl-2,3,4,5-tetrahydro-1,5-benzothiazepin-8-yl)oxy)propanoic acid;
3-((3,3-dibutyl-7-methoxy-1,1-dioxido-5-phenyl-2,3,4,5-tetrahydro-1,5-benzothiazepin-8-yl)oxy)propanoic acid;
3-((3,3-dibutyl-7-(methylthio)-1,1-dioxido-5-phenyl-2,3,4,5-tetrahydro-1,5-benzothiazepin-8-yl)oxy)-2-methoxypropanoic acid;
(R)-3-((3,3-dibutyl-7-(methylthio)-1,1-dioxido-5-phenyl-2,3,4,5-tetrahydro-1,5-benzothiazepin-8-yl)oxy)-2-methoxypropanoic acid;
(S)-3-((3,3-dibutyl-7-(methylthio)-1,1-dioxido-5-phenyl-2,3,4,5-tetrahydro-1,5-benzothiazepin-8-yl)oxy)-2-methoxypropanoic acid;
3-((3-butyl-3-ethyl-7-(methylthio)-1,1-dioxido-5-phenyl-2,3,4,5-tetrahydro-1,5-benzothiazepin-8-yl)oxy)-2-hydroxy-2-methylpropanoic acid;
(S)-3-(((R)-3-butyl-3-ethyl-7-(methylthio)-1,1-dioxido-5-phenyl-2,3,4,5-tetrahydro-1,5-benzothiazepin-8-yl)oxy)-2-hydroxy-2-methylpropanoic acid;
(R)-3-(((R)-3-butyl-3-ethyl-7-(methylthio)-1,1-dioxido-5-phenyl-2,3,4,5-tetrahydro-1,5-benzothiazepin-8-yl)oxy)-2-hydroxy-2-methylpropanoic acid;
(S)-3-(((S)-3-butyl-3-ethyl-7-(methylthio)-1,1-dioxido-5-phenyl-2,3,4,5-tetrahydro-1,5-benzothiazepin-8-yl)oxy)-2-hydroxy-2-methylpropanoic acid;
(R)-3-(((S)-3-butyl-3-ethyl-7-(methylthio)-1,1-dioxido-5-phenyl-2,3,4,5-tetrahydro-1,5-benzothiazepin-8-yl)oxy)-2-hydroxy-2-methylpropanoic acid;
3-((3-butyl-5-(4-fluorophenyl)-3-methyl-7-(methylthio)-1,1-dioxido-2,3,4,5-tetrahydro-1,5-benzothiazepin-8-yl)oxy)propanoic acid;
(S)-3-((3-butyl-5-(4-fluorophenyl)-3-methyl-7-(methylthio)-1,1-dioxido-2,3,4,5-tetrahydro-1,5-benzothiazepin-8-yl)oxy)propanoic acid;
(R)-3-((3-butyl-5-(4-fluorophenyl)-3-methyl-7-(methylthio)-1,1-dioxido-2,3,4,5-tetrahydro-1,5-benzothiazepin-8-yl)oxy)propanoic acid;
3-((3-butyl-5-(4-fluorophenyl)-3-methyl-7-(methylthio)-1,1-dioxido-2,3,4,5-tetrahydro-1,5-benzothiazepin-8-yl)oxy)-2-hydroxypropanoic acid;
(S)-3-(((R)-3-butyl-5-(4-fluorophenyl)-3-methyl-7-(methylthio)-1,1-dioxido-2,3,4,5-tetrahydro-1,5-benzothiazepin-8-yl)oxy)-2-hydroxypropanoic acid;
(R)-3-(((R)-3-butyl-5-(4-fluorophenyl)-3-methyl-7-(methylthio)-1,1-dioxido-2,3,4,5-tetrahydro-1,5-benzothiazepin-8-yl)oxy)-2-hydroxypropanoic acid;
(S)-3-(((S)-3-butyl-5-(4-fluorophenyl)-3-methyl-7-(methylthio)-1,1-dioxido-2,3,4,5-tetrahydro-1,5-benzothiazepin-8-yl)oxy)-2-hydroxypropanoic acid;
(R)-3-(((S)-3-butyl-5-(4-fluorophenyl)-3-methyl-7-(methylthio)-1,1-dioxido-2,3,4,5-tetrahydro-1,5-benzothiazepin-8-yl)oxy)-2-hydroxypropanoic acid;
3-((3-butyl-3-ethyl-7-(methylamino)-1,1-dioxido-5-phenyl-2,3,4,5-tetrahydro-1,5-benzothiazepin-8-yl)oxy)propanoic acid;
(S)-3-((3-butyl-3-ethyl-7-(methylamino)-1,1-dioxido-5-phenyl-2,3,4,5-tetrahydro-1,5-benzothiazepin-8-yl)oxy)propanoic acid; and
(R)-3-((3-butyl-3-ethyl-7-(methylamino)-1,1-dioxido-5-phenyl-2,3,4,5-tetrahydro-1,5-benzothiazepin-8-yl)oxy)propanoic acid;

or a pharmaceutically acceptable salt thereof.

9. A pharmaceutical composition comprising as the active ingredient a therapeutically effective amount of a compound according to claim 1, and at least one pharmaceutically acceptable excipient, carrier or diluent.

* * * * *

UNITED STATES PATENT AND TRADEMARK OFFICE
CERTIFICATE OF CORRECTION

| | |
|---|---|
| PATENT NO. | : 10,975,045 B2 |
| APPLICATION NO. | : 16/805153 |
| DATED | : April 13, 2021 |
| INVENTOR(S) | : Per-Göran Gillberg et al. |

It is certified that error appears in the above-identified patent and that said Letters Patent is hereby corrected as shown below:

On the Title Page

Item (73), Assignee, delete "Aibireo" and insert -- Albireo --.

Signed and Sealed this
Fifth Day of September, 2023

Katherine Kelly Vidal
*Director of the United States Patent and Trademark Office*